US006562823B1

(12) United States Patent
Dinsmore et al.

(10) Patent No.: US 6,562,823 B1
(45) Date of Patent: May 13, 2003

(54) INHIBITORS OF PRENYL-PROTEIN TRANSFERASE

(75) Inventors: Christopher J. Dinsmore, Schwenksville, PA (US); Jeffrey M. Bergman, Perkasie, PA (US); Samuel L. Graham, Schwenksville, PA (US); Diem N. Nguyen, North Wales, PA (US); Gerald E. Stokker, Gwynedd Valley, PA (US); Theresa M. Williams, Harleysville, PA (US); C. Blair Zartman, Hatfield, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/719,878

(22) PCT Filed: Jun. 29, 1999

(86) PCT No.: PCT/US99/14741

§ 371 (c)(1),
(2), (4) Date: Jun. 28, 2001

(87) PCT Pub. No.: WO00/01702

PCT Pub. Date: Jan. 13, 2000

Related U.S. Application Data

(60) Provisional application No. 60/091,629, filed on Jul. 2, 1998.

(51) Int. Cl.[7] ............... C07D 267/00; C07D 281/00; C07D 291/00; A61K 31/495
(52) U.S. Cl. .................... 514/250; 540/469
(58) Field of Search ............ 540/469; 514/250

(56) References Cited

U.S. PATENT DOCUMENTS

| | | | |
|---|---|---|---|
| 5,736,539 A | 4/1998 | Graham et al. | |
| 5,756,528 A | 5/1998 | Anthony et al. | |
| 5,773,616 A | 6/1998 | Yuan et al. | |
| 5,856,326 A | 1/1999 | Anthony et al. | |
| 6,329,376 B1 | * 12/2001 | Bergman et al. | 514/250 |

FOREIGN PATENT DOCUMENTS

| | | |
|---|---|---|
| EP | 0 670 314 A1 | 9/1995 |
| WO | WO 95/09001 | 4/1995 |
| WO | WO 97/27854 | 8/1997 |
| WO | WO 97/36591 | 10/1997 |
| WO | WO 97/36592 | 10/1997 |
| WO | WO 97/36593 | 10/1997 |
| WO | WO 97/36888 | 10/1997 |
| WO | WO 97/36889 | 10/1997 |
| WO | WO 99/09985 | 3/1999 |
| WO | WO 99/20609 | 4/1999 |

OTHER PUBLICATIONS

Williams, T. M., Inhibitors of protein prenylation, Exp. Opin. Ther. Patents, vol. 9 (9), pp. 1263–1280, 1999.
Williams, T. M., Inhibitors of protein farnesylation, Exp. Opin. Ther. Patents, vol. 8 (5), pp. 553–569, 1998.
Williams, T. M. et al., N–Arylpiperazinone Inhibitors of Farnesyltransferase: Discovery and Biological Activity, J. Med. Chem., vol. 42, No. 19, pp. 3779–3784, 1999.
Graham, S. L., Inhibitors of protein farnesylation: a new approach to cancer chemotherapy, Exp. Opin. Ther. Patents, vol. 5 (12), pp. 1269–1285, 1995.
Graham, S. L. et al., Inhibitors of protein farnesylation, Exp. Opin. Ther. Patents, vol. 6 (12), pp. 1295–1304, 1996.
Sepp–Lorenzino, et al., A Peptidomimetic Inhibiotr of Farneyl–Protein Transferase Blocks the Anchorage–dependent and –independent Growth of Human Tumor Cell Lines, Cancer Research, vol. 55, 5302–5309, 1995.
Kohl, et al., Inhibition of farnesyltransferase induces regression of mammary and salivary carcinomas in ras transgenic mice, Proc. Natl. Acad. Sci. USA, vol. 91, pp. 792–797, 1995.
Bolton et al., Ras Oncogene Directed Approaches in Cancer Chemotherapy, Ann. Reports Med. Chem., vol 29, pp. 165–174, 1994.
Balasubramanian et al., Recent Developments in Cancer Cytotoxics, Ann. Reports Med. Chem., vol. 33, pp. 151–162, 1998.
Kohl et al., Protein farnesyltransferase inhibitors block the growth of ras–dependent tumors in nude mice, Proc. Natl. Acad. Sci. USA vol. 91, pp. 9141–9145, Sep. 1994.

* cited by examiner

*Primary Examiner*—Bruck Kifle
*Assistant Examiner*—Hong Liu
(74) *Attorney, Agent, or Firm*—Matthew A. Leff; Mark R. Daniel

(57) ABSTRACT

The present invention is directed to peptidomimetic piperazine-containing macrocyclic compounds which inhibit prenyl-protein transferase and the prenylation of the oncogene protein Ras. The invention is further directed to chemotherapeutic compositions containing the compounds of this invention and methods for inhibiting prenyl-protein transferase and the prenylation of the oncogene protein Ras.

17 Claims, No Drawings

SEQUENCE LISTING

```
<160> NUMBER OF SEQ ID NOS: 25

<210> SEQ ID NO 1
<211> LENGTH: 4
<212> TYPE: PRT
<213> ORGANISM: Artificial Sequence
<220> FEATURE:
<223> OTHER INFORMATION: completely synthetic sequence

<400> SEQUENCE: 1

Cys Val Leu Leu
```

```
<210> SEQ ID NO 2
<211> LENGTH: 4
<212> TYPE: PRT
<213> ORGANISM: Artificial Sequence
<220> FEATURE:
<223> OTHER INFORMATION: completely synthetic sequence

<400> SEQUENCE: 2

Cys Val Leu Ser
  1

<210> SEQ ID NO 3
<211> LENGTH: 15
<212> TYPE: PRT
<213> ORGANISM: Artificial Sequence
<220> FEATURE:
<223> OTHER INFORMATION: completely synthetic sequence

<400> SEQUENCE: 3

Gly Lys Lys Lys Lys Lys Ser Lys Thr Lys Cys Val Ile Met
  1               5                  10                  15

<210> SEQ ID NO 4
<211> LENGTH: 52
<212> TYPE: DNA
<213> ORGANISM: Artificial Sequence
<220> FEATURE:
<223> OTHER INFORMATION: completely synthetic sequence

<400> SEQUENCE: 4
gagagggaat cgggcccctt cctgcatgct gctgctgctg ctgctgctgg gc           52

<210> SEQ ID NO 5
<211> LENGTH: 41
<212> TYPE: DNA
<213> ORGANISM: Artificial Sequence
<220> FEATURE:
<223> OTHER INFORMATION: completely synthetic sequence

<400> SEQUENCE: 5
gagagagctc gaggttaacc cgggtgcgcg gcgtcggtgg t                      41

<210> SEQ ID NO 6
<211> LENGTH: 42
<212> TYPE: DNA
<213> ORGANISM: Artificial Sequence
<220> FEATURE:
<223> OTHER INFORMATION: completely synthetic sequence

<400> SEQUENCE: 6
gagagagtct agagttaacc cgtggtcccc gcgttgcttc ct                     42

<210> SEQ ID NO 7
<211> LENGTH: 43
<212> TYPE: DNA
<213> ORGANISM: Artificial Sequence
<220> FEATURE:
<223> OTHER INFORMATION: completely synthetic sequence

<400> SEQUENCE: 7
gaagaggaag cttggtaccg ccactgggct gtaggtggtg gct                    43

<210> SEQ ID NO 8
<211> LENGTH: 27
```

```
<212> TYPE: DNA
<213> ORGANISM: Artificial Sequence
<220> FEATURE:
<223> OTHER INFORMATION: completely synthetic sequence

<400> SEQUENCE: 8
ggcagagctc gtttagtgaa ccgtcag                                              27

<210> SEQ ID NO 9
<211> LENGTH: 27
<212> TYPE: DNA
<213> ORGANISM: Artificial Sequence
<220> FEATURE:
<223> OTHER INFORMATION: completely synthetic sequence

<400> SEQUENCE: 9
gagagatctc aaggacggtg actgcag                                              27

<210> SEQ ID NO 10
<211> LENGTH: 86
<212> TYPE: DNA
<213> ORGANISM: Artificial Sequence
<220> FEATURE:
<223> OTHER INFORMATION: completely synthetic sequence

<400> SEQUENCE: 10
tctcctcgag gccaccatgg ggagtagcaa gagcaagcct aaggacccca gccagcgccg          60
gatgacagaa tacaagcttg tggtgg                                               86

<210> SEQ ID NO 11
<211> LENGTH: 33
<212> TYPE: DNA
<213> ORGANISM: Artificial Sequence
<220> FEATURE:
<223> OTHER INFORMATION: completely synthetic sequence

<400> SEQUENCE: 11
cacatctaga tcaggacagc acagacttgc agc                                       33

<210> SEQ ID NO 12
<211> LENGTH: 41
<212> TYPE: DNA
<213> ORGANISM: Artificial Sequence
<220> FEATURE:
<223> OTHER INFORMATION: completely synthetic sequence

<400> SEQUENCE: 12
tctcctcgag gccaccatga cagaatacaa gcttgtggtg g                              41

<210> SEQ ID NO 13
<211> LENGTH: 38
<212> TYPE: DNA
<213> ORGANISM: Artificial Sequence
<220> FEATURE:
<223> OTHER INFORMATION: completely synthetic sequence

<400> SEQUENCE: 13
cactctagac tggtgtcaga gcagcacaca cttgcagc                                  38

<210> SEQ ID NO 14
<211> LENGTH: 38
<212> TYPE: DNA
<213> ORGANISM: Artificial Sequence
<220> FEATURE:
<223> OTHER INFORMATION: completely synthetic sequence
```

```
<400> SEQUENCE: 14
gagagaattc gccaccatga cggaatataa gctggtgg                    38

<210> SEQ ID NO 15
<211> LENGTH: 33
<212> TYPE: DNA
<213> ORGANISM: Artificial Sequence
<220> FEATURE:
<223> OTHER INFORMATION: completely synthetic sequence

<400> SEQUENCE: 15
gagagtcgac gcgtcaggag agcacacact tgc                         33

<210> SEQ ID NO 16
<211> LENGTH: 22
<212> TYPE: DNA
<213> ORGANISM: Artificial Sequence
<220> FEATURE:
<223> OTHER INFORMATION: completely synthetic sequence

<400> SEQUENCE: 16
ccgccggcct ggaggagtac ag                                     22

<210> SEQ ID NO 17
<211> LENGTH: 38
<212> TYPE: DNA
<213> ORGANISM: Artificial Sequence
<220> FEATURE:
<223> OTHER INFORMATION: completely synthetic sequence

<400> SEQUENCE: 17
gagagaattc gccaccatga ctgagtacaa actggtgg                    38

<210> SEQ ID NO 18
<211> LENGTH: 32
<212> TYPE: DNA
<213> ORGANISM: Artificial Sequence
<220> FEATURE:
<223> OTHER INFORMATION: completely synthetic sequence

<400> SEQUENCE: 18
gagagtcgac ttgttacatc accacacatg gc                          32

<210> SEQ ID NO 19
<211> LENGTH: 21
<212> TYPE: DNA
<213> ORGANISM: Artificial Sequence
<220> FEATURE:
<223> OTHER INFORMATION: completely synthetic sequence

<400> SEQUENCE: 19
gttggagcag ttggtgttgg g                                      21
```

```
<210> SEQ ID NO 20
<211> LENGTH: 38
<212> TYPE: DNA
<213> ORGANISM: Artificial Sequence
<220> FEATURE:
<223> OTHER INFORMATION: completely synthetic sequence

<400> SEQUENCE: 20
gagaggtacc gccaccatga ctgaatataa acttgtgg                    38

<210> SEQ ID NO 21
<211> LENGTH: 36
<212> TYPE: DNA
<213> ORGANISM: Artificial Sequence
<220> FEATURE:
<223> OTHER INFORMATION: completely synthetic sequence

<400> SEQUENCE: 21
ctctgtcgac gtatttacat aattacacac tttgtc                      36

<210> SEQ ID NO 22
<211> LENGTH: 24
<212> TYPE: DNA
<213> ORGANISM: Artificial Sequence
<220> FEATURE:
<223> OTHER INFORMATION: completely synthetic sequence

<400> SEQUENCE: 22
gtagttggag ctgttggcgt aggc                                   24

<210> SEQ ID NO 23
<211> LENGTH: 38
<212> TYPE: DNA
<213> ORGANISM: Artificial Sequence
<220> FEATURE:
<223> OTHER INFORMATION: completely synthetic sequence

<400> SEQUENCE: 23
gagaggtacc gccaccatga ctgaatataa acttgtgg                    38

<210> SEQ ID NO 24
<211> LENGTH: 45
<212> TYPE: DNA
<213> ORGANISM: Artificial Sequence
<220> FEATURE:
<223> OTHER INFORMATION: completely synthetic sequence

<400> SEQUENCE: 24
ctctgtcgac agattacatt ataatgcatt ttttaatttt cacac            45

<210> SEQ ID NO 25
<211> LENGTH: 24
<212> TYPE: DNA
<213> ORGANISM: Artificial Sequence
<220> FEATURE:
<223> OTHER INFORMATION: completely synthetic sequence

<400> SEQUENCE: 25
gtagttggag ctgttggcgt aggc                                   24
```

INHIBITORS OF PRENYL-PROTEIN TRANSFERASE

This application claims the benefit of U.S. Provisional Application No. 60/091,629, filed Jul. 2, 1998.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase type I, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The term prenyl-protein transferase may be used to refer generally to farnesyl-protein transferase and geranylgeranyl-protein transferase type I. The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also famesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

It is, therefore, an object of this invention to develop peptidomimetic compounds that do not have a thiol moiety, and that will inhibit prenyl-protein transferase and thus, the post-translational prenylation of proteins. It is a further object of this invention to develop chemotherapeutic compositions containing the compounds of this invention and methods for producing the compounds of this invention.

SUMMARY OF THE INVENTION

The present invention comprises peptidomimetic piperazine-containing macrocyclic compounds which inhibit prenyl-protein transferase. Further contained in this invention are chemotherapeutic compositions containing these prenyl-protein transferase inhibitors and methods for their production.

The compounds of this invention are illustrated by the formula A:

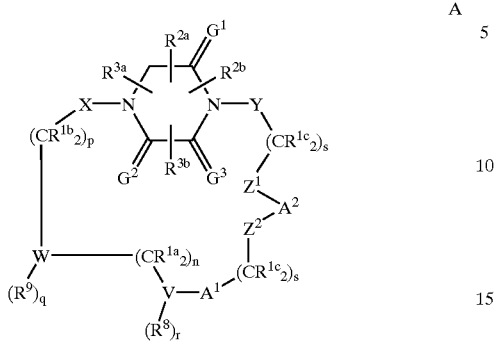

DETAILED DESCRIPTION OF THE INVENTION

The compounds of this invention are useful in the inhibition of prenyl-protein transferase and the prenylation of the oncogene protein Ras. In a first embodiment of this invention, the inhibitors of prenyl-protein transferase are illustrated by the formula A:

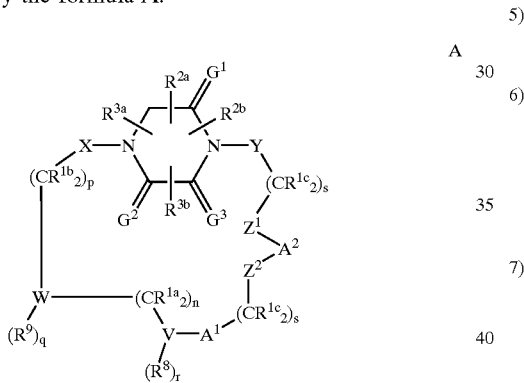

wherein:

$R^{1a}$, $R^{1b}$, $R^{1c}$ and $R^{1d}$ are independently selected from:
  a) hydrogen,
  b) aryl, heterocycle, cycloalkyl, alkenyl, alkynyl, $R^{10}O-$, $R^{11}S(O)_m-$, $R^{10}C(O)NR^{10}-$, $(R^{10})_2N-C(O)-$, CN, $NO_2$, $(R^{10})_2N-C(NR^{10})-$, $R^{10}C(O)-$, $R^{10}C(O)-$, $N_3$, $-N(R^{10})_2$, or $R^{11}OC(O)NR^{10}-$,
  c) unsubstituted or substituted $C_1-C_6$ alkyl wherein the substitutent on the substituted $C_1-C_6$ alkyl is selected from unsubstituted or substituted aryl, heterocyclic, cycloalkyl, alkenyl, alkynyl, $R^{10}O-$, $R^{11}S(O)_m-$, $R^{10}C(O)NR^{10}-$, $(R^{10})_2N-C(O)-$, CN, $(R^{10})_2N-C(NR^{10})-$, $R^{10}C(O)-$, $R^{10}OC(O)-$, $N_3$, $-N(R^{10})_2$, and $R^{11}OC(O)-NR^{10}-$,
or two $R^{1a}$s, two $R^{1b}$s, two $R^{1c}$s or two $R^{1d}$s, on the same carbon atom may be combined to form $-(CH_2)_t-$;

$R^{2a}$, $R^{2b}$, $R^{3a}$ and $R^{3b}$ are independently selected from H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

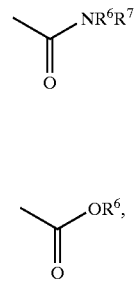

or

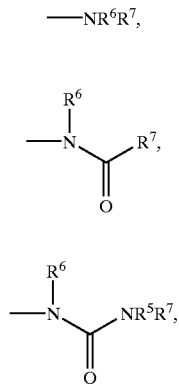

wherein the substituted group is substituted with one or more of:
1) aryl or heterocycle, unsubstituted or substituted with:
   a) $C_{1-4}$ alkyl,
   b) $(CH_2)_pOR^6$,
   c) $(CH_2)_pNR^6R^7$,
   d) halogen,
   e) CN,
2) $C_{3-6}$ cycloalkyl,
3) $OR^6$,
4) $SR^4$, $S(O)R^4$, $SO_2R^4$,
5) $-NR^6R^7$,
6) 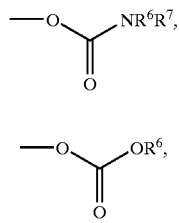
7) 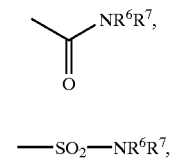
8) 
9) 
10) 
11) 
12) 
13)

-continued

14) 

15) 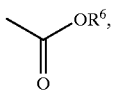

16) N₃, or

F; or

R²ᵃ and R³ᵃ are attached to the same C atom and are combined to form —(CH₂)ᵤ— wherein one of the carbon atoms is optionally replaced by a moiety selected from O, S(O)ₘ, —NC(O)—, and —N(COR¹⁰)—;

and R²ᵃ and R³ᵃ are optionally attached to the same carbon atom;

R⁴ is selected from C₁₋₄ alkyl, C₃₋₆ cycloalkyl, heterocycle, aryl, unsubstituted or substituted with:
a) C₁₋₄ alkoxy,
b) aryl or heterocycle,
c) halogen,
d) HO,
e)

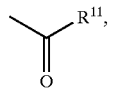

f) —SO₂R¹¹
g) N(R¹⁰)₂, or
h) C₁₋₄ perfluoroalkyl;

R⁵, R⁶ and R⁷ are independently selected from:
1) hydrogen,
2) R¹⁰C(O)—, or R¹⁰OC(O)—, and
3) C₁–C₆ alkyl, C₂–C₆ alkenyl, C₂–C₆ alkynyl, C₃₋₆ cycloalkyl, heterocycle, aryl, aroyl, heteroaroyl, arylsulfonyl, heteroarylsulfonyl, C₆–C₁₀ multicyclic alkyl ring, unsubstituted or substituted with one or more substituents selected from:
a) R¹⁰O—,
b) aryl or heterocycle,
c) halogen,
d) R¹⁰C(O)NR¹⁰—,
e)

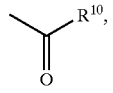

f) —SO₂R¹¹
g) N(R¹⁰)₂,
h) C₃₋₆ cycloalkyl,
i) C₆–C₁₀ multicyclic alkyl ring,
j) C₁–C₆ perfluoroalkyl,
k) (R¹⁰)₂N—C(NR¹⁰)—,
l) R¹⁰OC(O)—,
m) R¹¹OC(O)NR¹⁰—, n) CN, and
o) NO₂; or R⁶ and R⁷ may be joined in a ring; and independently, R⁵ and R⁷ may be joined in a ring;

R⁸ is independently selected from:
a) hydrogen,
b) unsubstituted or substituted aryl, unsubstituted or substituted heterocycle, C₃–C₁₀ cycloalkyl, C₂–C₆ alkenyl, C₂–C₆ alkynyl, perfluoroalkyl, F, Cl, Br, R¹²O—, R¹¹S(O)ₘ—, R¹⁰C(O)NR¹⁰—, (R¹⁰)₂NC(O)—, R¹⁰₂N—C(NR¹⁰)—, CN, NO₂, R¹⁰C(O)—, R¹⁰OC(O)—, N₃, —N(R¹⁰)₂, or R¹¹OC(O)NR¹⁰—, and
c) C₁–C₆ alkyl unsubstituted or substituted by unsubstituted or substituted aryl, unsubstituted or substituted heterocycle, C₃–C₁₀ cycloalkyl, C₂–C₆ alkenyl, C₂–C₆ alkynyl, perfluoroalkyl, F, Cl, Br, R¹⁰O—, R¹¹S(O)ₘ—, R¹⁰C(O)NH—, (R¹⁰)₂NC(O)—, R¹⁰₂N—C(NR¹⁰)—, CN, R¹⁰C(O)—, R¹⁰OC(O)—, N₃, —N(R¹⁰)₂, or R¹⁰OC(O)NH—;

R⁹ is selected from:
a) hydrogen,
b) C₂–C₆ alkenyl, C₂–C₆ alkynyl, perfluoroalkyl, F, Cl, Br, R¹⁰O—, R¹¹S(O)ₘ—, R¹⁰C(O)NR¹⁰—, (R¹⁰)₂NC(O)—, R¹⁰₂N—C(NR¹⁰)—, CN, NO₂, R¹⁰C(O)—, R¹⁰OC(O)—, N₃, —N(R¹⁰)₂, or R¹¹OC(O)NR¹⁰—, and
c) C₁–C₆ alkyl unsubstituted or substituted by perfluoroalkyl, F, Cl, Br, R¹⁰O—, R¹¹S(O)ₘ—, R¹⁰C(O)NR¹⁰—, (R¹⁰)₂NC(O)—, R¹⁰₂N—C(NR¹⁰)—, CN, R¹⁰C(O)—, R¹⁰OC(O)—, N₃, —N(R¹⁰)₂, or R¹¹OC(O)NR¹⁰—;

R¹⁰ is independently selected from hydrogen, C₁–C₆ alkyl, benzyl, unsubstituted or substituted aryl and unsubstituted or substituted heterocycle;

R¹¹ is independently selected from C₁–C₆ alkyl unsubstituted or substituted aryl and unsubstituted or substituted heterocycle;

R¹² is independently selected from hydrogen, C₁–C₆ alkyl, C₁–C₃ perfluoroalkyl, unsubstituted or substituted benzyl, unsubstituted or substituted aryl, unsubstituted or substituted heterocycle, and C₁–C₆ alkyl substituted with unsubstituted or substituted aryl or unsubstituted or substituted heterocycle;

A¹ is selected from a bond, —C(O)—, —C(O)NR¹⁰—, —NR¹⁰C(O)—, O, —N(R¹⁰)—, —S(O)₂N(R¹⁰)—, —N(R¹⁰)S(O)₂—, and S(O)ₘ;

A² is selected from a bond, —C(O)—, —C(O)NR¹⁰—, —NR¹⁰C(O)—, O, —N(R¹⁰)—, —S(O)₂N(R¹⁰)—, —N(R¹⁰)S(O)₂—, S(O)ₘ and —C(R¹ᵈ)₂—;

G¹, G² and G³ are independently selected from H₂ and O;

W is heterocycle;

V is selected from:
a) heterocycle, and
b) aryl;

X and Y are independently selected from a bond, —C(=O)— or —S(=O)ₘ;

Z¹ is selected from unsubstituted or substituted aryl and unsubstituted or substituted heterocycle, wherein the substituted aryl or substituted heterocycle is substituted with one or more of:
1) C₁₋₈ alkyl, C₂₋₈ alkenyl or C₂₋₈ alkynyl, unsubstituted or substituted with:
a) C₁₋₄ alkoxy,
b) NR⁶R⁷, c) $C_{3-6}$ cycloalkyl,
d) aryl or heterocycle,
e) HO,
f) —S(O)$_m$R$^4$,
g) —C(O)NR$^6$R$^7$,
h) —Si(C$_{1-4}$ alkyl)$_3$, or
i) C$_{1-4}$ perfluoroalkyl;
2) substituted or unsubstituted aryl or substituted or unsubstituted heterocycle,
3) halogen,
4) OR$^6$,
5) NR$^6$R$^7$,
6) CN,
7) NO$_2$,
8) CF$_3$;
9) —S(O)$_m$R$^4$,
10) —OS(O)$_2$R$^4$,
11) —C(O)NR$^6$R$^7$,
12) —C(O)OR$^6$, or
13) $C_3$–$C_6$ cycloalkyl;

$Z^2$ is selected from a bond, unsubstituted or substituted aryl and unsubstituted or substituted heterocycle, wherein the substituted aryl or substituted heterocycle is substituted with one or more of:
1) C1–8 alkyl, C2–8 alkenyl or C2–8 alkynyl, unsubstituted or substituted with:
a) $C_{1-4}$ alkoxy,
b) NR$^6$R$^7$,
c) $C_{3-6}$ cycloalkyl,
d) aryl or heterocycle,
e) HO,
f) —S(O)$_m$R$^4$,
g) —C(O)NR$^6$R$^7$,
h) —Si(C$_{1-4}$ alkyl)3, or
i) (C$_{1-4}$ perfluoroalkyl;
2) substituted or unsubstituted aryl or substituted or unsubstituted heterocycle,
3) halogen,
4) OR$^6$,
5) NR$^6$R$^7$,
6) CN,
7) NO$_2$,
8) CF$_3$,
9) —S(O)$_m$R$^4$,
10) —OS(O)$_2$R$^4$,
11) —C(O)NR$^6$R$^7$,
12) —C(O)OR$^6$, or
13) $C_3$–$C_6$ cycloalkyl;

m is 0, 1 or 2;
n is 0, 1, 2, 3 or 4;
p is 0, 1, 2, 3 or 4;
q is 1 or 2;
r is 0 to 5;
s is independently 0, 1, 2 or 3;
t is 2 to 6; and
u is 4 or 5;
or a pharmaceutically acceptable salt or stereoisomer thereof.

In another embodiment of this invention, the inhibitors of prenyl-protein transferase are illustrated by the formula A:

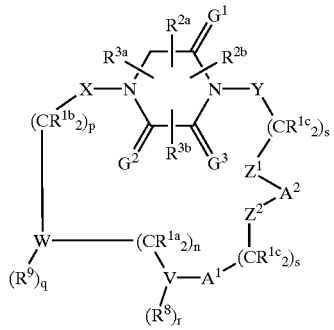

wherein:
$R^{1a}$, $R^{1b}$, $R^{1c}$ and $R^{1d}$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^{10}$O—, $R^{11}$S(O)$_m$—, $R^{10}$C(O)NR$^{10}$—, (R$^{10}$)$_2$N—C(O)—, CN, NO$_2$, (R$^{10}$)$_2$N—C(NR$^{10}$)—, R$^{10}$C(O)—, R$^{10}$OC(O)—, N$_3$, —N(R$^{10}$)$_2$, or R$^{11}$OC(O)NR$^{10}$—,
c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}$O—, $R^{11}$S(O)$_m$—, $R^{10}$C(O)NR$^{10}$—, (R$^{10}$)$_2$N—C(O)—, CN, (R$^{10}$)$_2$N—C(NR$^{10}$)—, R$^{10}$C(O)—, R$^{10}$OC(O)—, N$_3$, —N(R$^{10}$)$_2$, and R$^{11}$OC(O)—NR$^{10}$—;

$R^{2a}$, $R^{2b}$, $R^{3a}$ and $R^{3b}$ are independently selected from H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

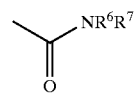

or

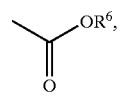

wherein the substituted group is substituted with one or more of:
1) aryl or heterocycle, unsubstituted or substituted with:
a) $C_{1-4}$ alkyl,
b) (CH$_2$)$_p$OR$^6$,
c) (CH$_2$)$_p$NR$^6$R$^7$,
d) halogen,
e) CN,
2) $C_{3-6}$ cycloalkyl,
3) OR$^6$,
4) SR$^4$, S(O)R$^4$, SO$_2$R$^4$,
5) —NR$^6$R$^7$, -continued 6)
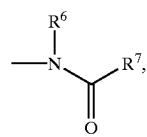

7)
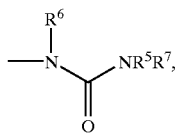

8)
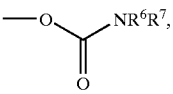

9)
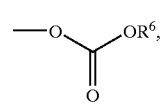

10)
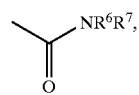

11)
—SO$_2$—NR$^6$R$^7$,

12)
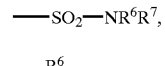

13)
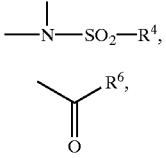

14)
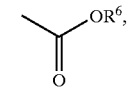

15)
N$_3$, or

16)
F; or

R$^{2a}$ and R$^{3a}$ are attached to the same C atom and are combined to form —(CH$_2$)$_u$— wherein one of the carbon atoms is optionally replaced by a moiety selected from O, S(O)$_m$, —NC(O)—, and —N(COR$^{10}$)—;

and R$^{2a}$ and R$^{3a}$ are optionally attached to the same carbon atom;

R$^4$ is selected from C$_{1-4}$ alkyl, C$_{3-6}$ cycloalkyl, heterocycle, aryl, unsubstituted or substituted with:
a) C$_{1-4}$ alkoxy,
b) aryl or heterocycle,
c) halogen,
d) HO,
e)

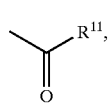

f) —SO$_2$R$^{11}$, or
g) N(R$^{10}$)$_2$;

R$^5$, R$^6$ and R$^7$ are independently selected from H; C$_{1-4}$ alkyl, C$_{3-6}$ cycloalkyl, heterocycle, aryl, aroyl, heteroaroyl, arylsulfonyl, heteroarylsulfonyl, unsubstituted or substituted with:
a) C$_{1-4}$ alkoxy,
b) aryl or heterocycle,
c) halogen,
d) HO,
e)

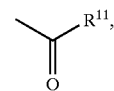

f) —SO$_2$R$^{11}$, or
g) N(R$^{10}$)$_2$; or

R$^6$ and R$^7$ may be joined in a ring; and independently, R$^5$ and R$^7$ may be joined in a ring;

R$^8$ is independently selected from:
a) hydrogen,
b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, R$^{10}$OC(O)—, N$_3$, —N(R$^{10}$)$_2$, or R$^{11}$OC(O)NR$^{10}$—, and
c) C$_1$–C$_6$ alkyl unsubstituted or substituted by unsubstituted or substituted aryl, unsubstituted or substituted heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NH—, (R$^{10}$)$_2$NC(O)—, R$^{10}$$_2$N—C(NR$^{10}$)—, CN, R$^{10}$C(O)—, R$^{10}$OC(O)—, N$_3$, —N(R$^{10}$)$_2$, or R$^{10}$OC(O)NH—;

R$^9$ is selected from:
a) hydrogen,
b) C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, R$^{10}$OC(O)—, N$_3$, —N(R$^{10}$)$_2$, or R$^{11}$OC(O)NR$^{10}$—, and
c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, R$^{10}$OC(O)—, N$_3$, —N(R$^{10}$)$_2$, or R$^{11}$OC(O)NR$^{10}$—;

R$^{10}$ is independently selected from hydrogen, C$_1$–C$_6$ alkyl, benzyl, unsubstituted or substituted aryl and unsubstituted or substituted heterocycle;

R$^{11}$ is independently selected from C$_1$–C$_6$ alkyl unsubstituted or substituted aryl and unsubstituted or substituted heterocycle;

A$^1$ is selected from a bond, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, and S(O)$_m$;

A$^2$ is selected from a bond, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, S(O)$_m$ and —C(R$^{1d}$)$_2$—;

G$^1$, G$^2$ and G$^3$ are independently selected from H$_2$ and O;

W is heterocycle;

V is selected from:
a) heterocycle, and
b) aryl;

X and Y are independently selected from a bond, —C(=O)— or —S(=O)$_m$;

Z$^1$ is selected from unsubstituted or substituted aryl and unsubstituted or substituted heterocycle, wherein the substituted aryl or substituted heterocycle is substituted with one or more of:
1) $C_{1-4}$ alkyl, unsubstituted or substituted with:
    a) $C_{1-4}$ alkoxy,
    b) $NR^6R^7$,
    c) $C_{3-6}$ cycloalkyl,
    d) aryl or heterocycle,
    e) HO,
    f) —$S(O)_mR^4$, or
    g) —$C(O)NR^6R^7$,
2) aryl or heterocycle,
3) halogen,
4) $OR^6$,
5) $NR^6R^7$,
6) CN,
7) $NO_2$,
8) $CF_3$,
9) —$S(O)_mR^4$,
10) —$C(O)NR^6R^7$, or
11) $C_3$–C6 cycloalkyl;

$Z^2$ is selected from a bond, unsubstituted or substituted aryl and unsubstituted or substituted heterocycle, wherein the substituted aryl or substituted heterocycle is substituted with one or more of:
1) $C_{1-4}$ alkyl, unsubstituted or substituted with:
    a) $C_{1-4}$ alkoxy,
    b) $NR^6R^7$,
    c) $C_{3-6}$ cycloalkyl,
    d) aryl or heterocycle,
    e) HO,
    f) —$S(O)_mR^4$, or
    g) —$C(O)NR^6R^7$,
2) aryl or heterocycle,
3) halogen,
4) $OR^6$,
5) $NR^6R^7$,
6) CN,
7) $NO_2$,
8) $CF_3$,
9) —$S(O)_mR^4$,
10) —$C(O)NR^6R^7$, or
11) $C_3$–C6 cycloalkyl;

m is 0, 1 or 2;
n is 0, 1, 2, 3 or 4;
p is 0, 1, 2, 3 or 4;
q is 1 or 2;
r is 0 to 5;
s is independently 0, 1, 2 or 3; and
u is 4 or 5;

or a pharmaceutically acceptable salt or stereoisomer thereof.

In a third embodiment of this invention, the inhibitors of prenyl-protein transferase are illustrated by the formula A:

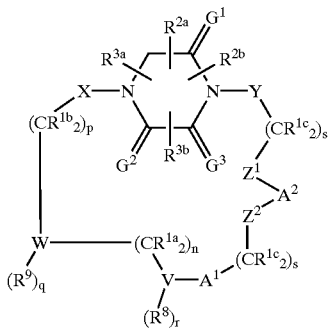

wherein:
$R^{1a}$ and $R^{1d}$ is independently selected from hydrogen and $C_1$–$C_6$ alkyl;
$R^{1b}$ and $R^{1c}$ are independently selected from:
    a) hydrogen,
    b) aryl, heterocycle, cycloalkyl, $R^{10}O$—, —$N(R^{10})_2$ or $C_2$–$C_6$ alkenyl, and
    c) unsubstituted or substituted $C_1$–$C_6$ alkyl wherein the substitutent on the substituted $C_1$–$C_6$ alkyl is selected from unsubstituted or substituted aryl, heterocycle, cycloalkyl, alkenyl, $R^{10}O$— and —$N(R^{10})_2$;
$R^{2b}$, $R^{3a}$ and $R^{3b}$ are independently selected from H and $CH_3$;
$R^{2a}$ is independently selected from H;

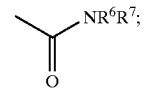

or $C_{1-5}$ alkyl, unbranched or branched, unsubstituted or substituted with one or more of:
1) aryl,
2) heterocycle,
3) $OR^6$,
4) $SR^4$, $SO_2R^4$, or
5)

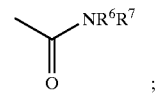
;

and $R^{2a}$ and $R^{3a}$ are optionally attached to the same carbon atom;
$R^4$ is selected from $C_{1-4}$ alkyl and $C_{3-6}$ cycloalkyl, unsubstituted or substituted with:
    a) $C_{1-4}$ alkoxy,
    b) halogen, or
    c) aryl or heterocycle;
$R^6$ and $R^7$ are independently selected from H; $C_{1-4}$ alkyl, $C_{3-6}$ cycloalkyl, aryl and heterocycle, unsubstituted or substituted with:
    a) $C_{1-4}$ alkoxy,
    b) halogen, or
    c) aryl or heterocycle;
$R^8$ is independently selected from:
    a) hydrogen,
    b) unsubstituted or substituted aryl, unsubstituted or substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and c) $C_1$–$C_6$ alkyl substituted by: unsubstituted or substituted aryl, unsubstituted or substituted heterocycle, $C_1$–$C_6$ perfluoroalkyl, $R^{10}O$—, $R^{10}C(O)NR^{10}$—, $(R^{10})_2N$—C$(NR^{10})$—, $R^{10}C(O)$—, —$N(R^{10})_2$, or $R^{11}OC(O)NR^{10}$—;

$R^9$ is selected from:
a) hydrogen,
b) $C_2$–$C_6$ alkenyl, $C_2$–$C_6$ alkynyl, $C_1$–$C_6$ perfluoroalkyl, F, Cl, $R^{10}O$—, $R^{11}S(O)_m$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl unsubstituted or substituted by $C_1$–$C_6$ perfluoroalkyl, F, Cl, $R^{10}O$—, $R^{11}S(O)_m$—, $R^{10}C(O)NR^{10}$—, CN, $(R^{10})_2N$—$C(NR^{10})$—, $R^{10}C(O)$—, —$N(R^{10})_2$, or $R^{11}OC(O)NR^{10}$—;

$R^{10}$ is independently selected from hydrogen, $C_1$–$C_6$ alkyl, benzyl, unsubstituted or substituted aryl and unsubstituted or substituted heterocycle;

$R^{11}$ is independently selected from $C_1$–$C_6$ alkyl, unsubstituted or substituted aryl and unsubstituted or substituted heterocycle;

$A^1$ is selected from a bond, —C(O)—, —C(O)$NR^{10}$—, —$NR^{10}$C(O)—, O, —$N(R^{10})$—, —$S(O)_2N(R^{10})$—, —$N(R^{10})S(O)_2$—, and $S(O)_m$;

$A^2$ is selected from a bond, —C(O)—, —C(O)$NR^{10}$—, —$NR^{10}$C(O)—, O, —$N(R^{10})$—, —$S(O)_2N(R^{10})$—, —$N(R^{10})S(O)_2$—, $S(O)_m$ and —$C(R^{14})_2$—;

$G^1$, $G^2$ and $G^3$ are independently selected from $H_2$ and O;

V is selected from:
a) heterocycle selected from pyrrolidinyl, imidazolyl, pyridinyl, thiazolyl, pyridonyl, 2-oxopiperidinyl, indolyl, quinolinyl, isoquinolinyl, and thienyl, and
b) aryl;

W is a heterocycle selected from pyrrolidinyl, imidazolyl, pyridinyl, thiazolyl, pyridonyl, 2-oxopiperidinyl, indolyl, quinolinyl, or isoquinolinyl;

X is a bond or —C(=O)—;

Y is a bond or —C(=O)—;

$Z^1$ is selected from unsubstituted or substituted aryl or unsubstituted or substituted heterocycle, wherein the substituted aryl or substituted heterocycle is independently substituted with one or two of:
1) $C_{1-4}$ alkyl, unsubstituted or substituted with:
  a) $C_{1-4}$ alkoxy,
  b) $NR^6R^7$,
  c) $C_{3-6}$ cycloalkyl,
  d) aryl or heterocycle,
  e) HO,
  f) —$S(O)_mR^4$, or
  g) —$C(O)NR^6R^7$,
2) aryl or heterocycle,
3) halogen,
4) $OR^6$,
5) $NR^6R^7$,
6) CN,
7) $NO_2$,
8) $CF_3$;
9) —$S(O)_mR^4$,
10) —$C(O)NR^6R^7$, or
11) $C_3$–C6 cycloalkyl;

$Z^2$ is selected from a bond, unsubstituted or substituted aryl and unsubstituted or substituted heterocycle, wherein the substituted aryl or substituted heterocycle is substituted independently with one or two of:
1) $C_{1-4}$ alkyl, unsubstituted or substituted with:
  a) $C_{1-4}$ alkoxy,
  b) $NR^6R^7$,
  c) $C_{3-6}$ cycloalkyl,
  d) aryl or heterocycle,
  e) HO,
  f) —$S(O)_mR^4$, or
  g) —$C(O)NR^6R^7$,
2) aryl or heterocycle,
3) halogen,
4) $OR^6$,
5) $NR^6R^7$,
6) CN,
7) $NO_2$,
8) $CF_3$,
9) —$S(O)_mR^4$,
10) —$C(O)NR^6R^7$, or
11) $C_3$–C6 cycloalkyl;

m is 0, 1 or 2;
n is 0, 1, 2, 3 or 4;
p is 0, 1, 2, 3 or 4;
q is 1 or 2;
r is 0 to 5;
s is independently 0, 1, 2 or 3; and
u is 4 or 5;

or a pharmaceutically acceptable salt or stereoisomer thereof.

In a fourth embodiment of this invention, the inhibitors of prenyl-protein transferase are illustrated by the formula B:

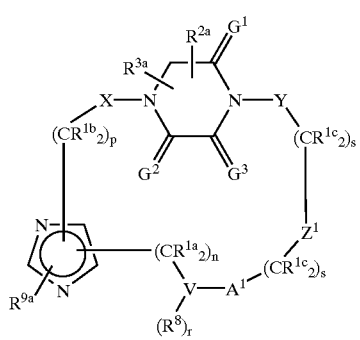

B wherein:
$R^{1a}$, $R^{1b}$ and $R^{1c}$ is independently selected from:
a) hydrogen,
b) aryl, heterocycle, cycloalkyl, $R^{10}O$—, —$N(R^{10})_2$ or $C_2$–$C_6$ alkenyl, and
c) $C_1$–$C_6$ alkyl unsubstituted or substituted by aryl, heterocycle, cycloalkyl, alkenyl, $R^{10}O$—, or —$N(R^{10})_2$;

$R^{3a}$ is selected from H and $CH_3$;
$R^{2a}$ is selected from H;

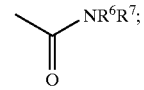

and $C_{1-5}$ alkyl, unbranched or branched, unsubstituted or substituted with one or more of:
1) aryl, 2) heterocycle,
3) OR$^6$,
4) SR$^4$, SO$_2$R$^4$, or
5)

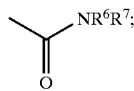

and any two of R$^{2a}$ and R$^{3a}$ are optionally attached to the same carbon atom;

R$^4$ is selected from:
C$_{1-4}$ alkyl and C$_{3-6}$ cycloalkyl, unsubstituted or substituted with:
a) C$_{1-4}$ alkoxy,
b) halogen, or
c) aryl or heterocycle;

R$^6$ and R$^7$ are independently selected from H; C$_{1-6}$ alkyl, C$_{3-6}$ cycloalkyl, C$_6$–C$_{10}$ multicyclic alkyl ring, heterocycle, aryl, aroyl, heteroaroyl, arylsulfonyl, heteroarylsulfonyl, unsubstituted or substituted with one or two:
a) C$_{1-4}$ alkoxy,
b) aryl or heterocycle,
c) halogen,
d) HO,
e)

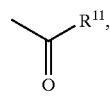

f)

—SO$_2$R$^{11}$, g) N(R$^{10}$)$_2$,
h) C$_{3-6}$ cycloalkyl,
i) C$_6$–C$_{10}$ multicyclic alkyl ring; or R$^8$ is independently selected from:
a) hydrogen,
b) unsubstituted or substituted aryl, C$_1$–C$_6$ alkyl, C$_2$–C$_6$ alkenyl, C$_2$–C$_6$ alkynyl, C$_1$–C$_6$ perfluoroalkyl, F, Cl, R$^{12}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
c) C$_1$–C$_6$ alkyl substituted by: unsubstituted or substituted aryl, C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

R$^{9a}$ is hydrogen or methyl;

R$^{10}$ is independently selected from hydrogen, C$_1$–C$_6$ alkyl, benzyl and unsubstituted or substituted aryl;

R$^{11}$ is independently selected from C$_1$–C$_6$ alkyl and unsubstituted or substituted aryl;

R$^{12}$ is independently selected from hydrogen, C$_1$–C$_6$ alkyl, unsubstituted or substituted benzyl, unsubstituted or substituted aryl, unsubstituted or substituted heterocycle, and C$_1$–C$_6$ alkyl substituted with unsubstituted or substituted aryl or unsubstituted or substituted heterocycle;

A$^1$ is selected from a bond, —C(O)— and O;
G$_1$, G$_2$ and G$_3$ are independently selected from H$_2$ and O;

V is selected from:
a) heterocycle selected from pyrrolidinyl, imidazolyl, pyridinyl, thiazolyl, pyridonyl, 2-oxopiperidinyl, indolyl, quinolinyl, isoquinolinyl, and thienyl, and
b) aryl;

X is a bond or —C(=O)—;

Y is a bond or —C(=O)—;

Z$^1$ is selected from unsubstituted or substituted aryl or unsubstituted or substituted heterocycle, wherein the substituted aryl or substituted heterocycle is independently substituted with one or two of:
1) C$_{1-8}$ alkyl, C$_2$–C$_8$ alkenyl or C$_{2-8}$ alkynyl, unsubstituted or substituted with:
a) C$_{1-4}$ alkoxy,
b) NR$^6$R$^7$,
c) C$_{3-6}$ cycloalkyl,
d) aryl or heterocycle,
e) HO,
f) —S(O)$_m$R$^4$,
g) —C(O)NR$^6$R$^7$,
h) —Si(C$_{1-4}$ alkyl)$_3$, or
i) C$_{1-4}$ perfluoroalkyl;
2) substituted or unsubstituted aryl or substituted or unsubstituted heterocycle,
3) halogen,
4) OR$^6$,
5) NR$^6$R$^7$,
6) CN,
7) NO$_2$,
8) CF$_3$,
9) —S(O)$_m$R$^4$,
10) —OS(O)$_2$R$^4$,
11) —C(O)NR$^6$R$^7$,
12) —C(O)OR$^6$, or
13) C$_3$–C6 cycloalkyl;

m is 0, 1 or 2;
n is 0, 1, 2, 3 or 4;
p is 0, 1, 2, 3 or 4;
r is 0 to 5; and
s is independently 0, 1, 2 or 3;
or a pharmaceutically acceptable salt or stereoisomer thereof.

In a fifth embodiment of this invention, the inhibitors of prenyl-protein transferase are illustrated by the formula B:

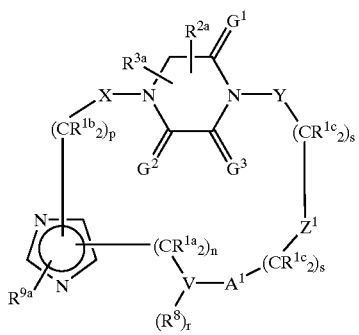

B wherein:
R$^{1a}$ is selected from: hydrogen or C$_1$–C$_6$ alkyl;
R$^{1b}$ and R$^{1c}$ is independently selected from:
a) hydrogen,
b) aryl, heterocycle, cycloalkyl, R$^{10}$O—, —N(R$^{10}$)$_2$ or C$_2$–C$_6$ alkenyl, and c) $C_1$–$C_6$ alkyl unsubstituted or substituted by aryl, heterocycle, cycloalkyl, alkenyl, $R^{10}O$—, or —$N(R^{10})_2$;

$R^{3a}$ is selected from H and $CH_3$;

$R^{2a}$ is selected from H;

$$\underset{O}{\overset{}{\diagdown}}\!\!\!\!\!\!\!\!\!\diagup NR^6R^7;$$

and $C_{1-5}$ alkyl, unbranched or branched, unsubstituted or substituted with one or more of:
1) aryl,
2) heterocycle,
3) $OR^6$,
4) $SR^4$, $SO_2R^4$, or
5)

$$\underset{O}{\overset{}{\diagdown}}\!\!\!\!\!\!\!\!\!\diagup NR^6R^7;$$

and any two of $R^{2a}$ and $R^{3a}$ are optionally attached to the same carbon atom;

$R^4$ is selected from $C_{1-4}$ alkyl and $C_{3-6}$ cycloalkyl, unsubstituted or substituted with:
a) $C_{1-4}$ alkoxy,
b) halogen, or
c) aryl or heterocycle;

$R^6$ and $R^7$ are independently selected from:
a) hydrogen,
b) $C_1$–$C_6$ alkyl, $C_2$–$C_6$ alkenyl, $C_2$–$C_6$ alkynyl, $R^{10}C(O)$— or $R^{10}OC(O)$— and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR10)$—, $R^{10}C(O)$—, $R^{10}OC(O)$—, —$N(R^{10})_2$, or $R^{11}OC(O)NR^{10}$—;

$R^8$ is independently selected from:
a) hydrogen,
b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by: unsubstituted or substituted aryl, $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^{9a}$ is hydrogen or methyl;

$R^{10}$ is independently selected from hydrogen, $C_1$–$C_6$ alkyl, benzyl and unsubstituted or substituted aryl;

$R^{11}$ is independently selected from $C_1$–$C_6$ alkyl and unsubstituted or substituted aryl;

$A^1$ is selected from a bond, —C(O)— and O;

$G^1$, $G^2$ and $G^3$ are independently selected from $H_2$ and O;

V is selected from:
a) heterocycle selected from pyrrolidinyl, imidazolyl, pyridinyl, thiazolyl, pyridonyl, 2-oxopiperidinyl, indolyl, quinolinyl, isoquinolinyl, and thienyl, and
b) aryl;

X is a bond or —C(=O)—;

Y is a bond or —C(=O)—;

$Z^1$ is selected from unsubstituted or substituted aryl or unsubstituted or substituted heterocycle, wherein the substituted aryl or substituted heterocycle is independently substituted with one or two of:
1) $C_1$–$C_4$ alkyl, unsubstituted or substituted with:
   a) $C_{1-4}$ alkoxy,
   b) $NR^6R^7$,
   c) $C_{3-6}$ cycloalkyl,
   d) aryl or heterocycle,
   e) HO,
   f) —$S(O)_mR^4$, or
   g) —$C(O)NR^6R^7$,
2) aryl or heterocycle,
3) halogen,
4) $OR^6$,
5) $NR^6R^7$,
6) CN,
7) $NO_2$,
8) $CF_3$,
9) —$S(O)_mR^4$,
10) —$C(O)NR^6R^7$, or
11) $C_3$–$C6$ cycloalkyl;

m is 0, 1 or 2;
n is 0, 1, 2, 3 or 4;
p is 0, 1, 2, 3 or 4;
r is 0 to 5; and
s is independently 0, 1, 2 or 3;

or a pharmaceutically acceptable salt or stereoisomer thereof.

A preferred embodiment of the compounds of this invention is illustrated by the formula C-1:

C-1 wherein:

$R^{1a}$, $R^{1b}$ and $R^{1c}$ is independently selected from:
a) hydrogen,
b) aryl, heterocycle, cycloalkyl, $R^{10}O$—, —$N(R^{10})_2$ or $C_2$–$C_6$ alkenyl, and
c) $C_1$–$C_6$ alkyl unsubstituted or substituted by aryl, heterocycle, cycloalkyl, alkenyl, $R^{10}O$—, or —$N(R^{10})_2$;

$R^{3a}$ is selected from H and $CH_3$;

$R^{2a}$ is selected from H;

$$\underset{O}{\overset{}{\diagdown}}\!\!\!\!\!\!\!\!\!\diagup NR^6R^7;$$

and $C_{1-5}$ alkyl, unbranched or branched, unsubstituted or substituted with one or more of:
1) aryl, 2) heterocycle,
3) OR$^6$,
4) SR$^4$, SO$_2$R$^4$, or
5)

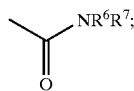

and any two of R$^{2a}$ and R$^{3a}$ are optionally attached to the same carbon atom;

R$^4$ is selected from C$_{1-4}$ alkyl and C$_{3-6}$ cycloalkyl, unsubstituted or substituted with:
 a) C$_{1-4}$ alkoxy,
 b) halogen, or
 c) aryl or heterocycle;

R$^6$ and R$^7$ are independently selected from H; C$_{1-6}$ alkyl, C$_{3-6}$ cycloalkyl, C$_6$–C$_{10}$ multicyclic alkyl ring, heterocycle, aryl, aroyl, heteroaroyl, arylsulfonyl, heteroarylsulfonyl, unsubstituted or substituted with one or two:
 a) C$_{1-4}$ alkoxy,
 b) aryl or heterocycle,
 c) halogen,
 d) HO,
 e)

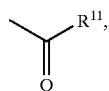

f) —SO$_2$R$^{11}$,
 g) N(R$^{10}$)$_2$,
 h) C$_{3-6}$ cycloalkyl,
 i) C$_6$–C$_{10}$ multicyclic alkyl ring; or R$^8$ is independently selected from:
 a) hydrogen,
 b) unsubstituted or substituted aryl, C$_1$–C$_6$ alkyl, C$_2$–C$_6$ alkenyl, C$_2$–C$_6$ alkynyl, C$_1$–C$_6$ perfluoroalkyl, F, Cl, R$^{12}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
 c) C$_1$–C$_6$ alkyl substituted by unsubstituted or substituted aryl, C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{10}$OC(O)NR$^{10}$—;

R$^{9a}$ is hydrogen or methyl;

R$^{10}$ is independently selected from hydrogen, C$_1$–C$_6$ alkyl, benzyl and unsubstituted or substituted aryl;

R$^{12}$ is independently selected from C$_1$–C$_6$ alkyl and unsubstituted or substituted aryl;

R$^{12}$ is independently selected from hydrogen, C$_1$–C$_6$ alkyl, unsubstituted or substituted benzyl, unsubstituted or substituted aryl, unsubstituted or substituted heterocycle, and C$_1$–C$_6$ alkyl substituted with unsubstituted or substituted aryl or unsubstituted or substituted heterocycle;

A$^1$ is selected from a bond, —C(O)—, O and S(O)$_m$;
V is phenyl or pyridyl;
X is a bond or —C(=O)—;
Y is a bond or —C(=O)—;
Z$^1$ is selected from unsubstituted or substituted aryl or unsubstituted or substituted heterocycle, wherein the substituted aryl or substituted heterocycle is substituted with one or two of:

1) C$_{1-8}$ alkyl, C$_{2-8}$ alkenyl or C$_{2-8}$ alkynyl, unsubstituted or substituted with:
  a) C$_{1-4}$ alkoxy,
  b) NR$^6$R$^7$,
  c) C$_{3-6}$ cycloalkyl,
  d) aryl or heterocycle,
  e) HO,
  f) —S(O)$_m$R$^4$,
  g) —C(O)NR$^6$R$^7$,
  h) —Si(C$_{1-4}$ alkyl)$_3$, or
  i) C$_{1-4}$ perfluoroalkyl;
 2) substituted or unsubstituted aryl or substituted or unsubstituted heterocycle,
 3) halogen,
 4) OR$^6$,
 5) NR$^6$R$^7$,
 6) CN,
 7) NO$^2$,
 8) CF$_3$,
 9) —S(O)$_m$R$^4$,
 10) —OS(O)$_2$R$^4$,
 11) —C(O)NR$^6$R$^7$,
 12) —C(O)OR$^6$, or
 13) C$_3$–C6 cycloalkyl;

m is 0, 1 or 2;
n is 0, 1, 2, 3 or 4;
p is 0, 1, 2, 3 or 4;
r is 0 to 5; and
s is independently 0, 1, 2 or 3;

or a pharmaceutically acceptable salt or stereoisomer thereof.

Another preferred embodiment of the compounds of this invention is illustrated by the formula C:

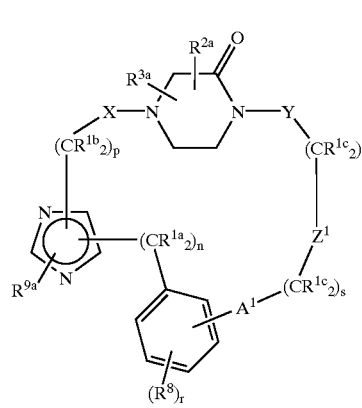

wherein:

R$^{1a}$ is selected from hydrogen and C$_1$–C$_6$ alkyl;

R$^{1b}$ and R$^{1c}$ is independently selected from:
 a) hydrogen,
 b) aryl, heterocycle, cycloalkyl, R$^{10}$O—, —N(R$^{10}$)$^2$ or C$_2$–C$_6$ alkenyl, and
 c) C$_1$–C$_6$ alkyl unsubstituted or substituted by aryl, heterocycle, cycloalkyl, alkenyl, R$^{10}$O—, or —N(R$^{10}$)$^2$;

R$^{3a}$ is selected from H and CH$_3$;

$R^{2a}$ is selected from H;

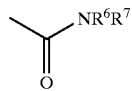

and $C_{1-5}$ alkyl, unbranched or branched, unsubstituted or substituted with one or more of:
1) aryl,
2) heterocycle,
3) $OR^6$,
4) $SR^4$, $SO^2R^4$, or
5)

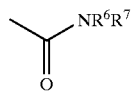

and any two of $R^{2a}$ and $R^{3a}$ are optionally attached to the same carbon tom;

$R^4$ is selected from $C_{1-4}$ alkyl and $C_{3-6}$ cycloalkyl, unsubstituted or substituted with:
a) $C_{1-4}$ alkoxy,
b) halogen, or
c) aryl or heterocycle;

$R^6$ and $R^7$ are independently selected from:
a) hydrogen,
b) $C_1$–$C_6$ alkyl, $C_2$–$C_6$ alkenyl, $C_2$–$C_6$ alkynyl, $R^{10}C(O)$— or $R^{10}OC(O)$— and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^8$ is independently selected from:
a) hydrogen,
b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by unsubstituted or substituted aryl, $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^{9a}$ is hydrogen or methyl;

$R^{10}$ is independently selected from hydrogen, $C_1$–$C_6$ alkyl, benzyl and unsubstituted or substituted aryl;

$R^{11}$ is independently selected from $C_1$–$C_6$ alkyl and unsubstituted or substituted aryl;

$A^1$ is selected from a bond, —C(O)— and O;

X is a bond or —C(=O)—;

Y is a bond or —C(=O)—;

$Z^1$ is selected from unsubstituted or substituted aryl or unsubstituted or substituted heterocycle, wherein the substituted aryl or substituted heterocycle is substituted with one or two of:
1) $C_{1-4}$ alkyl, unsubstituted or substituted with:
a) $C_{1-4}$ alkoxy,
b) $NR^6R^7$,
c) $C_{3-6}$ cycloalkyl,
d) aryl or heterocycle,
e) HO,
f) —$S(O)_mR^4$, or
g) —$C(O)NR^6R^7$,
2) aryl or heterocycle,
3) halogen,
4) $OR^6$,
5) $NR^6R^7$,
6) CN,
7) $NO_2$,
8) $CF_3$,
9) —$S(O)_mR^4$,
10) —$C(O)NR^6R^7$, or
11) $C_3$–$C_6$ cycloalkyl;

m is 0, 1 or 2;

n is 0, 1, 2, 3 or 4;

p is 0, 1, 2, 3 or 4;

r is 0 to 5; and s is independently 0, 1, 2 or 3;

or a pharmaceutically acceptable salt or stereoisomer thereof.

In another embodiment of this invention, the inhibitors of prenyl-protein transferase are illustrated by the formula D:

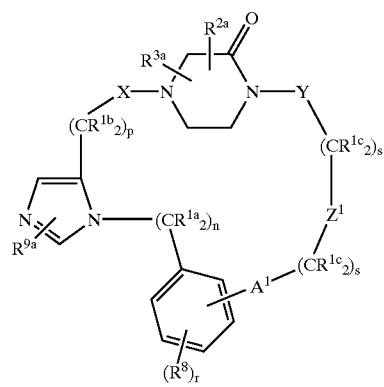

D wherein:

$R^{1a}$, $R^{1b}$ and $R^{1c}$ is independently selected from:
a) hydrogen,
b) aryl, heterocycle, cycloalkyl, $R^{10}O$—, —$N(R^{10})_2$ or $C_2$–$C_6$ alkenyl, and
c) $C_1$–$C_6$ alkyl unsubstituted or substituted by aryl, heterocycle, cycloalkyl, alkenyl, $R^{10}O$—, or —$N(R^{10})_2$;

$R^{3a}$ is selected from H and $CH_3$;

$R^{2a}$ is selected from H;

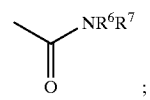

and $C_{1-5}$ alkyl, unbranched or branched, unsubstituted or substituted with one or more of:
1) aryl,
2) heterocycle,
3) $OR^6$,
4) $SR^4$, $SO_2R^4$, or

5)

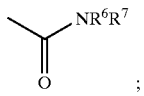

and any two of $R^2$ and $R^3$ are optionally attached to the same carbon atom;

$R^4$ is selected from $C_{1-4}$ alkyl and $C_{3-6}$ cycloalkyl, unsubstituted or substituted with:
 a) $C_{1-4}$ alkoxy,
 b) halogen, or
 c) aryl or heterocycle;

$R^6$ and $R^7$ are independently selected from H; $C_{1-6}$ alkyl, $C_{3-6}$ cycloalkyl, $C_6$–$C_{10}$ multicyclic alkyl ring, aryl, aroyl, arylsulfonyl, unsubstituted or substituted with one or two:
 a) $C_{1-4}$ alkoxy,
 b) aryl,
 c) halogen,
 d) HO,
 e)

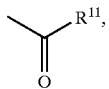

f) —$SO_2R^{11}$
 g) $N(R^{10})_2$,
 h) $C_{3-6}$ cycloalkyl,
 i) $C_6$–$C_{10}$ multicyclic alkyl ring; or $R^8$ is independently selected from:
 a) hydrogen,
 b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{12}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
 c) $C_1$–$C_6$ alkyl substituted by unsubstituted or substituted aryl, $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^{9a}$ is hydrogen or methyl;

$R^{10}$ and $R^{12}$ are independently selected from hydrogen, $C_1$–$C_6$ alkyl, benzyl and unsubstituted or substituted aryl;

$R^{11}$ is independently selected from $C_1$–$C_6$ alkyl and unsubstituted or substituted aryl;

$A^1$ is selected from a bond, —C(O)—, O and $S(O)_m$;

X is a bond;

Y is a bond;

$Z^1$ is selected from unsubstituted or substituted aryl or unsubstituted or substituted heterocycle, wherein the substituted aryl or substituted heterocycle is substituted with one or two of:
 1) $C_{1-8}$ alkyl, $C_{2-8}$ alkenyl or $C_{2-8}$ alkynyl, unsubstituted or substituted with:
  a) $C_{1-4}$ alkoxy,
  b) $NR^6R^7$,
  c) $C_{3-6}$ cycloalkyl,
  d) aryl or heterocycle,
  e) HO,
  f) —$S(O)_mR^4$,
  g) —$C(O)NR^6R^7$,
  h) —$Si(C_{1-4}$ alkyl$)_3$, or
  i) $C_{1-4}$ perfluoroalkyl;
 2) substituted or unsubstituted aryl or substituted or unsubstituted heterocycle,
 3) halogen,
 4) $OR^6$,
 5) $NR^6R^7$,
 6) CN,
 7) $NO_2$,
 8) $CF_3$,
 9) —$S(O)_mR^4$,
 10) —$OS(O)_2R^4$,
 11) —$C(O)NR^6R^7$,
 12) —$C(O)OR^6$, or
 13) $C_3$–$C_6$ cycloalkyl;

m is 0, 1 or 2;

n is 0, 1, 2, 3 or 4;

p is 0, 1, 2, 3 or 4;

r is 0 to 5; and s is independently 0, 1, 2 or 3;

or a pharmaceutically acceptable salt or stereoisomer thereof.

In a further embodiment of this invention, the inhibitors of prenyl-protein transferase are illustrated by the formula D:

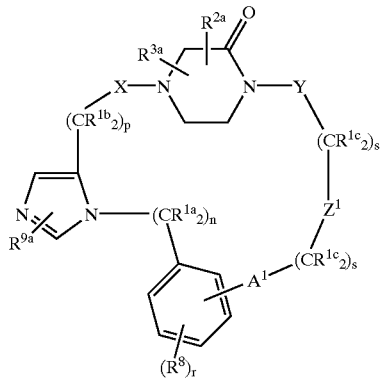

D wherein:

$R^{1a}$ is selected from hydrogen and $C_1$–$C_6$ alkyl;

$R^{1b}$ and $R^{1c}$ is independently selected from:
 a) hydrogen,
 b) aryl, heterocycle, cycloalkyl, $R^{10}O$—, —$N(R^{10})_2$ or $C_2$–$C_6$ alkenyl, and
 c) $C_1$–$C_6$ alkyl unsubstituted or substituted by aryl, heterocycle, cycloalkyl, alkenyl, $R^{10}O$—, or —$N(R^{10})_2$;

$R^{3a}$ is selected from H and $CH_3$;

$R^{2a}$ is selected from H;

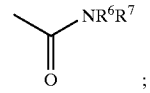

and $C_{1-5}$ alkyl, unbranched or branched, unsubstituted or substituted with one or more of:
 1) aryl,
 2) heterocycle,
 3) $OR^6$, 4) SR$^4$, SO$_2$R$^4$, or
5)

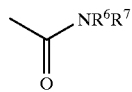

and any two of R$^2$ and R$^3$ are optionally attached to the same carbon tom;

R$^4$ is selected from C$_{1-4}$ alkyl and C$_{3-6}$ cycloalkyl, unsubstituted or substituted with:
 a) C$_{1-4}$ alkoxy,
 b) halogen, or
 c) aryl or heterocycle;

R$^6$ and R$^7$ are independently selected from:
 a) hydrogen,
 b) C$_1$–C$_6$ alkyl, C$_2$–C$_6$ alkenyl, C$_2$–C$_6$ alkynyl, R$^{10}$C(O)— or R$^{10}$OC(O)— and
 c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—; R$^8$ is independently selected from:
 a) hydrogen,
 b) unsubstituted or substituted aryl, C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
 c) C$_1$–C$_6$ alkyl substituted by unsubstituted or substituted aryl, C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

R$^{9a}$ is hydrogen or methyl;
R$^{10}$ is independently selected from hydrogen, C$_1$–C$_6$ alkyl, benzyl and unsubstituted or substituted aryl;
R$^{11}$ is independently selected from C$_1$–C$_6$ alkyl and unsubstituted or substituted aryl;
A$^1$ is selected from a bond, —C(O)— and O;
X is a bond;
Y is a bond;
Z$^1$ is selected from unsubstituted or substituted aryl or unsubstituted or substituted heterocycle, wherein the substituted aryl or substituted heterocycle is substituted with one or two of:
 1) C$_{1-4}$ alkyl, unsubstituted or substituted with:
  a) C$_{1-4}$ alkoxy,
  b) NR$^6$R$^7$,
  c) C$_{3-6}$ cycloalkyl,
  d) aryl or heterocycle,
  e) HO,
  f) —S(O)$_m$R$^4$, or
  g) —C(O)NR$^6$R$^7$,
 2) aryl or heterocycle,
 3) halogen,
 4) OR$^6$,
 5) NR$^6$R$^7$,
 6) CN,
 7) NO$_2$,
 8) CF$_3$,
 9) —S(O)$_m$R$^4$,
 10) —C(O)NR$^6$R$^7$, or
 11) C$_3$–C$_6$ cycloalkyl;
m is 0, 1 or 2;
n is 0, 1, 2, 3 or 4;
p is 0, 1, 2, 3 or 4;
r is 0 to 5; and
s is independently 0, 1, 2 or 3;
or a pharmaceutically acceptable salt or stereoisomer thereof.

In a further preferred embodiment of this invention, the inhibitors of prenyl-protein transferase are illustrated by the formula E:

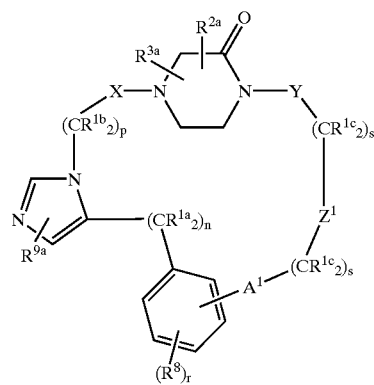

wherein:
R$^{1a}$, R$^{1b}$ and R$^{1c}$ is independently selected from:
 a) hydrogen,
 b) aryl, heterocycle, cycloalkyl, R$^{10}$O—, —N(R$^{10}$)$_2$ or C$_2$–C$_6$ alkenyl, and
 c) C$_1$–C$_6$ alkyl unsubstituted or substituted by aryl, heterocycle, cycloalkyl, alkenyl, R$^{10}$—, or —N(R$^{10}$)$_2$;
R$^{3a}$ is selected from H and CH$_3$;
R$^{2a}$ is selected from H;

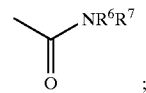

and C$_{1-5}$ alkyl, unbranched or branched, unsubstituted or substituted with one or more of:
 1) aryl,
 2) heterocycle,
 3) OR$^6$,
 4) SR$^4$, SO$_2$R$^4$, or
 5)

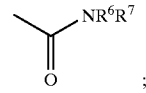

and any two of R$^2$ and R$^3$ are optionally attached to the same carbon atom;

R$^4$ is selected from C$_{1-4}$ alkyl and C$_{3-6}$ cycloalkyl, unsubstituted or substituted with:
 a) C$_{1-4}$ alkoxy,
 b) halogen, or
 c) aryl or heterocycle;

R$^6$ and R$^7$ are independently selected from H; C$_{1-6}$ alkyl, C$_{3-6}$ cycloalkyl, C$_6$–C$_{10}$ multicyclic alkyl ring, aryl, aroyl, arylsulfonyl, unsubstituted or substituted with one or two:

a) $C_{1-4}$ alkoxy,
b) aryl,
c) halogen,
d) HO,
e)

$$\underset{O}{\overset{R^{11}}{\bigwedge}},$$

f) —$SO_2R^{11}$
g) $N(R^{10})_2$,
h) $C_{3-6}$ cycloalkyl,
i) $C_6$–$C_{10}$ multicyclic alkyl ring; or $R^8$ is independently selected from:
   a) hydrogen,
   b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{12}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
   c) $C_1$–$C_6$ alkyl substituted by unsubstituted or substituted aryl, $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^{9a}$ is hydrogen or methyl;
$R^{10}$ and $R^{12}$ are independently selected from hydrogen, $C_1$–$C_6$ alkyl, benzyl and unsubstituted or substituted aryl;
$R^{11}$ is independently selected from $C_1$–$C_6$ alkyl and unsubstituted or substituted aryl;
$A^1$ is selected from a bond, —C(O)— and O;
X is a bond;
Y is a bond;
$Z^1$ is selected from unsubstituted or substituted aryl or unsubstituted or substituted heterocycle, wherein the substituted aryl or substituted heterocycle is substituted with one or two of:
   1) $C_{1-8}$ alkyl, $C_{2-8}$ alkenyl or $C_{2-8}$ alkynyl, unsubstituted or substituted with:
      a) $C_{1-4}$ alkoxy,
      b) $NR^6R^7$,
      c) $C_{3-6}$ cycloalkyl,
      d) aryl or heterocycle,
      e) HO,
      f) —$S(O)_mR^4$,
      g) —$C(O)NR^6R^7$,
      h) —$Si(C_{1-4}$ alkyl$)_3$, or
      i) $C_{1-4}$ perfluoroalkyl;
   2) substituted or unsubstituted aryl or substituted or unsubstituted heterocycle,
   3) halogen,
   4) $OR^6$,
   5) $NR^6R^7$,
   6) CN,
   7) $NO_2$,
   8) $CF_3$,
   9) —$S(O)_mR^4$,
   10) —$OS(O)_2R^4$,
   11) —$C(O)NR^6R^7$,
   12) —$C(O)OR^6$, or
   13) $C_{3-6}$ cycloalkyl;
m is 0, 1 or 2;
n is 0, 1, 2, 3 or 4;
p is 2, 3 or 4;
r is 0 to 5; and
s is independently 0, 1, 2 or 3;
or a pharmaceutically acceptable salt or stereoisomer thereof.

In a still further embodiment of this invention, the inhibitors of prenyl-protein transferase are illustrated by the formula E:

E wherein:
$R^{1a}$ is selected from hydrogen and $C_1$–$C_6$ alkyl;
$R^{1b}$ and $R^{1c}$ is independently selected from:
   a) hydrogen,
   b) aryl, heterocycle, cycloalkyl, $R^{10}O$—, —$N(R^{10})_2$ or $C_2$–$C_6$ alkenyl, and
   c) $C_1$–$C_6$ alkyl unsubstituted or substituted by aryl, heterocycle, cycloalkyl, alkenyl, $R^{10}O$—, or —$N(R^{10})_2$;
$R^{3a}$ is selected from H and $CH_3$;
$R^{2a}$ is selected from H;

$$\underset{O}{\overset{NR^6R^7}{\bigwedge}};$$

and $C_{1-5}$ alkyl, unbranched or branched, unsubstituted or substituted with one or more of:
   1) aryl,
   2) heterocycle,
   3) $OR^6$,
   4) $SR^4$, $SO_2R^4$, or
   5)

$$\underset{O}{\overset{NR^6R^7}{\bigwedge}};$$

and any two of $R^2$ and $R^3$ are optionally attached to the same carbon atom;
$R^4$ is selected from $C_{1-4}$ alkyl and $C_{3-6}$ cycloalkyl, unsubstituted or substituted with:
   a) $C_{1-4}$ alkoxy,
   b) halogen, or
   c) aryl or heterocycle;
$R^6$ and $R^7$ are independently selected from:
   a) hydrogen,
   b) $C_1$–$C_6$ alkyl, $C_2$–$C_6$ alkenyl, $C_2$–$C_6$ alkynyl, $R^{10}C(O)$— or $R^{10}OC(O)$— and c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—;

R$^8$ is independently selected from:
  a) hydrogen,
  b) unsubstituted or substituted aryl, C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
  c) C$_1$–C$_6$ alkyl substituted by unsubstituted or substituted aryl, C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

R$^{9a}$ is hydrogen or methyl;

R$^{10}$ is independently selected from hydrogen, C$_1$–C$_6$ alkyl, benzyl and unsubstituted or substituted aryl;

R$^{11}$ is independently selected from C$_1$–C$_6$ alkyl and unsubstituted or substituted aryl;

A$^1$ is selected from a bond, —C(O)— and O;

X is a bond;

Y is a bond;

Z$^1$ is selected from unsubstituted or substituted aryl or unsubstituted or substituted heterocycle, wherein the substituted aryl or substituted heterocycle is substituted with one or two of:
  1) C$_{1-4}$ alkyl, unsubstituted or substituted with:
    a) C$_{1-4}$ alkoxy,
    b) NR$^6$R$^7$,
    c) C$_{3-6}$ cycloalkyl,
    d) aryl or heterocycle,
    e) HO,
    f) —S(O)$_m$R$^4$, or
    g) —C(O)NR$^6$R$^7$,
  2) aryl or heterocycle,
  3) halogen,
  4) OR$^6$,
  5) NR$^6$R$^7$,
  6) CN,
  7) NO$_2$,
  8) CF$_3$,
  9) —S(O)$_m$R$^4$,
  10) —C(O)NR$^6$R$^7$, or
  11) C$_3$–C$_6$ cycloalkyl;

m is 0, 1 or 2;

n is 0, 1, 2, 3 or 4;

p is 2, 3 or 4;

r is 0 to 5; and s is independently 0, 1, 2 or 3;

or a pharmaceutically acceptable salt or stereoisomer thereof.

The preferred compounds of this invention are as follows:

19,20-Dihydro-19-oxo-5H,17H-18,21-ethano-6,10:12,16-dimetheno-22H-imidazo[3,4-h][1,8,11,14]oxatriazacycloeicosine-9-carbonitrile (1), 19-Chloro-22,23-dihydro-22-oxo-5H-21,24-ethano-6,10-metheno-25H-dibenzo[b,e]imidazo[4,3-l][1,4,7,10,13]dioxatriaza-cyclononadecine-9-carbonitrile (2), 22,23-Dihydro-22-oxo-5H-21,24-ethano-6,10-metheno-25H-dibenzo[b,e]imidazo[4,3-l][1,4,7,10,13]dioxatriazacyclononadecine-9-carbonitrile (3), 20-Chloro-23,24-dihydro-23-oxo-5H-22,25-ethano-6,10:12,16-dimetheno-12H,26H-benzo[b]imidazo[4,3-i][1,17,4,7,10]dioxatriazacyclodocosine-9-carbonitrile (4), (S)-20-Chloro-23,24-dihydro-27-[2-(methylsulfonyl)ethyl]-23-oxo-5H-22,25-ethano-6,10:12,16-dimetheno-12H,26H-benzo[b]imidazo[4,3-i][1,17,4,7,10]dioxatriazacyclodocosine-9-carbonitrile (5), (±)-19,20-Dihydro-19-oxo-5H-18,21-ethano-12,14-etheno-6,10-metheno-22H-benzo[d]imidazo[4,3-k][1,6,9,12]oxatriaza-cyclooctadecine-9-carbonitrile (6), (+)-19,20-Dihydro-19-oxo-5H-18,21-ethano-12,14-etheno-6,10-metheno-22H-benzo[d]imidazo[4,3-k][1,6,9,12]oxatriazacyclooctadecine-9-carbonitrile ((+)-6), (−)-19,20-Dihydro-19-oxo-5H-18,21-ethano-12,14-etheno-6,10-metheno-22H-benzo[d]imidazo[4,3-k][1,6,9,12]oxatriazacyclooctadecine-9-carbonitrile ((−)-6), 19,20-dihydro-5H,17H-18,21-Ethano-6,10:12,16-dimetheno-22H-imidazo[3,4-h][1,8,11,14]oxatriazacycloeicosin-20-one (7), (±)-19,20-Dihydro-3-methyl-19-oxo-5H-18,21-ethano-12,14-etheno-6,10-metheno-22H-benzo[d]imidazo[4,3-k][1,6,9,12]oxatriazacyclooctadecine-9-carbonitrile (8), (+)-19,20-Dihydro-3-methyl-19-oxo-5H-18,21-ethano-12,14-etheno-6,10-metheno-22H-benzo[d]imidazo[4,3-k][1,6,9,12]oxatriaza-cyclooctadecine-9-carbonitrile ((+)-8), (−)-19,20-Dihydro-3-methyl-19-oxo-5H-18,21-ethano-12,14-etheno-6,10-metheno-22H-benzo[d]imidazo[4,3-k][1,6,9,12]oxatriaza-cyclooctadecine-9-carbonitrile ((−)-8), (±)-19,20-Dihydro-19,22-dioxo-5H-18,21-ethano-12,14-etheno-6,10-metheno-22H-benzo[d]imidazo[4,3-k][1,6,9,12]oxatriazacyclooctadecine-9-carbonitrile (10), (+)-19,20-Dihydro-19,22-dioxo-5H-18,21-ethano-12,14-etheno-6,10-metheno-22H-benzo[d]imidazo[4,3-k][1,6,9,12]oxatriazacyclooctadecine-9-carbonitrile ((+)-10), (−)-19,20-Dihydro-19,22-dioxo-5H-18,21-ethano-12,14-etheno-6,10-metheno-22H-benzo[d]imidazo[4,3-k][1,6,9,12]oxatriazacyclooctadecine-9-carbonitrile ((−)-10), (±)-1-Bromo-19,20-dihydro-19-oxo-5H-18,21-ethano-12,14-etheno-6,10-metheno-22H-benzo[d]imidazo[4,3-k][1,6,9,12]oxatriazacyclooctadecine-9-carbonitrile (11), (+)-1-Bromo-19,20-dihydro-3-methyl-19-oxo-5H-18,21-ethano-12,14-etheno-6,10-metheno-22H-benzo[d]imidazo[4,3-k][1,6,9,12]oxatriaza-cyclooctadecine-9-carbonitrile (12), (−)-1-Bromo-19,20-dihydro-3-methyl-19-oxo-5H-18,21-ethano-12,14-etheno-6,10-metheno-22H-benzo[d]imidazo[4,3-k][1,6,9,12]oxatriazacyclo-octadecine-9-carbonitrile (12), 19,20-Dihydro-5H-18,21-ethano-12,14-etheno-6,10-metheno-22H-benzo[d]imidazo[4,3-k][1,6,9,12]oxatriaza-cyclooctadecine-9-carbonitrile (13)

(±)(5RS)-19,20-Dihydro-5-methyl-19-oxo-5H-18,21-ethano-12,14-etheno-6,10-metheno-22H-benzo[d]imidazo[4,3-k][1,6,9,12]oxatriazacyclooctadecine-9-carbonitrile (14), (5R,R)-19,20-Dihydro-5S-methyl-19-oxo-5H-18,21-ethano-12,14-etheno-6,10-metheno-22H-benzo[d]imidazo[4,3-k][1,6,9,12]oxatriaza-cyclooctadecine-9-carbonitrile, (5S,S)-19,20-Dihydro-5S-methyl-19-oxo-5H-18,21-ethano-12,14-etheno-6,10-metheno-22H-benzo[d]imidazo[4,3-k][1,6,9,12]oxatriaza-cyclooctadecine-9-carbonitrile, (5R,S)-19,20-Dihydro-5R-methyl-19-oxo-5H-18,21-ethano-12,14-etheno-6,10-metheno-22H-benzo[d]imidazo[4,3-k][1,6,9,12]oxatriaza-cyclooctadecine-9-carbonitrile, (5S,R)-19,20-Dihydro-5-methyl-19-oxo-5H-18,21-ethano-12,14-etheno-6,10-metheno-22H-benzo[d]imidazo[4,3-k][1,6,9,12]oxatriaza-cyclooctadecine-9-carbonitrile, (±)-18,19-Dihydro-18-oxo-5H-6,9:11,13-dietheno-17,20-ethano-9H,21H-benzo[d]imidazo[4,3-k][1,6,9,12]oxatriaza-cycloheptadecine-8-carbonitrile (16), (R,R)-18,19-Dihydro-18-oxo-5H-6,9:11,13-dietheno-17,20-ethano-9H,21H-benzo[d]imidazo[4,3-k][1,6,9,12]oxatriaza-cycloheptadecine-8-carbonitrile (R,S)-18,19-Dihydro-18-oxo-5H-6,9:11,13-dietheno-17,20-ethano-9H,21H-benzo[d]imidazo[4,3-k][1,6,9,12]oxatriaza-cycloheptadecine-8-carbonitrile (S,R)-18,19-Dihydro-18-oxo-5H-6,9:11,13-dietheno-17,20-ethano-9H,21H-benzo[d]imidazo[4,3-k][1,6,9,12]oxatriaza-cycloheptadecine-8-carbonitrile (S,S)-18,19-Dihydro-18-oxo-5H-6,9:11,13-dietheno-17,20-ethano-9H,21H-benzo[d]imidazo[4,3-k][1,6,9,12]oxatriaza-cycloheptadecine-8-carbonitrile 18-Chloro-21,22-dihydro-21-oxo-5H-20,23-ethano-6,9-etheno-9H,24H-dibenzo[b,]imidazo[4,3-l][1,4,7,10,13]dioxatriaza-cyclooctadecine-8-carbonitrile (18), 8-Chloro-19,20-dihydro-19-oxo-5H-18,21-ethano-12,14-etheno-6,10-metheno-22H-benzo[d]imidazo[4,3-k][1,6,9,12]oxatriaza-cyclooctadecine-9-carbonitrile (19), 19,20-Dihydro-19-oxo-8-phenoxy-5H-18,21-ethano-12,14-etheno-6,10-metheno-22H-benzo[d]imidazo[4,3-k][1,6,9,12]oxatriaza-yclooctadecine-9-carbonitrile (20), 18-Oxo-17,18,20,21-tetrahydro-5H-19,22-ethano-6,10:12,16-dimetheno-23H-imidazo[3,4-h][1,8,11,14]oxatriazacycloheneicosine-9-carbonitrile (21), Spiro[cyclohexane-1', 17-18-oxo-17,18,20,21-tetrahydro-5H-19,22-ethano-6,10:12,16-dimetheno-23H-imidazo[3,4-h][1,8,11,14]oxatriazacycloheneicosine-9-carbonitrile] (22), (±)-19,20-Dihydro-19-oxo-17-propyl-5H,17H-18,21-ethano-6,10:12,16-dimetheno-22H-imidazo[3,4-h][1,8,11,14]oxatriaza-cycloeicosine-9-carbonitrile (23), (+)-19,20-Dihydro-19-oxo-17-propyl-5H,17H-18,21-ethano-6,10:12,16-dimetheno-22H-imidazo[3,4-h][1,8,11,14]oxatriaza-cycloeicosine-9-carbonitrile ((+)-23), (−)-19,20-Dihydro-19-oxo-17-propyl-5H,17H-18,21-ethano-6,10:12,16-dimetheno-22H-imidazo[3,4-h][1,8,11,14]oxatriaza-cycloeicosine-9-carbonitrile ((−)-23), 15-Bromo-19,20-dihydro-19-oxo-5H,17H-18,21-ethano-6,10:12,16-dimetheno-22H-imidazo[3,4-h][1,8,11,14]oxatriaza-cycloeicosine-9-carbonitrile (24), 15-Bromo-19,20-dihydro-3-methyl-19-oxo-5H,17H-18,21-ethano-6,10:12,16-dimetheno-22H-imidazo[3,4-h][1,8,11,14]oxatriaza-cycloeicosine-9-carbonitrile (25), 19,20-Dihydro-15-iodo-3-methyl-19-oxo-5H,17H-18,21-ethano-6,10:12,16-dimetheno-22H-imidazo[3,4-h][1,8,11,14]oxatriaza-cycloeicosine-9-carbonitrile (26), 19,20-Dihydro-3-methyl-19-oxo-5H,17H-18,21-ethano-12,16-imino-6,10-metheno-22H-imidazo[3,4-h][1,8,11,14]oxatriaza-cycloeicosine-9-carbonitrile (27), 15-Bromo-19,20-dihydro-3-methyl-19-oxo-5H,17H-18,21-ethano-12,16-imino-6,10-metheno-22H-imidazo[3,4-h][1,8,11,14]oxatriaza-cycloeicosine-9-carbonitrile (28), 15-Bromo-19,20-dihydro-3-methyl-17-oxo-5H,17H-18,21-ethano-6,10:12,16-dimetheno-22H-imidazo[3,4-h][1,8,11,14]oxatriaza-cycloeicosine-9-carbonitrile (29), 15-[(2-Cyclobutyl)ethynyl]-19,20-dihydro-3-methyl-17-oxo-5H,17H-18,21-ethano-6,10:12,16-dimetheno-22H-imidazo[3,4-h][1,8,11,14]oxatriazacycloeicosine-9-carbonitrile (30), 15-[(2-Cyclobutyl)ethyl]-19,20-dihydro-3-methyl-17-oxo-5H,17H-18,21-ethano-6,10:12,16-dimetheno-22H-imidazo[3,4-h][1,8,11,14]oxatriazacycloeicosine-9-carbonitrile (31), 15-[(2-Cyclopropyl)ethyl]-19,20-dihydro-3-methyl-17-oxo-5H,17H-18,21-ethano-6,10:12,16-dimetheno-22H-imidazo[3,4-h][1,8,11,14]oxatriazacycloeicosine-9-carbonitrile (32), 19,20-Dihydro-15-(3,3-dimethyl-1-butynyl)-19-oxo-5H,17H-18,21-ethano-6,10:12,16-dimetheno-22H-imidazo[3,4-h][1,8,11,14]oxatriazacycloeicosine-9-carbonitrile (33), 19,20-Dihydro-19-oxo-15-(2-phenylethynyl)-5H,17H-18,21-ethano-6,10:12,16-dimetheno-22H-imidazo[3,4-h][1,8,11,14]oxatriaza-cycloeicosine-9-carbonitrile (34), 15-(Cyclohexylethynyl)-19,20-dihydro-19-oxo-5H,17H-18,21-ethano-6,10:12,1-dimetheno-22H-imidazo[3,4-h][1,8,11,14]oxatriaza-cycloeicosine-9-carbonitrile (35), 19,20-Dihydro-19-oxo-15-[2-(trimethylsilyl)ethynyl]-5H,17H-18,21-ethano-6,10:12,16-dimetheno-22H-imidazo[3,4-h][1,8,11,14]oxatriazacycloeicosine-9-carbonitrile (36), 19,20-Dihydro-15-(ethynyl)-19-oxo-5H,17H-18,21-ethano-6,10:12,16-dimetheno-22H-imidazo[3,4-h][1,8,11,14]oxatriaza-cycloeicosine-9-carbonitrile (37), 19,20-Dihydro-3-methyl-19-oxo-5H,17H-18,21-ethano-6,10:12,16-dimetheno-22H-imidazo[3,4-h][1,8,11,14]oxatriaza-cycloeicosine-9-carbonitrile (38), 15-(Cyclohexylethynyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (39), 19,20-Dihydro-3-methyl-15-(1-octynyl)-19-oxo-5H,17H-18,21-ethano-6,10:12,16-dimetheno-22H-imidazo[3,4-h][1,8,11,14]oxatriaza-cycloeicosine-9-carbonitrile (40), 15-(3-Cyclohexyl-1-propynyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (41), 15-(3-Cyclobutylethynyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (42), 15-(3-Cyclopropylethynyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (43), 19,20-Dihydro-3-methyl-19-oxo-15-(5,5,5-trifluoro-1-pentynyl)-5H,17H-18,21-ethano-6,10:12,16-dimetheno-22H-imidazo[3,4-h][1,8,11,14]oxatriazacycloeicosine-9-carbonitrile (44), 19,20-Dihydro-3-methyl-19-oxo-15-(5,5,5-trifluoro-1-pentynyl)-5H,17H-18,21-ethano-12,16-imino-6,10-metheno-22H-imidazo[3,4-h][1,8,11,14]oxatriazacycloeicosine-9-carbonitrile (45), 19,20-Dihydro-19-oxo-15-(2-propenyl)-5H,17H-18,21-ethano-6,10:12,16-dimetheno-22H-imidazo[3,4-h][1,8,11,14]oxatriaza-cycloeicosine-9-carbonitrile (46), 19,20-Dihydro-3-methyl-19-oxo-15-(2-propenyl)-5H,17H-18,21-ethano-6,10:12,16-dimetheno-22H-imidazo[3,4-h][1,8,11,14]oxatriazacycloeicosine-9-carbonitrile (47), 15-(Cyclopropyl)methyl-19,20-dihydro-19-oxo-5H,17H-18,21-ethano-6,10:12,16-dimetheno-22H-imidazo[3,4-h][1,8,11,14]oxatriazacycloeicosine-9-carbonitrile (48), 19,20-Dihydro-15-methyl-19-oxo-5H,17H-18,21-ethano-6,10:12,16-dimetheno-22H-imidazo[3,4-h][1,8,11,14]oxatriaza-cycloeicosine-9-carbonitrile (49), 19,20-Dihydro-3-methyl-19-oxo-15-pentyl-5H,17H-18,21-ethano-12,16-imino-6,10-metheno-22H-imidazo[3,4-h][1,8,11,14]oxatriazacycloeicosine-9-carbonitrile (50), 19,20-Dihydro-15-(3,3-dimethyl-1-butyl)-19-oxo-5H,17H-18,21-ethano-6,10:12,16-dimetheno-22H-imidazo[3,4-h][1,8,11,14]oxatriazacycloeicosine-9-carbonitrile (51), 15-(2-Cyclohexyl-1-ethyl)-19,20-dihydro-19-oxo-5H,17H-18,21-ethano-6,10:12,16-dimetheno-22H-imidazo[3,4-h][1,8,11,14]oxatriazacycloeicosine-9-carbonitrile (52), 19,20-Dihydro-15-ethyl-19-oxo-5H,17H-18,21-ethano-6,10:12,16-dimetheno-22H-imidazo[3,4-h][1,8,11,14]oxatriazacycloeicosine-9-carbonitrile (53), 19,20-Dihydro-19-oxo-15-propyl-5H,17H-18,21-ethano-6,10:12,16-dimetheno-22H-imidazo[3,4-h][1,8,11,14]oxatriazacycloeicosine-9-carbonitrile (54), 19,20-Dihydro-3-methyl-15-octyl-19-oxo-5H,17H-18,21-ethano-6,10:12,16-dimetheno-22H-imidazo[3,4-h][1,8,11,14]oxatriazacycloeicosine-9-carbonitrile (55), 15-(2-Cyclohexyl-1-ethyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (56), cis-15-(2-Cyclopropyl-1-ethenyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (57), 15-(2-Cyclopropyl-1-ethyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (58), 19,20-Dihydro-3-methyl-19-oxo-15-(5,5,5-trifluoropentyl)-5H,17H-18,21-ethano-6,10:12,16-dimetheno-22H-imidazo[3,4-h][1,8,11,14]oxatriazacycloeicosine-9-carbonitrile (59), 19,20-Dihydro-3-methyl-19-oxo-15-(5,5,5-trifluoropentyl)-5H,17H-18,21-ethano-12,16-imino-6,10-metheno-22H-imidazo[3,4-h][1,8,11,14]oxatriazacycloeicosine-9-carbonitrile (60), 9-Cyano-19,20-dihydro-19-oxo-5H,17H-18,21-ethano-6,10:12,16-dimetheno-22H-imidazo[3,4-h][1,8,11,14]oxatriaza-cycloeicosine-15-carboxylic acid methyl ester (61), 9-Cyano-19,20-dihydro-19-oxo-5H,17H-18,21-ethano-6,10:12,16-dimetheno-22H-imidazo[3,4-h][1,8,11,14]oxatriaza-cycloeicosine-15-carboxylate, lithium salt (62)

N-(2-Adamantyl)-9-cyano-19,20-dihydro-19-oxo-5H,17H-18,21-ethano-6,10:12,16-dimetheno-22H-imidazo[3,4-h][1,8,11,14]oxatriazacycloeicosine-15-carboxamide (63), (±)-19,20-Dihydro-15-(2,3-dihydroxy-1-propyl)-19-oxo-5H,17H-18,21-ethano-6,10:12,16-dimetheno-22H-imidazo[3,4-h][1,8,11,14]oxatriazacycloeicosine-9-carbonitrile (64), (±)-19,20-Dihydro-15-(2,3-dihydroxy-1-propyl)-3-methyl-19-oxo-5H,17H-18,21-ethano-6,10:12,16-dimetheno-22H-imidazo[3,4-h][1,8,11,14]oxatriazacycloeicosine-9-carbonitrile (65)

(±)-19,20-Dihydro-15-[(2,2-dimethyl-1,3-dioxolano)-4-methyl]-19-oxo-5H,17H-18,21-ethano-6,10:12,16-dimetheno-22H-imidazo[3,4-h][1,8,11,14]oxatriazacycloeicosine-9-carbonitrile (66)

(±)-19,20-Dihydro-15-[(2,2-dimethyl-1,3-dioxolano)-4-methyl]-3-methyl-19-oxo-5H,17H-18,21-ethano-6,10:12,16-dimetheno-22H-imidazo[3,4-h][1,8,11,14]oxatriazacycloeicosine-9-carbonitrile (67)

19,20-Dihydro-3-methyl-19-oxo-15-phenyl-5H,17H-18,21-ethano-6,10:12,16-dimetheno-22H-imidazo[3,4-h][1,8,11,14]oxatriaza-cycloeicosine-9-carbonitrile (68), 19,20-Dihydro-15-(2-methoxyphenyl)-3-methyl-19-oxo-5H,17H-18,21-ethano-6,10:12,16-dimetheno-22H-imidazo[3,4-h][1,8,11,14]oxatriazacycloeicosine-9-carbonitrile (69), 19,20-Dihydro-15-(3-methoxyphenyl)-3-methyl-19-oxo-5H,17H-18,21-ethano-6,10:12,16-dimetheno-22H-imidazo[3,4-h][1,8,11,14]oxatriazacycloeicosine-9-carbonitrile (70), 19,20-Dihydro-15-(4-methoxyphenyl)-3-methyl-19-oxo-5H,17H-18,21-ethano-6,10:12,16-dimetheno-22H-imidazo[3,4-h][1,8,11,14]oxatriazacycloeicosine-9-carbonitrile (71), 15-(2-Chlorophenyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (72), 15-(3-Chlorophenyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (73), 15-(4-Chlorophenyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (74), 15-(2,4-Dichlorophenyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (75), 5-(3,5-Dichlorophenyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (76), 19,20-Dihydro-3-methyl-19-oxo-15-(3-thienyl)-5H,17H-18,21-ethano-6,10:12,16-dimetheno-22H-imidazo[3,4-h][1,8,11,14]oxatriazacycloeicosine-9-carbonitrile (77), 15-(Benzo[b]furan-2-yl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (78), 19,20-Dihydro-15-[(methanesulfonyl)oxy]-19-oxo-5H,17H-18,21-ethano-6,10:12,16-dimetheno-22H-imidazo[3,4-h][1,8,11,14]oxatriazacycloeicosine-9-carbonitrile (79), 15-Benzyloxy-19,20-dihydro-19-oxo-5H,17H-18,21-ethano-6,10:12,16-dimetheno-22H-imidazo[3,4-h][1,8,11,14]oxatriazacycloeicosine-9-carbonitrile (80), 19,20-Dihydro-15-hydroxy-19-oxo-5H,17H-18,21-ethano-6,10:12,16-dimetheno-22H-imidazo[3,4-h][1,8,11,14]oxatriaza-cycloeicosine-9-carbonitrile (81)

15-[(Cyclohexylmethyl)oxy]-19,20-dihydro-19-oxo-5H,17H-18,21-ethano-6,10:12,16-dimetheno-22H-imidazo[3,4-h][1,8,11,14]oxatriazacycloeicosine-9-carbonitrile (82), 19,20-Dihydro-19-oxo-15-[(4,4,4-trifluoro-1-butyl)oxy]-5H,17H-18,21-ethano-6,10:12,16-dimetheno-22H-imidazo[3,4-h][1,8,11,14]oxatriazacycloeicosine-9-carbonitrile (83), 19,20-Dihydro-19-oxo-15-phenoxy-5H,17H-18,21-ethano-6,10:12,16-dimetheno-22H-imidazo[3,4-h][1,8,11,14]oxatriaza-cycloeicosine-9-carbonitrile (84), 19,20-Dihydro-14-[(methanesulfonyl)oxy]-19-oxo-5H,17H-18,21-ethano-6,10:12,16-dimetheno-22H-imidazo[3,4-h][1,8,11,14]oxatriazacycloeicosine-9-carbonitrile (85), 14-[(Cyclohexylmethyl)oxy]-19,20-dihydro-19-oxo-5H,17H-18,21-ethano-6,10:12,16-dimetheno-22H-imidazo[3,4-h][1,8,11,14]oxatriazacycloeicosine-9-carbonitrile (86), 14-[(Cyclopropylmethyl)oxy]-19,20-dihydro-19-oxo-5H,17H-18,21-ethano-6,10:12,16-dimetheno-22H-imidazo[3,4-h][1,8,11,14]oxatriazacycloeicosine-9-carbonitrile (87), 19,20-Dihydro-19-oxo-14-[(trifluoromethanesulfonyl)oxy]-5H,17H-18,21-ethano-6,10:12,16-dimetheno-22H-imidazo[3,4-h][1,8,11,14]oxatriazacycloeicosine-9-carbonitrile (88)

14-(3-Cyclopropylethynyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (89), 19-Oxo-19,20,22,23-tetrahydro-5H-18,21-ethano-12,14-etheno-6,10-metheno-benzo[d]imidazo[4,3-l][1,6,9,13]oxatriaza-cyclononadecine-9-carbonitrile (90), 9-Bromo-19,20,22,23-tetrahydro-5H-18,21-ethano-12,14-etheno-6,10-metheno-benzo[d]imidazo[4,3-l][1,6,9,13]oxatriaza-cyclononadecine-19-one (91), 19,20,22,23-Tetrahydro-9-[4-(trifluoromethyl)phenyl]-5H-18,21-ethano-12,14-etheno-6,10-metheno-benzo[d]imidazo[4,3-l][1,6,9,13]oxatriazacyclononadecine-19-one (92), 8-Chloro-19-oxo-19,20,22,23-tetrahydro-5H-18,21-ethano-12,14-etheno-6,10-metheno-benzo[d]imidazo[4,3-l][1,6,9,13]oxatriaza-cyclononadecine-9-carbonitrile (93), 3-Methyl-19-oxo-19,20,22,23-tetrahydro-5H-18,21-ethano-12,14-etheno-6,10-metheno-benzo[d]imidazo[4,3-l][1,6,9,13]oxatriaza-cyclononadecine-9-carbonitrile (94), 18-Oxo-18,19,20,21,22,23-hexaahydro-5H-19,22-ethano-12,14-etheno-6,10-metheno-benzo[d]imidazo[4,3-l][1,7,10,13]oxatriaza-cyclononadecine-9-carbonitrile (95), 18-Oxo-18,19,20,21,22,23-hexaahydro-5H-19,22-ethano-12,14-etheno-6,10-metheno-24H-benzo[d]imidazo[4,3-m][1,7,10,14]oxatriazacycloeicosine-9-carbonitrile (96), 15-Bromo-18-oxo-18,19,20,21,22,23-hexaahydro-5H-19,22-ethano-12,14-etheno-6,10-metheno-24H-benzo[d]imidazo[4,3-m][1,7,10,14]oxatriazacycloeicosine-9-carbonitrile (97), 5,6,20,21,22,23,24,25-Octahydro-21-Oxo-7H-20,23-ethano-14,16-etheno-8,12-metheno-benzo[d]imidazo[4,3-1 ][1,6,9,13]oxatriaza-cycloheneicosine-11-carbonitrile (98), 15-Chloro-19,20-dihydro-3-methyl-19-oxo-5H,17H-18,21-ethano-6,10:12,16-dimetheno-22H-imidazo[3,4-h][1,8,11,14]oxatriaza-cycloeicosine-9-carbonitrile (99),

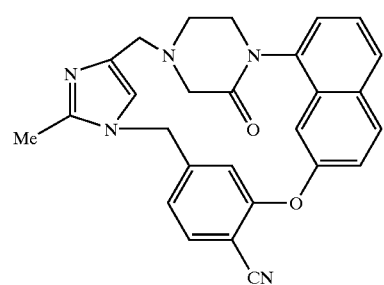

9 or a pharmaceutically acceptable salt or stereoisomer thereof.

Specific examples of the compounds of the invention are:

(+)-19,20-Dihydro-19-oxo-5H-18,21-ethano-12,14-etheno-6,10-metheno-22H-benzo[d]imidazo[4,3-k][1,6,9,12]oxatriazacyclooctadecine-9-carbonitrile ((+)-6),

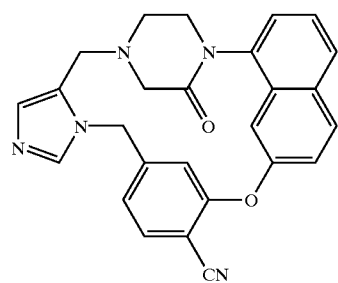

6

15-Bromo-19,20-dihydro-3-methyl-19-oxo-5H,17H-18,21-ethano-6,10:12,16-dimetheno-22H-imidazo[3,4-h][1,8,11,14]oxatriaza-cycloeicosine-9-carbonitrile (25)

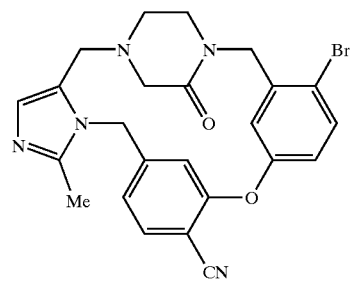

25

15-[(2-Cyclobutyl)ethyl]-19,20-dihydro-3-methyl-17-oxo-5H,17H-18,21-ethano-6,10:12,16-dimetheno-22H-imidazo[3,4-h][1,8,11,14]oxatriazacycloeicosine-9-carbonitrile (31),

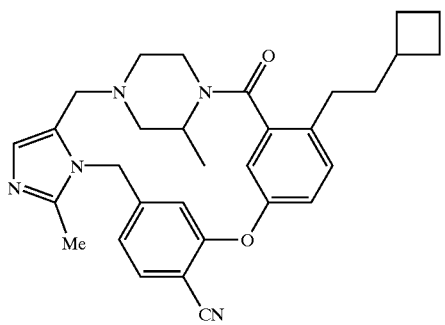

19,20-Dihydro-3-methyl-19-oxo-15-(5,5,5-trifluoropentyl)-5H,17H-18,21-ethano-6,10:12,16-dimetheno-22H-imidazo[3,4-h][1,8,11,14]oxatriazacycloeicosine-9-carbonitrile (59)

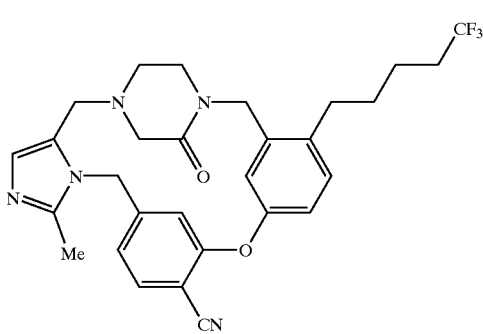

19-Oxo-19,20,22,23-tetrahydro-5H-18,21-ethano-12,14-etheno-6,10-metheno-benzo[d]imidazo[4,3-l][1,6,9,13]oxatriaza-cyclononadecine-9-carbonitrile (90)

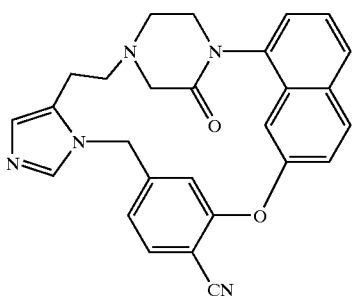

18-Oxo-18,19,20,21,22,23-hexaahydro-5H-19,22-ethano-12,14-etheno-6,10-metheno-24H-benzo[d]imidazo[4,3-m][1,7,10,14]oxatriazacycloeicosine-9-carbonitrile (96)

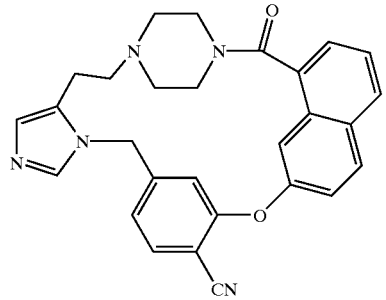

or a pharmaceutically acceptable salt or stereoisomer thereof.

The compounds of the present invention may have asymmetric centers, chiral axes and chiral planes, and occur as racemates, racemic mixtures, and as individual diastereomers, with all possible isomers, including optical isomers, being included in the present invention. (See E. L. Eliel and S. H. Wilen *Sterochemistry of Carbon Compounds* (John Wiley and Sons, New York 1994), in particular pages 1119–1190) When any variable (e.g. aryl, heterocycle, $R^{1a}$, $R^6$ etc.) occurs more than one time in any constituent, its definition on each occurence is independent at every other occurence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

Preferably, alkenyl is $C_2$–$C_6$ alkenyl.

Preferably, alkynyl is $C_2$–$C_6$ alkynyl.

As used herein, "cycloalkyl" is intended to include cyclic saturated aliphatic hydrocarbon groups having the specified number of carbon atoms. Preferably, cycloalkyl is $C_3$–$C_{10}$ cycloalkyl. Examples of such cycloalkyl elements include, but are not limited to, cyclopropyl, cyclobutyl, cyclopentyl, cyclohexyl and cycloheptyl.

As used herein, the term "$C_6$–$C_{10}$ multicyclic alkyl ring" in is intended to include polycyclic saturated and unsaturated aliphatic hydrocarbon groups having the specified number of carbon atoms. Examples of such cycloalkyl groups includes, but are not limited to:

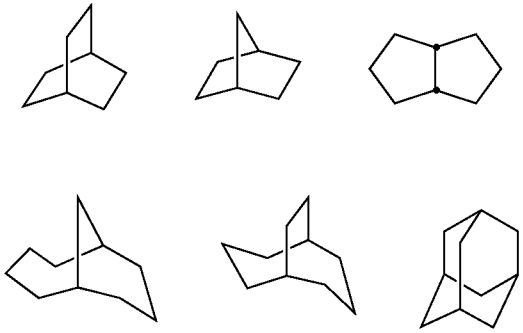

-continued

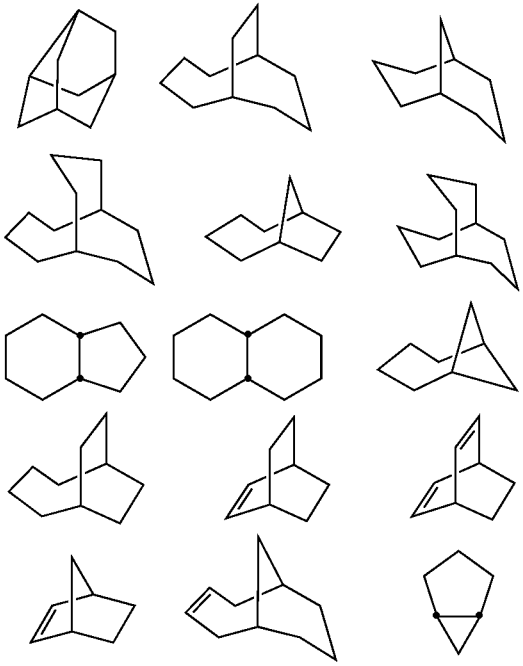

Preferably, $C_6$–$C_{10}$ multicyclic alkyl ring is adamantyl.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl moieties. Examples of such heterocyclic elements include, but are not limited to, azepinyl, benzimidazolyl, benzisoxazoly, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. An embodiment of the examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein, unless otherwise specifically defined, substituted alkyl, substituted cycloalkyl, substituted aroyl, substituted aryl, substituted heteroaroyl, substituted heteroaryl, substituted arylsulfonyl, substituted heteroarylsulfonyl and substituted heterocycle include moieties containing from 1 to 3 substituents in addition to the point of attachment to the rest of the compound. Preferably, such substituents are selected from the group which includes but is not limited to F, Cl, Br, $CF_3$, $NH_2$, $N(C_1$–$C_6$ alkyl$)_2$, $NO_2$, CN, $(C_1$–$C_6$ alkyl)O—, (aryl)O—, —OH, $(C_1$–$C_6$ alkyl)S$(O)_m$—, $(C_1$–$C_6$ alkyl)C(O)NH—, $H_2$N—C(NH)—, $(C_1$–$C_6$ alkyl)C(O)—, $(C_1$–$C_6$ alkyl)OC(O)—, $N_3$, $(C_1$–$C_6$ alkyl)OC(O)NH—, phenyl, pyridyl, imidazolyl, oxazolyl, isoxazolyl, thiazolyl, thienyl, furyl, isothiazolyl and $C_1$–$C_{20}$ alkyl.

As used herein in the definition of $R^2$ and $R^3$, the term "the substituted group" intended to mean a substituted $C_{1-8}$ alkyl, substituted $C_{2-8}$ alkenyl, substituted $C_{2-8}$ alkynyl, substituted aryl or substituted heterocycle from which the substitutent(s) $R^2$ and $R^3$ are selected.

Preferably, as used herein in the definition of R6 and R7, the substituted $C_{1-6}$ alkyl, substituted $C_{2-6}$ alkenyl, substituted $C_{2-6}$ alkynyl, substituted $C_{3-6}$ cycloalkyl, substituted aroyl, substituted aryl, substituted heteroaroyl, substituted arylsulfonyl, substituted heteroarylsulfonyl, substituted heterocycle and substituted $C_{6-10}$ multicyclic alkyl ring, include moieties containing from 1 to 3 substitutents in addition to the point of attachment to the rest of the compound.

The moiety formed when, in the definition of $R^{1a}$, $R^{1b}$, $R^{1c}$ and $R^{1d}$, two $R^{1a}$s, two $R^{1b}$s, two $R^{1c}$s or two $R^{1d}$s, on the same carbon atom are combined to form —$(CH_2)_t$— is illustrated by the following:

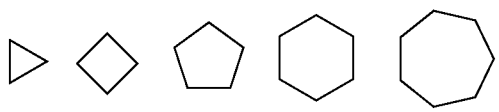

When $R^2$ and $R^3$ are combined to form $—(CH_2)_u—$, cyclic moieties are formed. Examples of such cyclic moieties include, but are not limited to:

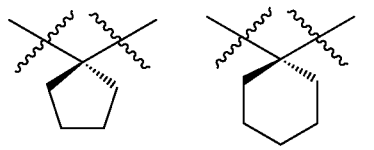

In addition, such cyclic moieties may optionally include a heteroatom(s). Examples of such heteroatom-containing cyclic moieties include, but are not limited to:

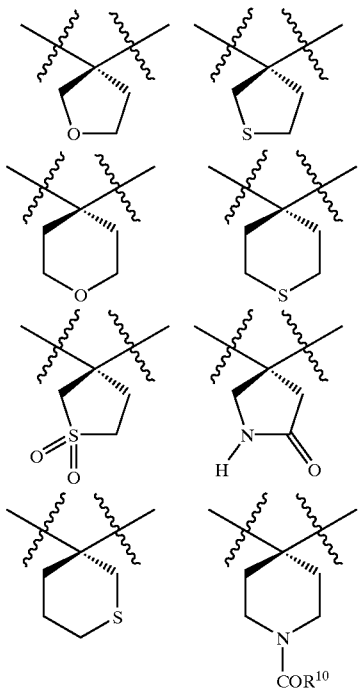

Lines drawn into the ring systems from substituents (such as from $R^2$, $R^3$, $R^4$ etc.) indicate that the indicated bond may be attached to any of the substitutable ring carbon atoms.

Preferably, $R^{1a}$ and $R^{1b}$ are independently selected from: hydrogen, $—N(R^{10})_2$, $R^{10}C(O)NR^{10}—$ or unsubstituted or substituted $C_1$–$C_6$ alkyl wherein the substituent on the substituted $C_1$–$C_6$ alkyl is selected from unsubstituted or substituted phenyl, $—N(R^{10})_2$, $R^{10}O—$ and $R^{10}C(O)NR^{10}—$.

Preferably, $R^{1c}$ and $R^{1d}$ are independently selected from: hydrogen, or unsubstituted or substituted $C_1$–$C_6$ alkyl wherein the substituent on the substituted $C_1$–$C_6$ alkyl is selected from unsubstituted or substituted phenyl, $—N(R^{10})_2$, $R^{10}O—$ and $R^{10}C(O)NR^{10}—$.

Preferably, $R^{2a}$ is selected from H,

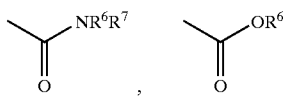

and an unsubstituted or substituted group, the group selected from $C_{1-8}$ alkyl, $C_{2-8}$ alkenyl and $C_{2-8}$ alkynyl;
wherein the substituted group is substituted with one or more of:
1) aryl or heterocycle, unsubstituted or substituted with:
   a) $C_{1-4}$ alkyl,
   b) $(CH_2)_pOR^6$,
   c) $(CH_2)_pNR^6R^7$,
   d) halogen,
2) $C_{3-6}$ cycloalkyl,
3) $OR^6$,
4) $SR^4$, $S(O)R^4$, $SO_2R^4$,

5) $—NR^6R^7$,

6) 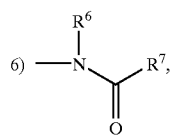

7) $—\overset{R^6}{\underset{}{N}}—\overset{O}{\underset{}{C}}—NR^7R^{7a}$,

8) 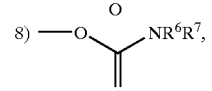

9) 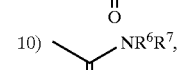

10) 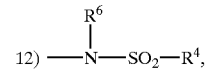

11) $—SO_2—NR^6R^7$,

12) $—\overset{R^6}{\underset{}{N}}—SO_2—R^4$,

13) 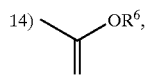

14) $\overset{O}{\underset{}{\overset{\|}{C}}}\!\!—OR^6$,

15) $N_3$, or
16) F.

Preferably, $R^{2b}$, $R^{3a}$ and $R^{3b}$ are independently selected from: hydrogen and $C_1$–$C_6$ alkyl.

Preferably, $R^4$ is unsubstituted or substituted $C_1$–$C_6$ alkyl, unsubstituted or substituted aryl and unsubstituted or substituted cycloalkyl.

Preferably, $R^5$, $R^6$ and $R^7$ is selected from: hydrogen, unsubstituted or substituted $C_1$–$C_6$ alkyl, unsubstituted or substituted aryl and unsubstituted or substituted cycloalkyl.

Preferably, $R^9$ is hydrogen or methyl.

Preferably, $R^{10}$ is selected from H, $C_1$–$C_6$ alkyl and benzyl.

Preferably, $A^1$ and $A^2$ are independently selected from: a bond, —C(O)NR$^{10}$—, —NR$^{10}$C(O)—, O, —N(R$^{10}$)—, —S(O)$_2$N(R$^{10}$)— and —N(R$^{10}$)S(O)$_2$—.

Preferably, $G^1$ is O. Preferably, $G^2$ and $G^3$ are hydrogen.

Preferably, V is selected from heteroaryl and aryl. More preferably, V is phenyl or pyridyl.

Preferably, X and Y are independently selected from: a bond and —C(=O)—. More preferably, X and Y are a bond.

Preferably, $Z^1$ and $Z^2$ are independently selected from unsubstituted or substituted phenyl, unsubstituted or substituted naphthyl, unsubstituted or substituted pyridyl, unsubstituted or substituted furanyl and unsubstituted or substituted thienyl. More preferably, $Z^1$ is selected from unsubstituted or substituted phenyl and unsubstituted or substituted naphthyl. More preferably, $Z^2$ is selected from a bond and unsubstituted or substituted phenyl.

Preferably, W is selected from imidazolinyl, imidazolyl, oxazolyl, pyrazolyl, pyyrolidinyl, thiazolyl and pyridyl. More preferably, W is selected from imidazolyl and pyridyl.

Preferably, n is 0, 1, or 2.
Preferably, r is 1 or 2.
Preferably p is 1, 2 or 3.
Preferably s is 0 or 1.
Preferably, the moiety

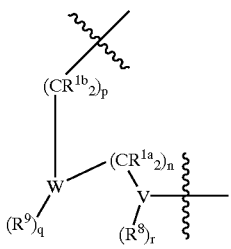

is selected from:

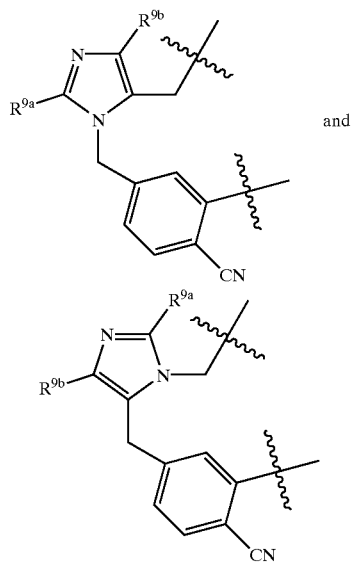

wherein $R^{9a}$ and $R^{9b}$ are independently selected from hydrogen or methyl.

It is intended that the definition of any substituent or variable (e.g., $R^{1a}$, $R^9$, n, etc.) at a particular location in a molecule be independent of its definitions elsewhere in that molecule. Thus, —N(R$^{10}$)$_2$ represents —NHH, —NHCH$_3$, —NHC$_2$H$_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Schemes 1–23, in addition to other standard manipulations such as ester hydrolysis, cleavage of protecting groups, etc., as may be known in the literature or exemplified in the experimental procedures. Substituents R, $R^a$, $R^b$ and $R^{sub}$, as shown in the Schemes, represent the substituents $R^2$, $R^3$, $R^4$, and $R^5$, and substituents on $Z^1$ and $Z^2$; however their point of attachment to the ring is illustrative only and is not meant to be limiting.

These reactions may be employed in a linear sequence to provide the compounds of the invention or they may be used to synthesize fragments which are subsequently joined by the alkylation reactions described in the Schemes.

SYNOPSIS OF SCHEMES 1–23

The requisite intermediates are in some cases commercially available, or can be prepared according to literature procedures. In Scheme 1, for example, the synthesis of macrocyclic compounds of the instant invention containing suitably substituted piperazines and the preferred benzylimidazolyl moiety is outlined. Preparation of the substituted piperazine intermediate is essentially that described by J. S. Kiely and S. R. Priebe in *Organic Preparations and Proceedings Int.*, 1990, 22, 761–768. Boc-protected amino acids I, available commercially or by procedures known to those skilled in the art, can be coupled to N-benzyl amino acid esters using a variety of dehydrating agents such as DCC (dicyclohexycarbodiimide) or EDC.HCl (1-ethyl-3-(3-dimethylaminopropyl)carbodiimide hydrochloride) in a solvent such as methylene chloride, chloroform, dichloroethane, or in dimethylformamide. The product II is then deprotected with acid, for example hydrogen chloride in chloroform or ethyl acetate, or trifluoroacetic acid in methylene chloride, and cyclized under weakly basic conditions to give the diketopiperazine III. Reduction of III with lithium aluminum hydride in refluxing ether gives the piperazine IV, which may then be deprotected by catalytic reduction to provide intermediate V. Intermediate V may then be coupled to intermediate VII, prepared from 4-imidazolylacetic acid VI in several step as illustrated. Once the amide bond is formed to yield the intermediate VIII, cesium carbonate nucleophilic aromatic substitution reaction conditions result in an intramolecular cyclization to yield compound IX of the instant invention. This cyclization reaction depends on the presence of an electronic withdrawing moiety (such as nitro, cyano, and the like) either ortho or para to the fluorine atom.

Scheme 2 illustrates the synthesis of instant compounds wherein an amido bond is formed between the piperazine nitrogen and the linker to the Y group. Thus, the protected piperazine X is coupled to a naphthoic acid having a suitably positioned benzyloxy moiety. Consecutive removal of the Boc and benzyl protecting groups provided intermediate XI, which may be coupled to a suitably substituted 1-benzylimidazole aldehyde XII to give intermediate XIII. Intramolecular cyclization takes place as previously described using the cesium carbonate conditions to provide instant compound XIV.

Scheme 3 illustrates the preparation of instant compounds which incorporate a piperazinone moiety in the macrocyclic ring. Thus the suitably substituted benzyloxybenzyl mesylate XV is reacted with a 4-protected 2-piperazinone XVI to provide the 1-benzyl-2-piperazinone intermediate XVII. Intermediate XVII is doubly deprotected in the presence of Boc anhydride to provide the N-Boc protected piperazinone, which is deprotected to give intermediate XVIII. Reductive N-alkylation of intermediate XVIII with a suitably substituted 1-benzylimidazole aldehyde XII provides intermediate XIX, which can undergo intramolecular cyclization under the cesium carbonate conditions to give compound XX of the instant invention.

Synthesis of compounds of the invention characterized by direct attachment of an aryl moiety to the piperazinone moiety and incorporation of a third aromatic carbocyclic moiety into the macrocycle is illustrated in Scheme 4. A benzyloxyphenoxyaniline XXII, prepared in three steps from a suitably substituted 2-benzyloxyphenol XXI and a suitably substituted nitrochlorobenzene XXII, is reacted with chloroacetyl chloride to provide intermediate XXIV. Intermediate XXIV is reacted with a suitably substituted ethanolamine and the resulting amido alcohol cyclized to form the piperazinone moiety of intermediate XXV. Intermediate XXV is reductively alkylated as described in Schemes 2 and 3 to provide intermediate XXVI. Deprotection, followed by intramolecular cyclization provides compound XXVII of the instant invention.

Scheme 5 illustrates expansion of the macrocyclic ring to a "18-membered" system by utilizing a suitably substituted 3-benzyloxyphenol XXVIII in the place of the 2-benzyloxyphenol XXI. Scheme 5 also illustrates the use of a reduced amino acid (such as methioninol) to provide substitution specifically at the 5-position of the piperazinone moiety.

Scheme 6 illustrates that the synthetic strategy of building the piperazinone onto a alcoholic aromatic amine can also be utilized to prepare compounds of the instant invention wherein a naphthyl group forms part of the macrocyclic backbone.

Scheme 7 illustrates the synthetic strategy that is employed when the $R^8$ substitutent is not an electronic withdrawing moiety either ortho or para to the fluorine atom. In the absence of the electronic withdrawing moiety, the intramolecular cyclization can be accomplished via an Ullmann reaction. Thus, the imidazolylmethylacetate XXXII is treated with a suitably substituted halobenzylbromide to provide the 1-benzylimidazolyl intermediate XXXIII. The acetate functionality of intermediate XXXIII was converted to an aldehyde which was then reductively coupled to intermediate XVIII, prepared as illustrated in Scheme 3. Coupling under standard Ullmann conditions provided compound XXXIV of the instant invention.

Illustrative examples of the preparation of compounds of the instant invention that incorporate a 2,5-diketopiperazine moiety and a 2,3-diketopiperazine moiety are shown in Schemes 8–9 and Schemes 10–11 respectively.

Scheme 12 illustrates the manipulation of a functional group on a side chain of an intermediate 2,5-diketopiperazine. The side chain of intermediate IIIa, obtained as illustrated in Scheme 1 from protected aspartic acid, may be comprehensively reduced and reprotected to afford intermediate XXXV, which can deprotected or can be alkylated first followed by deprotection to provide intermediate IVa having an ether sidechain. The intermediate IVa can be incorporated into the reaction sequence illustrated in Scheme 1.

Scheme 13 illustrates direct preparation of a symmetrically substituted piperazine intermediate from a suitably substituted aniline (such as intermediate XXIII from Scheme 4) and a suitably substituted bis-(chloroethyl)amine XXXVII. The intermediate XXXVIII can be utilized in the reaction sequence illustrated in Scheme I to produce compound IXL of the instant invention.

Preparation of a substituted piperazinone intermediate XVIIIa starting from a readily available N-protected amino acid XL is illustrated in Scheme 14.

Scheme 15 illustrates preparation of an intermediate piperazinone compound XLI having a substituent at the 3-position that is derived from the starting protected amino acid I.

Incorporation of a spirocyclic moiety (for example, when $R^2$ and $R^3$ are combined to form a ring) is illustrated in Scheme 16.

Scheme 17 illustrates the use of an optionally substituted homoserine lactone XLII to prepare a Boc-protected piperazinone XLIII. Intermediate XLIII may be deprotected and reductively alkylated or acylated as illustrated in the previous Schemes. Alternatively, the hydroxyl moiety of intermediate XLIII may be mesylated and displaced by a suitable nucleophile, such as the sodium salt of ethane thiol, to provide an intermediate XLIV. Intermediate XLIII may also be oxidized to provide the carboxylic acid on intermediate XLV, which can be utilized form an ester or amide moiety.

Amino acids of the general formula XL which have a sidechain not found in natural amino acids may be prepared by the reactions illustrated in Scheme 18 starting with the readily prepared imine XLVI.

Schemes 19–22 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.

Scheme 23 depicts the synthesis of compounds of the instant invention having an imidazolyl moiety incorporated into the macrocyclic ring via different points of attachement. Activated zinc is added to a fluoroaryl methylhalide in THF to form the arylmethyl zinc halide, which is subsequently coupled to an N-protected 4-iodoimidazole to give compound XLVII. Regiospecfic alkylation of the imidazole ring is accomplished with ethyl bromoacetate, with subsequent methanolysis of the intermediate imidazolium salt giving XLVIII. Elaboration of XLVIII to the primary amine proceeds through standard chemistry. Alkylation of the amine with suitably substituted N-aryl chloroaceamide (such as the intermediate illustrated in Scheme 6) provides the intermediate amide, which can be reductively alkyated with glycol aldehyde dimer to give hydroxyethyl compound. Ring closure under Mitsunobu conditions furnishes the piperazinone intermediate, which can then undergo cyclization as described above to provide the compound of the instant invention IL.

SCHEME 1

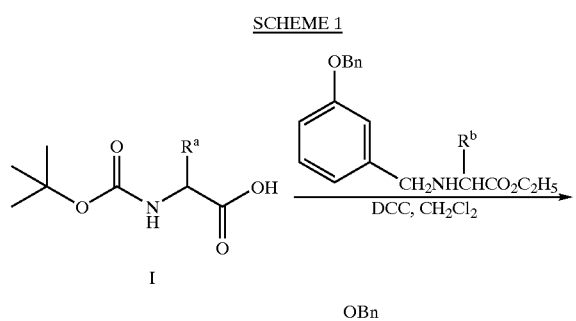

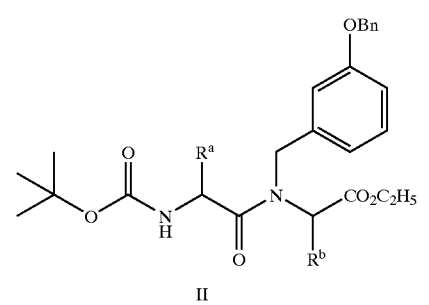

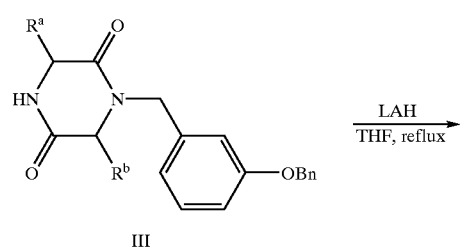

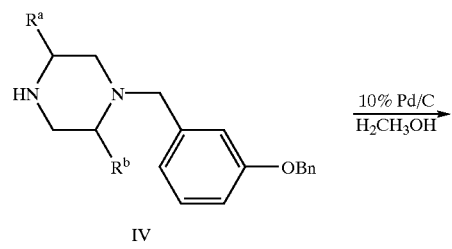

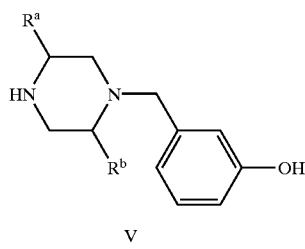

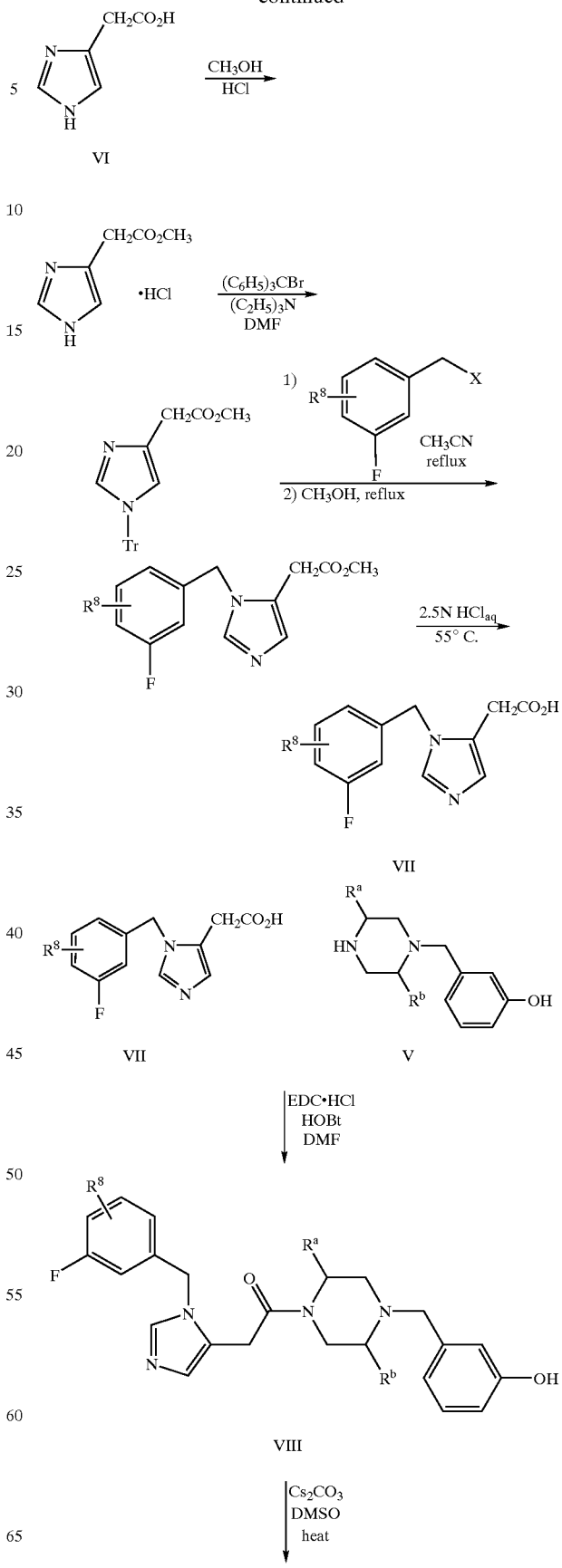

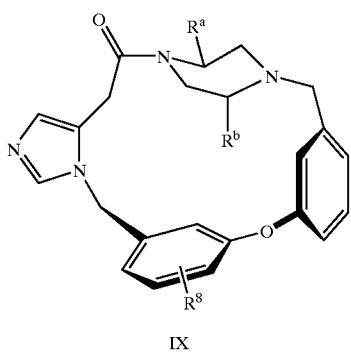
IX
SCHEME 2
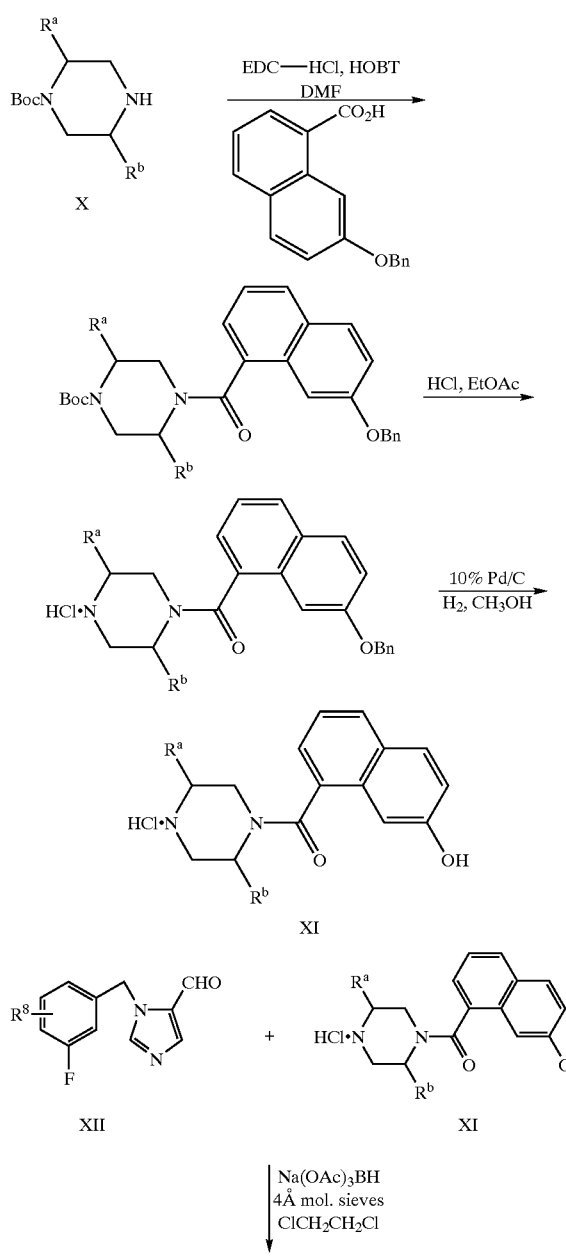
XIII
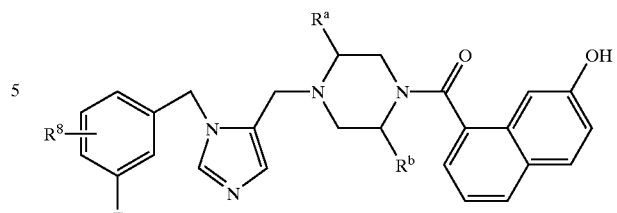
$Cs_2CO_3$
DMSO
heat
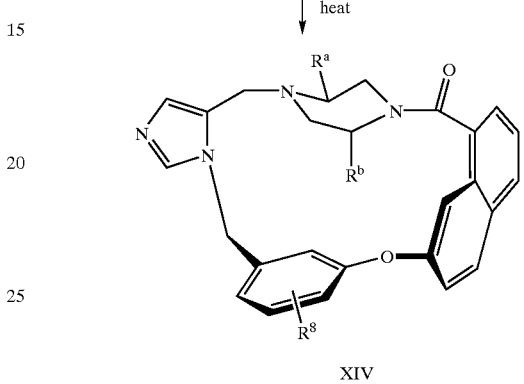
XIV
SCHEME 3
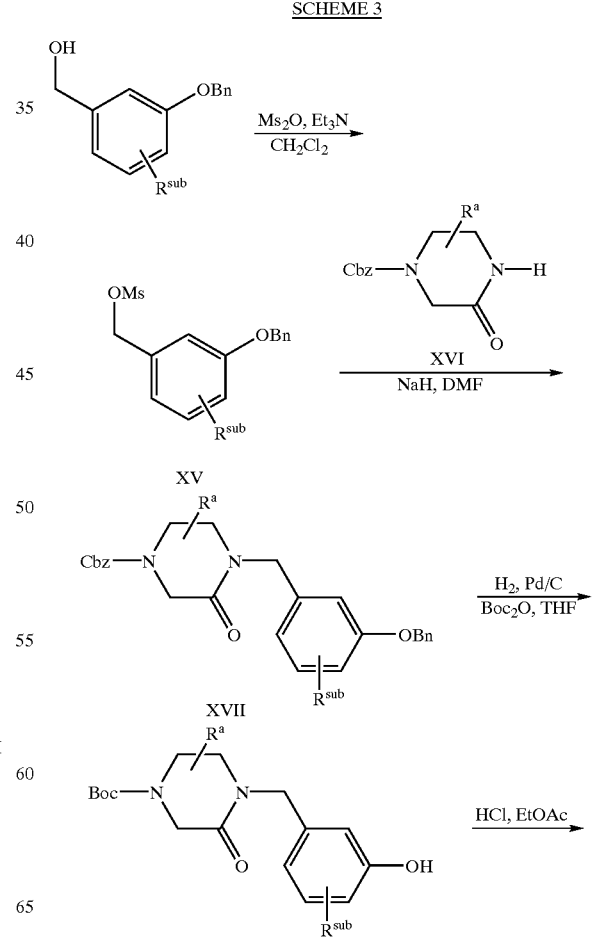

-continued
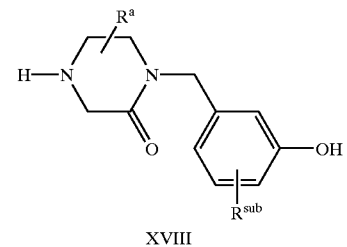
XVIII
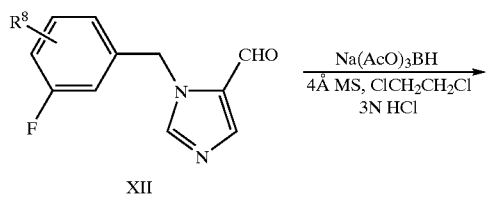
XII
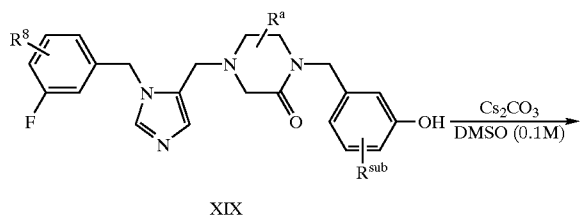
XIX
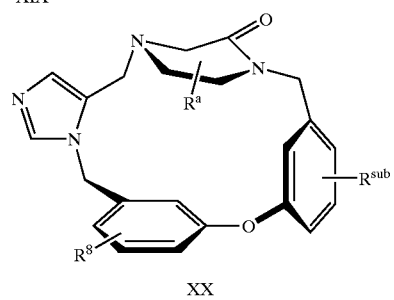
XX
SCHEME 4
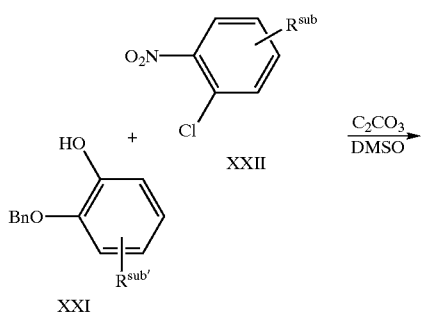
XXII
XXI
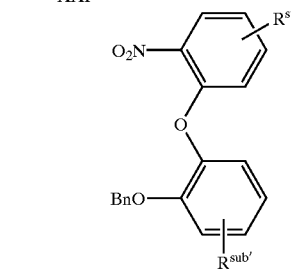
-continued
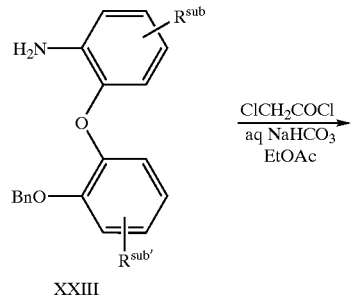
XXIII
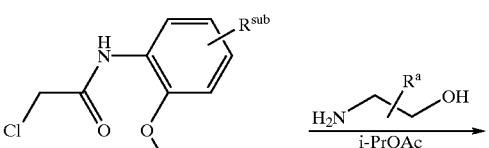
XXIV
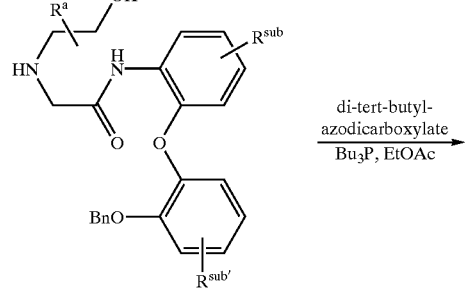
XXV
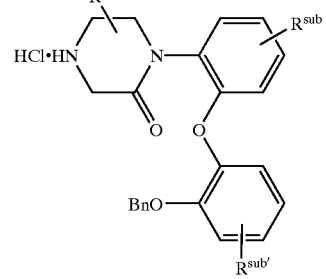
XXVI

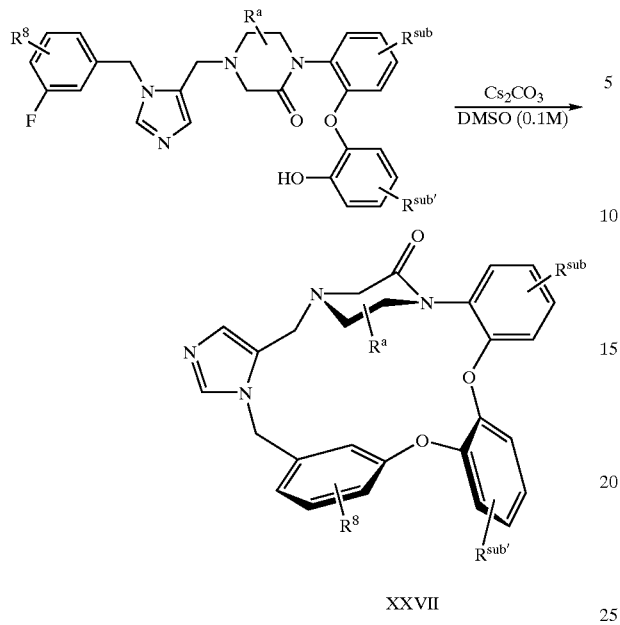
XXVII
SCHEME 5
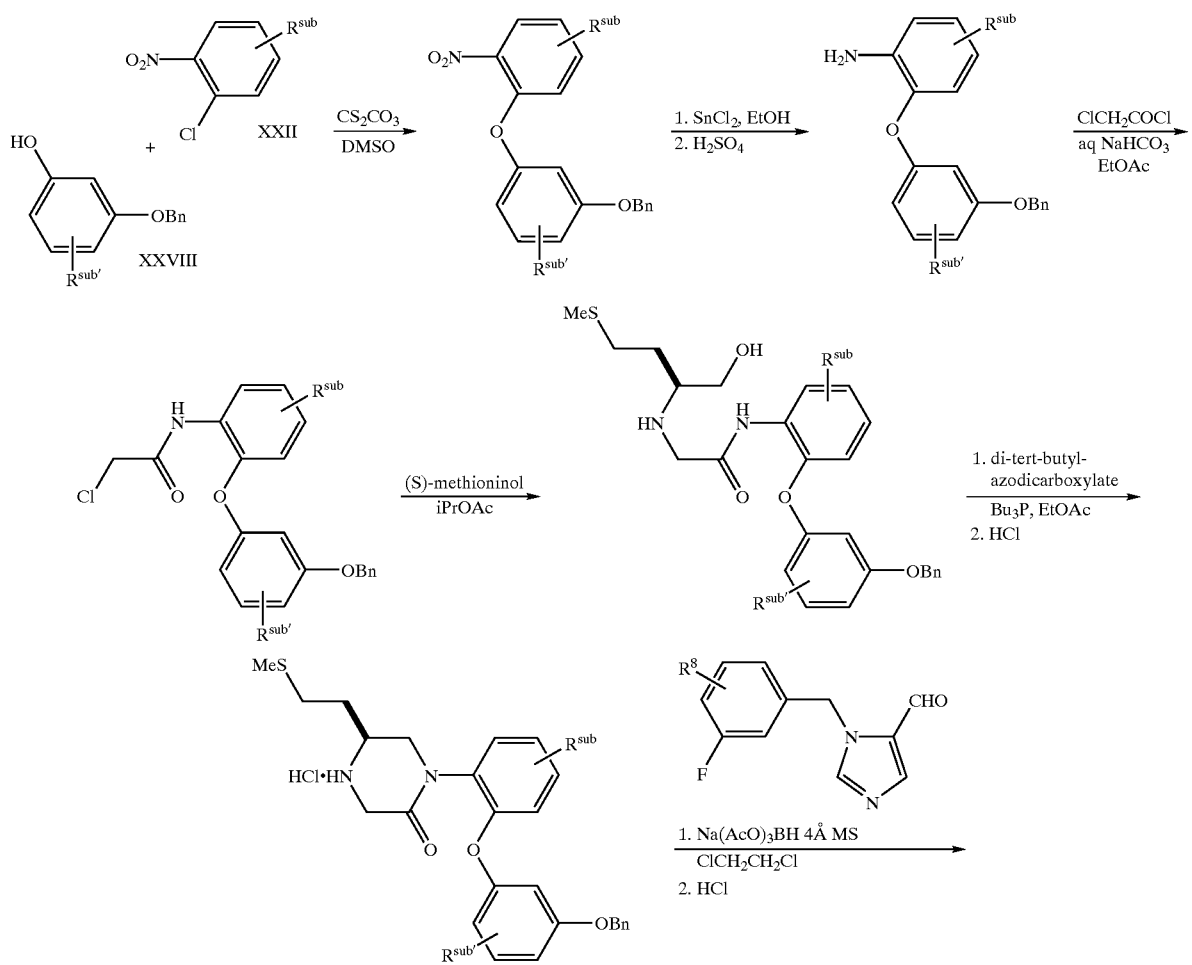

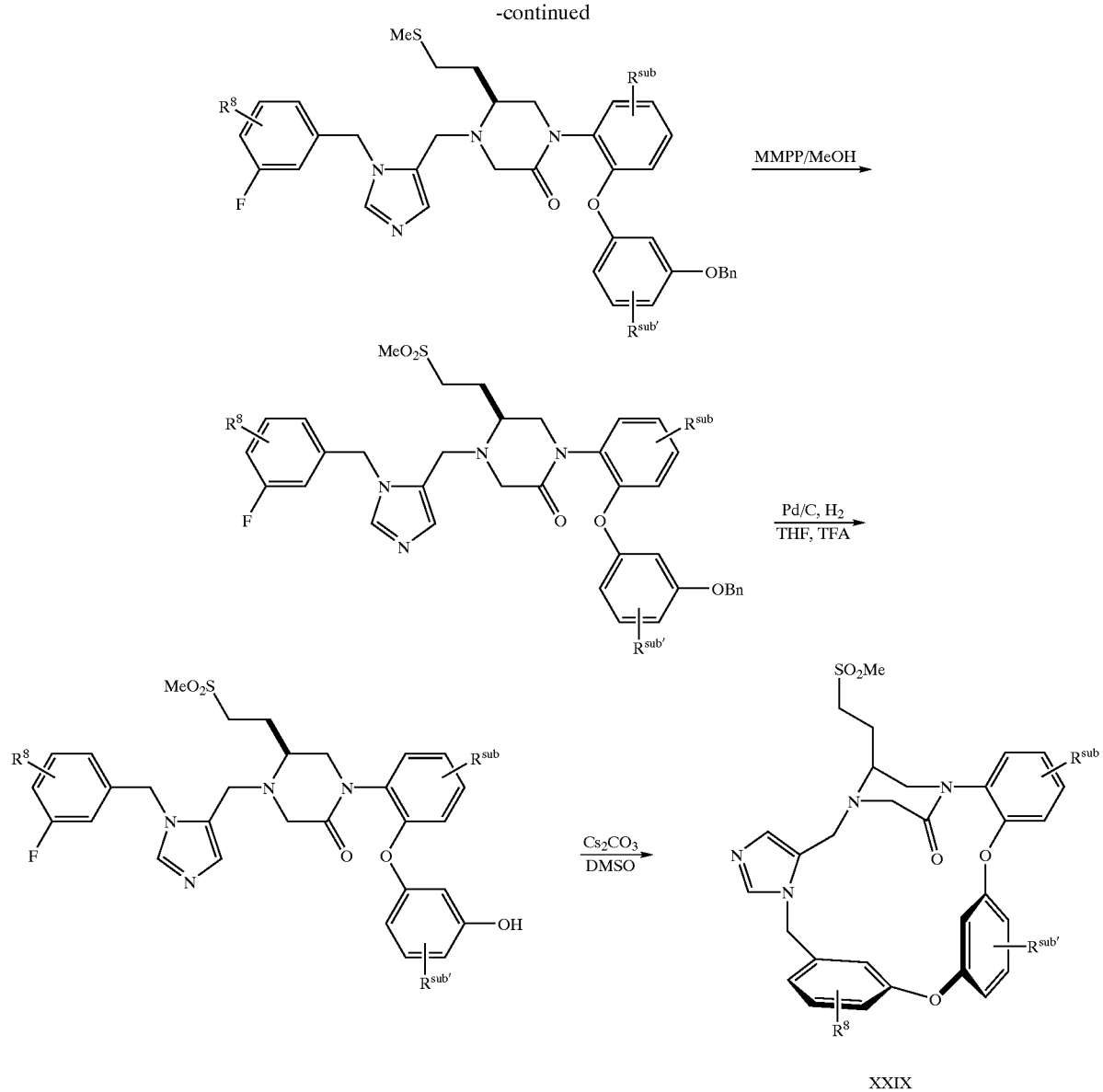
SCHEME 6
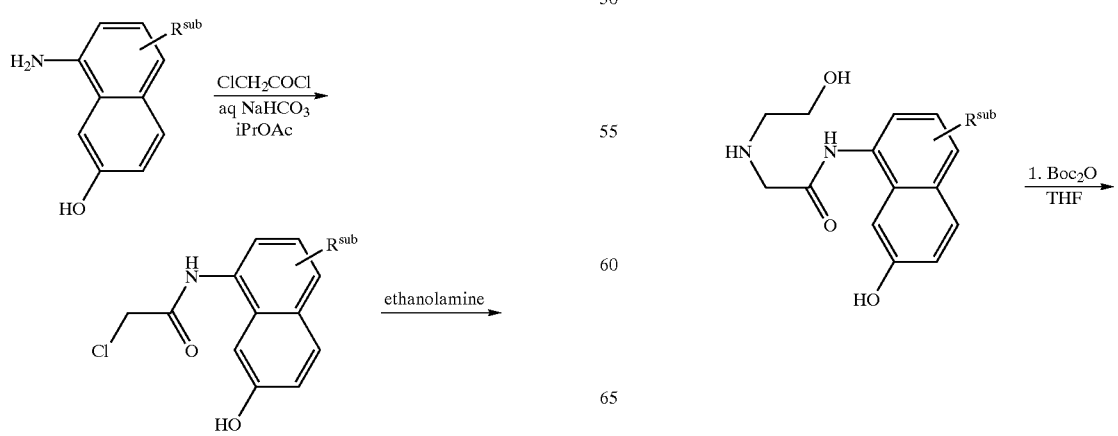

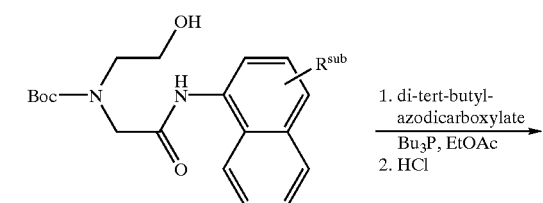
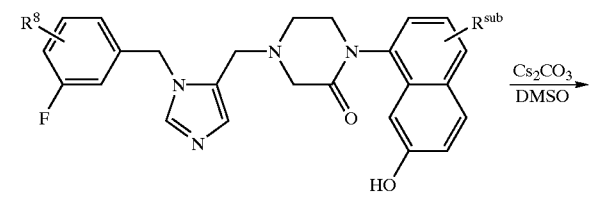
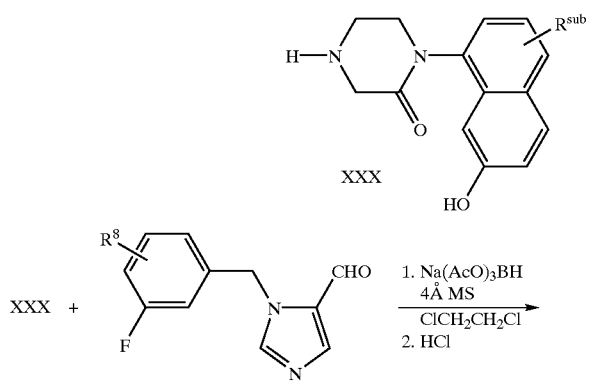
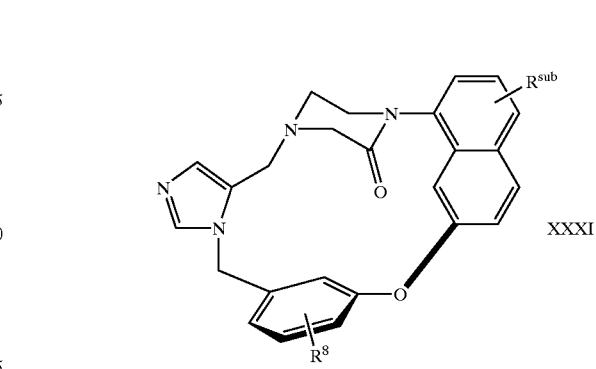
SCHEME 7
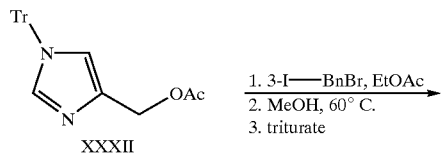
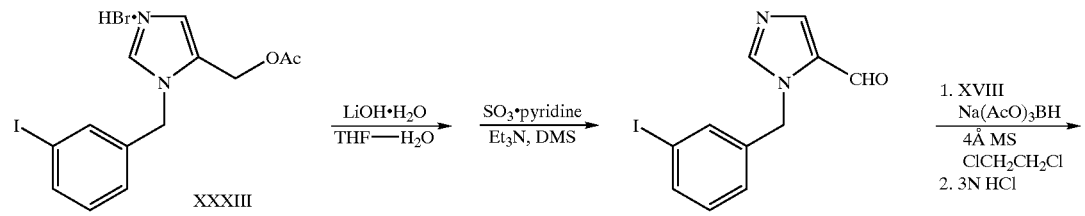
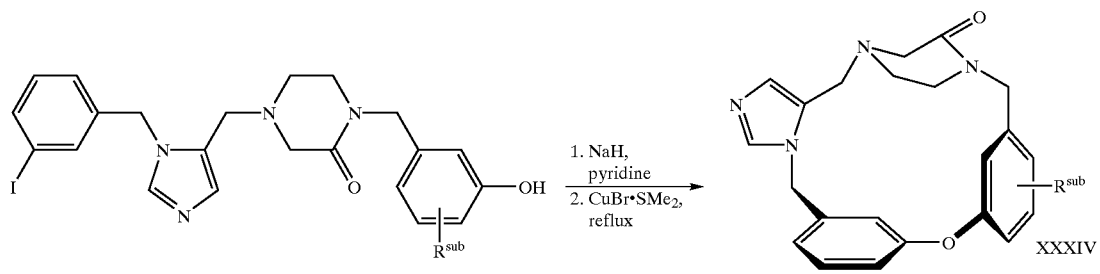

SCHEME 8
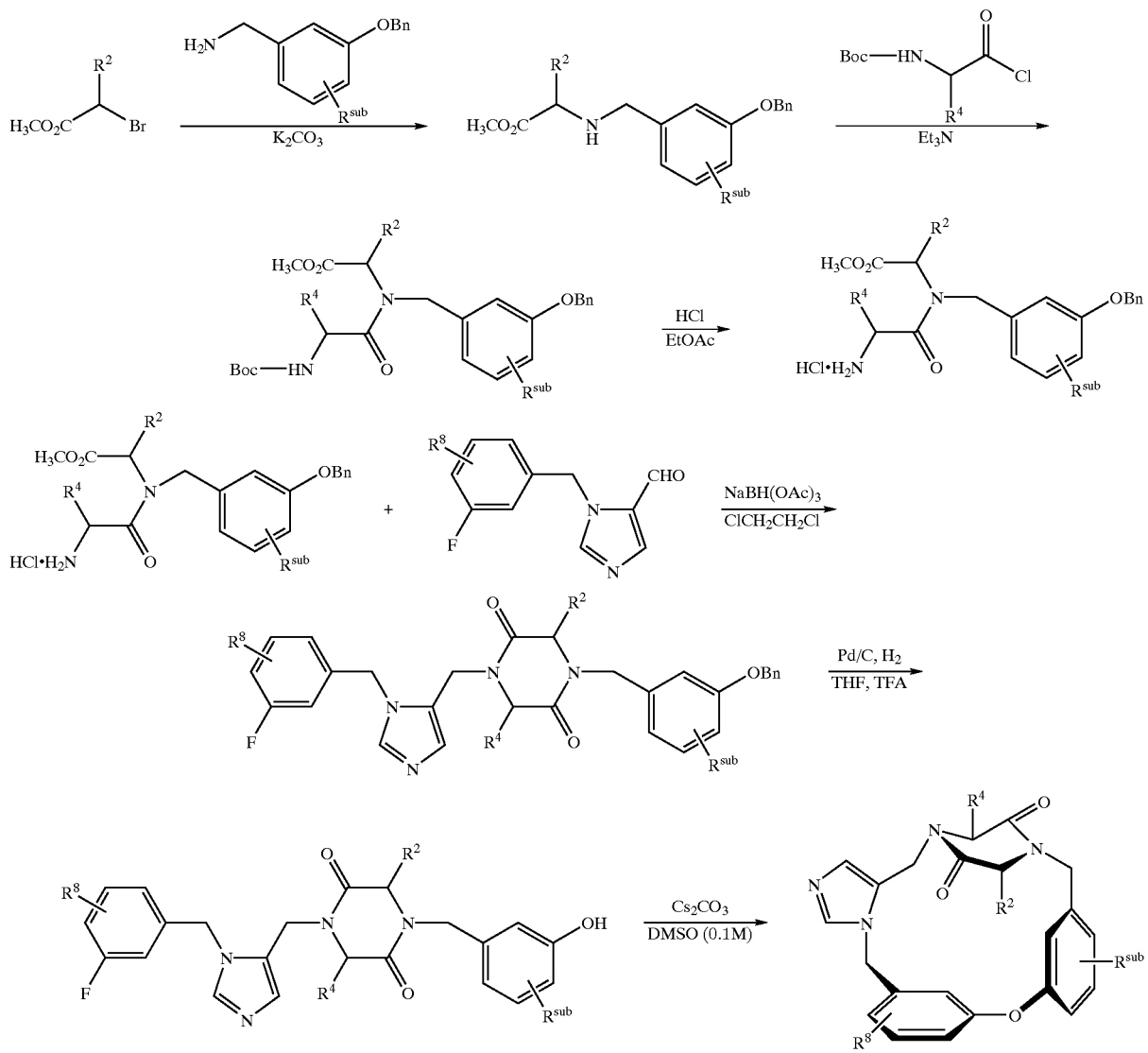
SCHEME 9
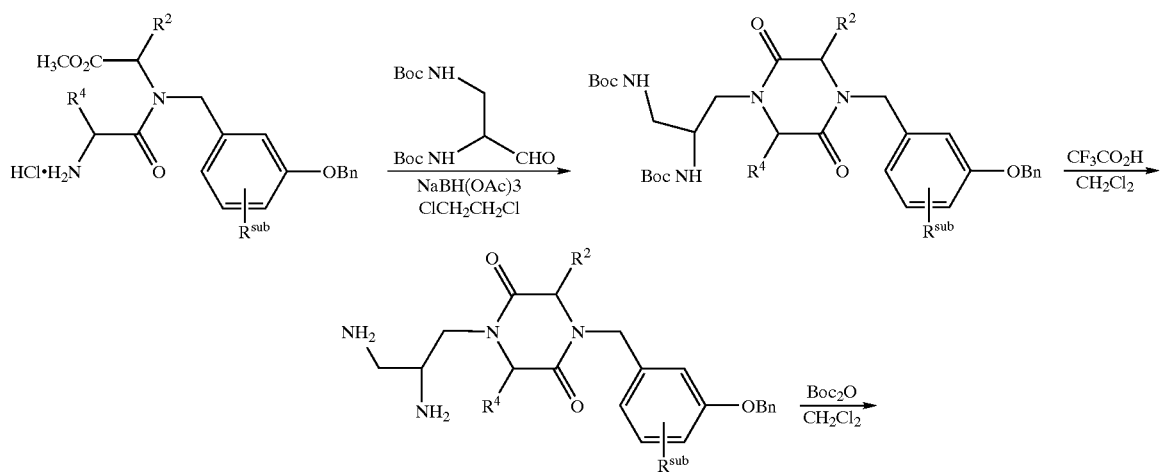

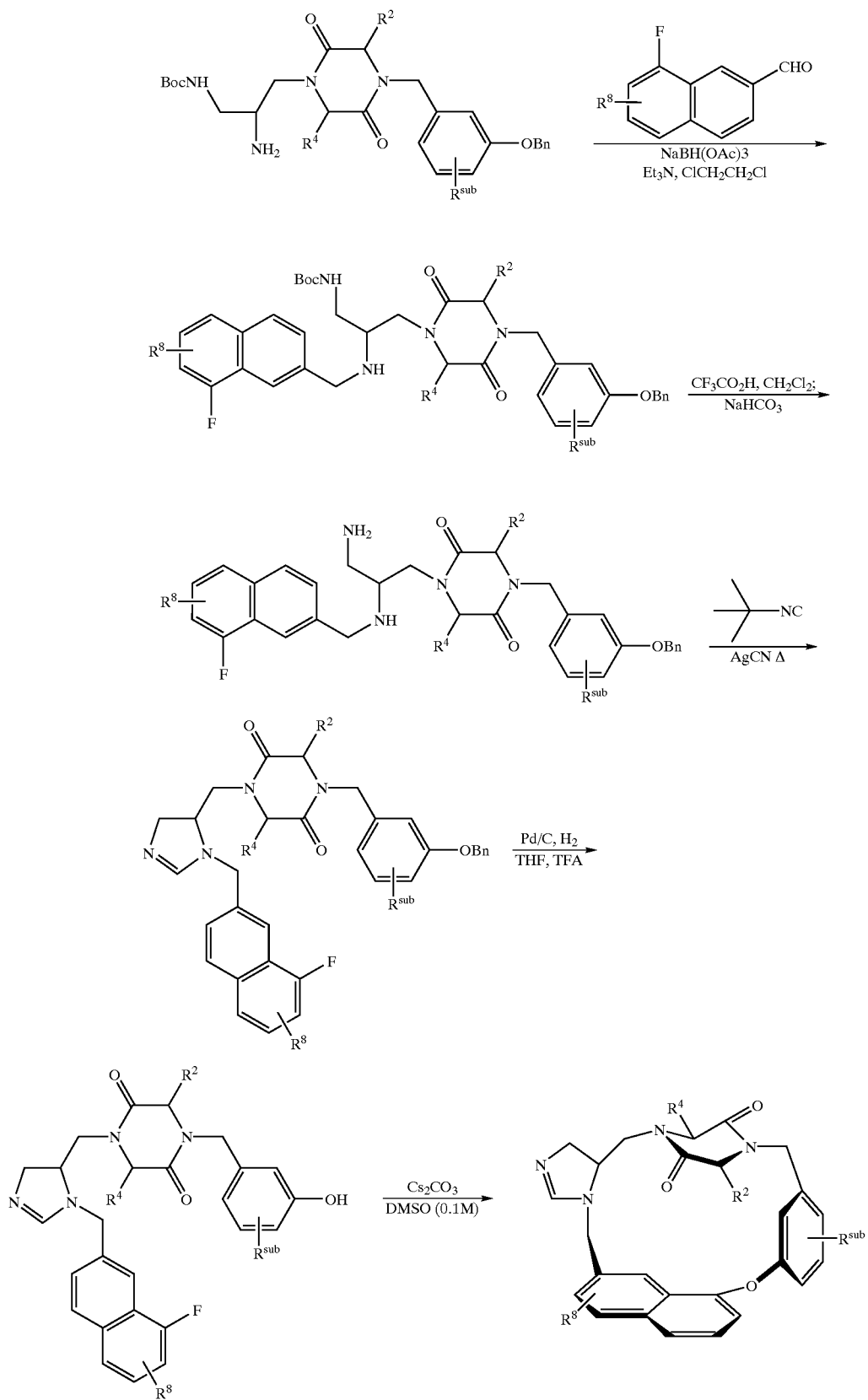

SCHEME 10
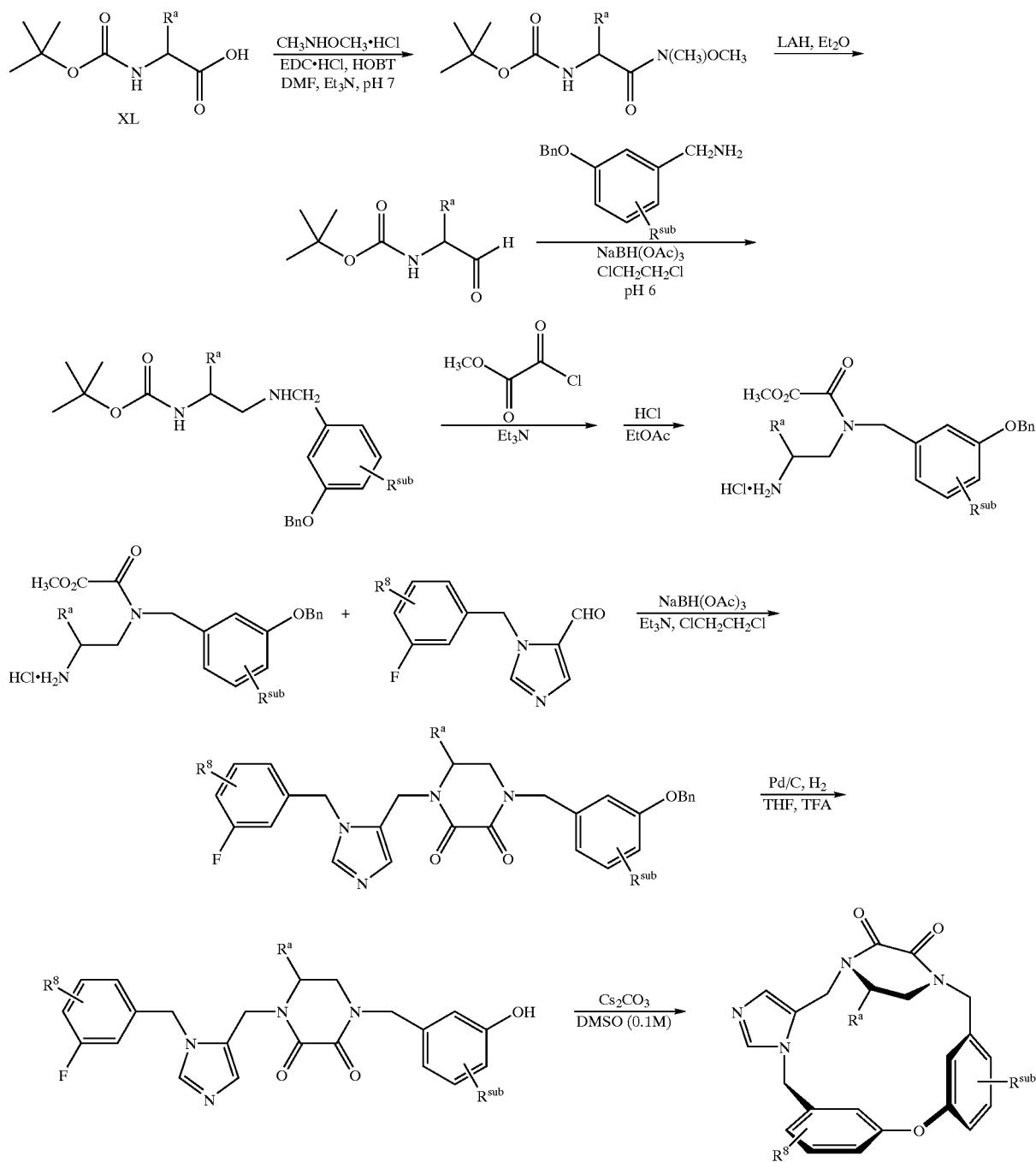
SCHEME 11
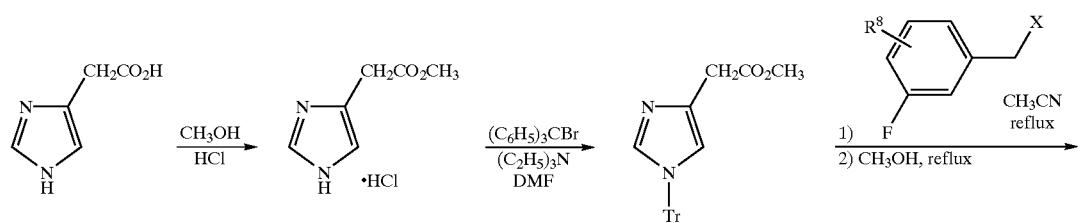

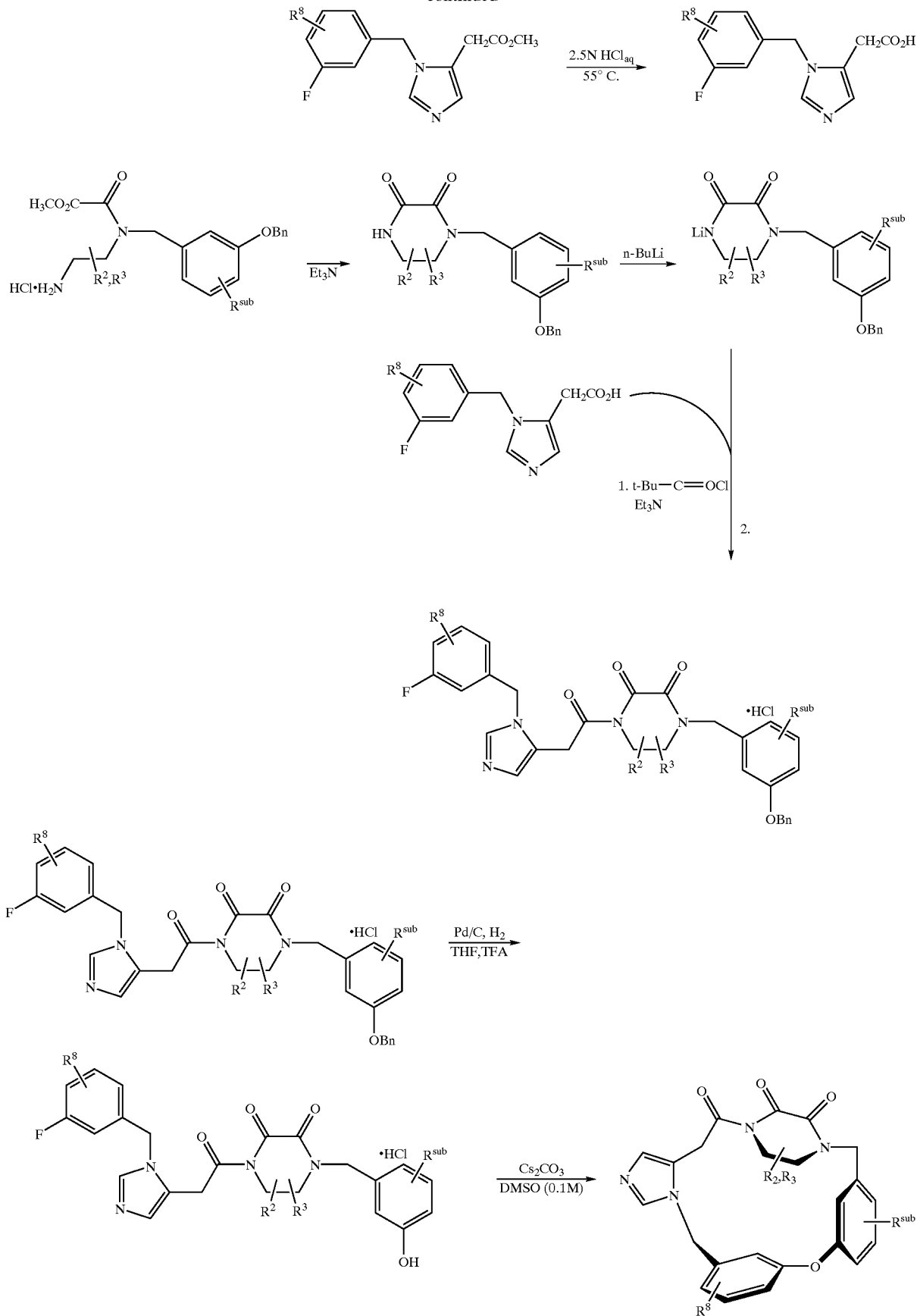

SCHEME 12
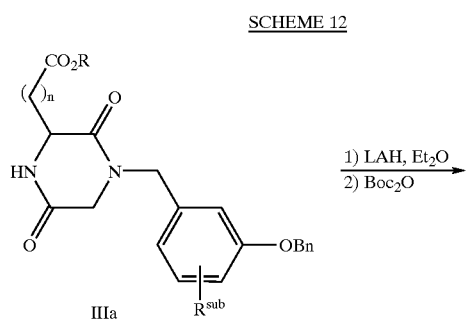
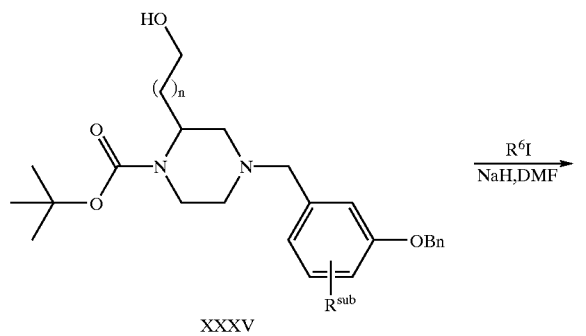
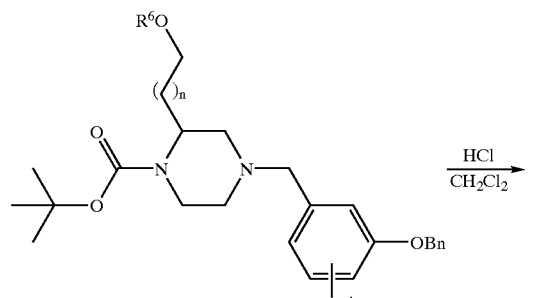
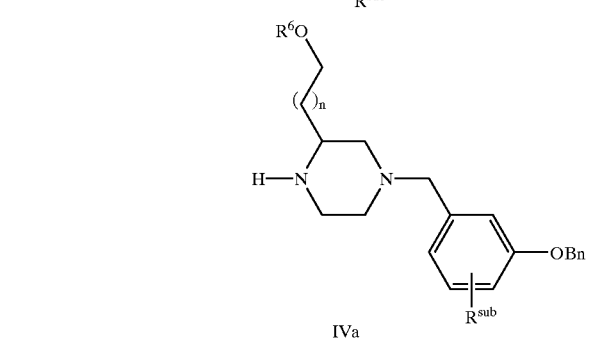
SCHEME 13
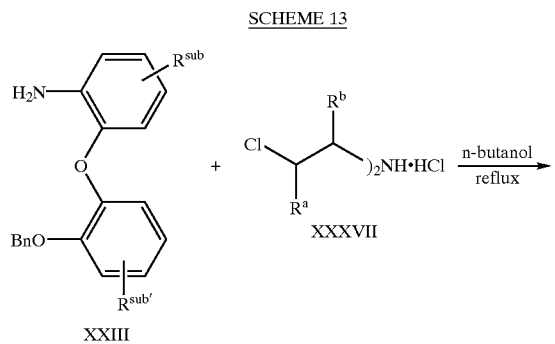
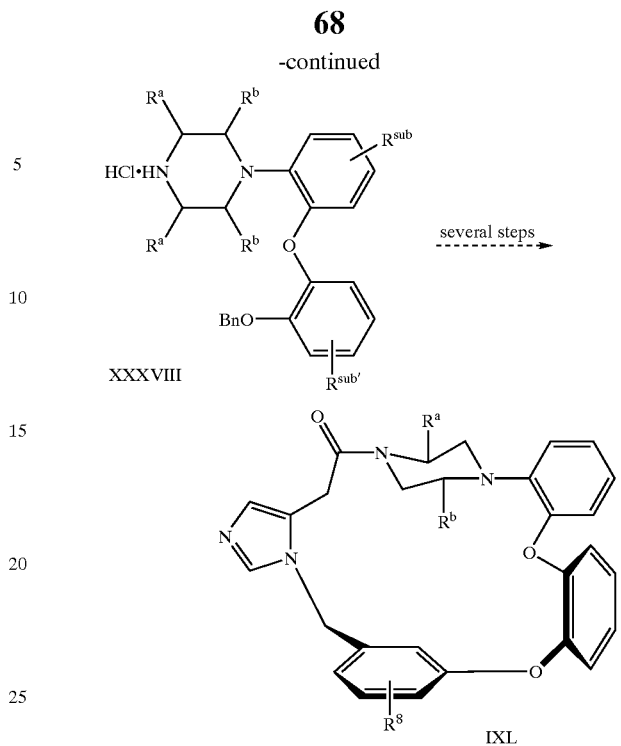
SCHEME 14
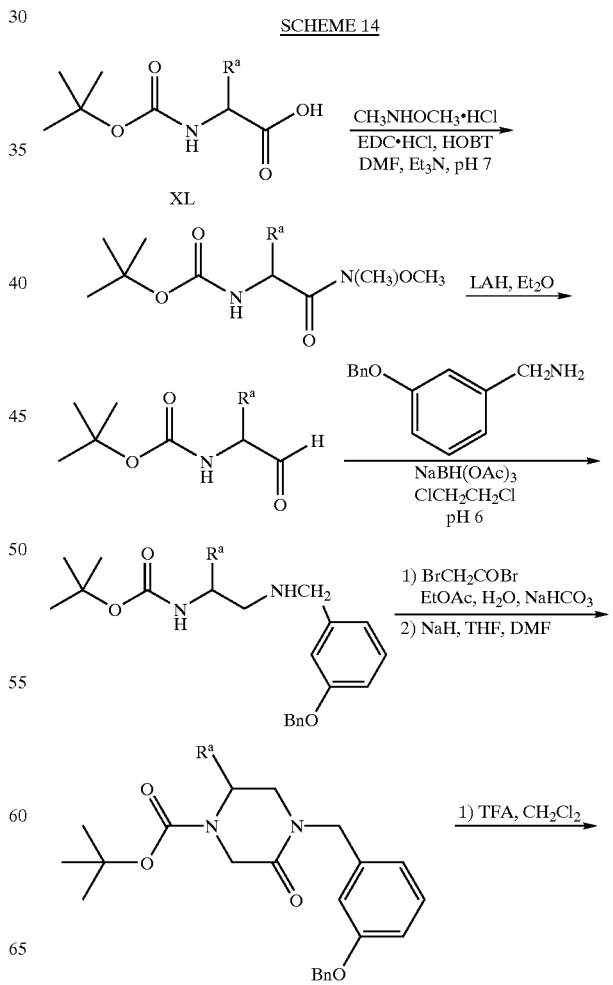

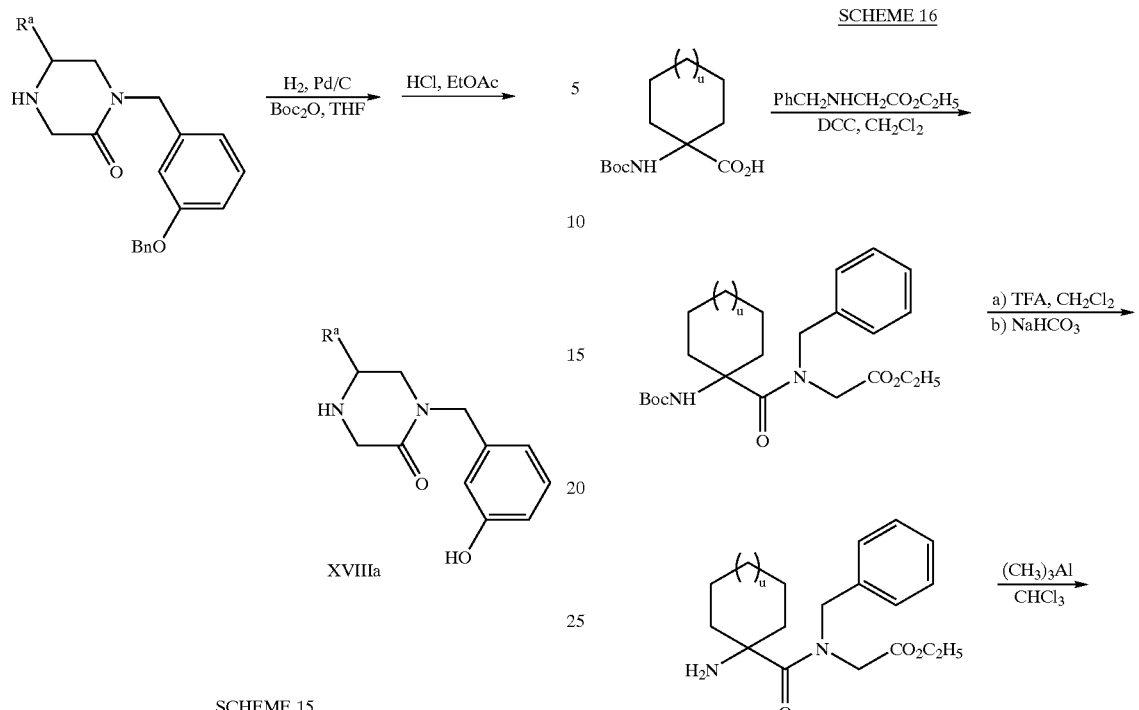
SCHEME 15
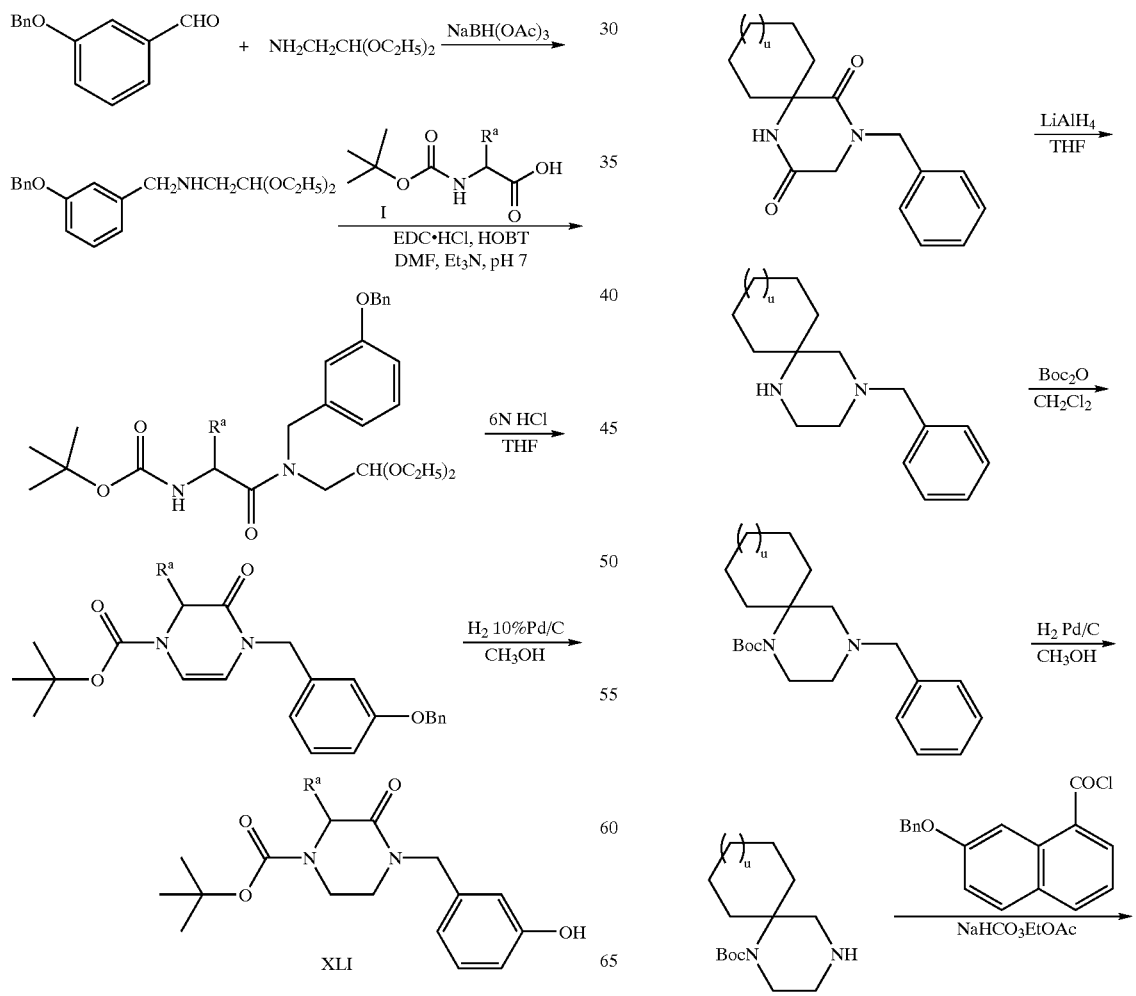
SCHEME 16

-continued
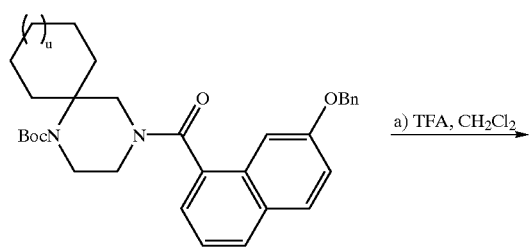
a) TFA, CH$_2$Cl$_2$
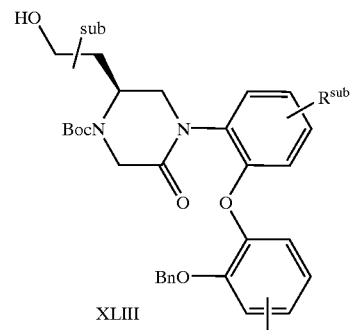
1. MsCl, iPr$_2$NEt
2. NaSEt, DMF
1. (COCl)$_2$, Et$_3$N DMSO
2. NaClO$_2$, t-BuOH 2-Me-2-butene NaH$_2$PO$_4$
XLIII
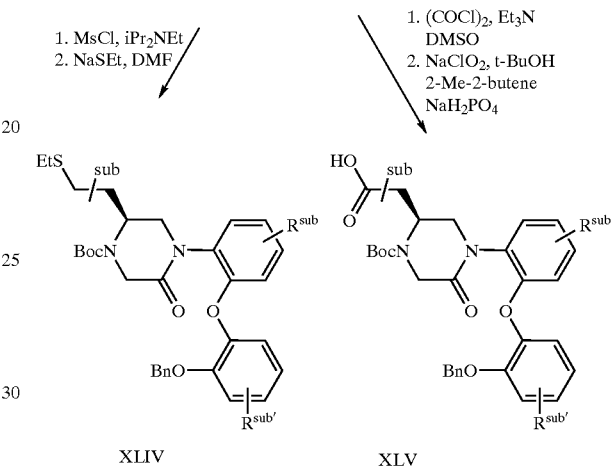
XLIV      XLV
SCHEME 17
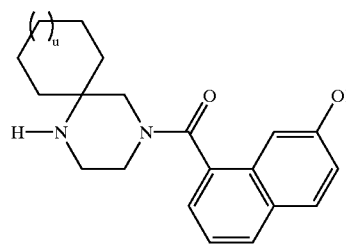
1. Boc$_2$O, i-Pr$_2$EtN
2. DIBAL
XLII
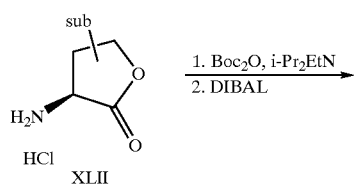
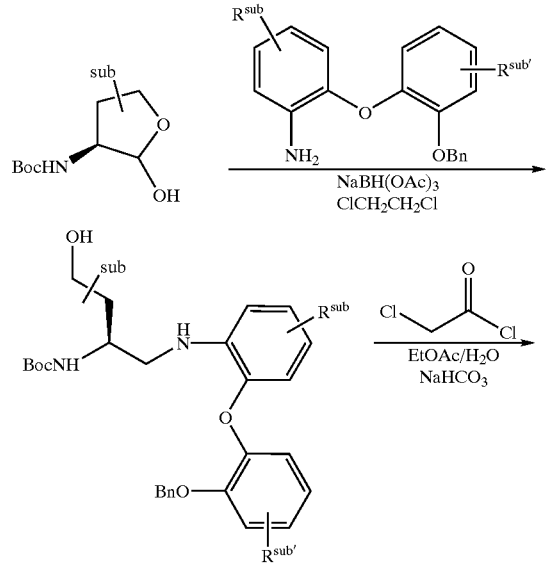
NaBH(OAc)$_3$
ClCH$_2$CH$_2$Cl
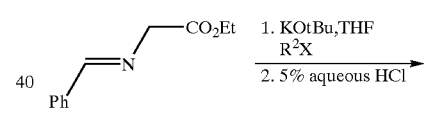
XLVII
SCHEME 18
1. KOtBu, THF
   R$^2$X
2. 5% aqueous HCl
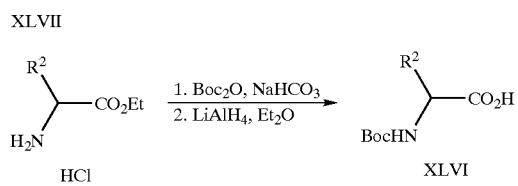
1. Boc$_2$O, NaHCO$_3$
2. LiAlH$_4$, Et$_2$O
XLVI
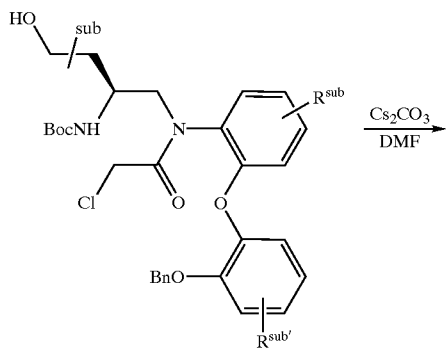
Cl-CH$_2$-COCl
EtOAc/H$_2$O
NaHCO$_3$
Cs$_2$CO$_3$
DMF
SCHEME 19
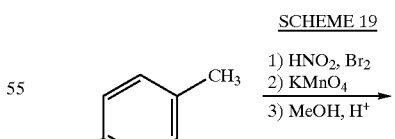
1) HNO$_2$, Br$_2$
2) KMnO$_4$
3) MeOH, H$^+$
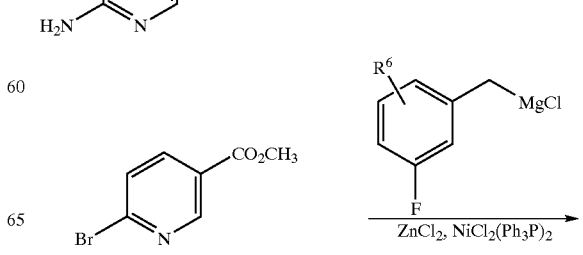
ZnCl$_2$, NiCl$_2$(Ph$_3$P)$_2$

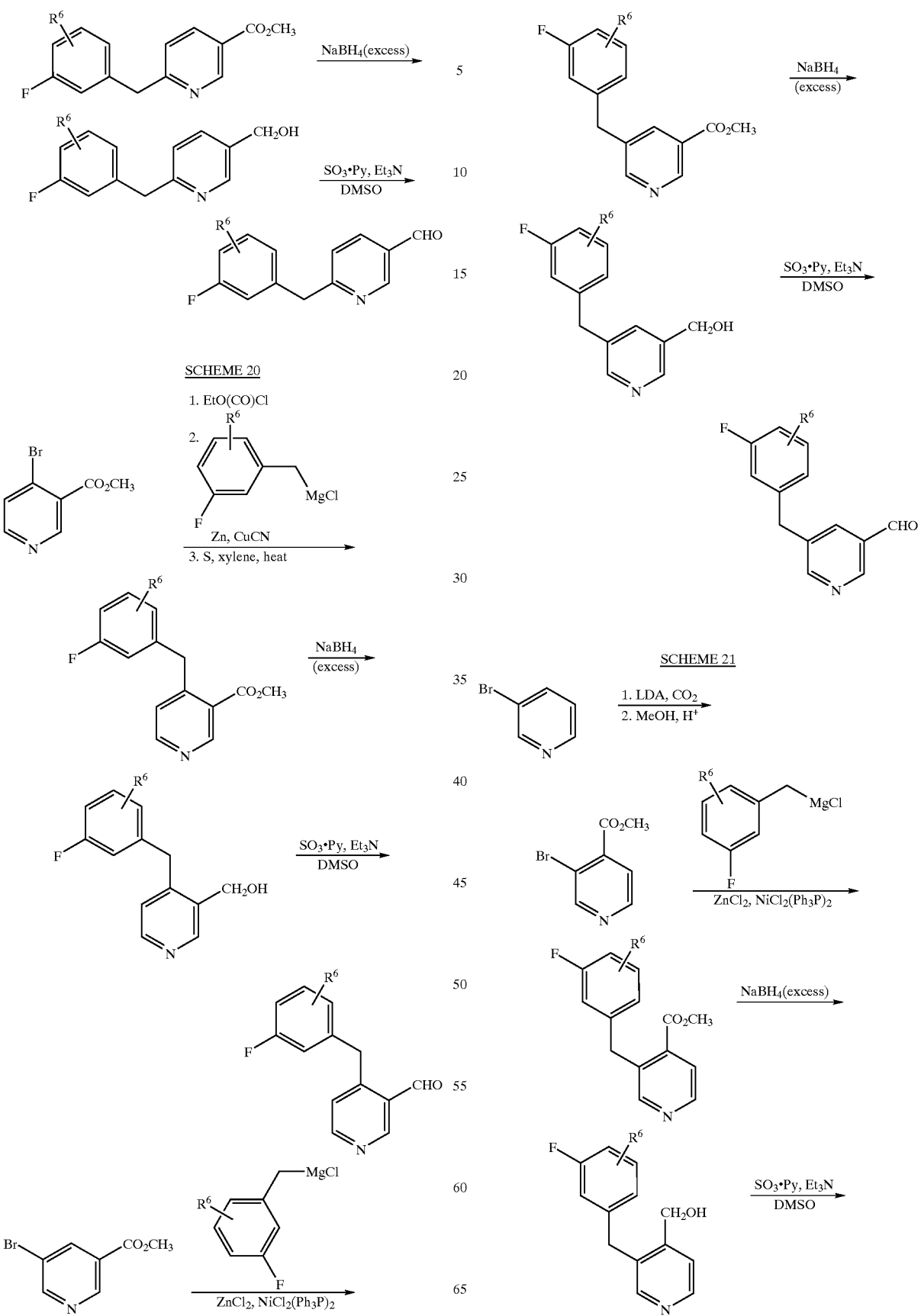

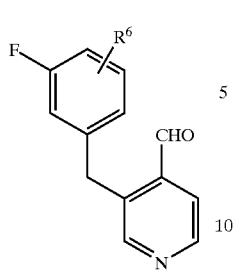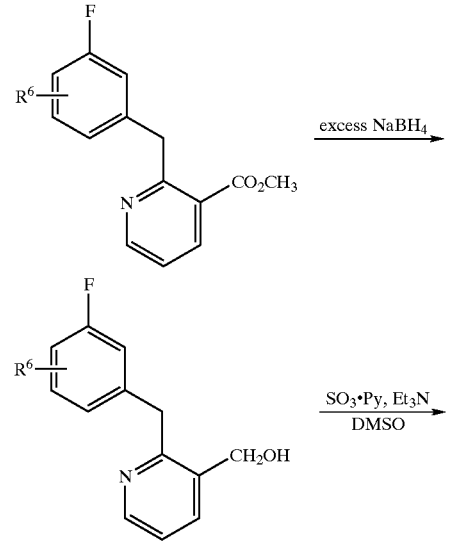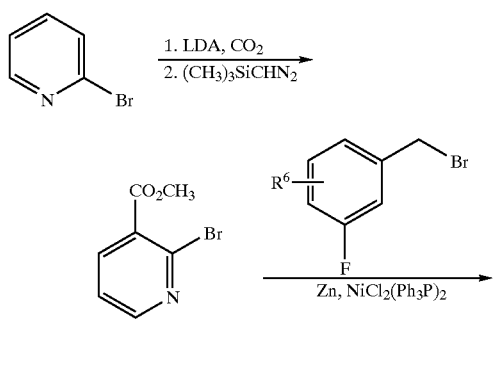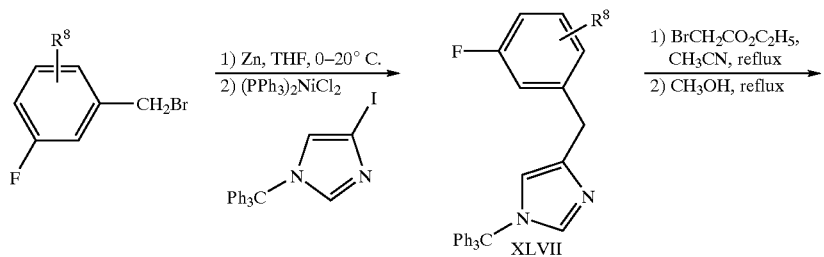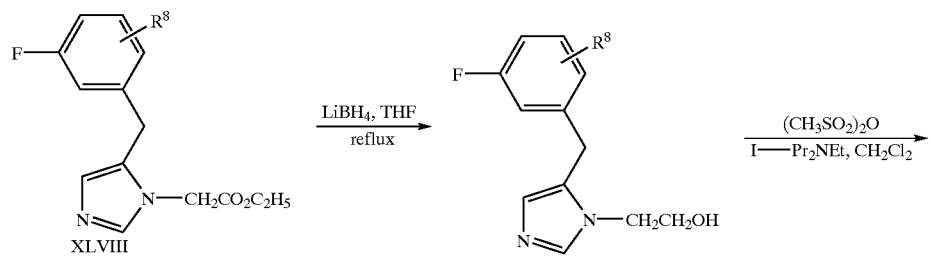

-continued

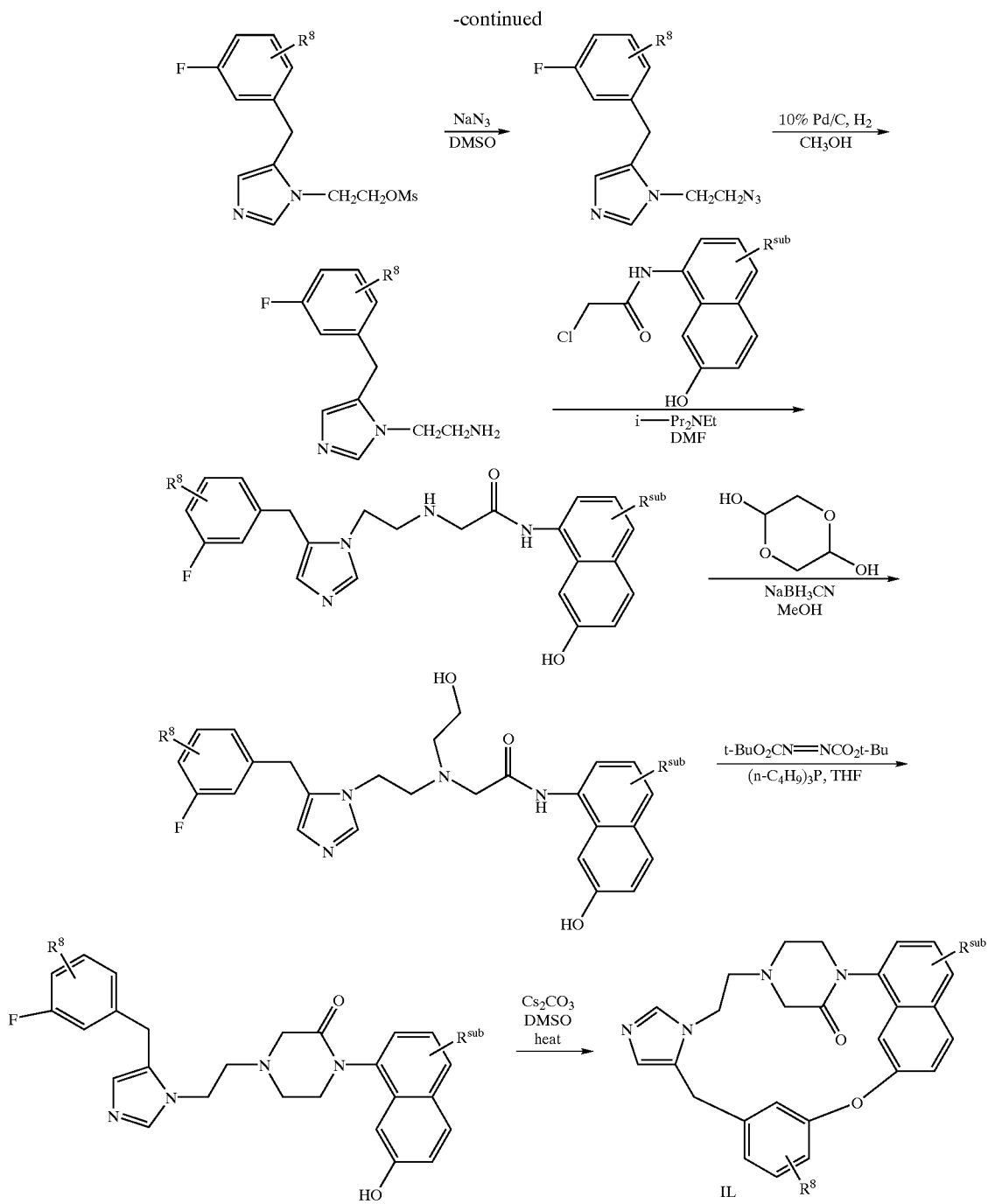

In a preferred embodiment of the instant invention the compounds of the invention are selective inhibitors of farnesyl-protein transferase. A compound is considered a selective inhibitor of farnesyl-protein transferase, for example, when its in vitro farnesyl-protein transferase inhibitory activity, as assessed by the assay described in Example 106, is at least 100 times greater than the in vitro activity of the same compound against geranylgeranyl-protein transferase-type I in the assay described in Example 107. Preferably, a selective compound exhibits at least 1000 times greater activity against one of the enzymatic activities when comparing geranylgeranyl-protein transferase-type I inhibition and farnesyl-protein transferase inhibition.

It is also preferred that the selective inhibitor of farnesyl-protein transferase is further characterized by:

a) an $IC_{50}$ (a measure of in vitro inhibitory activity) for inhibition of the prenylation of newly synthesized K-Ras protein more than about 100-fold higher than the $EC_{50}$ for the inhibition of the farnesylation of hDJ protein.

When measuring such $IC_{50}$s and $EC_{50}$s the assays described in Example 111 may be utilized.

It is also preferred that the selective inhibitor of farnesyl-protein transferase is further characterized by:

b) an $IC_{50}$ (a measurement of in vitro inhibitory activity) for inhibition of K4B-Ras dependent activation of MAP kinases in cells at least 100-fold greater than the $EC_{50}$ for inhibition of the farnesylation of the protein hDJ in cells.

It is also preferred that the selective inhibitor of farnesyl-protein transferase is further characterized by:

c) an $IC_{50}$ (a measurement of in vitro inhibitory activity) against H-Ras dependent activation of MAP kinases in cells at least 1000 fold lower than the inhibitory activity ($IC_{50}$) against H-ras-CVLL (SEQ.ID.NO.: 1) dependent activation of MAP kinases in cells. When measuring Ras dependent activation of MAP kinases in cells the assays described in Example 110 may be utilized.

In another preferred embodiment of the instant invention the compounds of the invention are dual inhibitors of farnesyl-protein transferase and geranylgeranyl-protein transferase type I. Such a dual inhibitor may be termed a Class II prenyl-protein transferase inhibitor and will exhibit certain characteristics when assessed in in vitro assays, which are dependent on the type of assay employed.

In a SEAP assay, such as described in Examples 110, it is preferred that the dual inhibitor compound has an in vitro inhibitory activity ($IC_{50}$) that is less than about 12 $\mu$M against K4B-Ras dependent activation of MAP kinases in cells.

The Class II prenyl-protein transferase inhibitor may also be characterized by:

a) an $IC_{50}$ (a measurement of in vitro inhibitory activity) for inhibiting K4B-Ras dependent activation of MAP kinases in cells between 0.1 and 100 times the $IC_{50}$ for inhibiting the farnesylation of the protein hDJ in cells; and b) an $IC_{50}$ (a measurement of in vitro inhibitory activity) for inhibiting K4B-Ras dependent activation of MAP kinases in cells greater than 5-fold lower than the inhibitory activity ($IC_{50}$) against expression of the SEAP protein in cells transfected with the pCMV-SEAP plasmid that constitutively expresses the SEAP protein.

The Class II prenyl-protein transferase inhibitor may also be characterized by:

a) an $IC_{50}$ (a measurement of in vitro inhibitory activity) against H-Ras dependent activation of MAP kinases in cells greater than 2 fold lower but less than 20,000 fold lower than the inhibitory activity ($IC_{50}$) against H-ras-CVLL (SEQ.ID.NO.: 1) dependent activation of MAP kinases in cells; and b) an $IC_{50}$ (a measurement of in vitro inhibitory activity) against H-ras-CVLL dependent activation of MAP kinases in cells greater than 5-fold lower than the inhibitory activity ($IC_{50}$) against expression of the SEAP protein in cells transfected with the pCMV-SEAP plasmid that constitutively expresses the SEAP protein.

The Class II prenyl-protein transferase inhibitor may also be characterized by:

a) an $IC_{50}$ (a measurement of in vitro inhibitory activity) against H-Ras dependent activation of MAP kinases in cells greater than 10-fold lower but less than 2,500 fold lower than the inhibitory activity ($IC_{50}$) against H-ras-CVLL (SEQ.ID.NO.: 1) dependent activation of MAP kinases in cells; and b) an $IC_{50}$ (a measurement of in vitro inhibitory activity) against H-ras-CVLL dependent activation of MAP kinases in cells greater than 5 fold lower than the inhibitory activity ($IC_{50}$) against expression of the SEAP protein in cells transfected with the pCMV-SEAP plasmid that constitutively expresses the SEAP protein.

A method for measuring the activity of the inhibitors of prenyl-protein transferase, as well as the instant combination compositions, utilized in the instant methods against Ras dependent activation of MAP kinases in cells is described in Example 110.

In yet another embodiment, a compound of the instant invention may be a more potent inhibitor of geranylgeranyl-protein transferase-type I than it is an inhibitor of farnesyl-protein transferase.

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, src, abl, lck, fyn) or by other mechanisms.

The compounds of the instant invention inhibit prenyl-protein transferase and the prenylation of the oncogene protein Ras. The instant compounds may also inhibit tumor angiogenesis, thereby affecting the growth of tumors (J. Rak et al. Cancer Research, 55:4575–4580 (1995)). Such anti-angiogenesis properties of the instant compounds may also be useful in the treatment of certain forms of vision deficit related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. Science, 256:1331–1333 (1992).

The compounds of the instant invention are also useful in the prevention of restenosis after percutaneous transluminal coronary angioplasty by inhibiting neointimal formation (C. Indolfi et al. Nature medicine, 1:541–545(1995).

The instant compounds may also be useful in the treatment and prevention of polycystic kidney disease (D. L. Schaffner et al. American Journal of Pathology, 142:1051–1060 (1993) and B. Cowley, Jr. et al.FASEB Journal, 2:A3160 (1988)).

The instant compounds may also be useful for the treatment of fungal infections.

The instant compounds may also be useful as inhibitors of proliferation of vascular smooth muscle cells and therefore useful in the prevention and therapy of arteriosclerosis and diabetic vascular pathologies.

The compounds of this invention may be administered to mammals, preferably humans, either alone or, preferably, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the instant invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula A are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention may also be co-administered with other well known therapeutic agents that are selected for their particular usefulness against the condition that is being treated. For example, the compounds of the instant invention may also be co-administered with other well known cancer therapeutic agents that are selected for their particular usefulness against the condition that is being treated. Included in such combinations of therapeutic agents are combinations of the instant prenyl-protein transferase inhibitors and an antineoplastic agent. It is also understood that such a combination of antineoplastic agent and inhibitor of prenyl-protein transferase may be used in conjunction with other methods of treating cancer and/or tumors, including radiation therapy and surgery.

Examples of an antineoplastic agent include, in general, microtubule-stabilizing agents (such as paclitaxel (also known as Taxol®), docetaxel (also known as Taxotere®), epothilone A, epothilone B, desoxyepothilone A, desoxyepothilone B or their derivatives); microtubule-disruptor agents; alkylating agents, anti-metabolites; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents, haematopoietic growth factors and antibodies (such as trastuzumab (Herceptin™)).

Example classes of antineoplastic agents include, for example, the anthracycline family of drugs, the vinca drugs, the mitomycins, the bleomycins, the cytotoxic nucleosides, the taxanes, the epothilones, discodermolide, the pteridine family of drugs, diynenes and the podophyllotoxins. Particularly useful members of those classes include, for example, doxorubicin, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, cisplatin, carboplatin, cyclophosphamide, bleomycin, tamoxifen, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

The preferred class of antineoplastic agents is the taxanes and the preferred antineoplastic agent is paclitaxel.

Radiation therapy, including x-rays or gamma rays which are delivered from either an externally applied beam or by implantation of tiny radioactive sources, may also be used in combination with the instant inhibitor of prenyl-protein transferase alone to treat cancer.

Additionally, compounds of the instant invention may also be useful as radiation sensitizers, as described in WO 97/38697, published on Oct. 23, 1997, and herein incorporated by reference.

The instant compounds may also be useful in combination with other inhibitors of parts of the signaling pathway that links cell surface growth factor receptors to nuclear signals initiating cellular proliferation. Thus, the instant compounds may be utilized in combination with a compound which has Rafantagonist activity. The instant compounds may also be co-administered with compounds that are selective inhibitors of famesyl-protein transferase, dual inhibitors of farnesyl-protein transferase and geranylgeranylprotein transferase type I or selective inhibitors of geranylgeranyl-protein transferase type I. Such a selective inhibitor or dual inhibitor may be an inhibitor that is competitive with the binding of the CAAX-containing protein substrate of farnesyl-protein transferase or may be farnesyl pyrophosphate competitive inhibitors.

In particular, the compounds disclosed in the following patents and publications may be useful as farnesyl pyrophosphate-competitive inhibitor component of the instant composition: U.S. Ser. Nos. 08/254,228 and 08/435,047. Those patents and publications are incorporated herein by reference.

In practicing methods of this invention, which comprise administering, simultaneously or sequentially or in any order, two or more of a protein substrate-competitive inhibitor and a prenyl pyrophosphate-competitive inhibitor, such administration can be orally or parenterally, including intravenous, intramuscular, intraperitoneal, subcutaneous, rectal and topical routes of administration. It is preferred that such administration be orally. It is more preferred that such administration be orally and simultaneously. When the protein substrate-competitive inhibitor and a prenyl pyrophosphate-competitive inhibitor are administered sequentially, the administration of each can be by the same method or by different methods.

The instant compounds may also be useful in combination with an integrin antagonist for the treatment of cancer, as described in U.S. Ser. No. 09/055,487, filed Apr. 6, 1998, which is incorporated herein by reference.

As used herein the term an integrin antagonist refers to compounds which selectively antagonize, inhibit or counteract binding of a physiological ligand to an integrin(s) that is involved in the regulation of angiogenisis, or in the growth and invasiveness of tumor cells. In particular, the term refers to compounds which selectively antagonize, inhibit or counteract binding of a physiological ligand to the αvβ3 integrin, which selectively antagonize, inhibit or counteract binding of a physiological ligand to the αvβ5 integrin, which antagonize, inhibit or counteract binding of a physiological ligand to both the αvβ3 integrin and the αvβ5 integrin, or which antagonize, inhibit or counteract the activity of the particular integrin(s) expressed on capillary endothelial cells. The term also refers to antagonists of the αvβ6, αvβ8, α1β1, α2β1, α5β1, α6β1 and α6β4 integrins. The term also refers to antagonists of any combination of αvβ3, αvβ5, αvβ6, αvβ8, α1β1, α2β1, α5β1, α6β1 and α6β4 integrins. The instant compounds may also be useful with other agents that inhibit angiogenisis and thereby inhibit the growth and invasiveness of tumor cells, including, but not limited to angiostatin and endostatin.

Similarly, the instant compounds may be useful in combination with agents that are effective in the treatment and prevention of NF-1, restenosis, polycystic kidney disease, infections of hepatitis delta and related viruses and fungal infections.

If formulated as a fixed dose, such combination products employ the combinations of this invention within the dosage range described below and the other pharmaceutically active agent(s) within its approved dosage range. Combinations of the instant invention may alternatively be used sequentially with known pharmaceutically acceptable agent(s) when a multiple combination formulation is inappropriate.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immuno-logical, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1

Preparation of 19,20-Dihydro-19-oxo-5H,17H-18, 21-ethano-6,10:12,16-dimetheno-22H-imidazo[3,4-h][1,8,11,14]oxatriazacycloeicosine-9-carbonitrile (1), Dihydrochloride

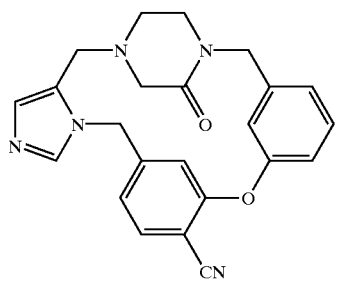

Step A: Preparation of 1-Triphenylmethyl-4-(hydroxymethyl)imidazole

To a solution of 4-(hydroxymethyl)imidazole hydrochloride (35.0 g, 260 mmol) in 250 mL of dry DMF at room temperature was added triethylamine (90.6 mL, 650 mmol). A white solid precipitated from the solution. Chlorotriphenylmethane (76.1 g, 273 mmol) in 500 mL of DMF was added dropwise. The reaction mixture was stirred for 20 hours, poured over ice, filtered, and washed with ice water. The resulting product was slurried with cold dioxane, filtered, and dried in vacuo to provide the titled product as a white solid which was sufficiently pure for use in the next step.

Step B: Preparation of 1-Triphenylmethyl-4-(acetoxymethyl)imidazole

Alcohol from Step A (260 mmol, prepared above) was suspended in 500 mL of pyridine. Acetic anhydride (74 mL, 780 mmol) was added dropwise, and the reaction was stirred for 48 hours during which it became homogeneous. The solution was poured into 2 L of EtOAc, washed with water (3×1 L), 5% aq. HCl soln. (2×1 L), sat. aq. NaHCO$_3$, and brine, then dried (Na$_2$SO$_4$), filtered, and concentrated in vacuo to provide the crude product. The acetate was isolated as a white powder which was sufficiently pure for use in the next reaction.

Step C: Preparation of 4-Cyano-3-fluorotoluene

To a degassed solution of 4-bromo-3-fluorotoluene (50.0 g, 264 mmol) in 500 mL of DMF was added Zn(CN)$_2$ (18.6 g, 159 mmol) and Pd(PPh$_3$)$_4$ (6.1 g, 5.3 mmol). The reaction was stirred at 80° C. for 6 hours, then cooled to room temperature. The solution was poured into EtOAc, washed with water, sat. aq. NaHCO$_3$, and brine, then dried (Na$_2$SO$_4$), filtered, and concentrated in vacuo to provide the crude product. Purification by silica gel chromatography (0–5% EtOAc/hexane) provided the titled product.

Step D: Preparation of 4-Cyano-3-fluorobenzylbromide

To a solution of the product from Step C (22.2 g, 165 mmol) in 220 mL of carbontetrachloride was added N-bromosuccinimide (29.2 g, 164 mmol) and benzoylperoxide (1.1 g). The reaction was heated to reflux for 30 minutes, then cooled to room temperature. The solution was concentrated in vacuo to one-third the original volume, poured into EtOAc, washed with water, sat. aq. NaHCO$_3$, and brine, then dried (Na$_2$SO$_4$), filtered, and concentrated in vacuo to provide the crude product. Analysis by 1H NMR indicated only partial conversion, so the crude material was resubjected to the same reaction conditions for 2.5 hours, using 18 g (102 mmol) of N-bromosuccinimide. After workup, the crude material was purified by silica gel chromatography (0–10% EtOAc/hexane) to provide the desired product.

Step E: Preparation of 1-(4-Cyano-3-fluorobenzyl)-5-(acetoxymethyl)-imidazole Hydrobromide A solution of the product from Step B (36.72 g, 96.14 mmol) and the product from Step D (20.67 g, 96.14 mmol) in 250 mL of EtOAc was stirred at 60° C. for 20 hours, during which a white precipitate formed. The reaction was cooled to room temperature and filtered to provide the solid imidazolium bromide salt. The filtrate was concentrated in vacuo to a volume of 100 mL, reheated at 60° C. for two hours, cooled to room temperature, and filtered again. The filtrate was concentrated in vacuo to a volume 40 mL, reheated at 60° C. for another two hours, cooled to room temperature, and concentrated in vacuo to provide a pale yellow solid. All of the solid material was combined, dissolved in 300 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid which was used in the next step without further purification.

Step F: Preparation of 1-(4-Cyano-3-fluorobenzyl)-5-(hydroxymethyl)imidazole

To a solution of the product from Step E (31.87 g, 89.77 mmol) in 300 mL of 2:1 THF/water at 0° C. was added lithium hydroxide monohydrate (7.53 g, 179 mmol). After two hours, the reaction was concentrated in vacuo to a 100 mL volume, stored at 0° C. for 30 minutes, then filtered and washed with 700 mL of cold water to provide a brown solid. This material was dried in vacuo next to P$_2$O$_5$ to provide the titled product as a pale brown powder which was sufficiently pure for use in the next step without further purification.

Step G: Preparation of 1-(4-Cyano-3-fluorobenzyl)-5-imidazolecarboxaldehyde

To a solution of the alcohol from Step F (2.31 g, 10.0 mmol) in 20 mL of DMSO at 0° C. was added triethylamine (5.6 mL, 40 mmol), then SO$_3$-pyridine complex (3.89 g, 25 mmol). After 30 minutes, the reaction was poured into EtOAc, washed with water and brine, dried (Na$_2$SO$_4$), filtered, and concentrated in vacuo to provide the aldehyde as a pale yellow powder which was sufficiently pure for use in the next step without further purification.

Step H: Preparation of 3-(Benzyloxy)benzylmethanesulfonate

To a solution of 3-(benzyloxy)benzyl alcohol (1.546 g, 7.21 mmol) in 20 mL of CH$_2$Cl$_2$ at 0° C. was added triethylamine (1.206 mL, 8.65 mmol) and methanesulfonic anhydride (1.257 g, 7.21 mmol). After 45 minutes, the solution was poured into EtOAc, washed with 10% HCl soln., sat. aq. NaHCO$_3$ and brine, dried (Na$_2$SO$_4$), filtered, and concentrated in vacuo to provide the titled product as a yellow oil.

Step I: Preparation of 1-[3-(Benzyloxy)benzyl]-4-(benzyloxy)carbonyl-2-piperazinone Sodium hydride (430 mg, 10.8 mmol as 60% dispersion in mineral oil) was triturated with hexanes, then suspended in 5 mL of DMF. After cooling to 0° C., 4-(benzyloxy)carbonyl-2-piperazinone was added (1.68 g, 7.18 mmol). After 15 minutes, a solution of the product from Step H (2.096 g, 7.18 mmol) in 2 mL of DMF was added, followed by a 1 mL DMF rinse. The reaction was warmed to room temperature, stirred for 30 minutes, then poured into EtOAc. The organic layer was washed with water, sat. aq. NaHCO$_3$ and brine, dried (Na$_2$SO$_4$), filtered, and concentrated in vacuo. The resulting product was purified by silica gel chromatography (60% EtAOAc/hexane) to produce the titled product as a pale yellow oil.

Step J: Preparation of 1-[3-(Hydroxy)benzyl]-4-(tert-Butyloxy)carbonyl-2-piperazinone A solution of the product from Step 1 (806 mg, 1.87 mmol) and di-tert-butyl dicarbonate (408 mg, 1.87 mmol) and 10% palladium on carbon (330 mg) were stirred in a solution of 10 mL of THF under a balloon atmosphere of hydrogen. After 20 hours, the solution was filtered through celite, and the filter pad was rinsed with THF. Concentration in vacuo provided the titled product as a white foam.

Step K: Preparation of 1-[3-(Hydroxy)benzyl]-2-piperazinone Hydrochloride

Through a solution of the product from Step J (68 mg, 0.22 mmol) in 3.0 mL of ethyl acetate at 0° C. was bubbled anhydrous HCl gas for 5 minutes. After 15 minutes, the solution was concentrated in vacuo to provide the titled salt as a white foam which was used in the next reaction without further purification.

Step L: Preparation of 4-[1-(4-Cyano-3-fluorobenzyl)-5-imidazolylmethyl]-1-[3-hydroxybenzyl]-2-piperazinone To a solution of the amine hydrochloride from Step K (theoretically 0.22 mmol) in 2 mL of 1,2-dichloroethane was added 4 Å powdered molecular sieves (100 mg), followed by sodium triacetoxyborohydride (70 mg, 0.33 mmol). The aldehyde from Step G (51 mg, 0.22 mmol) was added, and the reaction was stirred for 16 hours. The reaction was poured into EtOAc, washed with sat. aq. NaHCO$_3$ and brine, dried (Na$_2$SO$_4$), filtered, and concentrated in vacuo. The titled product was obtained as a pale yellow foam.

Step M: Preparation of Compound 1 Dihydrochloride

To a solution of the product from Step L (60.6 mg, 0.15 mol) in 1.5 mL of DMSO was added cesium carbonate (148 mg, 0.45 mmol). The reaction was warmed to 55° C. under argon for 20 minutes, then cooled to room temperature. The solution was poured into EtOAc and washed with water and brine, dried (Na$_2$SO$_4$), filtered, and concentrated in vacuo. The resulting product was purified by silica gel chromatography (5–6% MeOH/CH$_2$Cl$_2$), taken up in CH$_2$Cl$_2$ and treated with excess 1 M HCl/ether solution, and concentrated in vacuo to provide the titled product dihydrochloride as a white powder.

FAB mass spectrum m/e 400.0 (M+1). Analysis calculated for C$_{23}$H$_{21}$N$_5$O$_2$.2.70HCl.1.00H$_2$O: C, 53.55; H, 5.02; N, 13.57; Found: C, 53.64; H, 5.04; N, 13.05.

Example 2

Preparation of 19-Chloro-22,23-dihydro-22-oxo-5H-21,24-ethano-6,10-metheno-25H-dibenzo[b,e]imidazo[4,3-l][1,4,7,10,13]dioxatriaza-cyclononadecine-9-carbonitrile (2), Hydrochloride

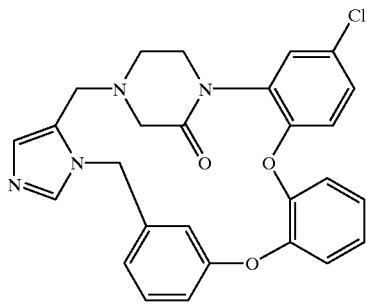

Step A: Preparation of 2-[2-(Benzyloxy)phenyl]-5-chloronitrobenzene

To a solution of 2-(benzyloxy)phenol (4.2736 g, 21.34 mmol) and 2,5-dichloronitrobenzene (4.302 g, 22.41 mmol) in 40 mL of DMSO was added cesium carbonate (13.8 g, 42.7 mmol). The reaction was heated to 70° C. under argon for one hour, then cooled to room temperature. The solution was poured into EtOAc, washed with water, sat. aq. NaHCO$_3$ and brine, dried (Na$_2$SO$_4$), filtered, and concentrated in vacuo. The titled product was obtained as a brown oil.

Step B: Preparation of 2-[2-(Benzyloxy)phenyl]-5-chloroaniline

To a solution of the product from Step A (7.69 g, 21.34 mmol) in 80 mL of ethanol was added stannous(II) chloride (20.17 g, 106.7 mmol). The solution was heated to 50° C. for one hour, then cooled to room temperature. The solution was poured into 10 mL of concentrated sulfuric acid, then heated to 90° C. for 30 minutes. After cooling, the solution was concentrated in vacuo, basified with 20% NaOH solution, and extracted with EtOAc. The organic layer was washed with water and brine, dried (Na$_2$SO$_4$), filtered, and concentrated in vacuo to provide the titled product as a brown oil.

Step C: Preparation of N-[2-(2-(Benzyloxy)phenyl)-5-chlorophenyl]-2-chloroacetamide To a solution of the product from Step B (6.200 g, 19.07 mmol) in 100 mL of EtOAc and 100 mL of saturated NaHCO$_3$ solution at 0° C. was added chloroacetyl chloride (2.28 mL, 28.6 mmol). After one hour, the solution was poured into EtOAc, washed with water and brine, dried (Na$_2$SO$_4$), filtered, and concentrated in vacuo. The titled product was obtained as a brown solid.

Step D: Preparation of N-[2-(2-(Benzyloxy)phenyl)-5-chlorophenyl]-2-[(2-(hydroxy)ethyl)amino]acetamide To a solution of the product from Step C (6.9165 g, 17.25 mmol) in 25 mL of isopropyl acetate was added ethanolamine (3.84 mL, 63.7 mmol). The reaction was warmed to 55° C. for 4 hours, then cooled to room temperature. The solution was poured into EtOAc, washed with sat. aq. NaHCO$_3$ and brine, dried (Na$_2$SO$_4$), filtered, and concentrated in vacuo. The titled product was obtained as a brown solid.

Step E: Preparation of 1-[2-(2-(Benzyloxy)phenyl)-5-chlorophenyl]-2-piperazinone Hydrochloride To a solution of di-tert-butylazodicarboxylate (5.557 g, 24.1 mmol) in 20 mL of EtOAc at 0° C. was added tributylphosphine (6.013 mL, 24.1 mmol) dropwise. After 10 minutes, a solution of the product from Step D (6.8548 g, 16.09 mmol) in 10 mL of EtOAc was added dropwise over 15 minutes, and the reaction was allowed to warm to room temperature. After one hour, the solution was poured into EtOAc, washed with sat. aq. NaHCO$_3$ and brine, dried (Na$_2$SO$_4$), filtered, and concentrated in vacuo. The crude product mixture was taken up in 30 mL of ether, 1N HCl/Ether was added (17 mL), and the solution was concentrated in vacuo. This was stirred in 50 mL of cold isopropanol over an ice bath for 30 minutes, and the resulting slurry was filtered and rinsed with cold isopropanol. The filtered solid was dried in vacuo next to P$_2$O$_5$ to provide the titled product as a white solid.

Step F: Preparation of 1-[2-(2-(Benzyloxy)phenyl)-5-chlorophenyl]-4-[1-(4-cyano-3-fluorobenzyl)-5-imidazolylmethyl]-2-piperazinone To a solution of the amine hydrochloride from Step E (320 mg, 0.720 mmol) in 3 mL of 1,2-dichloroethane was added 4 Å powdered molecular sieves (400 mg), followed by sodium triacetoxyborohydride (228 mg, 1.08 mmol). The aldehyde from Step G of Example 1 was added (165 mg, 0.720 mmol), and the reaction was stirred for 2 hours. The reaction was poured into EtOAc, washed with sat. aq. NaHCO$_3$ and brine, dried (Na$_2$SO$_4$), filtered, and concentrated in vacuo. The crude product was taken up in 2 mL of THF and 15 mL of 3N HCl solution, stirred for one hour, then partitioned between CH$_2$Cl$_2$ and sat. aq. NaHCO$_3$ solution. The aqueous layer was extracted twice with CH$_2$Cl$_2$, and the combined organic layers were dried (Na$_2$SO$_4$), filtered, and concentrated in vacuo. The titled product was obtained as a pale yellow foam.

Step G: Preparation of 1-[2-(2-Hydroxyphenyl)-5-chlorophenyl]-4-[1-(4-cyano-3-fluorobenzyl)-5-imidazolylmethyl]-2-piperazinone Trifluoroacetate To a solution of the benzyl ether from Step F (402 mg, 0.647 mmol) in 5 mL of 1:1 MeOH/EtOAc was added trifluoroacetic acid (0.10 mL) and 10% palladium on carbon (200 mg). The solution was stirred under a balloon atmosphere of hydrogen at room temperature. After 16 hours, the solution was filtered through celite, and the filter pad was rinsed with 1:1 MeOH/EtOAc. Concentration in vacuo provided the titled product as a white foam.

Step H: Preparation of Compound 2 Hydrochloride

To a solution of the product from Step G (290.8 mg, 0.546 mmol) in 5 mL of DMSO was added cesium carbonate (532 mg, 1.64 mmol). The reaction was warmed to 55° C. under argon for one hour, then cooled to room temperature. The solution was poured into EtOAc and washed with water and brine, dried (Na$_2$SO$_4$), filtered, and concentrated in vacuo. The resulting product was purified by silica gel chromatography (5–7% MeOH/CH$_2$Cl$_2$), taken up in CH$_2$Cl$_2$ and treated with excess 1 M HCl/ether solution, and concentrated in vacuo to provide the titled product dihydrochloride as a white powder.

FAB mass spectrum m/e 512.2 (M+1). Analysis calculated for C$_{28}$H$_{22}$ClN$_5$O$_3$·1.80HCl·1.20H$_2$O: C, 56.13; H, 4.41; N, 11.69; Found: C, 56.18; H, 4.43; N, 11.19.

Example 3

Preparation of 22,23-Dihydro-22-oxo-5H-21,24-ethano-6,10-metheno-25H-dibenzo[b,e]imidazo[4,3-1][1,4,7,10,13]dioxatriazacyclononadecine-9-carbonitrile (3), Hydrochloride

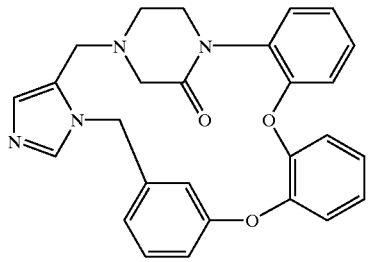

3

Step A: Preparation of Compound 3 Dihydrochloride

To a solution of Compound 2 from Example 2 (41 mg, 0.070 mmol) in 3 mL of isopropanol was added 0.5 mL of sat. aq. NaHCO₃ solution and 10% palladium on carbon (100 mg). The solution was stirred under a balloon atmosphere of hydrogen at room temperature. After 5 hours, the solution was filtered through celite, and the filter pad was rinsed with THF. The filtrate was taken up in $CH_2Cl_2$, washed with water, dried ($Na_2SO_4$), filtered, treated with excess 1 M HCl/ether solution, and concentrated in vacuo provided the titled product as a white foam.

FAB mass spectrum m/e 478.2 (M+1).

EXAMPLE 4

Preparation of 20-Chloro-23,24-dihydro-23-oxo-5H-22,25-ethano-6,10:12,16-dimetheno-12H,26H-benzo[b]imidazo[4,3-i][1,17,4,7,10]dioxatriazacyclodocosine-9-carbonitrile (4), Hydrochloride

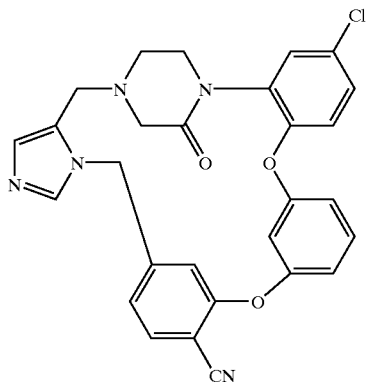

4

Step A: Preparation of 2-[3-(Benzyloxy)phenyl]-5-chloronitrobenzene

To a solution of 3-(benzyloxy)phenol (1.145 g, 5.72 mmol) and 2,5-dichloronitrobenzene (1.154 g, 6.01 mmol) in 15 mL of DMSO was added cesium carbonate (3.72 g, 11.4 mmol). The reaction was heated to 70° C. under argon for one hour, then cooled to room temperature. The solution was poured into EtOAc, washed with water, sat. aq. NaHCO₃ and brine, dried ($Na_2SO_4$), filtered, and concentrated in vacuo. The titled product was obtained as a brown oil.

Step B: Preparation of 2-[3-(Benzyloxy)phenyl]-5-chloroaniline

To a solution of the product from Step A (2.07 g, 5.72 mmol) in 20 mL of ethanol was added stannous(II) chloride (4.32 g, 22.8 mmol). The solution was heated to 50° C. for 45 minutes hour, then cooled to room temperature. The solution was poured into 2 mL of concentrated sulfuric acid, then heated to 90° C. for 30 minutes. After cooling, the solution was concentrated in vacuo, basified with 20% NaOH solution, and extracted with EtOAc. The organic layer was washed with water and brine, dried ($Na_2SO_4$), filtered, and concentrated in vacuo to provide the titled product as a brown oil.

Step C: Preparation of N-[2-(3-(Benzyloxy)phenyl)-5-chlorophenyl]-2-chloroacetamide To a solution of the product from Step B (1.79 g, 5.51 mmol) in 20 mL of EtOAc and 20 mL of saturated NaHCO₃ solution at 0° C. was added chloroacetyl chloride (1.09 mL, 13.8 mmol). After one hour, the solution was poured into EtOAc, washed with water and brine, dried ($Na_2SO_4$), filtered, and concentrated in vacuo. The titled product was obtained as a brown oil.

Step D: Preparation of N-[2-(3-(Benzyloxy)phenyl)-5-chlorophenyl]-2-[(2-hydroxyethyl)amino]acetamide To a solution of the product from Step C (1.07 g, 2.66 mmol) in 5 mL of isopropyl acetate was added ethanolamine (0.643 mL, 10.6 mmol). The reaction was warmed to 55° C. for 2 hours, then cooled to room temperature. The solution was poured into EtOAc, washed with sat. aq. NaHCO₃ and brine, dried ($Na_2SO_4$), filtered, and concentrated in vacuo. The titled product was obtained as a brown foam.

Step E: Preparation of 1-[2-(3-(Benzyloxy)phenyl)-5-chlorophenyl]-2-piperazinone Hydrochloride To a solution of di-tert-butylazodicarboxylate (733 mg, 3.2 mmol) in 5 mL of THF at 0° C. was added tributylphosphine (0.797 mL, 3.2 mmol) dropwise. After 10 minutes, a solution of the product from Step D (895 mg, 2.10 mmol) in 5 mL of THF was added dropwise over 15 minutes, and the reaction was allowed to warm to room temperature. After 16 hours, the solution was concentrated in vacuo. The crude product mixture was purified by silica gel chromatography (50% EtOAc/$CH_2Cl_2$, then 5% MeOH/$CH_2Cl_2$). The resulting product was taken up in ether, excess 1N HCl/Ether was added, and the solution was concentrated in vacuo. The titled product, containing tributylphosphine oxide impurity, was used in the next reaction without further purification.

Step F: Preparation of 1-[2-(3-(Benzyloxy)phenyl)-5-chlorophenyl]-4-[1-(4-cyano-3-fluorobenzyl)-5-imidazolylmethyl]-2-piperazinone Hydrochloride To a solution of the crude amine hydrochloride from Step E (ca. 2.14 mmol) in 4 mL of 1,2-dichloroethane was added 4 Å powdered molecular sieves (800 mg), followed by sodium triacetoxyborohydride (664 mg, 3.15 mmol). The aldehyde from Step G of Example 1 was added (385 mg, 1.68 mmol), and the reaction was stirred for 2 hours. The reaction was poured into EtOAc, washed with sat. aq. NaHCO₃ and brine, dried ($Na_2SO_4$), filtered, and concentrated in vacuo. The crude product was taken up in 2 mL of THF and 15 mL of 3N HCl solution, stirred for two hours, then concentrated in vacuo. The crude material containing the titled product was used in the next reaction without further purification.

Step G: Preparation of 1-[2-(3-Hydroxyphenyl)-5-chlorophenyl]-4-[1-(4-cyano-3-fluorobenzyl)-5-imidazolylmethyl]-2-piperazinone Trifluoroacetate To a solution of the crude product from Step F (ca 1.68 mmol) in 25 mL of 1:1 MeOH/EtOAc was added trifluoroacetic acid (0.10 mL) and 10% palladium on carbon (800 mg). The solution was stirred under a balloon atmosphere of hydrogen at room temperature. After 4 hours, the solution was filtered through celite, the filter pad was rinsed with 1:1 MeOH/THF, and the filtrate was concentrated in vacuo. The crude material containing the titled product was used in the next reaction without further purification.

Step H: Preparation of Compound 4 Hydrochloride

To a solution of the crude product from Step G (ca. 1.68 mmol) in 8 mL of DMSO was added cesium carbonate (1.65 g, 5.1 mmol). The reaction was warmed to 60° C. under argon for fifteen minutes, then warmed to 70° C. for 5 hours, then cooled to room temperature. The solution was poured into EtOAc and washed with water and brine, dried (Na$_2$SO$_4$), filtered, and concentrated in vacuo. The resulting product was purified by silica gel chromatography (5–7% MeOH/CH$_2$Cl$_2$), taken up in CH$_2$Cl$_2$ and treated with excess 1 M HCl/ether solution, and concentrated in vacuo to provide the titled product hydrochloride as a white powder.

FAB mass spectrum m/e 512 (M+1). Analysis calculated for C$_{28}$H$_{22}$ClN$_5$O$_3$.1.00 HCl.1.85 H$_2$O: C, 57.80; H, 4.63; N, 12.04; Found: C, 57.80; H, 4.77; N, 11.25.

EXAMPLE 5

Preparation of (S)-20-Chloro-23,24-dihydro-27-[2-(methylsulfonyl)ethyl]-23-oxo-5H-22,25-ethano-6,10:12,16-dimetheno-12H,26H-benzo[b]imidazo[4,3-i][1,17,4,7,10]dioxatriazacyclodocosine-9-carbonitrile (5), Dihydrochloride

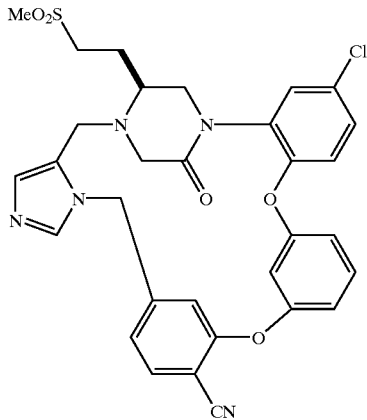

Step A: Preparation of (S)-N-[2-(3-(Benzyloxy)phenyl)-5-chlorophenyl]-2-[(1-hydroxy-4-methylthio-2-butyl)amino]acetamide To a solution of the product from Step C of Example 4 (1.012 g, 2.65 mmol) in 5 mL of isopropyl acetate was added (S)-methioninol (1.211 g, 8.95 mmol). The reaction was warmed to 80° C. for 2.5 hours, then cooled to room temperature. The solution was poured into EtOAc, washed with sat. aq. NaHCO$_3$ and brine, dried (Na$_2$SO$_4$), filtered, and concentrated in vacuo. The titled product was obtained as a brown oil.

Step B: Preparation of (S)-1-[2-(3-(Benzyloxy)phenyl)-5-chlorophenyl]-5-[2-(methylthio)ethyl]-2-piperazinone Hydrochloride To a solution of di-tert-butylazodicarboxylate (733 mg, 3.2 mmol) in 7 mL of THF at 0° C. was added tributylphosphine (0.797 mL, 3.2 mmol) dropwise. After 10 minutes, a solution of the product from Step A (1.062 mg, 2.12 mmol) in 4 mL of THF was added dropwise over 15 minutes, and the reaction was allowed to warm to room temperature. After 30 minutes, the solution was poured into EtOAc, washed with sat. aq. NaHCO$_3$ and brine, dried (Na$_2$SO$_4$), filtered, and concentrated in vacuo. The crude product mixture was purified by silica gel chromatography (5–7% MeOH/CH$_2$Cl$_2$). The resulting product was taken up in ether, excess 1N HCl/Ether was added, the solution was concentrated in vacuo, and the resulting residue was triturated with hexane. The titled product, containing tributylphosphine oxide impurity, was used in the next reaction without further purification.

Step C: Preparation of (S)-1-[2-(3-(Benzyloxy)phenyl)-5-chlorophenyl]-4-[1-(4-cyano-3-fluorobenzyl)-5-imidazolylmethyl]-5-[2-(methylthio)ethyl]-2-piperazinone Hydrochloride To a solution of the crude amine hydrochloride from Step B (ca. 2.12 mmol) in 6 mL of 1,2-dichloroethane was added 4 Å powdered molecular sieves (1.0 g), followed by sodium triacetoxyborohydride (835 mg, 3.95 mmol). The aldehyde from Step G of Example 1 was added (450 mg, 1.97 mmol), and the reaction was stirred for 16 hours. The reaction was poured into EtOAc, washed with sat. aq. NaHCO$_3$ and brine, dried (Na$_2$SO$_4$), filtered, and concentrated in vacuo. The crude product mixture was purified by silica gel chromatography (5–7% MeOH/CH$_2$Cl$_2$). The resulting material (1.28 g) containing the titled product and tributylphosphine oxide impurity was used in the next reaction without further purification.

Step D: Preparation of (S)-1-[2-(3-(Benzyloxy)phenyl)-5-chlorophenyl]-4-[1-(4-cyano-3-fluorobenzyl)-5-imidazolylmethyl]-5- [2-(methanesulfonyl)ethyl]-2-piperazinone Hydrochloride A solution of the crude sulfide from Step C (ca. 1.15 mmol) in 5 mL of methanol was added dropwise to a solution of magnesium monoperoxyphthalate (2.27 g, 4.60 mmol) at 0° C. The solution was warmed to room temperature. After 15 minutes, the reaction was poured into EtOAc, washed with sat. aq. NaHCO$_3$ and brine, dried (Na$_2$SO$_4$), filtered, and concentrated in vacuo. The crude product mixture was purified by silica gel chromatography (2–5% MeOH/CH$_2$Cl$_2$) to provide the titled compound as a white foam.

Step E: Preparation of (S)-1-[2-(3-Hydroxyphenyl)-5-chlorophenyl]-4-[1-(4-cyano-3-fluorobenzyl)-5-imidazolylmethyl]-5-[2-(methanesulfonyl)ethyl]-2-piperazinone Trifluoroacetate To a solution of the product from Step D (383 mg, 0.527 mmol) in 10 mL of 1:1 MeOH/EtOAc was added trifluoroacetic acid (0.10 mL) and 10% palladium on carbon (300 mg). The solution was stirred under a balloon atmosphere of hydrogen at room temperature. After 1.5 hours, the solution was filtered through celite, the filter pad was rinsed with 1:1 MeOH/THF, and the filtrate was concentrated in vacuo. The crude material containing the titled product was used in the next reaction without further purification.

Step F: Preparation of Compound 5 Dihydrochloride

To a solution of the crude product from Step E (ca. 0.527 mmol) in 4 mL of DMSO was added cesium carbonate (513 mg, 1.58 mmol). The reaction was warmed to 55° C. under argon for 2 hours, then cooled to room temperature. The solution was poured into EtOAc and washed with water and brine, dried (Na$_2$SO$_4$), filtered, and concentrated in vacuo. The resulting product was purified by silica gel chromatography (5–7% MeOH/CH$_2$Cl$_2$), taken up in CH$_2$Cl$_2$ and treated with excess 1 M HCl/ether solution, and concentrated in vacuo to provide the titled product hydrochloride as a pale yellow powder. Detailed $^1$H NMR and HPLC studies revealed that the product is composed of an inseparable 4:1 mixture of diastereomers.

FAB mass spectrum m/e 618 (M+1). Analysis calculated for $C_{31}H_{28}ClN_5O_5S \cdot 2.20HCl \cdot 1.00 H_2O$: C, 53.36; H, 4.36; N, 10.04; Found: C, 53.36; H, 4.32; N, 9.87.

EXAMPLE 6

Preparation of (±)-19,20-Dihydro-19-oxo-5H-18,21-ethano-12,14-etheno-6,10-metheno-22H-benzo[d]imidazo[4,3-k][1,6,9,12]oxatriazacyclooctadecine-9-carbonitrile (6), Dihydrochloride

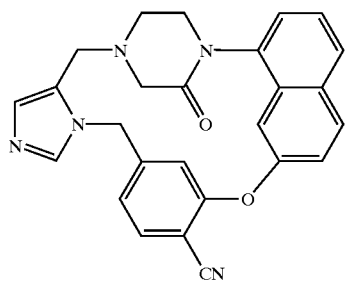

Step A: Preparation of N-(7-Hydroxy-1-naphthyl)-2-[(2-(hydroxy)ethyl)amino]acetamide To a solution of 8-amino-2-naphthol (15.00 g, 94.2 mmol) in 300 mL of isopropyl acetate and 250 mL of saturated NaHCO₃ solution at 0° C. was added chloroacetyl chloride (18.75 mL, 235 mmol). 30 minutes, the layers were separated, and the organic layer was filtered through a glass frit to remove insolubles. Ethanolamine was added (20.9 mL, 377 mmol), and the reaction was warmed to 50° C. for 2 hours, then cooled to room temperature. The solution was poured into EtOAc, washed with water and brine, dried (Na₂SO₄), filtered, and concentrated in vacuo. The titled product was obtained as a dark brown solid which was used in the next reaction without further purification.

Step B: Preparation of N-(7-Hydroxy-1-naphthyl)-2-[(2-hydroxyethyl)tert-butoxycarbonylamino]acetamide To a solution of the product from Step A (7.50 g, 28.8 mmol) in 100 mL of tetrahydrofuran at 0° C. was added di-tert-butyldicarbonate (6.29 g, 28.8 mmol). After 1.5 hours, the solution was concentrated in vacuo to provide the titled product as a dark brown foam which was used in the next reaction without further purification.

Step C: Preparation of 4-tert-Butoxycarbonyl-1-(7-hydroxy-1-naphthyl)-2-piperazinone To a solution of di-tert-butylazodicarboxylate (10.81 g, 43.2 mmol) in 60 mL of tetrahydrofuran at 0° C. was added tributylphosphine (10.76 mL, 43.2 mmol) dropwise. After 10 minutes, a solution of the crude product from Step B (ca. 28.8 mmol) in 30 mL of tetrahydrofuran was added dropwise, and the reaction was allowed to warm to room temperature. After two hours, HPLC analysis showed partial conversion. The solution was cooled to 0° C., and additional portions of tributylphosphine (3.0 mL, 18 mmol) and di-tert-butylazodicarboxylate (4.6 g, 18 mmol) were added. The reaction was warmed to room temperature, and stirred for 16 hours. The solution was concentrated in vacuo, and the resulting product was purified by isilica gel chromatography (0–5% MeOH/CH₂Cl₂) to provide the titled product as a dark brown foam, contaminated with tributylphosphine oxide impurity. This material was used in the next reaction without further purification.

Step D: Preparation of 1-(7-Benzyloxy-1-naphthyl)-4-tert-butoxycarbonyl-2-piperazinone To a solution of the product from Step C (ca. 28.8 mmol) in 150 mL of acetone was added potassium carbonate (20.0 g, 145 mmol), followed by benzyl bromide (3.45 mL, 29 mmol). The reaction was heated to reflux, and stirred for 18 hours. After cooling to room temperature, the solution was concentrated in vacuo to a 50 mL volume, poured into EtOAc, washed with sat. aq. NaHCO₃ and brine, dried (Na₂SO₄), filtered, and concentrated in vacuo. The crude product mixture was purified by silica gel chromatography (40–50% EtOAc/hexane) to provide the titled compound as a pale brown foam.

Step E: Preparation of 1-(7-Benzyloxy-1-naphthyl)-2-piperazinone Hydrochloride

Through a solution of the product from Step D (1.244 g, 2.88 mmol) in 50 mL of ethyl acetate at 0° C. was bubbled anhydrous HCl gas for 5 minutes. After 30 minutes, the solution was concentrated in vacuo to provide the titled salt as a brown powder (1.064 g) which was used in the next reaction without further purification.

Step F: Preparation of 1-(7-Benzyloxy-1-naphthyl)-4-[1-(4-cyano-3-fluorobenzyl)-5-imidazolylmethyl]-2-piperazinone To a solution of the crude amine hydrochloride from Step E (2.88 mmol) in 15 mL of 1,2-dichloroethane was added 4 Å powdered molecular sieves (2.0 g), followed by sodium triacetoxyborohydride (911 mg, 4.32 mmol). The aldehyde from Step G of Example 1 was added (659 mg, 2.88 mmol), and the reaction was stirred for 40 minutes. The reaction was poured into EtOAc, washed with sat. aq. NaHCO₃ and brine, dried (Na₂SO₄), filtered, and concentrated in vacuo. The titled product was obtained as a brown foam which was used in the next reaction without further purification.

Step G: Preparation of 1-(7-Hydroxy-1-naphthyl)-4-[1-(4-cyano-3-fluorobenzyl)-5-imidazolylmethyl]-2-piperazinone Trifluoroacetate To a solution of the benzyl ether from Step F (1.563 g, 2.85 mmol) in 25 mL of 1:1 MeOH/EtOAc was added trifluoroacetic acid (1.0 mL) and 10% palladium on carbon (900 mg). The solution was stirred under a balloon atmosphere of hydrogen at room temperature. After 8 hours, the solution was filtered through celite, and the filter pad was rinsed with 1:1 MeOH/THF. Concentration in vacuo provided the titled product as a white foam which was used in the next reaction without further purification.

Step H: Preparation of Compound 6 Dihydrochloride

To a solution of the product from Step G (ca. 2.85 mmol) in 50 mL of DMSO was added cesium carbonate (2.815 g, 8.64 mmol). The reaction was warmed to 55° C. under argon for 45 minutes, then cooled to room temperature. The solution was poured into EtOAc and washed with water and brine, dried (Na₂SO₄), filtered, and concentrated in vacuo. The resulting product was purified by silica gel chromatography (5–8% MeOH/CH₂Cl₂) to provide the product as a pale yellow foam. A portion of this was taken up in CH₂Cl₂, treated with excess 1 M HCl/ether solution, and concentrated in vacuo to provide the titled product dihydrochloride as a pale yellow powder.

FAB mass spectrum m/e 436.3 (M+1). Analysis calculated for $C_{26}H_{21}N_5O_2 \cdot 2.10 HCl \cdot 1.10 H_2O$: C, 58.77; H, 4.80; N, 13.18; Found: C, 58.82; H, 4.79; N, 12.67.

EXAMPLE 7

(+)-19,20-Dihydro-19-oxo-5H-18,21-ethano-12,14-etheno-6,10-metheno-22H-benzo[d]imidazo[4,3-k][1,6,9,12]oxatriazacyclooctadecine-9-carbonitrile (6), Enantiomer A Dihydrochloride

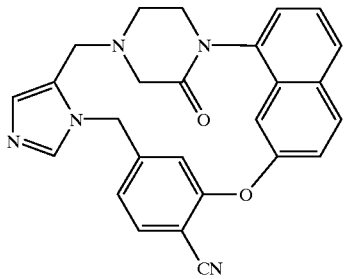

A sample of free base Compound 6 (96 mg in 3 mL of MeOH) was resolved by preparative chiral HPLC (Chiralcel OD 25×2 cm; 80–100% gradient: ethanol/0.1% diethylamine-hexane over 45 min; flow rate 8.0 mL/min; 310 nm). The faster eluting product was taken up in $CH_2Cl_2$, treated with excess 1 M HCl/ether solution, and concentrated in vacuo to provide the titled product dihydrochloride as a pale white powder. Assay for enantiomeric purity (retention time=8.04 min; Chiralcel OD 250×4.6 mm; 80% ethanol/0.1% diethylamine-hexane; flow rate 1.0 mL/min; 310 nm) indicated 96.4% enantiomeric excess.

$[\alpha]_D^{23}$ +236.1 (c 0.10, $CHCl_3$); Analysis calculated for $C_{26}H_{21}N_5O_2$.2.15 HCl.2.45 $H_2O$: C, 55.97; H, 5.07; N, 12.55; Found: C, 56.00; H, 5.11; N, 12.34.

EXAMPLE 8

(−)-19,20-Dihydro-19-oxo-5H-18,21-ethano-12,14-etheno-6,10-metheno-22H-benzo[d]imidazo[4,3-k][1,6,9,12]oxatriazacyclooctadecine-9-carbonitrile (6), Enantiomer B Dihydrochloride

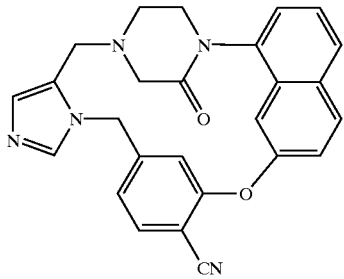

The titled product was produced under the same conditions described in Example 7. Assay of the slower-eluting product for enantiomeric purity (retention time=13.96 min; Chiralcel OD 250×4.6 mm; 80% ethanol/0.1% diethylamine-hexane; flow rate 1.0 mL/min; 310 nm) indicated >99% enantiomeric excess.

$[\alpha]_D^{23}$ −244.8 (c 0.10, $CHCl_3$); Analysis calculated for $C_{26}H_{21}N_5O_2$.2.00 HCl.2.30 $H_2O$: C, 56.79; H, 5.06; N, 12.74; Found: C, 56.80; H, 5.38; N, 12.58.

EXAMPLE 9

Preparation of 19,20-Dihydro-5H,17H-18,21-ethano-6,10:12,16-dimetheno-22H-imidazo[3,4-h][1,8,11,14]oxatriazacycloeicosin-20-one (7), Dihydrochloride

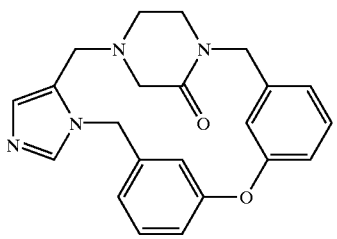

Step A: Preparation of 1-(3-Iodobenzyl)-5-(acetoxymethyl)-imidazole Hydrobromide A solution of the product from Step B of Example 1 (4.85 g, 13.1 mmol) and 3-iodobenzyl bromide (3.89 g, 13.1 mmol) in 50 mL of EtOAc was stirred at 60° C. for 16 hours, during which a white precipitate formed. The reaction was cooled to room temperature and filtered to provide the solid imidazolium bromide salt. The filtrate was concentrated in vacuo to a volume of 15 mL, reheated at 60° C. for two hours, cooled to room temperature, and filtered again. The filtrate was concentrated in vacuo to a volume 10 mL, reheated at 60° C. for another two hours, cooled to room temperature, and concentrated in vacuo to provide a pale yellow solid. All of the solid material was combined, dissolved in 50 mL of methanol, and warmed to 60° C. After 30 minutes, the solution was reconcentrated in vacuo to provide a white solid which was triturated with hexane to remove soluble materials. Removal of residual solvents in vacuo provided the titled product hydrobromide as a white powder which was used in the next step without further purification.

Step B: Preparation of 1-(3-Iodobenzyl)-5-(hydroxymethyl) imidazole

To a solution of the product from Step A (4.54 g, 10.4 mmol) in 100 mL of 3:1 THF/water at 0° C. was added lithium hydroxide 5 monohydrate (1.31 g, 41.9 mmol). After two hours, the reaction was concentrated in vacuo,then poured into aqueous $NaHCO_3$ and extracted three times with $CH_2Cl_2$. The extracts were dried ($Na_2SO_4$), filtered, and concentrated in vacuo to provide the crude product which was sufficiently pure for use in the next step without further purification.

Step C: Preparation of 1-(3-Iodobenzyl)-5-imidazolecarboxaldehyde

To a solution of the alcohol from Step B (ca. 10.4 mmol) in 100 mL of DMSO at room temperature was added triethylamine (14.5 mL, 104 mmol), then $SO_3$-pyridine complex (8.27 g, 52 mmol). After 40 minutes, the reaction was poured into EtOAc, washed with water and brine, dried ($Na_2SO_4$), filtered, and concentrated in vacuo to provide the aldehyde as an oily solid contaminated with triethylamine.

Step D: Preparation of 4-[1-(4-Cyano-3-fluorobenzyl)-5-imidazolylmethyl]-1-[3-hydroxybenzyl]-2-piperazinone To a solution of the amine hydrochloride from Step K of Example 1 (1.87 mmol) in 5 mL of 1,2-dichloroethane was added 4 Å powdered molecular sieves (500 mg), followed by sodium triacetoxyborohydride (592 mg, 2.80 mmol). The aldehyde from Step C (583 mg, 1.9 mmol) was added, and the reaction was stirred for 16 hours. The reaction was poured into EtOAc, washed with sat. aq. $NaHCO_3$ and brine, dried (Na$_2$SO$_4$), filtered, and concentrated in vacuo. The resulting material was purified by silica gel chromatography (5–6% MeOH/CH$_2$Cl$_2$) to provide the titled product as a white foam.

Step E: Preparation of Compound 7 Dihydrochloride

A suspension of NaH on mineral oil was triturated with hexane. Pyridine (5 mL) was added, followed by the product from Step D (251 mg, 0.500 mmol). After stirring for 15 minutes at room temperature, copper(I)bromide dimethylsulfide complex was added (205 mg, 1.00 mmol), and the reaction was heated to reflux. After 2 hours, the solution was poured into EtOAc and washed with water and brine, dried (Na$_2$SO$_4$), filtered, and concentrated in vacuo. The resulting product was purified by silica gel chromatography (1.5–6% MeOH/CH$_2$Cl$_2$) to provide the desired product, which was taken up in CH$_2$Cl$_2$ and treated with excess 1 M HCl/ether solution, and concentrated in vacuo to provide the titled product dihydrochloride as a white powder.

ES mass spectrum m/e 375.18 (M+1). Analysis calculated for C$_{22}$H$_{22}$N$_4$O$_2$.2.50 HCl.0.60 H$_2$O: C, 55.60; H, 5.45; N, 11.79; Found: C, 55.56; H, 5.40; N, 11.30.

EXAMPLE 10

Preparation of (±)-19,20-Dihydro-3-methyl-19-oxo-5H-18,21-ethano-12,14-etheno-6,10-metheno-22H-benzo[d]imidazo[4,3-k][1,6,9,12] oxatriazacyclooctadecine-9-carbonitrile (8), Dihydrochloride

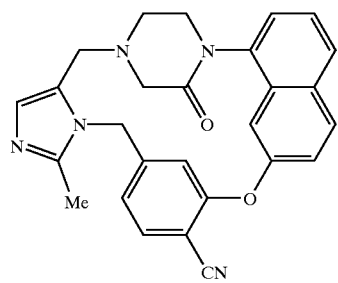

Step A: Preparation of 1-(4-Cyano-3-fluorobenzyl)-2-methyl-5-imidazolecarboxaldehyde To a solution of the bromide from Step D of Example 1 (1.26 g, 5.9 mmol) in 10 mL of DMF at 0° C. was added 4-formyl-2-methylimidazole (0.650 g, 5.9 mmol) and cesium carbonate (2.9 g, 8.9 mmol). After 2 hours, the reaction was poured into 2:1 EtOAc:hexane, washed with water and brine, dried (Na$_2$SO$_4$), filtered, and concentrated in vacuo to provide the crude product mixture. The material was purified by silica gel chromatography (2–5% MeOH/CHCl$_3$) to provide the titled product along with the regioisomer 1-(4-cyano-3-fluorobenzyl)-2-methyl-4-imidazolecarboxaldehyde and a mixed fraction.

Step B: Preparation of 1-(7-Benzyloxy-1-naphthyl)-4-[1-(4-cyano-3-fluorobenzyl)-2-methyl-5-imidazolylmethyl]-2-piperazinone To a solution of the amine hydrochloride from Step E of example 6 (464 mg, 1.26 mmol) in 8 mL of 1,2-dichloroethane was added 4 Å powdered molecular sieves (1.0 g), followed by sodium triacetoxyborohydride (401 mg, 1.89 mmol). The aldehyde from Step A was added (306 mg, 1.26 mmol), and the reaction was stirred for 16 hours. The reaction was poured into EtOAc, washed with sat. aq. NaHCO$_3$ and brine, dried (Na$_2$SO$_4$), and concentrated in vacuo. The crude material was purified by silica gel chromatography (2%MeOH/CHCl$_3$-5%MeOH/0.5%NH$_4$OH/CHCl$_3$) to provide the titled product.

Step C: Preparation of 1-(7-Hydroxy-1-naphthyl)-4-[1-(4-cyano-3-fluorobenzyl)-2-methyl-5-imidazolylmethyl]-2-piperazinone To a solution of the benzyl ether from Step B (419 mg, 0.75 mmol) in 6 mL of 1:1 MeOH/EtOAc was added 10% palladium on carbon (250 mg). The solution was stirred under a balloon atmosphere of hydrogen at room temperature. After 4 hours, another portion of Pd/C was added (250 mg). After 16 hours, the solution was filtered through celite. Concentration in vacuo provided the titled product which was used in the next reaction without further purification.

Step D: Preparation of Compound 8 Dihydrochloride

To a solution of the product from Step C (304 mg, 0.67 mmol) in 13 mL of DMSO was added cesium carbonate (422 mg, 1.29 mmol). The reaction was warmed to 55° C. under argon for one hour, then cooled to room temperature. The solution was poured into EtOAc and washed with water and brine, dried (Na$_2$SO$_4$), filtered, and concentrated in vacuo. The crude material was crystallized from EtOH/Et$_2$O to yield 187 mg of pure material along with 29 mg of impure material. A portion of the pure material (10 mg) was taken up in CH$_2$Cl$_2$, treated with excess 1 M HCl/ether solution, and concentrated in vacuo to provide the titled product dihydrochloride as a white powder.

FAB mass spectrum m/e 450.3 (M+1). Analysis calculated for C$_{27}$H$_{23}$N$_5$O$_2$.2.00 HCl.1.50 H$_2$O: C, 59.02; H, 5.14; N, 12.75; Found: C, 59.05; H, 5.26; N, 12.51.

EXAMPLE 11

(+) or (−)-19,20-Dihydro-3-methyl-19-oxo-5H-18,21-ethano-12,14-etheno-6,10-metheno-22H-benzo[d]imidazo[4,3-k][1,6,9,12] oxatriazacyclooctadecine-9-carbonitrile (8), Enantiomer A Dihydrochloride

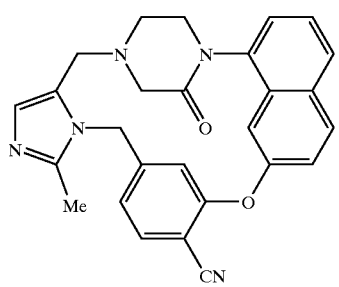

A sample of the racemic mixture of Compound 8 free base from Example 10, Step D (206 mg in MeOH) was resolved by preparative chiral HPLC (Chiralcel OD 25×2 cm; 80–100% gradient: ethanol/0.1% diethylamine-hexane over 45 min; flow rate 8.0 mL/min; 310 nm). The faster eluting product was taken up in CH$_2$Cl$_2$, treated with excess 1 M HCl/ether solution, and concentrated in vacuo to provide the titled product dihydrochloride as a pale white powder. Assay for enantiomeric purity (retention time=6.72 min; Chiralcel OD 250×4.6 mm; 80% ethanol/0.1% diethylamine-hexane; flow rate 1.0 mL/min; 310 nm) indicated >99% enantiomeric excess.

Analysis calculated for C$_{27}$H$_{23}$N$_5$O$_2$.2.00 HCl.1.75 H$_2$O: C, 58.54; H, 5.19; N, 12.64; Found: C, 58.51; H, 5.43; N, 12.67.

EXAMPLE 12

(−) or (+)-19,20-Dihydro-3-methyl-19-oxo-5H-18, 21-ethano-12,14-etheno-6,10-metheno-22H-benzo [d]imidazo[4,3-k][1,6,9,12] oxatriazacyclooctadecine-9-carbonitrile (8), Enantiomer B Dihydrochloride

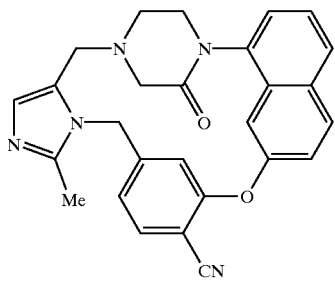

8

The titled product was produced under the same conditions described in Example 11. Assay of the slower-eluting product for enantiomeric purity (retention time=15.67 min; Chiralcel OD 250×4.6 mm; 80% ethanol/0.1% diethylamine-hexane; flow rate 1.0 mL/min; 310 nm) indicated >99% enantiomeric excess.

Analysis calculated for $C_{27}H_{23}N_5O_2 \cdot 2.00$ HCl$\cdot 1.45$ $H_2O$: C, 59.11; H, 5.13; N, 12.77; Found: C, 59.10; H, 5.34; N, 12.71.

EXAMPLE 13

Preparation of Compound 9 Dihydrochloride

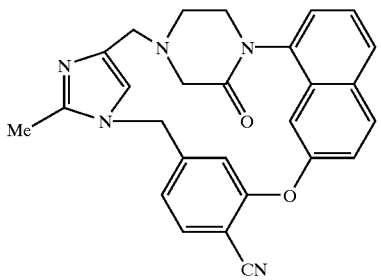

9

Step A: Preparation of 1-(4-Cyano-3-fluorobenzyl)-2-methyl-4-imidazolecarboxaldehyde The titled product was isolated from the reaction in Step A of Example 10.

Step B: Preparation of 1-(7-Benzyloxy-1-naphthyl)-4-[1-(4-cyano-3-fluorobenzyl)-2-methyl-4-imidazolylmethyl]-2-piperazinone To a solution of the amine hydrochloride from Step E of example 6 (200 mg, 0.54 mmol) in 5 mL of 1,2-dichloroethane was added 4Å powdered molecular sieves (0.5 g), followed by sodium triacetoxyborohydride (163 mg, 0.77 mmol). The aldehyde from Step A was added (125 mg, 0.51 mmol), and the reaction was stirred for 16 hours. The reaction was poured into EtOAc, washed with sat. aq. $NaHCO_3$ and brine, dried ($Na_2SO_4$), filtered, and concentrated in vacuo to provide the titled product.

Step C: Preparation of 1-(7-Hydroxy-1-naphthyl)-4-[1-(4-cyano-3-fluorobenzyl)-2-methyl-4-imidazolylmethyl]-2-piperazinone To a solution of the benzyl ether from Step B (240 mg, 0.43 mmol) in 4 mL of 1:1 MeOH/EtOAc was added 10% palladium on carbon (240 mg). The solution was stirred under a balloon atmosphere of hydrogen at room temperature. After 16 hours, the solution was filtered through celite. Concentration in vacuo provided the titled which was used in the next reaction without further purification.

Step D: Preparation of Compound 9 Dihydrochloride

To a solution of the product from Step C (172 mg, 0.37 mmol) in 10 mL of DMSO was added cesium carbonate (241 mg, 0.74 mmol). The reaction was warmed to 55° C. under argon for one hour, then at 85° C. for two hours, then cooled to room temperature. The solution was poured into EtOAc and washed with water and brine, dried ($Na_2SO_4$), filtered, and concentrated in vacuo. The crude material was purified on 2×1 mm preparative silica gel TLC plates, eluting with 90:10:1 $CHCl_3$:MeOH:$NH_4OH$. The product was taken up in $CH_2Cl_2$, treated with excess 1 M HCl/ether solution, and concentrated in vacuo to provide the titled product dihydrochloride as a white powder.

FAB mass spectrum m/e 450 (M+1).

EXAMPLE 14

Preparation of (±)-19,20-Dihydro-19,22-dioxo-5H-18,21-ethano-12,14-etheno-6,10-metheno-22H-benzo[d]imidazo[4,3-k][1,6,9,12] oxatriazacyclooctadecine-9-carbonitrile (10), Hydrochloride

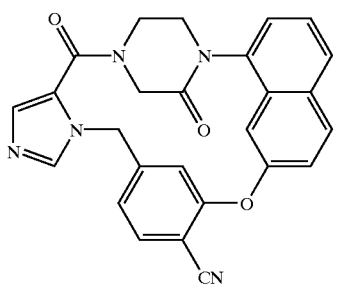

10

Step A: Preparation of 1-(4-Cyano-3-fluorobenzyl)-5-imidazolecarboxylic Acid Sodium Salt To a solution of the aldehyde from Step G of Example 1 (0.500 g, 2.18 mmol) in 15 mL of tert-butanol and 4 mL of 2-methyl-2-butene was added a solution of $NaH_2PO_4 \cdot H_2O$ (301 mg, 2.18 mmol) and $NaClO_4$ (236 mg, 2.62 mmol) in 5 mL of water. After 18 hours, another portion of $NaH_2PO_4 \cdot H_2O/NaClO_4$ (ca. 0.2 equiv) was added, and the reaction was stirred another 2 hours. The mixture was filtered, and the solids were rinsed with EtOAc to provide the titled product as a brown solid.

Step B: Preparation of 1-(7-Benzyloxy-1-naphthyl)-4-[1-(4-cyano-3-fluorobenzyl)-5-imidazolylcarbonyl]-2-piperazinone To a solution of the amine hydrochloride from Step E of Example 6 (297 mg, 0.81 mmol) in 5 mL of DMF at room temperature was added the carboxylic acid sodium salt from Step A (215 mg, 0.81 mmol), HOBt·$H_2O$ (131 mg, 0.97 mmol), and EDC·HCl (186 mg, 0.97 mmol). The reaction was stirred at room temperature for 4.5 hours, then poured into EtOAc, washed with sat. aq. $NaHCO_3$ and brine, dried ($Na_2SO_4$), filtered, and concentrated in vacuo. The resulting titled product was used without further purification.

Step C: Preparation of 1-(7-Hydroxy-1-naphthyl)-4-[1-(4-cyano-3-fluorobenzyl)-5-imidazolylcarbonyl]-2-piperazinone To a solution of the benzyl ether from Step B (430 mg, 0.77 mmol) in 10 mL of 1:1 MeOH/EtOAc was added 10% palladium on carbon (430 mg). The solution was stirred under a balloon atmosphere of hydrogen at room temperature overnight. Another portion of Pd/C was added (400 mg). After another 18 hours, the solution was filtered through celite. Concentration in vacuo provided the titled product which was used in the next reaction without further purification.

Step D: Preparation of Compound 10 Hydrochloride

To a solution of the product from Step C (230 mg, 0.49 mmol) in 10 mL of DMSO was added cesium carbonate (319 mg, 0.98 mmol). The reaction was warmed to 55° C. under argon for one hour, then at 80° C. for one hour, then cooled to room temperature. The solution was poured into EtOAc and washed with water and brine, dried ($Na_2SO_4$), filtered, and concentrated in vacuo. The crude material was purified on 2×1 mm preparative silica gel TLC plates, eluting with 90:10:1 $CHCl_3$:MeOH:$NH_4OH$. The product was taken up in $CH_2Cl_2$, treated with excess 1 M HCl/ether solution, and concentrated in vacuo to provide the titled product hydrochloride as a white powder.

FAB mass spectrum m/e 450 (M+1). Analysis calculated for $C_{26}H_{19}N_5O_3$.1.00 HCl.2.05 $H_2O$: C, 59.72; H, 4.65; N, 13.40; Found: C, 59.71; H, 4.91; N, 12.88.

EXAMPLE 15

(+)- or (−)-19,20-Dihydro-19,22-dioxo-5H-18,21-ethano-12,14-etheno-6,10-metheno-22H-benzo[d]imidazo[4,3-k][1,6,9,12]oxatriazacyclooctadecine-9-carbonitrile (10), Hydrochloride

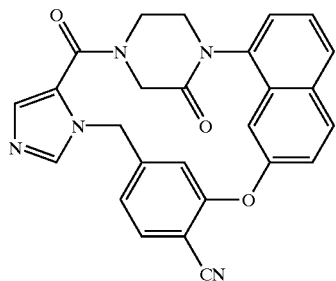

10

A sample of the racemic mixture of Compound 10 free base from Example 14, Step D (55 mg in MeOH) was resolved by preparative chiral HPLC (Chiralpak AD 25×2 cm; 80–100% gradient:

2-propanol/0.1% diethylamine-hexane over 45 min; flow rate 7.0 mL/min; 285 nm). The faster eluting product was taken up in $CH_2Cl_2$, treated with excess 1 M HCl/ether solution, and concentrated in vacuo to provide the titled product dihydrochloride as a pale white powder. Assay for enantiomeric purity (retention time=8.63 min; Chiralpak AD 250×4.6 mm; 80% ethanol/0.1% diethylamine-hexane; flow rate 1.0 mL/min; 260 nm) indicated ca. 96% enantiomeric excess.

FAB mass spectrum m/e 450 (M+1). Analysis calculated for $C_{26}H_{19}N_5O_3$.1.00 HCl.0.55 $H_2O$.0.30 $CHCl_3$: C, 59.41; H, 4.06; N, 13.17; Found: C, 59.39; H, 4.08; N, 13.09.

EXAMPLE 16

(−)- or (+)-19,20-Dihydro-19,22-dioxo-5H-18,21-ethano-12,14-etheno-6,10-metheno-22H-benzo[d]imidazo[4,3-k][1,6,9,12]oxatriazacyclooctadecine-9-carbonitrile (10), Hydrochloride

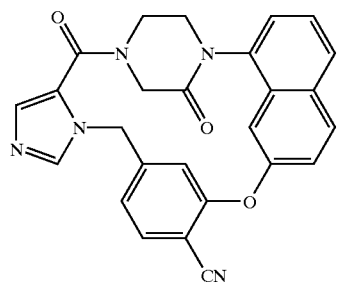

10

The titled product was produced from the product of Example 10 under the same conditions described in Example 15. Assay of the slower-eluting product for enantiomeric purity (retention time=9.42 min; Chiralpak AD 250×4.6 mm; 80% ethanol/0.1% diethylamine-hexane; flow rate 1.0 mL/min; 260 nm) indicated 94% enantiomeric excess.

FAB mass spectrum m/e 450 (M+1). Analysis calculated for $C_{26}H_{19}N_5O_3$.1.00 HCl.2.25 $H_2O$.0.05 $CHCl_3$: C, 58.76; H, 4.65; N, 13.15; Found: C, 59.74; H, 4.65; N, 12.96.

EXAMPLE 17

Preparation of (+)-1-Bromo-19,20-dihydro-19-oxo-5H-18,21-ethano-12,14-etheno-6,10-metheno-22H-benzo[d]imidazo[4,3-k][1,6,9,12]oxatriazacyclooctadecine-9-carbonitrile (11), Dihydrochloride

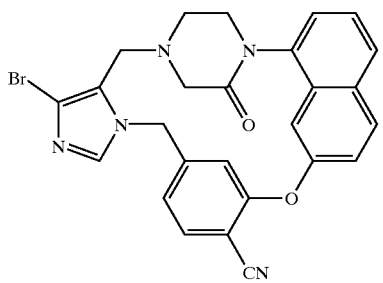

11

To a solution of the product of Example 6 (75 mg, 0.17 mmol) and sodium acetate (92 mg, 0.68 mmol) in 2 mL of acetic acid was added 0.17 mL of 1M bromine in acetic acid solution. After 1.5 hours, the reaction was diluted with EtOAc and basified with aq. $NaHCO_3$ solution. The organic layer was washed with aq. $NaHCO_3$ solution and brine, dried ($Na_2SO_4$), filtered, and concentrated in vacuo. The crude material was purified on 2×0.5 mm preparative silica gel TLC plates, eluting with 90:10:1 $CHCl_3$:MeOH:$NH_4OH$. The product was taken up in $CH_2Cl_2$, treated with excess 1 M HCl/ether solution, and concentrated in vacuo to provide the titled product dihydrochloride as a white powder.

FAB mass spectrum m/e 514 (M+1).

EXAMPLE 18

Preparation of (−)- or (+)-1-Bromo-19,20-dihydro-3-methyl-19-oxo-5H-18,21-ethano-12,14-etheno-6,10-metheno-22H-benzo[d]imidazo[4,3-k][1,6,9,12]oxatriazacyclooctadecine-9-carbonitrile (12), Dihydrochloride

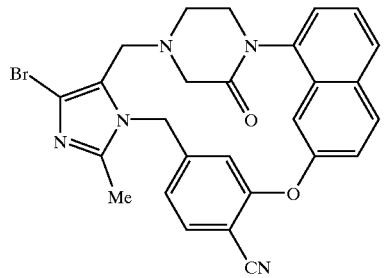

The titled compound was prepared from the product of Example 12 (100 mg, 0.22 mmol) using the same procedure as that described for the preparation and purification of Example 17. The product was isolated as a white powder.

ES mass spectrum m/e 528.12 (M+1).

EXAMPLE 19

Preparation of 19,20-Dihydro-5H-18,21-ethano-12,14-etheno-6,10-metheno-22H-benzo[d]imidazo[4,3-k][1,6,9,12]oxatriazacyclooctadecine-9-carbonitrile (13), Trihydrochloride

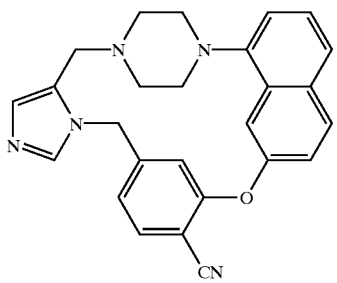

To a solution of the product of Example 6 (50 mg, 0.12 mmol) in 3 mL of tetrahydrofuran at reflux was added borontrifluoride etherate (0.030 mL, 0.24 mmol) under argon. Borane dimethylsulfide complex was added (0.130 mL, 0.13 mmol) and the solution was stirred at reflux for 3 hours. Additional portions of borontrifluoride etherate (0.030 mL, 0.24 mmol) and borane dimethylsulfide complex (0.130 mL, 0.13 mmol) were added. After one hour, the reaction was cooled to room temperature, quenched with 3N HCl solution, and basified with solid $Na_2SO_3$. The mixture was partitioned between EtOAc and water, and the organic phase was washed with brine, dried ($Na_2SO_4$), filtered, and concentrated in vacuo. The crude material was purified on three 0.5 mm preparative silica gel TLC plates, eluting with 90:10:1 $CHCl_3$:MeOH:$NH_4OH$. The product was taken up in $CH_2Cl_2$, treated with excess 1 M HCl/ether solution, and concentrated in vacuo to provide the titled product dihydrochloride as a white powder.

FAB mass spectrum m/e 422 (M+1).

EXAMPLE 20

Preparation of (±)-19,20-Dihydro-5-methyl-19-oxo-5H-18,21-ethano-12,14-etheno-6,10-metheno-22H-benzo[d]imidazo[4,3-k][1,6,9,12]oxatriazacyclooctadecine-9-carbonitrile (14), Diastereomer A Dihydrochloride

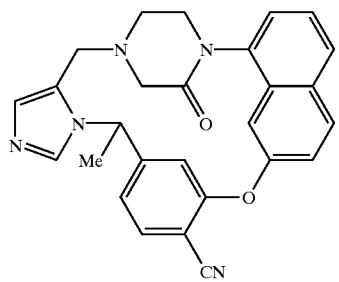

To a solution of the product of Example 6 (48.6 mg, 0.111 mmol) in 1 mL of 1:1 THF/DMSO at 0° C. was added n-butyllithium (0.223 mL, 0.558 mmol, 2.5 M in hexane). After 5 minutes, iodomethane was added (0.069 mL, 1.11 mmol), and the reaction was stirred at 0° C. for 30 minutes. The solution was diluted with EtOAc, washed with brine, dried ($Na_2SO_4$), filtered, and concentrated in vacuo. The resulting product was purified by silica gel chromatography (5–8% MeOH/$CH_2Cl_2$) to provide the faster eluting product, which was taken up in $CH_2C_{12}$ and treated with excess 1 M HCl/ether solution, and concentrated in vacuo to provide the titled product dihydrochloride (3.1 mg) as a white powder. $^1$H NMR analysis indicated the presence of 20% of the Example 21 diastereomer.

HRMS (ES) calculated for M+H$^+$: 450.1924. Found 450.1927.

EXAMPLE 21

(±)-19,20-Dihydro-5-methyl-19-oxo-5H-18,21-ethano-12,14-etheno-6,10-metheno-22H-benzo[d]imidazo[4,3-k][1,6,9,12]oxatriazacyclooctadecine-9-carbonitrile (14), Diastereomer B Dihydrochloride

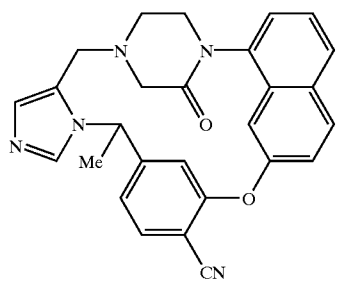

The titled compound (3.0 mg) was isolated from the reaction described for the preparation of Example 20 as a slower eluting product of column chromatography. $^1$H NMR analysis indicated the presence of 20% of the Example 20 diastereomer.

HRMS (ES) calculated for M+H$^+$: 450.1924. Found 450.1924.

EXAMPLE 22

Preparation of (±)-18,19-Dihydro-18-oxo-5H-6, 9:11,13-dietheno-17,20-ethano-9H,21H-benzo[d] imidazo[4,3-k][1,6,9,12]oxatriazacycloheptadecine-8-carbonitrile (16), Atropisomer A Dihydrochloride

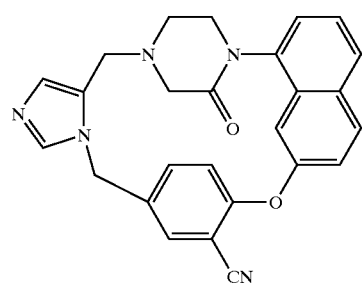

Step A: Preparation of 1-(3-Cyano-4-fluorobenzyl)-5-imidazolecarboxaldehyde

The titled product was prepared from 3-cyano-4-fluorotoluene using the same procedures as those described in Example 1, Steps D through G for the preparation of 1-(4-cyano-3-fluorobenzyl)-5-imidazolecarboxaldehyde, except that 3-cyano-4-fluorotoluene was used in place of 4-cyano-3-fluorotoluene in Step D.

Step B: Preparation of 1-(7-Benzyloxy-1-naphthyl)-4-[1-(3-cyano-4-fluorobenzyl)-5-imidazolylmethyl]-2-piperazinone The titled compound was prepared from the product of Step A (322 mg, 1.4 mmol) and the product of Example 6 Step E using the same procedure as that described in Step F for Example 6. The product (580 mg, 76%) was used without further purification.

Step C: Preparation of 1-(7-Hydroxy-1-naphthyl)-4-[1-(3-cyano-4-fluorobenzyl)-5-imidazolylmethyl]-2-piperazinone Trifluoroacetate To a solution of the benzyl ether from Step B (251 mg, 0.460 mmol) in 10 mL of MeOH was added 20% palladium hydroxide on carbon (200 mg). The solution was stirred under a balloon atmosphere of hydrogen at room temperature. After 45 minutes, the solution was filtered through celite, and the filter pad was rinsed with MeOH. Concentration in vacuo provided the titled product as a white foam (193 mg) which was used in the next reaction without further purification.

Step D: Preparation of Compound 16 Dihydrochloride

To a solution of the product from Step C (183 mg, 0.40 mmol) in 10 mL of DMSO was added cesium carbonate (261 mg, 0.80 mmol). The reaction was warmed to 55° C. under argon for 1.5 hours, then cooled to room temperature. The solution was poured into EtOAc and washed with water and brine, dried ($Na_2SO_4$), filtered, and concentrated in vacuo. The crude material was purified on seven 0.5 mm preparative silica gel TLC plates, eluting with 90:10:1 $CHCl_3$:MeOH:$NH_4OH$. The faster eluting product was taken up in $CHCl_3$, treated with excess 1 M HCl/ether solution, and concentrated in vacuo to provide the titled product dihydrochloride as a white powder.

FAB mass spectrum m/e 436.2 (M+1). Analysis calculated for $C_{26}H_{21}N_5O_2 \cdot 2.0$ HCl$\cdot 1.20$ $H_2O \cdot 0.05$ $CHCl_3$: C, 58.37; H, 4.79; N, 13.07; Found: C, 58.38; H, 4.79; N, 12.67.

EXAMPLE 23

(±)-18,19-Dihydro-18-oxo-5H-6,9:11,13-dietheno-17,20-ethano-9H,21H-benzo[d]imidazo[4,3-k][1,6,9,12]oxatriaza-cycloheptadecine-8-carbonitrile (16), Atropisomer B Dihydrochloride

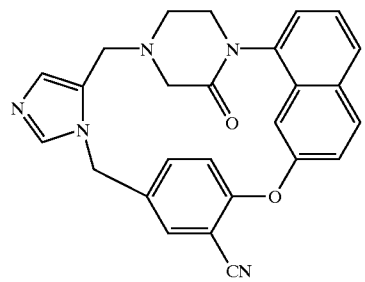

The compound was isolated from the reaction described in Step D of Example 22 as a slower eluting product of column chromatography. The product was taken up in $CHCl_3$, treated with excess 1 M HCl/ether solution, and concentrated in vacuo to provide the titled product dihydrochloride as a white powder.

FAB mass spectrum m/e 436.2 (M+1). Analysis calculated for $C_{26}H_{21}N_5O_2 \cdot 2.0$ HCl$\cdot 1.00$ $H_2O$: C, 59.32; H, 4.79; N, 13.30; Found: C, 59.28; H, 4.76; N, 13.49.

EXAMPLE 24

Preparation of 18-Chloro-21,22-dihydro-21-oxo-5H-20,23-ethano-6,9-etheno-9H,24H-dibenzo[b, eimidazo[4,3-l][1,4,7,10,13] dioxatriazaclooctadecine-8-carbonitrile (18), Dihydrochloride

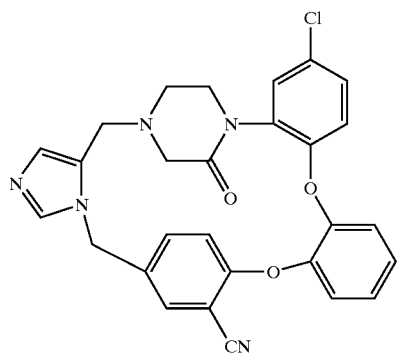

Step A: Preparation of 1-[2-(2-(Benzyloxy)phenyl)-5-chlorophenyl]-4-[1-(3-cyano-4-fluorobenzyl)-5-imidazolylmethyl]-2-piperazinone The titled compound was prepared from the product of Example 22 Step A (280 mg, 1.22 mmol) and the product of Example 2 Step E using the same procedure as that described in Example 2 Step F. The product was used without further purification.

Step B: Preparation of 1-[2-(2-Hydroxyphenyl)-5-chlorophenyl]-4-[1-(3-cyano-4-fluorobenzyl)-5-imidazolylmethyl]-2-piperazinone The titled compound was prepared from the product of Step A (651 mg, 1.05 mmol) using the same procedure as that described in Example 22 Step C. The crude product (480 mg) was used in the next reaction without further purification.

Step C: Preparation of Compound 18 Dihydrochloride

To a solution of the product from Step B (480 mg, 0.90 mmol) in 20 mL of DMSO was added cesium carbonate (588 mg, 1.8 mmol). The reaction was warmed to 55° C. under argon for one hour, then stirred at 80° C. for 2 hours, then cooled to room temperature. The solution was poured into EtOAc and washed with water and brine, dried (Na$_2$SO$_4$), filtered, and concentrated in vacuo. The crude material was purified on 0.5 mm preparative silica gel TLC plates, eluting with 90:10:1 CHCl$_3$:MeOH:NH$_4$OH. The product was taken up in CHCl$_3$, treated with excess 1 M HCl/ether solution, and concentrated in vacuo to provide the titled product dihydrochloride as a white powder.

FAB mass spectrum m/e 512.2 (M+1). Analysis calculated for C$_{28}$H$_{22}$ClN$_5$O$_3$.2.0 HCl.1.25 H$_2$O: C, 55.36; H, 4.40; N, 11.53; Found: C, 55.36; H, 4.75; N, 10.67.

EXAMPLE 25

Preparation of 8-Chloro-19,20-dihydro-19-oxo-5H-18,21-ethano-12,14-etheno-6,10-metheno-22H-benzo[d]imidazo[4,3-k][1,6,9,12]oxatriazacyclooctadecine-9-carbonitrile (19), Dihydrochloride

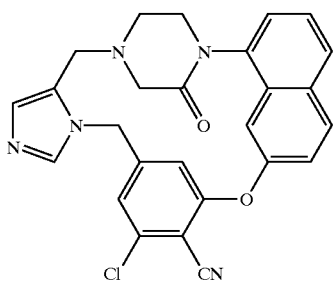

19

Step A: Preparation of 2,6-Dichloro-4-methylphenyl Trifluoromethanesulfonate

To a solution of 2,6-dichloro-p-cresol (25.20 g, 142 mmol) in 250 mL of dichloromethane at 0° C. was added pyridine (17.3 mL, 213 mmol), followed by dropwise addition of trifluoromethanesulfonic anhydride (23.9 mL, 142 mmol). The solution was allowed to warm to room temperature overnight, and was then concentrated to a 100 mL volume in vacuo. The solution was poured into 0.5 L of EtOAc, washed with saturated NH$_4$Cl solution, saturated NaHCO$_3$ solution and brine, dried (Na$_2$SO$_4$), filtered, and concentrated in vacuo to provide the titled product which was used in the next step without further purification.

Step B: Preparation of 2,6-Dichloro-p-tolunitrile

To a degassed solution of the triflate from Step A (40.92 g, 132.8 mmol) in 250 mL of DMF was added Zn(CN)$_2$ (15.6 g, 132.8 mmol) and Pd(PPh$_3$)$_4$ (7.67 g, 6.64 mmol). The reaction was stirred at 80° C. for three days. Another portion of Zn(CN)$_2$ (10 g) and Pd(PPh$_3$)$_4$ (5 g) was added the reaction was stirred at 80° C. for 24 hours, then cooled to room temperature. The solution was poured into EtOAc, washed with water, sat. aq. NaHCO$_3$, and brine, then dried (Na$_2$SO$_4$), filtered, and concentrated in vacuo to provide the crude product. Purification by crystallization (10% EtOAc/hexane) provided the titled product as white needles.

Step C: Preparation of 4-Cyano-3,5-dichlorobenzyl Bromide

To a solution of the product from Step B (1.16 g, 6.28 mmol) in 30 mL of carbontetrachloride was added N-bromosuccinimide (0.877 g, 6.91 mmol) and AIBN (103 mg, 0.63 mmol). The reaction was heated to reflux overnight. Additional portions of N-bromosuccinimide (430 mg) and AIBN (100 mg) were added, the reaction was refluxed for 4 hours, then cooled to room temperature. The solution was concentrated in vacuo, then triturated with 10% EtOAc/hexane and filtered. The filtrate was concentrated in vacuo, and purified by silica gel chromatography (8–10% EtOAc/hexane) to provide the titled product as a white solid.

Step D: Preparation of 1-(4-Cyano-3,5-dichlorobenzyl)-5-imidazolecarboxaldehyde

The titled product was prepared from the product of Step C using the same procedures as those described in Example 1, Steps D through G for the preparation of 1-(4-cyano-3-fluorobenzyl)-5-imidazolecarboxaldehyde.

Step E: Preparation of 1-(7-Hydroxy-1-naphthyl)-4-[1-(4-cyano-3,5-dichlorobenzyl)-5-imidazolylmethyl]-2-piperazinone The titled compound was prepared from the product of Step D and the product of Example 6 Step C using the same procedures as those described in Steps E and F for Example 6.

Step F: Preparation of Compound 19 Dihydrochloride

To a solution of the product from Step E (109 mg, 0.216 mmol) in 4 mL of DMSO was added cesium carbonate (210 mg, 0.647 mmol). The reaction was warmed to 60° C. under argon for 15 minutes, then to 80° C. for 15 minutes, then cooled to room temperature. The solution was poured into EtOAc and washed with water and brine, dried (Na$_2$SO$_4$), filtered, and concentrated in vacuo. The resulting product was purified by silica gel chromatography (3–5% MeOH/CH$_2$Cl$_2$) to provide the product as a pale brown foam. A portion of this was taken up in CH$_2$Cl$_2$, treated with excess 1 M HCl/ether solution, and concentrated in vacuo to provide the titled product dihydrochloride as a pale yellow powder.

FAB mass spectrum m/e 470.1 (M+1). Analysis calculated for C$_{26}$H$_{20}$ClN$_5$O$_2$.2.50 HCl.1.65 H$_2$O: C, 52.96; H, 4.41; N, 11.88; Found: C, 52.92; H, 4.32; N, 11.21.

EXAMPLE 26

Preparation of 19,20-Dihydro-19-oxo-8-phenoxy-5H-18,21-ethano-12,14-etheno-6,10-metheno-22H-benzo[d]imidazo[4,3-k][1,6,9,12]oxatriazacyclooctadecine-9-carbonitrile (20), Dihydrochloride

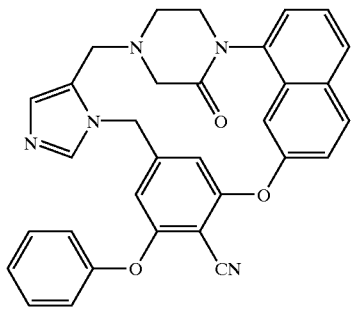

20

To a solution of the product of Example 25 (31.4 mg, 0.067 mmol) and phenol (31.5 mg, 0.33 mmol) in in 1 mL of DMSO was added cesium carbonate (107 mg, 0.33 mmol). The reaction was warmed to 80° C. under argon for 40 minutes, then cooled to room temperature. The solution was poured into EtOAc and washed with water and brine, dried (Na₂SO₄), filtered, and concentrated in vacuo. The resulting product was purified by silica gel chromatography (3–6% MeOH/CH₂Cl₂) to provide the product as a pale yellow foam. This was taken up in CH₂Cl₂, treated with excess 1 M HCl/ether solution, and concentrated in vacuo to provide the titled product dihydrochloride as a pale yellow powder.

FAB mass spectrum m/e 528 (M+1).

EXAMPLE 27

Preparation of 18-oxo-17,18,20,21-Tetrahydro-5H-19,22-ethano-6,10:12,16-dimetheno-23H-imidazo[3,4-h][1,8,11,14]oxatriazacycloheneicosine-9-carbonitrile (21), Dihydrochloride

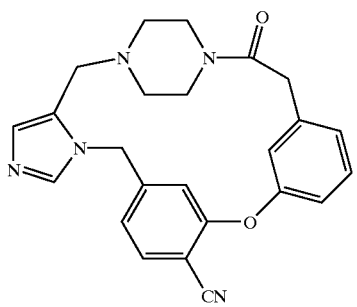

21

Step A: Preparation of 1-tert-Butyloxycarbonyl-4-[(3-hydroxyphenyl)acetyl]piperazine To a solution of N-tert-Butyloxycarbonylpiperazine (9.80 g, 52.6 mmol) and 3-(hydroxyphenyl)acetic acid (8.16 g, 152 mmol) in 100 mL of dimethylformamide at 0° C. was added 1-hydroxybenzotriazole hydrate (9.94 g, 73.6 mmol) and 1-(dimethylaminopropyl)-3-ethylcarbodiimide hydrochloride (13.06 g, 68.3 mmol). The solution was allowed to warm to room temperature. After 30 minutes, the reaction was poured into EtOAc and washed with water, saturated NH₄Cl solution, saturated NaHCO₃ solution, and brine, dried (Na₂SO₄), filtered, and concentrated in vacuo. The product was isolated as a white foam which was used without further purification.

Step B: Preparation of 1-tert-Butyloxycarbonyl-4-[(3-(methanesulfonyloxy)phenyl)acetyl]piperazine To a solution of the crude product from Step A (52.6 mmol) in 150 mL of dichloromethane at 0° C. was added triethylamine (14.66 mL, 105 mmol), followed by methanesulfonyl chloride (6.52 mL, 84.3 mmol). After 30 minutes, the reaction was poured into EtOAc and washed with water, saturated NH₄Cl solution, saturated NaHCO₃ solution, and brine, dried (Na₂SO₄), filtered, and concentrated in vacuo. The product was isolated as a white solid which was used without further purification.

Step C: Preparation of 1-[(3-(Methanesulfonyloxy)phenyl)-acetyl]piperazine, Hydrochloride Through a solution of the product from Step B (2.07 g, 5.22 mmol) in 75 mL of ethyl acetate at 0° C. was bubbled anhydrous HCl gas for 5 minutes. After 15 minutes, the reaction was concentrated in vacuo to produce the titled product as a white foam.

Step D: Preparation of 4-[1-(4-Cyano-3-fluorobenzyl)-5-imidazolylmethyl]-1-[(3-(methanesulfonyloxy)phenyl)-acetyl]piperazine To a solution of the amine hydrochloride from Step C (165 mg, 0.494 mmol) and the aldehyde from Example 1 Step G (102 mg, 0.445 mmol) in 3 mL of 1,2-dichloroethane was added 4 Å powdered molecular sieves (350 mg), followed by sodium triacetoxyborohydride (180 mg, 0.99 mmol). The reaction was stirred for 1.5 hours, then poured into EtOAc, washed with sat. aq. NaHCO₃ and brine, dried (Na₂SO₄), filtered, and concentrated in vacuo. The product was taken up in THF and 3N HCl, and stirred for 45 minutes. The solution was basified with aq NaHCO₃, extracted (4×) with chloroform, dried (Na₂SO₄), filtered, and concentrated in vacuo to produce the product as a white foam that was used without further purification.

Step E: Preparation of Compound 21 Dihydrochloride

A solution of the product from Step D (180 mg, 0.376 mmol) in 10 mL of DMSO was added via syringe pump over the course of 10 hours to a 90° C. solution of cesium carbonate (611 mg, 1.88 mmol) in 28 mL of DMSO. After an additional 5 hours, the reaction was cooled to room temperature and poured into EtOAc. The solution was washed with water and brine, dried (Na₂SO₄), filtered, and concentrated in vacuo. The resulting product was purified by silica gel chromatography (7–10% MeOH/CH₂Cl₂), taken up in CH₂Cl₂ and treated with excess 1 M HCl/ether solution, and concentrated in vacuo to provide the titled product dihydrochloride as a white powder.

FAB mass spectrum m/e 414.19 (M+1). Analysis calculated for C₂₄H₂₃N₅O₂.2.0 HCl.2.50 H₂O: C, 54.52; H, 5.71; N, 13.25; Found: C, 54.56; H, 5.79; N, 12.60.

EXAMPLE 28

Preparation of Spiro[cyclohexane-1',17-18-oxo-17,18,20,21-tetrahydro-5H-19,22-ethano-6,10:12,1 6-dimetheno-23H-imidazo[3,4-h][1,8,11,14]oxatriazacycloheneicosine-9-carbonitrile] (22), Dihydrochloride

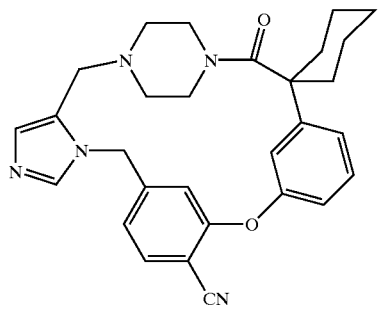

22

Step A: Preparation of Methyl-1-[1-(3-methoxyphenyl)-1-cyclohexyl]carboxylate

A solution of methyl 3-methoxyphenylacetate (9.0 g, 50 mmol) and 1,5-dibromopentane (6.75 mL, 50 mmol) in dry DMF (50 mL) was added dropwise (over a 6 h period) to a stirred mixture of hexane-washed 60% NaH (5.0 g, 110 mmol) in dry DMF (50 mL) at room temperature under argon. The mixture was gradually heated to 50° C. and stirred at this temperature for 16 hours. The reaction mixture was quenched with sat. NH₄Cl and then partitioned between EtOAc and H₂O. The organic layer was washed twice with H₂O, brine, and dried (Na₂SO₄). The solution was filtered and evaporated in vacuo. The crude product was chromatographed (CHCl₃) to give titled compound as a nearly colorless oil.

ES MS Calcd for C₁₅H₂₀O₃Na⁺ 271.314, found 271.14.

Step B: Preparation of 1-(3-Hydroxyphenyl)-1-cyclohexanecarboxylic Acid

The ester (320 mg, 1.3 mmol) from Step A was dissolved in HOAc (1.5 mL)-48% HBr (3 mL) and the mixture was refluxed for 4 hours. The clear solution was evaporated in vacuo to provide titled compound.

FAB MS Calcd for $C_{13}H_{16}O_3$ 221.1 (MH$^+$), found 221.1; (M—CO$_2$H) 175.1.

Step C: Preparation of 4-(tert-Butyloxycarbonyl)-1-[1-(3-hydroxyphenyl)-1-cyclohexylcarbonyl]-piperazine The titled compound was prepared from the product from Step B and N-tert-butyloxycarbonyl piperazine using the procedure described in Example 27 Step A.

FAB MS Calcd for $C_{22}H_{32}N_2O_4$ 389.5 (MH$^+$), found 389.3 (M-tBu) 333.2.

Step D: Preparation of 1-[1-(3-Hydroxyphenyl)-1-cyclohexylcarbonyl]piperazine Hydrochloride The carbamate from Step C was treated with EtOAc saturated with HCl at 0° C. for 30 minutes. Evaporation in vacuo provided the titled compound as a white powder.

FAB MS Calcd for $C_{17}H_{24}N_2O_2$ 289.3 (MH$^+$), found 289.1.

Step E: Preparation of 4-[1-(4-Cyano-3-fluorobenzyl)-5-imidazolylmethyl]-1-[1-(3-hydroxyphenyl)-1-cyclohexylcarbonyl]piperazine The titled compound was prepared from the product from Step D and the aldehyde from Example 1 Step G using the procedure described in Example 27 Step D.

FAB MS Calcd for $C_{29}H_{32}FN_5O_2$ 502.6 (MH$^+$), found 502.2. Analysis calculated for $C_{29}H_{32}FN_5O_2$.0.60 CHCl$_3$: C, 62.06; H, 5.73; N, 12.22; Found: C, 62.37; H, 5.72; N, 11.86.

Step F: Preparation of Compound 22 Dihydrochloride

The titled compound was prepared from the product from Step E using the procedure described in Example 27 Step E without converting to the hydrochloride.

FAB HRMS exact mass Calcd for $C_{29}H_{31}N_5O_2$ 482.2562 (MH$^+$), found 482.2550.

EXAMPLE 29

Preparation of (±)-19,20-Dihydro-19-oxo-17-propyl-5H,17H-18,21-ethano-6,10:12,16-dimetheno-22H-imidazo[3,4-h][1,8,11,14]oxatriazacycloeicosine-9-carbonitrile (23), Hydrochloride

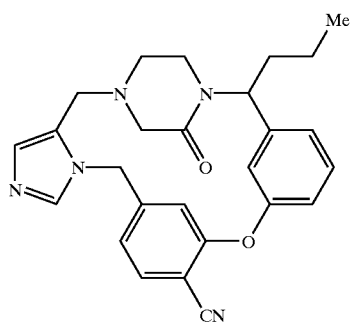

23

Step A: Preparation (±)-3-Benzyloxy-1-(1-hydroxy-3-buten-1-yl)benzene

To a solution of 3-(benzyloxy)benzaldehyde (4.25 g, 20.0 mmol) in 50 mL of dry diethyl ether at 0° C. was added allylmagnesium bromide (23.0 mL, 23.0 mmol, 1.0 M ether) dropwise. The solution was allowed to warm to room temperature overnight. The solution was concentrated in vacuo, then partitioned between EtOAc and saturated NaHCO$_3$ soln. The organic phase was washed with brine, dried (Na$_2$SO$_4$), filtered, and concentrated in vacuo to give the titled product as a yellow oil.

Step B: Preparation (±)-3-Benzyloxy-1-(1-methanesulfonyloxy-3-buten-1-yl)benzene To a solution of the product from Step A (4.93 g, 19.4 mmol) and triethylamine (8.10 mL, 58.3 mmol) in 40 mL of dichloroethane at 0° C. was added methanesulfonic anhydride (6.0 g, 34 mmol). When TLC analysis showed disappearance of starting alcohol, the reaction was partitioned between EtOAc and saturated NH$_4$Cl solution. The organic phase was washed with saturated NaHCO$_3$ soln and brine, dried (Na$_2$SO$_4$), filtered, and concentrated in vacuo to give the titled product as a yellow oil.

Step C: Preparation (±)-4-Benzyloxycarbonyl-1-[1-(3-(benzyloxy)phenyl)-3-buten-1-yl]-2-piperazinone Sodium hydride (1.20 g, 30.0 mmol, 60% mineral oil dispersion) was triturated with hexane. The flask was charged with 15 mL of dimethylformamide and cooled to 0° C. 4-Benzyloxycarbonyl-2-piperazinone was added (4.55 g, 19.4 mmol), and the reaction was stirred for 15 minutes at 0° C. A solution of the product from Step B (4.83 g, 14.5 mmol) in 15 mL of dimethylformamide was added slowly, and the reaction was allowed to warm to room temperature. After 3 days, the solution was concentrated in vacuo, and partitioned between EtOAc and saturated NaHCO$_3$ solution. The aqueous phase was extracted with EtOAc, and the combined organics were washed with saturated NaHCO$_3$ soln and brine, dried (Na$_2$SO$_4$), filtered, and concentrated in vacuo. The resulting product was purified by silica gel chromatography (10% EtOAc/hexane, then 5% MeOH/CH$_2$Cl$_2$) to provide the titled product as a yellow oil.

Step D: Preparation (±)-1-[1-(3-Hydroxyphenyl)-1-butyl]-2-piperazinone

To a solution of the product from Step C (0.55 g, 1.2 mmol) in 40 mL of methanol was added 10% palladium on carbon (0.655 g). The solution was stirred at room temperature under an atmosphere of hydrogen for 24 hours, then purged with argon. The mixture was filtered through celite, the filter pad was washed with methanol, and the filtrate was concentrated in vacuo to produce the titled product as a white solid.

Step E: Preparation of (±)-4-[1-(4-cyano-3-fluorobenzyl)-5-imidazolylmethyl]-1-[1-(3-hydroxyphenyl)-1-butyl]-2-piperazinone To a solution of the amine from Step D (245 mg, 0.99 mmol) and the aldehyde from Example 1 Step G (240 mg, 1.00 mmol) in 2 mL of 1,2-dichloroethane and 1 mL of methanol was added 4 Å powdered molecular sieves (320 mg), followed by sodium triacetoxyborohydride (470 mg, 2.22 mmol). After stirring overnight, there was no reaction. Sodium cyanoborohydride was added (138 mg, 2.22 mmol), and the reaction was allowed to stir until complete as judged by HPLC. The solution was poured into EtOAc, washed with sat. aq. NaHCO$_3$ and brine, dried (Na$_2$SO$_4$), filtered, and concentrated in vacuo. The resulting product was purified by silica gel chromatography (50% acetone/CH$_2$Cl$_2$, then 5% MeOH/CH$_2$Cl$_2$) to provide the titled product as a white solid.

Step F: Preparation of Compound 23 Hydrochloride

The product from Step E (243 mg, 0.526 mmol) was converted to the titled compound using the same procedure as that described in Step M of Example 1. The product was obtained as a white solid.

HRMS (ES) calculated for M+H$^+$: 442.2237. Found 442.2232. Analysis calculated for $C_{26}H_{27}N_5O_2$.1.45 HCl.1.65 H$_2$O: C, 59.58; H, 6.11; N, 12.01; Found: C, 59.55; H, 6.11; N, 13.36.

EXAMPLE 30

Preparation of (+)- or (−)-19,20-Dihydro-19-oxo-17-propyl-5H,17H-18,21-ethano6,10:12,16-dimetheno-22H-imidazo[3,4-h][1,8,11,14]oxatriaza-cycloeicosine-9-carbonitrile (23), Enantiomer A Hydrochloride

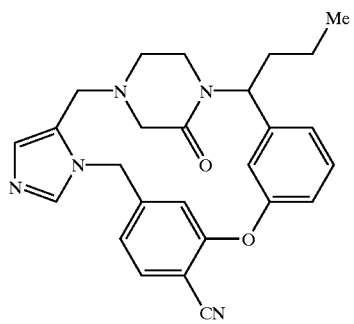

23

A sample of the racemic mixture of the free-base product from Example 29, Step F (243 mg in MeOH) was resolved by preparative chiral HPLC (Chiralpak AD 25×2 cm; 60% ethanol/0.1% diethylamine-hexane; flow rate 7.0 mL/min; 270 nm). The faster eluting product was taken up in $CH_2Cl_2$, treated with excess 1 M HCl/ether solution, and concentrated in vacuo to provide the titled product dihydrochloride as a pale white powder. Assay for enantiomeric purity (retention time=5.64 min; Chiralpak AD 250×4.6 mm; 70% ethanol/0.1% diethylamine-hexane; flow rate 1.0 mL/min; 270 nm) indicated 98.6% enantiomeric excess.

HRMS (ES) calculated for M+H$^+$: 442.2237. Found 442.2251. Analysis calculated for $C_{26}H_{27}N_5O_2 \cdot 0.75$ HCl $\cdot 2.45$ $H_2O$: C, 60.87; H, 6.42; N, 13.65; Found: C, 60.83; H, 6.43; N, 12.78.

EXAMPLE 31

Preparation of (−)- or (+)-19,20-Dihydro-19-oxo-17-propyl-5H,17H-18,21-ethano-6,10:12,16-dimetheno-22H-imidazo[3,4-h][1,8,11,14]oxatriaza-cycloeicosine-9-carbonitrile (23), Enantiomer B Hydrochloride

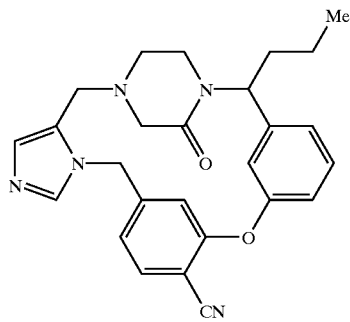

23

The titled product was produced from the product of Example 29 under the same conditions described in Example 30. Assay of the slower-eluting product for enantiomeric purity (retention time=8.20 min; Chiralpak AD 250×4.6 mm; 70% ethanol/0.1% diethylamine-hexane; flow rate 1.0 mL/min; 270 nm) indicated 97.2% enantiomeric excess.

HRMS (ES) calculated for M+H$^+$: 442.2237. Found 442.2234. Analysis calculated for $C_{26}H_{27}N_5O_2 \cdot 0.95$ HCl $\cdot 2.25$ $H_2O$: C, 60.43; H, 6.33; N, 13.55; Found; C, 60.43; H, 6.32; N, 12.59.

EXAMPLE 32

Preparation of 15-Bromo-19,20-dihydro-19-oxo-5H,17H-18,21-ethano-6,10:12,16-dimetheno-22H-imidazo[3,4-h][1,8,11,14]oxatriazacycloeicosine-9-carbonitrile (24), Hydrochloride

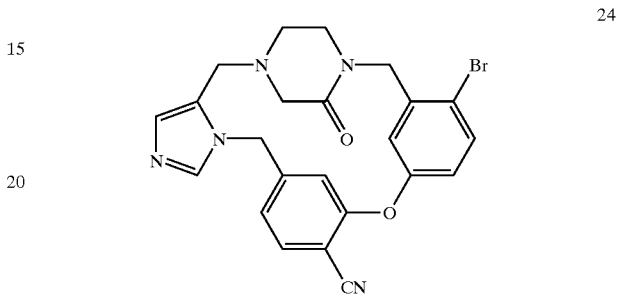

24

Step A: Preparation of 4-Bromo-1-[methanesulfonyloxy]-3-methylbenzene

To a solution of 4-bromo-3-methylphenol (10.2 g, 54.5 mmol) in 100 mL of dichloromethane at 0° C. was added triethylamine (15.2 mL, 109 mmol), followed by methanesulfonyl chloride (6.33 mL, 81.8 mmol). The reaction was stirred overnight, allowing it to warm to room temperature. The solution was poured into EtOAc, washed with water, saturated $NH_4Cl$ solution, saturated aq. $NaHCO_3$ and brine, dried ($Na_2SO_4$), filtered, and concentrated in vacuo. The resulting product was isolated as a white solid which required no further purification.

Step B: Preparation of 4-Bromo-3-bromomethyl-1-[methanesulfonyloxy]benzene

To a solution of the product from Step A (10.38 g, 39.2 mmol) and N-bromosuccinimide (8.61 g, 48.4 mmol) in 80 mL of carbontetrachloride was added 2,2'-azobisisobutyronitrile (0.89 g, 5.4 mmol), and the reaction was heated at reflux overnight under argon. The solution was cooled to room temperature, concentrated in vacuo, slurried with 30% EtOAc/hexane solution, and filtered. The filtrate was washed with saturated aq. $NaHCO_3$ and brine, dried ($Na_2SO_4$), filtered, and concentrated in vacuo to provide a 2:1 mixture of the titled product and a tribromide as a yellow oil.

Step C: Preparation of 4-tert-Butoxycarbonyl-2-piperazinone

To a solution of 4-benzyloxycarbonyl-2-piperazinone (9.44 g, 40.3 mmol) and di-tert-butyldicarbonate (8.80 g, 40.3 mmol) in 100 mL of ethanol was added 10% palladium on carbon (1.5 g). The solution was stirred at room temperature under an atmosphere of hydrogen for 3 days, then purged with argon. The mixture was filtered through celite, the filter pad was washed with ethanol/THF, and the filtrate was concentrated in vacuo to produce the titled product as a white solid.

Step D: Preparation of 1-[2-Bromo-5-((methanesulfonyl)oxy)benzyl]-4-tert-butoxycarbonyl-2-piperazinone Sodium hydride (0.89 g, 22.2 mmol, 60% mineral oil dispersion) was triturated with hexane. The flask was charged with 30 mL of dimethylformamide and cooled to 0° C. The product from Step C was added (3.65 g, 18.2 mmol), and the reaction was stirred for 15 minutes at 0° C. A solution of the crude product from Step B (14.7 g, ca. 24 mmol) in 40 mL of dimethylformamide was added slowly, and the reaction was allowed to warm to room temperature. After 24 hours, the solution was concentrated in vacuo, and partitioned between EtOAc and saturated NaHCO$_3$ solution. The aqueous phase was extracted with EtOAc, and the combined organics were washed with saturated NaHCO$_3$ soln and brine, dried (Na$_2$SO$_4$), filtered, and concentrated in vacuo. The resulting product was purified by silica gel chromatography (50–75% EtOAc/hexane) to provide the titled product as a yellow solid.

Step E: Preparation of 1-[2-Bromo-5-((methanesulfonyl)oxy)benzyl]-2-piperazinone Hydrochloride Through a solution of the product from Step D (7.71 g, 16.6 mmol) in 100 mL of ethyl acetate at 0° C. was bubbled anhydrous HCl gas for 10 minutes. After 30 minutes, the solution was concentrated in vacuo to provide the titled salt as a white foam which was used in the next reaction without further purification.

Step F: Preparation of 4-[1-(4-Cyano-3-fluorobenzyl)-5-imidazolylmethyl]-1-[2-bromo-5-((methanesulfonyl)-oxy)benzyl]-2-piperazinone To a solution of the amine hydrochloride from Step E (6.53 g, 16.3 mmol) and the aldehyde from Step G of Example 1 (4.62 g, 20.2 mmol) in 70 mL of 1,2-dichloroethane was added 4 Å powdered molecular sieves (4.6 g), followed by sodium triacetoxyborohydride (6.30 g, 29.7 mmol). After 3 hours, the reaction was poured into EtOAc, washed with sat. aq. NaHCO$_3$ and brine, dried (Na$_2$SO$_4$), filtered, and concentrated in vacuo. The resulting product was purified by silica gel chromatography (1–6% MeOH/CH$_2$Cl$_2$) to provide the titled product as a white solid.

Step G: Preparation of Compound 24 Hydrochloride

To a solution of the product from Step F (6.26 g, 10.9 mmol) in 220 mL of DMSO was added cesium carbonate (17.8 g, 54.7 mmol). The reaction was warmed to 80° C. under argon for 3 hours, then cooled to room temperature. The solution was poured into EtOAc and washed with water and brine, dried (Na$_2$SO$_4$), filtered, and concentrated in vacuo. The resulting product was purified by silica gel chromatography (2–6% MeOH/CH$_2$Cl$_2$) to provide the desired product as a white powder. A portion of this was taken up in CH$_2$Cl$_2$ and treated with excess 1 M HCl//ether solution, and concentrated in vacuo to provide the titled product dihydrochloride as a white powder.

HRMS (ES) calculated for M+H$^+$: 478.6873. Found 478.6890. Analysis calculated for C$_{23}$H$_{20}$BrN$_5$O$_2$.1.55 HCl.1.75 H$_2$O: C, 48.77; H, 4.46; N, 12.37; Found: C, 48.82; H, 4.46; N, 11.74.

EXAMPLE 33

Preparation of 15-Bromo-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (25), Dihydrochloride

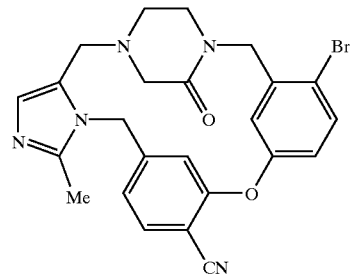

25

Step A: Preparation of 4-[1-(4-Cyano-3-fluorobenzyl)-2-methyl-5-imidazolylmethyl]-1-[2-bromo-5-((methanesulfonyl)-oxy)benzyl]-2-piperazinone The titled compound was prepared from the amine hydrochloride product of Step E of Example 32 (2.34 g, 5.73 mmol) and the product aldehyde from Step A of Example 10 (1.68 g, 6.91 mmol), using the procedure described in Step F of Example 32. The product was isolated as a white powder.

Step B: Preparation of Compound 25 Dihydrochloride

The titled compound was prepared from the product of Step A (2.97 g, 3.98 mmol) using the procedure described in Step G of Example 32. The resulting product (2.07 g, 95%) was isolated as a yellow solid. A portion of this was taken up in CH$_2$Cl$_2$ and treated with excess 1 M HCl/ether solution, and concentrated in vacuo to provide the titled product dihydrochloride as a yellow powder.

HRMS (ES) calculated for M+H$^+$: 492.1030. Found 492.1029. Analysis calculated for C$_{24}$H$_{22}$BrN$_5$O$_2$.2.50 HCl.0.20 hexane: C, 50.38; H, 4.58; N, 11.66; Found: C, 50.30; H, 4.75; N, 11.42.

EXAMPLE 34

Preparation of 19,20-Dihydro-15-iodo-3-methyl-19-oxo-5H,17H-18,21-ethano-6,10:12,16-dimetheno-22H-imidazo[3,4-h][1,8,11,14]oxatriazacycloeicosine-9-carbonitrile (26), Hydrochloride

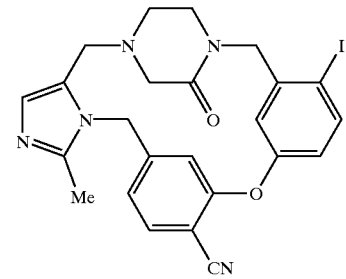

26

Step A: Preparation of 4-Iodo-3-methylphenol

To a solution of 4-amino-meta-cresol (20.59 g, 167 mmol) in 90 mL of tetrahydrofuran and 280 mL of 3M HCl solution at 0° C. was added a solution of NaNO$_2$ (12.73 g, 184 mmol) in 40 mL of water dropwise over 5 minutes. After 25 minutes, a solution of potassium iodide (112.5 g, 678 mmol)

in 85 mL of water was added, and stirring was continued for 15 minutes. The solution was poured into EtOAc and the organic layer was washed with water and brine, dried ($Na_2SO_4$), filtered, and concentrated in vacuo. The resulting product was purified by silica gel chromatography (0–50% EtOAc/hexane) to provide the desired product as a dark crystalline solid.

Step B: Preparation of Compound 26 Hydrochloride

The titled compound was prepared from the product of Step A using the procedures described in Steps A through G of Example 32, except that in Step F the aldehyde was substituted with the product aldehyde from Step A of Example 10. The resulting product was isolated as a white solid. A portion of this was taken up in $CH_2Cl_2$ and treated with excess 1 M HCl/ether solution, and concentrated in vacuo to provide the titled product hydrochloride as a white powder.

HRMS (ES) calculated for M+H$^+$: 540.0891. Found 540.0887. Analysis calculated for $C_{24}H_{22}IN_5O_2 \cdot 1.70$ HCl$\cdot 1.10$ hexane: C, 47.35; H, 4.45; N, 11.00; Found: C, 47.35; H, 4.33; N, 10.94.

EXAMPLE 35

Preparation of 19,20-Dihydro-3-methyl-19-oxo-5H,17H-18,21-ethano-12,16-imino-6,10-metheno-22H-imidazo[3,4-h][1,8,11,14]oxatriazacycloeicosine-9-carbonitrile (27), Dihydrochloride

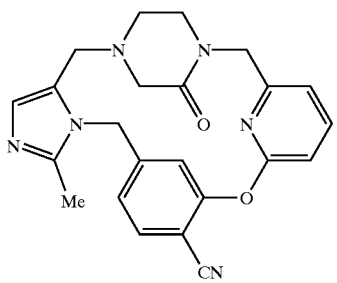

27

Step A: Preparation of 6-(2-Allyloxy)picolinic Acid, Allyl Ester

To a solution of 6-hydroxypicolinic acid (4.48 g, 32.2 mmol) in 50 mL of dimethylformamide was added potassium carbonate (13.3 g, 96.6 mmol) and allyl iodide (6.48 mL, 70.9 mmol). The reaction was heated at 80° C. for 1.5 hours, then cooled to room temperature. The solution was poured into EtOAc and the organic layer was washed with water and brine, dried ($Na_2SO_4$), filtered, and concentrated in vacuo. The resulting product was purified by silica gel chromatography (15–50% EtOAc/hexane) to provide the desired product as a yellow oil.

Step B: Preparation of 2-(2-Allyloxy)-6-(hydroxymethyl) pyridine

To a 0° C. solution of lithium aluminum hydride (553 mg, 14.6 mmol) in 10 mL of tetrahydrofuran was added dropwise via addition funnel a solution of the product from Step A (3.19 g, 14.6 mmol) in 10 mL of tetrahydrofuran, followed by a 5 mL tetrahydrofuran rinse. After 15 minutes, the reaction was quenched by the careful addition of EtOAc and saturated $NH_4Cl$ solution. The solution was partitioned between EtOAc and saturated $NaHCO_3$ solution, and the aqueous phase was reextracted with EtOAc. The combined organic layers were washed with brine, dried ($Na_2SO_4$), filtered, and concentrated in vacuo to provide the desired product as a colorless oil.

Step C: Preparation of 2-(2-Allyloxy)-6-[((methanesulfonyl)-oxy)methyl]pyridine

To a 0° C. solution of the alcohol from Step B (2.12 g, 12.8 mmol) in 20 mL of dichloromethane was added triethylamine (3.58 mL, 25.7 mmol), followed by methanesulfonic anhydride (2.46 g, 14.1 mmol). After 45 minutes, the solution was poured into EtOAc, washed with sat. aq. $NaHCO_3$ and brine, dried ($Na_2SO_4$), filtered, and concentrated in vacuo to provide the desired product as a yellow oil.

Step D: Preparation of 1-[2-(Allyloxy)-6-pyridylmethyl]-4-tert-butoxycarbonyl-2-piperazinone The titled compound was prepared from the product of Step C (2.47 g, 10.0 mmol) and the product of Step C of Example 32 (2.57 g, 12.85 mmol) using the procedure described in Step D of Example 32. The product was isolated as a yellow oil.

Step E: Preparation of 4-[1-(4-Cyano-3-fluorobenzyl)-2-methyl-5-imidazolylmethyl]-1-[2-(allyloxy)-6-pyridylmethyl]-2-piperazinone The titled compound was prepared from the product of Step D (223 mg, 0.664 mmol) using the procedures described in Steps E and F of Example 32 except that in Step F the aldehyde was substituted with the product aldehyde from Step A of Example 10. The resulting product was purified by silica gel chromatography (3–4% MeOH/$CH_2Cl_2$) to provide the desired product as a yellow foam.

Step F: Preparation of 4-[1-(4-Cyano-3-fluorobenzyl)-2-methyl-5-imidazolylmethyl]-1-(2-hydroxy-6-pyridylmethyl)-2-piperazinone To a solution of the allyl ether from Step E (89.6 mg, 0.189 mmol) in 2 mL of tetrahydrofuran was added tetrakis (triphenylphosphine)palladium (4.3 mg, 0.0037 mmol). After 5 minutes, sodium borohydride was added (10.7 mg, 0.283 mmol), and the reaction was stirred at room temperature for 30 minutes. The reaction was quenched with saturated $NH_4Cl$ solution, then partitioned between EtOAc and saturated $NaHCO_3$ solution. The organic layer was washed with brine, dried ($Na_2SO_4$), filtered, and concentrated in vacuo to provide the desired product as a yellow foam.

Step G: Preparation of Compound 27 Dihydrochloride

The titled compound was prepared from the product of Step F (65.6 mg, 0.151 mmol) using the procedure described in Step G of Example 32. The resulting product hydrochloride was isolated as a white powder.

HMRS (ES) calculated for M+H$^+$: 415.1877. Found 415.1820. Analysis calculated for $C_{23}H_{22}N_6O_2 \cdot 2.10HCl \cdot 1.30H_2O$: C, 53.75; H, 5.24; N, 16.35; Found: C, 53.74; H, 5.23; N, 14.79.

Example 36

Preparation of 15-Bromo-19,20-dihydro-3-methyl-19-oxo-5H,17H-18,21-ethano-12,16-imino-6,10-metheno-22H-imidazo[3,4-h][1,8,11,14]oxatriaza-cycloeicosine-9-carbonitrile (28), Dihydrochloride

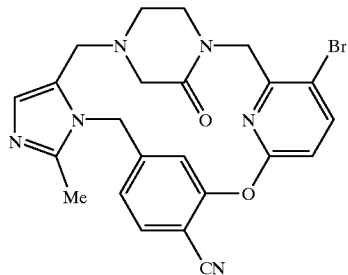

28

Step A: Preparation of 1-(2-Hydroxy-6-pyridylmethyl)-4-tert-butoxycarbonyl-2-piperazinone The titled compound was prepared from the product of Step D of Example 35 (2.02 g, 5.82 mmol) using the procedure described in Step F of Example 35. The product was isolated as a yellow solid.

Step B: Preparation of 1-(5-Bromo-2-hydroxy-6-pyridylmethyl)-4-tert-butoxycarbonyl-2-piperazinone To a solution of the product from Step A (511 mg, 1.66 mmol) in 10 mL of chloroform at 0° C. was added N-bromosuccinimide (296 mg, 1.66 mmol). After 30 minutes, the solution was concentrated in vacuo. The resulting product was purified by silica gel chromatography (3–4% MeOH/CH$_2$Cl$_2$) to provide the desired product.

Step C: Preparation of 4-[1-(4-Cyano-3-fluorobenzyl)-2-methyl-5-imidazolylmethyl]-1-(5-bromo-2-hydroxy-6-pyridylmethyl)-2-piperazinone The titled compound was prepared from the product of Step B (544 mg, 1.41 mmol) using the procedures described in Steps E and F of Example 32 except that in Step F the aldehyde was substituted with the product aldehyde from Step A of Example 10. The resulting product was purified by silica gel chromatography (5–10% MeOH/CH$_2$Cl$_2$) to provide the desired product as a white foam.

Step D: Preparation of Compound 28 Dihydrochloride

The titled compound was prepared from the product of Step C (200 mg, 0.391 mmol) using the procedure described in Step G of Example 32. The resulting product was isolated as a white solid (75 mg). A portion of this was taken up in CH$_2$Cl$_2$ and treated with excess 1 M HCl/ether solution, and concentrated in vacuo to provide the titled product dihydrochloride as a white powder.

HMRS (ES) calculated for M+H$^+$: 493.0982. Found 493.0991.

Example 37

Preparation of 15-Bromo-19,20-dihydro-3-methyl-17-oxo-5H,17H-18,21-ethano-6,10:12,16-dimetheno-22H-imidazo[3,4-h][1,8,11,14]oxatriaza-cycloeicosine-9-carbonitrile (29)

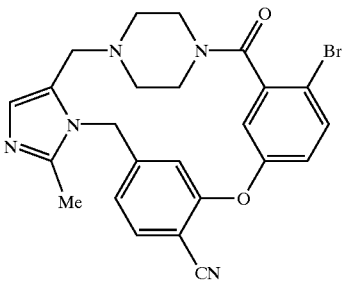

29

Step A: Preparation of 6-Bromo-3-[(methanesulfonyl)oxy]benzoic Acid

To a solution of the product from Step A of Example 32 (809 mg, 3.04 mmol) in 6 mL of pyridine and 6 mL of water was added potassium permanganate (961 mg, 6.08 mmol), and the reaction was heated to 90° C. Over the course of 24 hours, three additional portions of potassium permanganate (480 mg each, 3.04 mmol each) were added. The solution was filtered through celite, and the filter pad washed with 1:1 EtOH/water. The filtrate was concentrated in vacuo, acidified with concentrated HCl solution, and filtered. The filter cake was washed with cold water, and dried in vacuo next to P$_2$O$_5$ to provide the titled product as a white solid.

Step B: Preparation of 4-[6-Bromo-3-((methanesulfonyl)oxy)benzoyl]-1-(tert-butoxycarbonyl)piperazine To a solution the product from Step A (858 mg, 2.89 mmol), N-tert-butoxycarbonylpiperazine (540 mg, 2.89 mmol), and 1-hydroxybenzotriazole hydrate (546 mg, 4.05 mmol) in 4 mL of dimethylformamide was added 1-(dimethylaminopropyl)-3-ethylcarbodiimide hydrochloride (718 mg, 3.75 mmol). After 30 minutes, the reaction was poured into EtOAc and washed with water, 3N HCl solution, saturated NaHCO$_3$ solution, and brine, dried (Na$_2$SO$_4$), filtered, and concentrated in vacuo. The product was isolated as a white foam which was used without further purification.

Step C: Preparation of 4-[1-(4-Cyano-3-fluorobenzyl)-2-methyl-5-imidazolylmethyl]-1-[6-bromo-3-((methanesulfonyl)oxy)benzoyl]-2-piperazinone The titled compound was prepared from the product of Step B (1.08 g, 2.32 mmol) using the procedures described in Steps E and F of Example 32 except that in Step F the aldehyde was substituted with the product aldehyde from Step A of Example 10. The resulting product was taken up in 1:1 THF/3N HCl solution and stirred for 1 hour, then basified with NaHCO$_3$. The solution was extracted with dichloromethane, dried (Na$_2$SO$_4$), filtered, and concentrated in vacuo. The product was isolated as a white foam which was used without further purification.

Step D: Preparation of Compound 29

The titled compound was prepared from the product of Step C (507 mg, 0.859 mmol) using the procedure described in Step E of Example 27. The resulting product was purified by silica gel chromatography (5–6% MeOH/CH$_2$Cl$_2$) to afford the titled compound as white solid.

Example 38

Preparation of 15-[(2-Cyclobutyl)ethynyl]-19,20-dihydro-3-methyl-17-oxo-5H,17H-18,21-ethano-6,10:12,16-dimetheno-22H-imidazo[3,4-h][1,8,11,14]oxatriazacycloeicosine-9-carbonitrile (30), Dihydrochloride

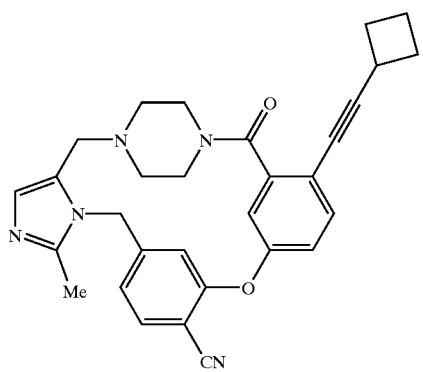

30

Step A: Preparation of [2-(tri-n-Butylstannyl)-1-ethynyl]cyclobutane

To a solution of n-BuLi/hexane (7.28 mL, 18.2 mmol, 2.5 M) at −5° C. was added tetrahydrofuran dropwise, maintaining the temperature below +9° C. 6-Chloro-1-hexyne (1.00 mL, 8.92 mmol) was added at +5° C., and the solution was stirred for six hours. The reaction was quenched by the addition of tri-n-butyltin chloride (2.66 mL, 9.81 mmol), and was allowed to stir for an additional 10 minutes. The solution was poured into hexane, washed with saturated NaHCO$_3$ solution and brine, dried (Na$_2$SO$_4$), filtered, and concentrated in vacuo. The product was isolated as a colorless liquid which was used without further purification.

Step B: Preparation of Compound 30 Dihydrochloride

To a solution of the product from Step A (202 mg, 0.547 mmol) and the Example 37 aryl bromide (90.0 mg, 0.182 mmol) in 1.0 mL of dimethylformamide in a sealed tube was added tetrakis(triphenylphosphine)palladium (31 mg, 0.027 mmol). The solution was heated to 110° C. After 3 hours, additional portions of stannane and catalyst were added, and the reaction was stirred for another 7 hours. The solution was poured into EtOAc and washed with saturated NaHCO$_3$ solution and brine, dried (Na$_2$SO$_4$), filtered, and concentrated in vacuo. The resulting product was purified by silica gel chromatography (5–10% MeOH/CH$_2$Cl$_2$) to provide the desired product as a pale yellow foam. A portion of this was taken up in CH$_2$Cl$_2$ and treated with excess 1 M HCl/ether solution, and concentrated in vacuo to provide the titled product dihydrochloride as a pale yellow powder.

HMRS (ES) calculated for M+H$^+$: 492.2394. Found 492.2411.

Example 39

Preparation of 15-[(2-Cyclobutyl)ethyl]-19,20-dihydro-3-methyl-17-oxo-5H,17H-18,21-ethano-6,10:12,16-dimetheno-22H-imidazo[3,4-h][1,8,11,14]oxatriazacycloeicosine-9-carbonitrile (31), Dihydrochloride

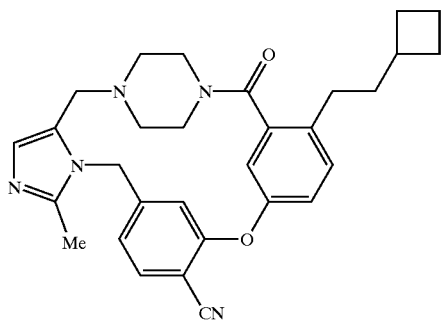

31

To a solution of the Example 38 alkyne product (39.7 mg, 0.070 mmol) in 2.0 mL of 1:1 methanol/EtOAc was added 10% palladium on carbon (50 mg). The solution was stirred under an atmosphere of hydrogen for 3 days, then purged with argon. The mixture was filtered through celite, the filter pad was washed with methanol/THF, and the filtrate was concentrated in vacuo. The resulting product was taken up in CH$_2$Cl$_2$ and treated with excess 1 M HCl/ether solution, and concentrated in vacuo to provide the titled product dihydrochloride as a pale yellow powder.

HMRS (ES) calculated for M+H$^+$: 496.2707. Found 496.2707.

Example 40

Preparation of 15-[(2-Cyclopropyl)ethyl]-19,20-dihydro-3-methyl-17-oxo-5H,17H-18,21-ethano-6,10:12,16-dimetheno-22H-imidazo[3,4-h][1,8,11,14]oxatriazacycloeicosine-9-carbonitrile (32), Dihydrochloride

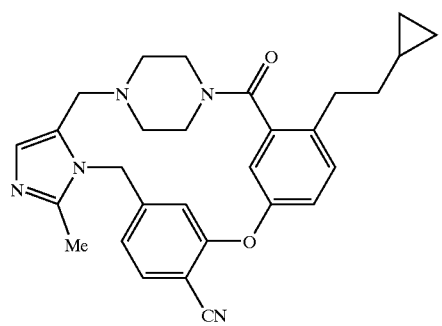

32

Step A: Preparation of [2-(tri-n-Butylstannyl)-1-ethynyl]cyclopropane

The titled compound was prepared using the procedure described in Step A of Example 38, substituting 5-chloro-1-pentyne for 6-chloro-1-hexyne.

Step B: Preparation of 4-[6-(2-Cyclopropyl)ethynyl-3-[(methanesulfonyl)oxy]benzoyl]-1-(tert-butoxycarbonyl)-piperazine The titled compound was prepared from the stannane product of Step A and the aryl bromide from Step B of Example 37 (500 mg, 1.08 mmol) using the procedure described in Step B of Example 38. The resulting product was purified by silica gel chromatography (35–90% EtOAc/hexane) to afford the titled compound as a white solid.

Step C: Preparation of 4-[1-(4-Cyano-3-fluorobenzyl)-2-methyl-5-imidazolylmethyl]-1-[6-(2-cyclopropyl)ethynyl-3-((methanesulfonyl)oxy)benzoyl]-2-piperazinone The titled compound was prepared from the product of Step B (351 mg, 0.78 mmol) using the procedures described in Steps E and F of Example 32 except that in Step F the aldehyde was substituted with the product aldehyde from Step A of Example 10. The resulting product was purified by silica gel chromatography (80–100% acetone/$CH_2Cl_2$) to afford the titled compound as a white solid.

Step D: Preparation of 4-[1-(4-Cyano-3-fluorobenzyl)-2-methyl-5-imidazolylmethyl]-1-[6-(2-cyclopropyl)ethyl-3-((methanesulfonyl)oxy)benzoyl]-2-piperazinone The titled compound was prepared from the product of Step C (57 mg, 0.10 mmol) using the procedure described for the preparation of Example 39. The crude product (23 mg) was used in the next step without further purification.

Step E: Preparation of Compound 32 Dihydrochloride

The titled compound was prepared from the product of Step D (23 mg, 0.040 mmol) using the procedure described in Step E of Example 27. The crude material was purified on 2×0.5 mm preparative silica gel TLC plates, eluting with 90:10:1 $CHCl_3$:MeOH:$NH_4OH$. The product was taken up in $CH_2Cl_2$, treated with excess 1 M HCl/ether solution, and concentrated in vacuo to provide the titled product dihydrochloride as a white powder.

FAB mass spectrum m/e 484 (M+1).

Example 41

Preparation of 19,20-Dihydro-15-(3,3-dimethyl-1-butynyl)-19-oxo-5H,17H-18,21-ethano-6,10:12,16-dimetheno-22H-imidazo[3,4-h][1,8,11,14]oxatriazacycloeicosine-9-carbonitrile (33), Hydrochloride

33

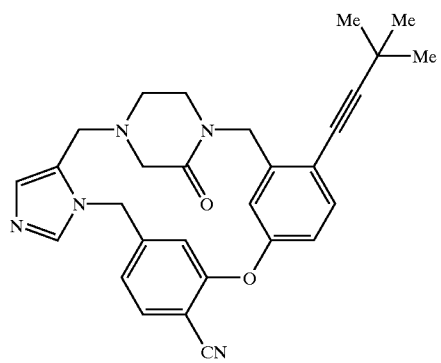

To a solution of the Example 32 aryl bromide (76.2 mg, 0.159 mmol) in 3 mL of dimethylformamide was added triethylamine (2.0 mL), copper(I) iodide (3.6 mg, 0.019 mmol), (bis)triphenylphosphinepalladium dichloride (5.2 mg, 0.008 mmol), and 3,3-dimethyl-1-butyne (0.040 mL, 0.325 mmol). The reaction was heated to 90° C. Over the course of 24 hours, additional portions of copper(I) iodide, (bis)triphenylphosphine palladium dichloride, and 3,3-dimethyl-1-butyne were added on three occasions. The solution was poured into EtOAc and washed with saturated $NaHCO_3$ solution and brine, dried ($Na_2SO_4$), filtered, and concentrated in vacuo. The resulting product was purified by silica gel chromatography (2.5% MeOH/$CH_2Cl_2$) to a pale yellow foam. A portion of this was taken up in $CH_2Cl_2$ and treated with excess 1 M HCl/ether solution, concentrated in vacuo, and truturated with hexane to provide the titled product hydrochloride as a pale brown powder.

HMRS (ES) calculated for M+H$^+$: 480.2394. Found 480.2401. Analysis calculated for $C_{29}H_{29}N_5O_2 \cdot 1.70HCl \cdot 2.50H_2O$: C, 59.37; H, 6.13; N, 11.94; Found: C, 59.38; H, 6.36; N, 9.25.

Example 42

Preparation of 19,20-Dihydro-19-oxo-15-(2-phenylethynyl)-5H,17H-18,21-ethano-6,10:12,16-dimetheno-22H-imidazo[3,4-h][1,8,11,14]oxatriazacycloeicosine-9-carbonitrile (34), Hydrochloride

34

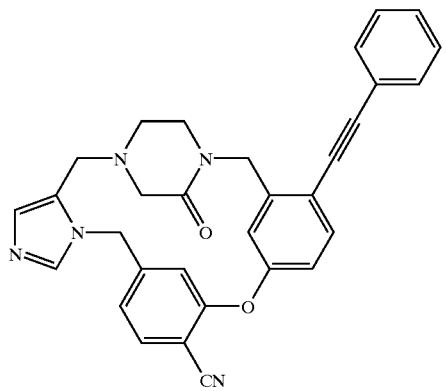

To a solution of the Example 32 aryl bromide (188 mg, 0.394 mmol) in 0.5 mL of dimethylformamide was added triethylamine (0.5 mL), copper(I) iodide (10.0 mg, 0.052 mmol), (bis)triphenylphosphinepalladium dichloride (22.4 mg, 0.032 mmol), triphenylphosphine (6.7 mg, 0.026 mmol), and phenylacetylene (0.087 mL, 0.792 mmol). The reaction was heated to 90° C. Over the course of 48 hours, additional portions of phenylacetylene (0.5 mL) were added on three occasions. The solution was poured into EtOAc and washed with saturated $NaHCO_3$ solution and brine, dried ($Na_2SO_4$), filtered, and concentrated in vacuo. The resulting product was purified by silica gel chromatography (50–60% acetone/$CH_2Cl_2$), followed by preparative reversed-phase HPLC. A portion of the product was taken up in $CH_2Cl_2$ and treated with excess 1 M HCl/ether solution, and concentrated in vacuo to provide the titled product hydrochloride as a white solid.

HRMS (ES) calculated for M+H$^+$: 500.2081. Found 500.2066. Analysis calculated for $C_{31}H_{25}N_5O_2 \cdot 1.50HCl \cdot 2.15H_2O$: C, 62.78; H, 5.24; N, 11.81; Found: C, 62.82: H, 5.23; N, 11.26.

Example 43

Preparation of 15-(Cyclohexylethynyl)-19,20-dihydro-19-oxo-5H,17H-18,21-ethano-6,10:12,16-dimetheno-22H-imidazo[3,4-h][1,8,11,14]oxatriaza-cycloeicosine-9-carbonitrile (35), Dihydrochloride

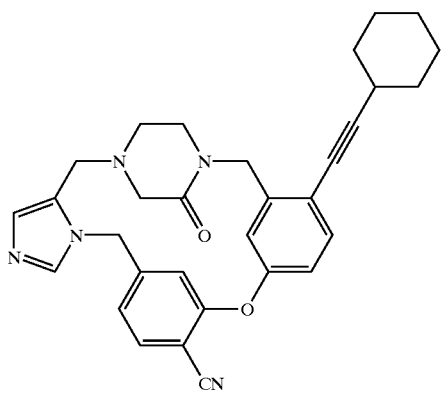

35

To a solution of the Example 32 aryl bromide (280 mg, 0.585 mmol) in 2 mL of dimethylformamide was added triethylamine (1.0 mL), copper(I) iodide (117 mg, 0.616 mmol), and (bis)triphenylphosphinepalladium dichloride (826 mg, 1.18 mmol). The reaction was heated to 90° C., and ethynylcyclohexane (1.0 mL mL) was added. After 1.5 hours, the solution was poured into EtOAc and washed with saturated NaHCO$_3$ solution and brine, dried (Na$_2$SO$_4$), filtered, and concentrated in vacuo. The resulting product was purified by silica gel chromatography (50–60% acetone/CH$_2$Cl$_2$, then 5–10% MeOH/CH$_2$Cl$_2$), followed by preparative reversed-phase HPLC. A portion of the product was taken up in CH$_2$Cl$_2$ and treated with excess 1 M HCl/ether solution, and concentrated in vacuo to provide the titled product dihydrochloride as a white solid.

HMRS (ES) calculated for M+H$^+$: 506.2550. Found 506.2553. Analysis calculated for $C_{31}H_{31}N_5O_2 \cdot 2.50HCl \cdot 1.90H_2O$: C, 59.00; H, 5.96; N, 11.10; Found: C, 59.03; H, 5.95; N, 9.57.

Example 44

Preparation of 19,20-Dihydro-19-oxo-15-[2-(trimethylsilyl)ethynyl]-5H,17H-18,21-ethano-6,10:12,16-dimetheno-22H-imidazo[3,4-h][1,8,11,14]oxatriazacycloeicosine-9-carbonitrile (36), Dihydrochloride

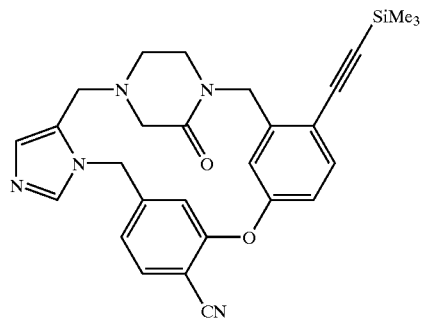

36

The titled product was prepared from the Example 32 aryl bromide (250 mg, 0.523 mmol) using the procedure described for Example 43, using trimethylsilylacetylene in place of ethynylcyclohexane. The product (138 mg, 53%) was isolated as a white solid. A portion of this was taken up in CH$_2$Cl$_2$ and treated with excess 1 M HCl/ether solution, and concentrated in vacuo to provide the titled product dihydrochloride as a white solid.

HMRS (ES) calculated for M+H$^+$: 496.2163. Found 496.2163. Analysis calculated for $C_{28}H_{29}N_5O_2Si \cdot 2.50HCl \cdot 2.40H_2O$: C, 53.37; H, 5.81; N, 11.12; Found: C, 53.36; H, 5.42; N, 10.30.

Example 45

Preparation of 19,20-Dihydro-15-(ethynyl)-19-oxo-5H,17H-18,21-ethano-6,10:12,16-dimetheno-22H-imidazo[3,4-h][1,8,11,14]oxatriaza-cycloeicosine-9-carbonitrile (37), Hydrochloride

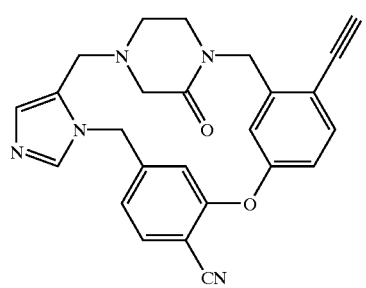

37

To a solution of the product of Example 44 (120 mg, 0.242 mmol) in 1 mL of methanol was added potassium carbonate (169 mg, 1.22 mmol). After 4 hours, the solution was poured into EtOAc and washed with saturated NaHCO$_3$ solution and brine, dried (Na$_2$SO$_4$), filtered, and concentrated in vacuo. The resulting product was taken up in CH$_2$Cl$_2$ and treated with excess 1 M HCl/ether solution, and concentrated in vacuo to provide the titled product hydrochloride as a white solid.

HMRS (ES) calculated for M+H$^+$: 424.1768. Found 424.1779. Analysis calculated for C$_{25}$H$_{21}$N$_5$O$_2$.1.20HCl.1.80H$_2$O: C, 60.09; H, 5.20; N, 14.02; Found: C, 60.08; H, 5.21; N, 13.18.

Example 46

Preparation of 19,20-Dihydro-3-methyl-19-oxo-5H, 17H-18,21-ethano-6,10:12,16-dimetheno-22H-imidazo[3,4-h][1,8,11,14]oxatriaza-cycloeicosine-9-carbonitrile (38), Dihydrochloride

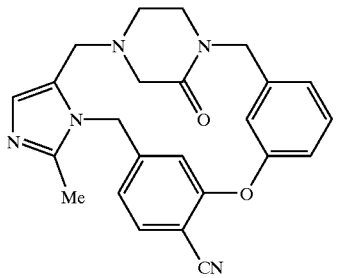

38

To a solution of the product of Example 33 (99.7 mg, 0.202 mmol) in 6 mL of 2-propanol was added saturated NaHCO$_3$ solution (0.5 mL) and 10% palladium on carbon (160 mg). The reaction was stirred under an atmosphere of hydrogen gas for 4 hours, then purged with argon. The solution was filtered through celite, and the filter pad was washed with methanol. The filtrate was concentrated in vacuo, taken up in dichloromethane, washed with water and brine, dried (Na$_2$SO$_4$), filtered, and concentrated in vacuo. The product was taken up in CH$_2$Cl$_2$, treated with excess 1 M HCl/ether solution, and concentrated in vacuo to provide the titled product dihydrochloride as a white solid.

HMRS (ES) calculated for M+H$^+$: 414.1924. Found 414.1924. Analysis calculated for C$_{24}$H$_{23}$N$_5$O$_2$.2.45HCl.0.50Et2O: C, 57.84; H, 5.69; N, 12.97; Found: C, 57.81; H, 5.57; N, 12.81.

Example 47

Preparation of 15-(Cyclohexylethynyl)-19,20-dihydro-3-methyl-19-oxo-5H,17H-18,21-ethano-6, 10:12,16-dimetheno-22H-imidazo[3,4-h][1,8,11,14] oxatriazacycloeicosine-9-carbonitrile (39), Dihydrochloride

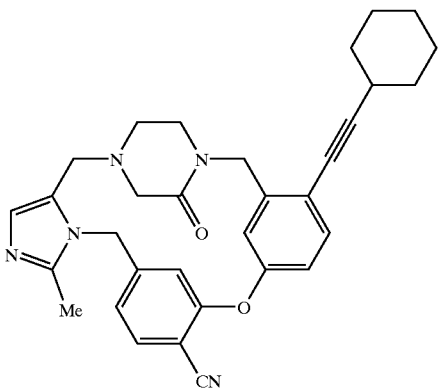

39

The titled product was prepared from the Example 33 aryl bromide (170 mg, 0.344 mmol) using the procedure described for Example 41, using ethynylcyclohexane in place of 3,3-dimethyl-1-butyne, and running the reaction in a sealed tube. The product (110 mg, 61%) was isolated as a white solid. A portion of this was taken up in CH$_2$Cl$_2$ and treated with excess 1 M HCl/ether solution, and concentrated in vacuo to provide the titled product dihydrochloride as a white solid.

HMRS (ES) calculated for M+H$^+$: 520.2707. Found 520.2729. Analysis calculated for C$_{32}$H$_{33}$N$_5$O$_2$.2.05HCl.1.85H$_2$O: C, 61.22; H, 6.22; N, 11.16; Found: C, 61.37; H, 6.22; N, 10.77.

Example 48

Preparation of 19,20-Dihydro-3-methyl-15-(1-octynyl)-19-oxo-5H,17H-18,21-ethano-6,10:12,16-dimetheno-22H-imidazo[3,4-h][1,8,11,14]oxatriaza-cycloeicosine-9-carbonitrile (40), Dihydrochloride

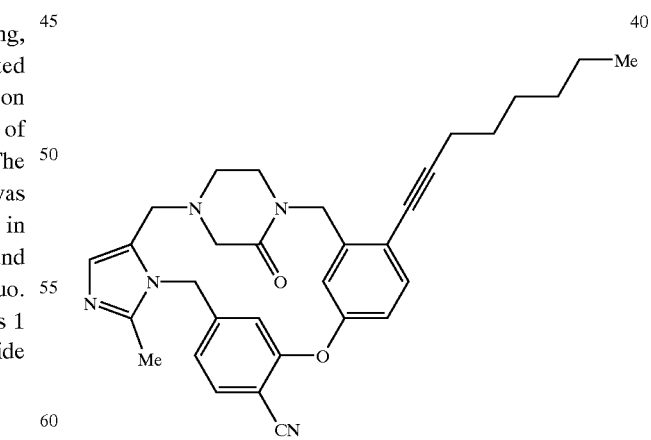

40

The titled product was prepared from the Example 33 aryl bromide (124 mg, 0.252 mmol) using the procedure described for Example 41, using 1-octyne in place of 3,3-dimethyl-1-butyne, and running the reaction in a sealed tube. The product (74 mg, 56%) was isolated as a white solid. A portion of this was taken up in CH₂Cl₂ and treated with excess 1 M HCl/ether solution, and concentrated in vacuo to provide the titled product dihydrochloride as a white solid.

HMRS (ES) calculated for M+H⁺: 522.2863. Found 522.2847. Analysis calculated for $C_{32}H_{35}N_5O_2 \cdot 2.50HCl \cdot 0.95Et2O$: C, 62.93; H, 6.93; N, 10.25; Found: C, 62.74; H, 6.69; N, 10.25.

Example 49

Preparation of 15-(3-Cyclohexyl-1-propynyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (41), Dihydrochloride

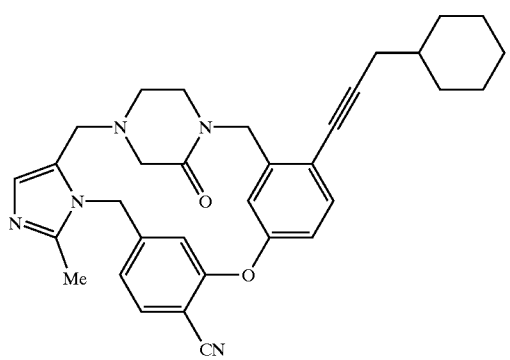

The titled product was prepared from the Example 33 aryl bromide (118 mg, 0.239 mmol) using the procedure described for Example 41, using 2-propyn-1-ylcyclohexane in place of 3,3-dimethyl-1-butyne, and running the reaction in a sealed tube. The product (60 mg, 44%) was isolated as a white solid. A portion of this was taken up in CH₂Cl₂ and treated with excess 1 M HCl/ether solution, and concentrated in vacuo to provide the titled product dihydrochloride as a white solid.

HMRS (ES) calculated for M+H⁺: 534.2863. Found 534.2865. Analysis calculated for $C_{33}H_{35}N_5O_2 \cdot 2.30HCl \cdot 1.80H_2O$: C, 60.98; H, 6.34; N, 10.78; Found: C, 60.94; H, 6.34; N, 9.51.

Example 50
Preparation of 15-(3-Cyclobutylethynyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (42), Hydrochloride

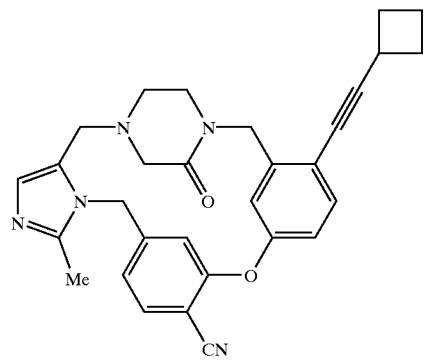

The titled product was prepared from the Example 33 aryl bromide (115 mg, 0.234 mmol) and the stannane described in Step A of Example 38, using the procedure described in Step B of Example 38. The resulting product was purified by preparative reversed-phase HPLC to give 55.6 mg (48%) as a white solid. A portion of the product was taken up in CH₂Cl₂ and treated with excess 1 M HCl/ether solution, and concentrated in vacuo to provide the titled product hydrochloride as a white solid.

HMRS (ES) calculated for M+H⁺: 492.2394. Found 492.2411. Analysis calculated for $C_{30}H_{29}N_5O_2 \cdot 1.85HCl \cdot 2.35H_2O$: C, 59.91; H, 5.96; N, 11.65; Found: C, 59.89; H, 5.96; N, 10.04.

Example 51
Preparation of 15-(3-Cyclopropylethynyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (43), Hydrochloride

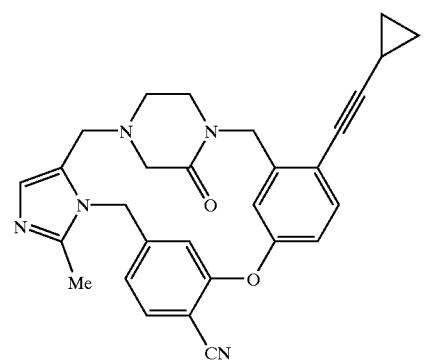

The titled product was prepared from the Example 33 aryl bromide (119 mg, 0.241 mmol) and the stannane described in Step A of Example 40, using the procedure described in Step B of Example 38. The resulting product was purified by preparative reversed-phase HPLC to give a white solid. A portion of the product was taken up in CH₂Cl₂ and treated with excess 1 M HCl/ether solution, and concentrated in vacuo to provide the titled product hydrochloride as a white solid.

HMRS (ES) calculated for M+H⁺: 478.2237. Found 478.2246. Analysis calculated for $C_{29}H_{27}N_5O_2 \cdot 1.40HCl \cdot 2.45H_2O$: C, 60.81; H, 5.86; N, 12.23; Found: C, 61.08; H, 5.99; N, 11.83.

Example 52

Preparation of 19,20-Dihydro-3-methyl-19-oxo-15-(5,5,5-trifluoro-1-pentynyl)-5H,17H-18,21-ethano-6,10:12,16-dimetheno-22H-imidazo[3,4-h][1,8,11,14]oxatriazacycloeicosine-9-carbonitrile (44), Hydrochloride

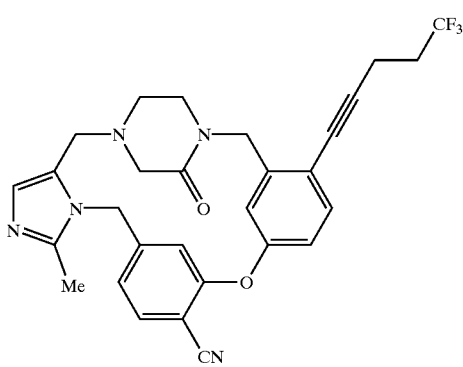

44

Step A: Preparation of 1,1-Dibromo-5,5,5-trifluoro-1-pentene

To a −78° C. solution of oxalyl chloride (4.13 mL, 47.4 mmol) in 60 mL of dichloromethane was added dimethylsulfoxide (4.76 mL, 67.1 mmol). After 10 minutes, 4,4,4-trifluorobutanol was added dropwise (5.059 g, 39.49 mmol), followed by dropwise addition of triethylamine (11.01 mL, 78.9 mmol). The solution was alowed to warm to room temperature over 30 minutes, and was quenched by the addition of saturated $NH_4Cl$ solution. The organic layer was separated and washed with brine to provide a solution of 4,4,4-trifluoro-1-butanal. To a second solution containing triphenylphosphine (31.1 g, 118 mmol) and carbontetrabromide (19.65 g, 59.2 mmol) in 50 mL of dichloromethane a 0° C. was added dropwise the aldehyde solution described above. Five minutes after complete addition, the reaction was diluted with 250 mL of hexane and 500 mL of water. The Organic layer was dried ($Na_2SO_4$), filtered, and concentrated in vacuo. The resulting material was triturated repeatedly with diethyl ether to remove triphenylphosphine oxide, giving the titled product.

Step B: Preparation of 5,5,5-Trifluoro-1-pentynyl-tri(n-butyl)stannane

To a −78° C. solution the product from Step A (0.935 mg, 3.31 mmol) in 10 mL of tetrahydrofuran was added n-BuLi solution (2.65 mL, 6.63 mmol, 2.5 M hexanes) dropwise. The reaction was stirred at −78° C. for one hour, then allowed to warm to room temperature for one hour. The solution was cooled to 0° C., and tributyltin chloride (0.898 mL, 3.31 mmol) was added. After 10 minutes, the solution was poured into hexane, washed with saturated $NaHCO_3$ solution and brine, dried ($Na_2SO_4$), filtered, and concentrated in vacuo. The product was isolated as a brown liquid which was used without further purification.

Step C: Preparation of Compound 44 Hydrochloride

To a solution of the product from Step B (250 mg, 0.618 mmol) and the Example 33 aryl bromide (101.7 mg, 0.206 mmol) in 1.0 mL of dimethylformamide in a sealed tube was added tetrakis(triphenylphosphine)palladium (36 mg, 0.031 mmol). The solution was heated to 110° C. After 14 hours, the solution was poured into EtOAc and washed with saturated $NaHCO_3$ solution and brine, dried ($Na_2SO_4$), filtered, and concentrated in vacuo. The resulting product was purified by silica gel chromatography (5–7% MeOH/ $CH_2Cl_2$) to provide the desired product (74 mg, 67%) as a brown solid. A portion of this was taken up in $CH_2Cl_2$ and treated with excess 1 M HCl/ether solution, and concentrated in vacuo to provide the titled product dihydrochloride as a pale yellow powder.

HMRS (ES) calculated for M+H$^+$: 534.2111. Found 534.2114. Analysis calculated for $C_{29}H_{26}F_3N_5O_2 \cdot 1.85HCl \cdot 2.50H_2O$: C, 53.94; H, 5.13; N, 10.85; Found: C, 54.33; H, 5.21; N, 9.85.

Example 53

Preparation of 19,20-Dihydro-3-methyl-19-oxo-15-(5,5,5-trifluoro-1-pentynyl)-5H,17H-18,21-ethano-12,16-imino-6,10-metheno-22H-imidazo[3,4-h][1,8,11,14]oxatriazacycloeicosine-9-carbonitrile (45), Dihydrochloride

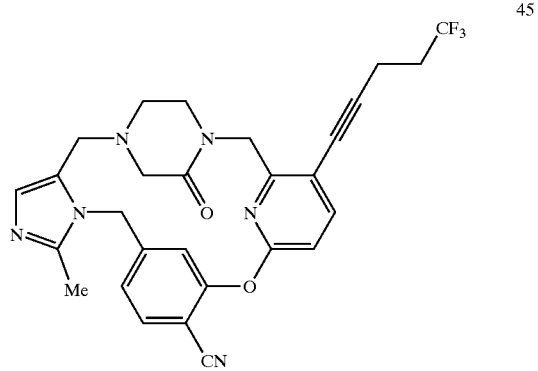

45

The titled compound was prepared from the Example 36 pyridyl bromide (111 mg, 0.225 mmol) using the procedure described in Step C of Example 52. The resulting product was purified by silica gel chromatography (0–6% MeOH/ $CH_2Cl_2$) to provide the desired product (95 mg, 80%) as a brown foam. A portion of this was taken up in $CH_2Cl_2$ and treated with excess 1 M HCl/ether solution, and concentrated in vacuo to provide the titled product dihydrochloride as a pale yellow powder.

HMRS (ES) calculated for M+H$^+$: 535.2069. Found 535.2064.

Example 54

Preparation of 19,20-Dihydro-19-oxo-15-(2-propenyl)-5H,17H-18,21-ethano-6,10:12,16-dimetheno-22H-imidazo[3,4-h][1,8,11,14]oxatriazacycloeicosine-9-carbonitrile (46), Hydrochloride

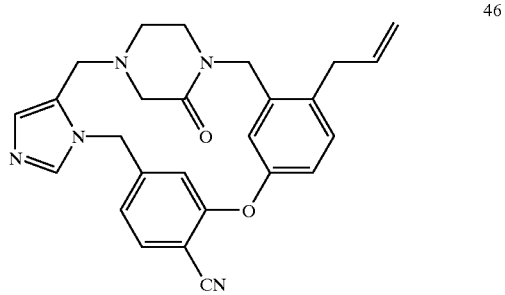

46

The titled product was prepared from the Example 32 aryl bromide (1.089 g, 2.28 mmol) using the procedure described in Step B of Example 38, except that allyltributylstannane was used in place of the alkynylstannane. The resulting material was purified by preparative reversed-phase HPLC to give the product as a white solid. A portion of the product was taken up in $CH_2Cl_2$ and treated with excess 1 M HCl/ether solution, and concentrated in vacuo to provide the titled product hydrochloride as a white solid.

HMRS (ES) calculated for M+H$^+$: 440.2081. Found 440.2106. Analysis calculated for $C_{26}H_{25}N_5O_2$.1.30HCl.2.15H$_2$O: C, 59.40; H, 5.87; N, 13.32; Found: C, 59.42; H, 5.86; N, 12.44.

Example 55

Preparation of 19,20-Dihydro-3-methyl-19-oxo-15-(2-propenyl)-5H,17H-18,21-ethano-6,10:12,16-dimetheno-22H-imidazo[3,4-h][1,8,11,14]oxatriazacycloeicosine-9-carbonitrile (47), Dihydrochloride

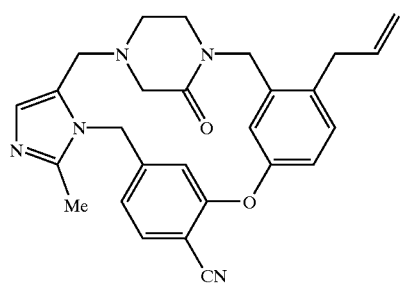

47

The titled product was prepared from the Example 33 aryl bromide (439 mg, 0.734 mmol) using the procedure described in Example 54. The resulting product was purified by silica gel chromatography (5% MeOH/CH$_2$Cl$_2$) to provide the desired product (270 mg, 68%) as a white solid. A portion of this was taken up in $CH_2Cl_2$ and treated with excess 1 M HCl/ether solution, and concentrated in vacuo to provide the titled product dihydrochloride as a white powder.

HMRS (ES) calculated for M+H$^+$: 454.2237. Found 454.2240.

Example 56

Preparation of 15-(Cyclopropyl)methyl-19,20-dihydro-19-oxo-5H,17H-18,21-ethano-6,10:12,16-dimetheno-22H-imidazo[3,4-h][1,8,11,14]oxatriazacycloeicosine-9-carbonitrile (48), Dihydrochloride

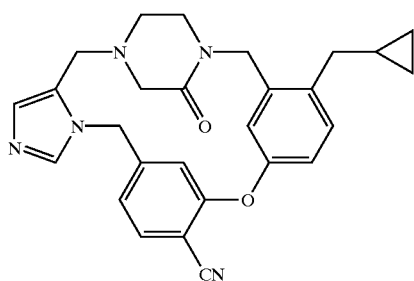

48

To a solution of the Example 54 olefin (89.0 mg, 0.202 mmol) in 1.5 mL of EtOAc at 0° C. containing Pd(OAc)$_2$ (3.5 mg, 0.016 mmol) was added excess ethereal diazomethane solution. After disappearance of the starting material as assessed by analytical HPLC, the solution was poured into EtOAc and washed with saturated NaHCO$_3$ solution and brine, dried (Na$_2$SO$_4$), filtered, and concentrated in vacuo. The resulting material was purified by preparative reversed-phase HPLC, then taken up in CH$_2$Cl$_2$ and treated with excess 1 M HCl/ether solution, and concentrated in vacuo to provide the titled product hydrochloride as a white solid.

HMRS (ES) calculated for M+H$^+$: 454.2237. Found 454.2239.

Example 57

Preparation of 19,20-Dihydro-15-methyl-19-oxo-5H,17H-18,21-ethano-6,10:12,16-dimetheno-22H-imidazo[3,4-h][1,8,11,14]oxatriazacycloeicosine-9-carbonitrile (49), Trihydrochloride

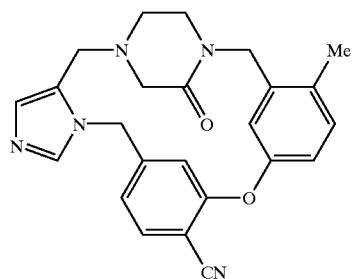

49

To a solution of the Example 32 aryl bromide (61.9 mg, 0.129 mmol) in 0.5 mL of HMPA and 0.5 mL DMF was added benzyl-bis-(triphenylphosphine)palladium dichloride (15 mg, 0.018 mmol) followed by tetramethylstannane (0.060 mL, 0.426 mmol). The reaction was heated at 120° C. for 24 hours. The solution was poured into EtOAc and washed with saturated NaHCO$_3$ solution and brine, dried (Na$_2$SO$_4$), filtered, and concentrated in vacuo. The resulting product was purified by silica gel chromatography (5–7% MeOH/CH$_2$Cl$_2$), then taken up in CH$_2$Cl$_2$ and treated with excess 1 M HCl/ether solution, and concentrated in vacuo to provide the titled product trihydrochloride as a white powder.

HMRS (ES) calculated for M+H$^+$: 414.1924. Found 414.1926. Analysis calculated for $C_{24}H_{23}N_5O_2$.3.60HCl.2.25H$_2$O: C, 49.31; H, 5.37; N, 11.98; Found: C, 49.28; H, 5.37; N, 12.50.

Example 58

Preparation of 19,20-Dihydro-3-methyl-19-oxo-15-pentyl-5H,17H-18,21-ethano-12,16-imino-6,10-metheno-22H-imidazo[3,4-h][1,8,11,14]oxatriazacycloeicosine-9-carbonitrile (50), Dihydrochloride

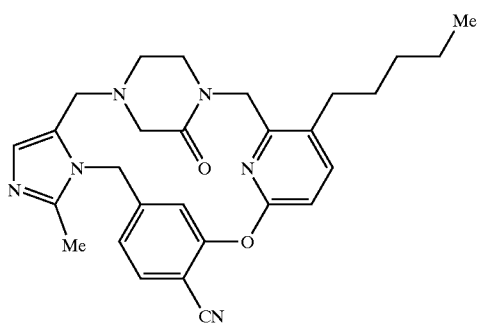

The titled compound was prepared from the Example 36 pyridyl bromide (35.4 mg, 0.072 mmol) using the procedure described for the preparation of Example 57, except that tetrapentylstannane was use instead of tetramethylstannane. The resulting product was purified by silica gel chromatography (3–5% MeOH/CH$_2$Cl$_2$), then taken up in CH$_2$Cl$_2$ and treated with excess 1 M HCl/ether solution, and concentrated in vacuo to provide the titled product dhydrochloride as a white powder.

HMRS(ES) calculated for M+H$^+$: 485.2659. Found 485.2677.

Example 59

Preparation of 19,20-Dihydro-15-(3,3-dimethyl-1-butyl)-19-oxo-5H,17H-18,21-ethano-6,10:12,16-dimetheno-22H-imidazo[3,4-h][1,8,11,14]oxatriazacycloeicosine-9-carbonitrile (51), Dihydrochloride

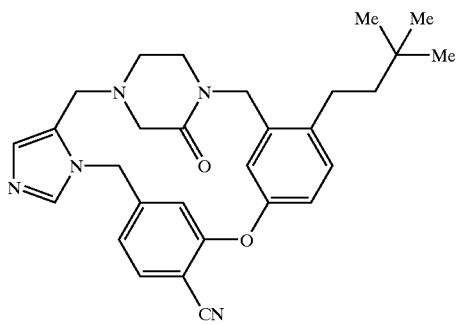

To a solution of the Example 41 alkyne (12.5 mg, 0.017 mmol) in 2 mL of ethanol was added 10% palladium on carbon (17.7 mg). The solution was stirred at room temperature under an atmosphere of hydrogen for 24 hours, then purged with argon. The mixture was filtered through celite, the filter pad was washed with methanol, and the filtrate was concentrated in vacuo to produce the crude material. This was taken up in CH$_2$Cl$_2$ and treated with excess 1 M HCl/ether solution, and concentrated in vacuo to provide the titled product dhydrochloride as a gray powder.

FAB mass spectrum m/e 484.3 (M+1).

Example 60

Preparation of 15-(2-Cyclohexyl-1-ethyl)-19,20-dihydro-19-oxo-5H,17H-18,21-ethano-6,10:12,16-dimetheno-22H-imidazo[3,4-h][1,8,11,14]oxatriazacycloeicosine-9-carbonitrile (52), Dihydrochloride

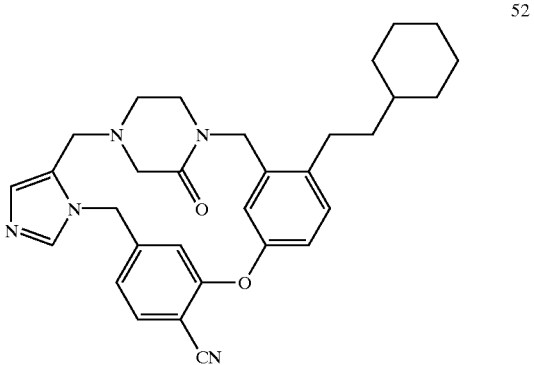

The titled product was prepared from the Example 43 alkyne (114.3 mg, 0.181 mmol) using the procedure described for the preparation of Example 59. The resulting material was purified by preparative reversed-phase HPLC, then taken up in CH$_2$Cl$_2$ and treated to with excess 1 M HCl/ether solution, and concentrated in vacuo to provide the titled product dihydrochloride as a white solid.

HMRS (ES) calculated for M+H$^+$: 510.2963. Found 510.2834. Analysis calculated for $C_{31}H_{35}N_5O_2$.2.25HCl.2.00H$_2$O: C, 58.46; H, 6.57; N, 11.00; Found: C, 58.43; H, 6.33; N, 9.24.

Example 61

Preparation of 19,20-Dihydro-15-ethyl-19-oxo-5H,17H-18,21-ethano-6,10:12,16-dimetheno-22H-imidazo[3,4-h][1,8,11,14]oxatriazacycloeicosine-9-carbonitrile (53), Dihydrochloride

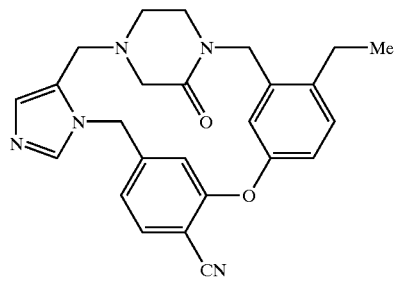

The titled product was prepared from the Example 45 alkyne (94.7 mg, 0.224 mmol) using the procedure described for the preparation of Example 59. The resulting material was taken up in CH$_2$Cl$_2$ and treated with excess 1 M HCl/ether solution, and concentrated in vacuo to provide the titled product dihydrochloride as a white solid.

HMRS (ES) calculated for M+H$^+$: 428.2081. Found 428.2090. Analysis calculated for $C_{25}H_{25}N_5O_2$.2.15HCl.1.25H$_2$O: C, 56.82; H, 5.66; N, 13.25; Found: C, 56.87; H. 5.66; N, 12.65.

Example 62

Preparation of 19,20-Dihydro-19-oxo-15-propyl-5H, 17H-18,21-ethano-6,10:12,16-dimetheno-22H-imidazo[3,4-h][1,8,11,14]oxatriazacycloeicosine-9-carbonitrile (54), Dihydrochloride

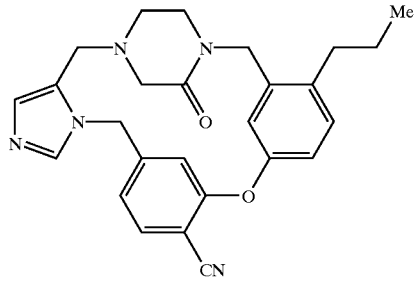

54

The titled product was prepared from the Example 54 olefin (82.0 mg, 0.187 mmol) using the procedure described for the preparation of Example 59. The resulting material was taken up in $CH_2Cl_2$ and treated with excess 1 M HCl/ether solution, and concentrated in vacuo to provide the titled product dihydrochloride as a white solid.

HMRS (ES) calculated for M+H$^+$: 442.2237. Found 442.2242. Analysis calculated for $C_{26}H_{27}N_5O_2 \cdot 2.15HCl \cdot 1.95H_2O$: C, 56.26; H, 6.00; N, 12.62; Found: C, 56.23; H, 6.00; N, 11.87.

Example 63

Preparation of 19,20-Dihydro-3-methyl-15-octyl-19-oxo-5H,17H-18,21-ethano-6,10:12,16-dimetheno-22H-imidazo[3,4-h][1,8,11,14]oxatriazacycloeicosine-9-carbonitrile (55), Dihydrochloride

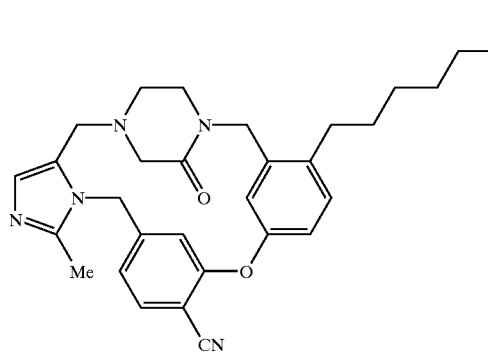

55

The titled product was prepared from the Example 48 alkyne (60.0 mg, 0.115 mmol) using the procedure described for the preparation of Example 59. The resulting material was taken up in $CH_2Cl_2$ and treated with excess 1 M HCl/ether solution, and concentrated in vacuo to provide the titled product dihydrochloride as a white solid.

HMRS (ES) calculated for M+H$^+$: 526.3176. Found 526.3168.

Example 64

Preparation of 15-(2-Cyclohexyl-1-ethyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (56), Dihydrochloride

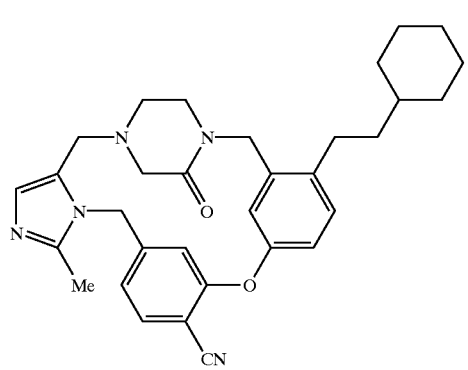

56

The titled product was prepared from the Example 47 alkyne (84.1 mg, 0.162 mmol) using the procedure described for the preparation of Example 59. The resulting material was taken up in $CH_2Cl_2$ and treated with excess 1 M HCl/ether solution, and concentrated in vacuo to provide the titled product dihydrochloride as a white solid.

HMRS (ES) calculated for M+H$^+$: 524.3020. Found 524.3040.

Example 65

Preparation of cis-15-(2-Cyclopropyl-1-ethenyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (57),

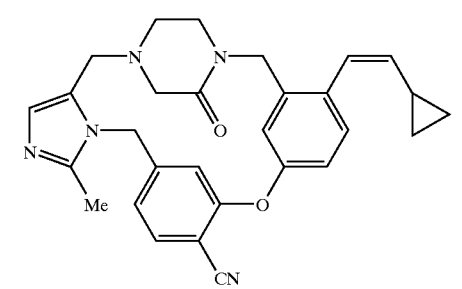

57

To a solution of the Example 51 alkyne (57 mg, 0.119 mmol) in ca. 10 mL of 1:1 dichloromethane/methanol was added palladium black (17 mg). The solution was stirred at room temperature under an atmosphere of hydrogen for one hour, then purged with argon. The mixture was filtered through celite, the filter pad was washed with methanol, and the filtrate was concentrated in vacuo to produce the crude material.

ES mass spectrum m/e 480.3 (M+1).

Example 66

Preparation of 15-(2-Cyclopropyl-1-ethyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (58), Dihydrochloride

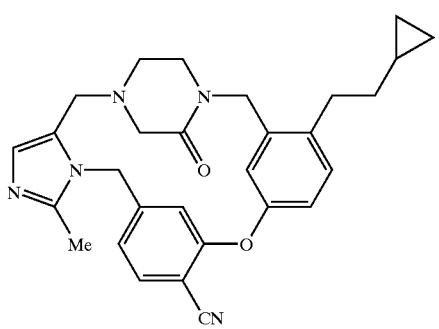

58

The titled product was prepared from the Example 65 olefin (60 mg) using the procedure described for the preparation of Example 65 (3 day reaction time). The resulting material was purified by preparative reversed-phase HPLC, then taken up in $CH_2Cl_2$/MeOH and treated with excess 1 M HCl/ether solution, and concentrated in vacuo to provide the titled product dihydrochloride as a white solid.

HMRS (ES) calculated for M+H$^+$: 482.2550. Found 482.2550. Analysis calculated for $C_{29}H_{31}N_5O_2$·2.50HCl·2.20CH$_3$OH: C, 58.25; H, 6.63; N, 10.89; Found: C, 58.25; H, 6.20; N, 10.53.

Example 67

Preparation of 19,20-Dihydro-3-methyl-19-oxo-15-(5,5,5-trifluoropentyl)-5H,17H-18,21-ethano-6,10:12,16-dimetheno-22H-imidazo[3,4-h][1,8,11,14]oxatriazacycloeicosine-9-carbonitrile (59), Dihydrochloride

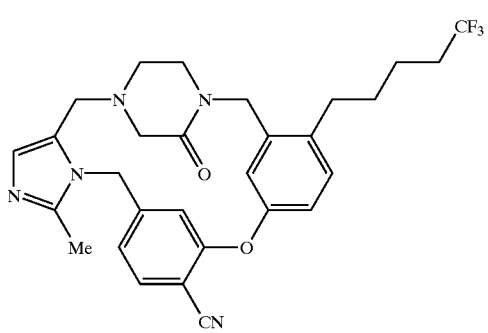

59

To a solution of the Example 52 alkyne (62 mg, 0.116 mmol) in 5 mL of 3:2 EtOH/EtOAc was added palladium black (40 mg). The solution was stirred at room temperature under an atmosphere of hydrogen for 20 hours, then purged with argon. The mixture was filtered through celite, the filter pad was washed with methanol/EtOAc, and the filtrate was concentrated in vacuo to produce the crude material. This was taken up in $CH_2Cl_2$ and treated with excess 1 M HCl/ether solution, and concentrated in vacuo to provide the titled product dihydrochloride as a brown powder.

HMRS (ES) calculated for M+H$^+$: 538.2435. Found 538.2437.

Example 68

Preparation of 19,20-Dihydro-3-methyl-19-oxo-15-(5,5,5-trifluoropentyl)-5H,17H-18,21-ethano-12,16-imino-6,10-metheno-22H-imidazo[3,4-h][1,8,11,14]oxatriazacycloeicosine-9-carbonitrile (60), Dihydrochloride

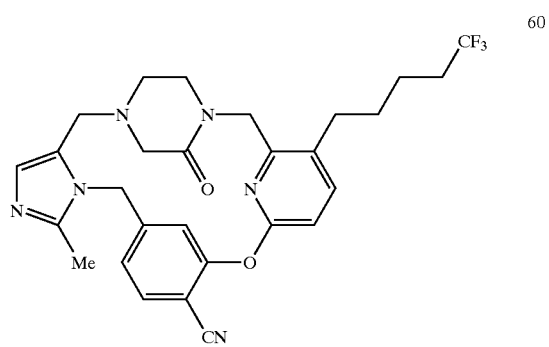

60

To a solution of the Example 53 alkyne (84 mg, 0.157 mmol) in 10 mL of 1:1 EtOH/EtOAc was added 10% palladium on carbon (110 mg). The solution was stirred at room temperature under an atmosphere of hydrogen for 48 hours, then purged with argon. The mixture was filtered through celite, the filter pad was washed with copious methanol/EtOAc, and the filtrate was concentrated in vacuo to produce the crude material. This was purified by silica gel chromatography (5–10% MeOH/$CH_2Cl_2$), then taken up in $CH_2Cl_2$ and treated with excess 1 M HCl/ether solution, and concentrated in vacuo to provide the titled product dhydrochloride as a white powder.

HRMS (FAB) calculated for M+H$^+$: 539.2382. Found 539.2383.

Example 69

Preparation of 9-Cyano-19,20-dihydro-19-oxo-5H,17H-18,21-ethano-6,10:12,16-dimetheno-22H-imidazo[3,4-h][1,8,11,14]oxatriazacycloeicosine-15-carboxylic Acid Methyl Ester (61), Hydrochloride

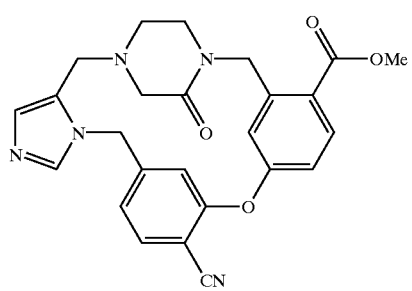

61

To a solution of the Example 32 aryl bromide (505 mg, 1.06 mmol) in 6 mL of methanol and 3 mL of DMSO was added triethylamine (0.60 mL, 4.3 mmol), Pd(OAc)$_2$ (50 mg, 0.22 mmol), and 1,3-bis-(diphenylphosphine)propane (90 mg, 0.22 mmol). The reaction was heated at 60° C. under an atmosphere of carbon monoxide for 26 hours, cooled to room temperature, and then treated with excess trimethylsilyldiazomethane. The solution was poured into EtOAc and washed with saturated NaHCO$_3$ solution and brine, dried (Na$_2$SO$_4$), filtered, and concentrated in vacuo. The resulting product was purified by silica gel chromatography (50% acetone/CH$_2$Cl$_2$, then 10% MeOH/CH$_2$Cl$_2$) to give a white solid (167 mg, 31%). A portion of this was taken up in CH$_2$Cl$_2$ and treated with excess 1 M HCl/ether solution, concentrated in vacuo, and truturated with hexane to provide the titled product hydrochloride as a white powder.

HMRS (ES) calculated for M+H$^+$: 458.1823. Found 458.1827. Analysis calculated for C$_{29}$H$_{29}$N$_5$O$_2$.0.85HCl.1.95H$_2$O: C, 57.34; H, 5.34; N, 13.38; Found: C, 57.33; H, 5.34; N, 12.41.

Example 70

Preparation of 9-Cyano-19,20-dihydro-19-oxo-5H,17H-18,21-ethano-6,10:12,16-dimetheno-22H-imidazo[3,4-h][1,8,11,14]oxatriazacycloeicosine-15-carboxylate, Lithium Salt (62)

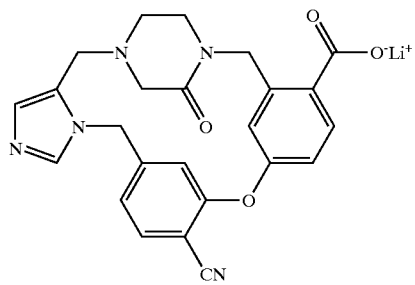

62

To a solution of the Example 69 methyl ester (64.2 mg, 0.140 mmol) in 0.60 mL of 2:1 tetrahydrofuran/water at 0° C. was added lithium hydroxide hydrate (6.4 mg, 0.153 mmol). The solution was stirred at 0° C. for 5 hours, then concentrated in vacuo to provide the titled product.

HRMS (FAB) calculated for M+H$^+$: 444.1666. Found 444.1657.

Example 71

Preparation of N-(2-Adamantyl)-9-cyano-19,20-dihydro-19-oxo-5H,17H-18,21-ethano-6,10:12,16-dimetheno-22H-imidazo[3,4-h][1,8,11,14]oxatriazacycloeicosine-15-carboxamide (63), Hydrochloride

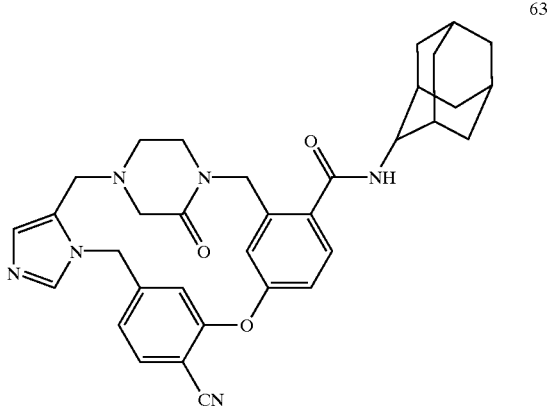

63

To a solution of the Example 71 lithium carboxylate salt (32.8 mg, 0.023 mmol) and 2-adamantanamine hydrochloride (20.8 mg, 0.111 mmol) in 0.50 mL of dimethylformamide was added triethylamine (0.031 mL, 0.222 mmol), 1-hydroxybenzotriazole hydrate (15.7 mg, 0.116 mmol) and 1-(dimethylaminopropyl)-3-ethylcarbodiimide hydrochloride (19.7 mg, 0.103 mmol). The solution was stirred for 2 days, then partitioned between EtOAc and saturated NaHCO$_3$ solution. The organic layer was washed with water and brine, dried (Na$_2$SO$_4$), filtered, and concentrated in vacuo. The resulting material was taken up in CH$_2$Cl$_2$ and treated with excess 1 M HCl/ether solution, and concentrated in vacuo to provide the titled product hydrochloride as a white powder.

HMRS (ES) calculated for M+H$^+$: 577.2921. Found 577.2918. Analysis calculated for C$_{34}$H$_{36}$N$_6$O$_3$.0.80HCl.2.50H$_2$O: C, 62.73; H, 6.47; N, 12.91; Found: C, 62.69; H, 6.93; N, 10.48.

Example 72

Preparation of (±)-19,20-Dihydro-15-(2,3-dihydroxy-1-propyl)-19-oxo-5H,17H-18,21-ethano-6,10:12,16-dimetheno-22H-imidazo[3,4-h][1,8,11,14]oxatriazacycloeicosine-9-carbonitrile (64), Hydrochloride

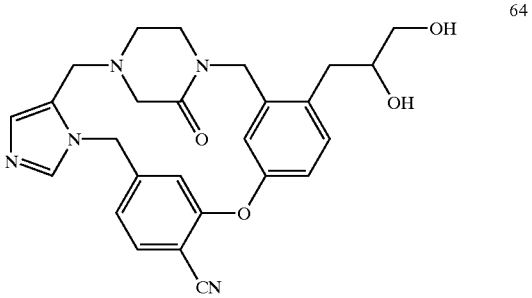

64

To a solution of $K_2OsO_4 \cdot 2H_2O$ (15.2 mg, 0.041 mmol), $K_3Fe(CN)_6$ (364 mg, 1.11 mmol) and quinuclidine (6.4 mg, 0.063 mmol) in 9 mL of 1:1 tert-butanol/water at 0° C. was added a solution of the Example 54 olefin (160 mg, 0.364 mmol) in 7 mL of 1:1 tert-butanol/water. Two additional portions of reagents were added over the course of 48 hours to drive the reaction to completion. The solution was poured into EtOAc and washed with saturated $NaHCO_3$ solution and brine, dried ($Na_2SO_4$), filtered, and concentrated in vacuo. A portion of this was taken up in $CH_2Cl_2/MeOH$ and treated with excess 1 M HCl/ether solution, concentrated in vacuo, and triturated with hexane to provide the titled product hydrochloride as a white powder.

HMRS (ES) calculated for M+H$^+$: 474.2135. Found 474.2115. Analysis calculated for $C_{26}H_{27}N_5O_4 \cdot 1.95HCl \cdot 1.90CH_3OH$: C, 55.34; H, 6.08; N, 11.57; Found: C, 55.33; H, 5.68; N, 11.54.

Example 73

Preparation of (±)-19,20-Dihydro-15-(2,3-dihydroxy-1-propyl)-3-methyl-19-oxo-5H,17H-18,21-ethano-6,10:12,16-dimetheno-22H-imidazo[3,4-h][1,8,11,14]oxatriazacycloeicosine-9-carbonitrile (65)

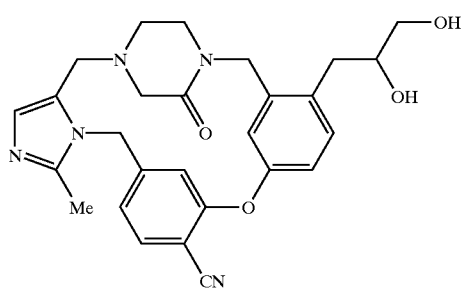

65

The titled product was prepared from the Example 55 olefin (469 mg, 0.826 mmol) using the procedure described for the preparation of Example 72. The titled product was isolated as a white solid.

Example 74

Preparation of (±)-19,20-Dihydro-15-[(2,2-dimethyl-1,3-dioxolano)-4-methyl]-19-oxo-5H,17H-18,21-ethano-6,10:12,16-dimetheno-22H-imidazo[3,4-h][1,8,11,14]oxatriazacycloeicosine-9-carbonitrile (66)

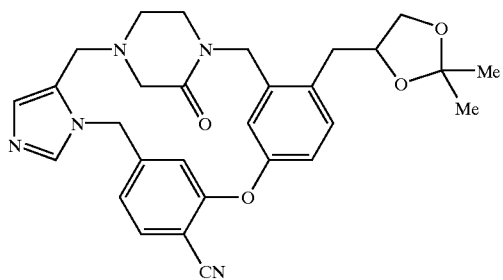

66

A solution of the Example 72 diol (51.8 mg, 0.109 mmol) and camphorsulfonic acid (37.3 mg, 0.161 mmol) in 10 mL of acetone was heated to reflux. After four hours, the solution was poured into EtOAc and washed with saturated $NaHCO_3$ solution and brine, dried ($Na_2SO_4$), filtered, and concentrated in vacuo. The titled product was isolated as a white solid.

HMRS (ES) calculated for M+H$^+$: 514.2449. Found 514.2467.

Example 75

Preparation of (±)-19,20-Dihydro-15-[(2,2-dimethyl-1,3-dioxolano)-4-methyl]-3-methyl-19-oxo-5H,17H-18,21-ethano-6,10:12,16-dimetheno-22H-imidazo[3,4-h][1,8,11,14]oxatriazacycloeicosine-9-carbonitrile (67)

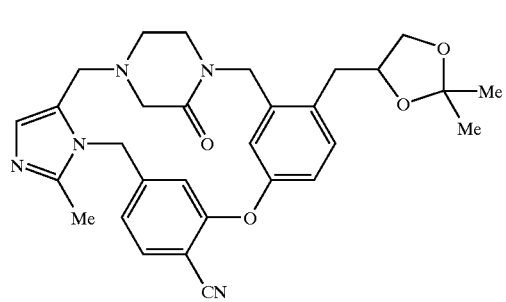

67

The titled product was prepared from the Example 73 diol (335 mg, 0.686 mmol) using the procedure described for the preparation of Example 74. The titled product was purified by silica gel chromatography (5% MeOH/$CH_2Cl_2$) to give the titled product as a white solid.

HRMS (FAB) calculated for M+H$^+$: 528.2611. Found 528.2622.

Example 76

Preparation of 19,20-Dihydro-3-methyl-19-oxo-15-phenyl-5H,17H-18,21-ethano-6,10:12,16-dimetheno-22H-imidazo[3,4-h][1,8,11,14]oxatriazacycloeicosine-9-carbonitrile (68), Dihydrochloride

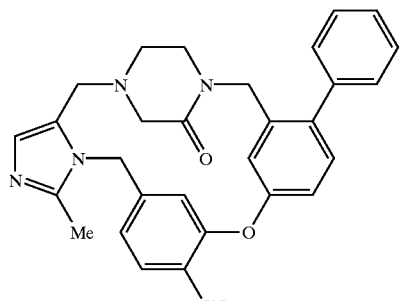

68

To the Example 34 aryl iodide (64.7 mg, 0.120 mmol) in 1.5 mL of 2:1 DME/water was added phenylboronic acid (33.3 mg, 0.273 mmol), potassium carbonate (81.4 mg, 0.589 mmol), and Pd(PPh$_3$)$_4$ (27.9 mg, 0.024 mmol). The solution was heated to 80° C. for 2.5 hours, then cooled to room temperature. The solution was poured into EtOAc and washed with saturated $NaHCO_3$ solution and brine, dried ($Na_2SO_4$), filtered, and concentrated in vacuo. The resulting product was purified by silica gel chromatography (5%

MeOH/CH$_2$Cl$_2$), then taken up in CH$_2$Cl$_2$ and treated with excess 1 M HCl/ether solution, and concentrated in vacuo to provide the titled product dihydrochloride as a white solid.

HRMS (FAB) calculated for M+H$^+$: 490.2247. Found 490.2257. Analysis calculated for C$_{30}$H$_{27}$N$_5$O$_2$·2.30HCl·0.65 DME: C, 61.95; H, 5.71; N, 11.08; Found: C, 61.96; H, 5.71; N, 11.09.

Example 77

Preparation of 19,20-Dihydro-15-(2-methoxyphenyl)-3-methyl-19-oxo-5H,17H-18,21-ethano-6,10:12,16-dimetheno-22H-imidazo[3,4-h][1,8,11,14]oxatriazacycloeicosine-9-carbonitrile (69), Dihydrochloride

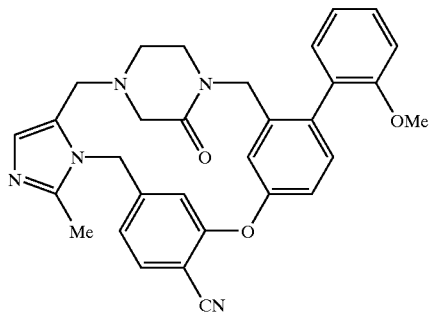

69

The titled product was prepared from the Example 34 aryl iodide (64.7 mg, 0.120 mmol) using the procedure described for the preparation of Example 76, except that 2-methoxyphenylboronic acid was used instead of phenylboronic acid. The titled dihydrochloride was isolated as a white solid.

HRMS (FAB) calculated for M+H$^+$: 520.2343. Found 520.2316. Analysis calculated for C$_{31}$H$_{29}$N$_5$O3·2.50HCl·2.50H$_2$O: C, 56.77; H, 5.61; N, 10.68; Found: C, 56.79; H, 5.15; N, 10.12.

Example 78

Preparation of 19,20-Dihydro-15-(3-methoxyphenyl)-3-methyl-19-oxo-5H,17H-18,21-ethano-6,10:12,16-dimetheno-22H-imidazo[3,4-h][1,8,11,14]oxatriazacycloeicosine-9-carbonitrile (70), Dihydrochloride

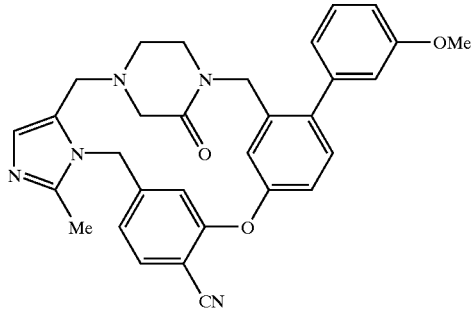

70

The titled product was prepared from the Example 34 aryl iodide (53.8 mg, 0.100 mmol) using the procedure described for the preparation of Example 76, except that 3-methoxyphenylboronic acid was used instead of phenylboronic acid. The titled dihydrochloride was isolated as a white solid.

HRMS (FAB) calculated for M+H$^+$: 520.2343. Found 520.2326. Analysis calculated for C$_{31}$H$_{29}$N$_5$O$_3$·2.50HCl·1.00H$_2$O: C, 59.20; H, 5.37; N, 11.14; Found: C, 59.20; H, 5.38; N, 10.25.

Example 79

Preparation of 19,20-Dihydro-15-(4-methoxyphenyl)-3-methyl-19-oxo-5H,17H-18,21-ethano-6,10:12,16-dimetheno-22H-imidazo[3,4-h][1,8,11,14]oxatriazacycloeicosine-9-carbonitrile (71), Dihydrochloride

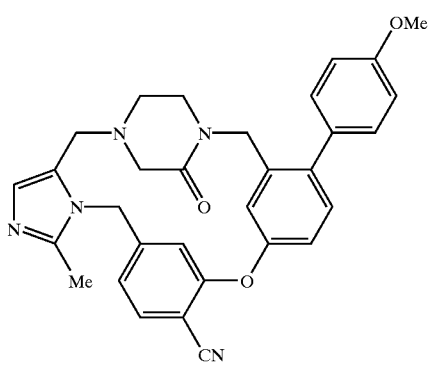

71

The titled product was prepared from the Example 34 aryl iodide (54.1 mg, 0.100 mmol) using the procedure described for the preparation of Example 76, except that 4-methoxyphenylboronic acid was used instead of phenylboronic acid. The titled dihydrochloride was isolated as a white solid.

HRMS (FAB) calculated for M+H$^+$: 520.2343. Found 520.2350.

Example 80

Preparation of 15-(2-Chlorophenyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (72), Hydrochloride

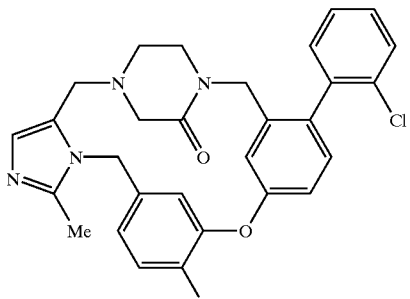

72

The titled product was prepared from the Example 34 aryl iodide (65.1 mg, 0.122 mmol) using the procedure described for the preparation of Example 76, except that 2-chlorophenylboronic acid was used instead of phenylboronic acid. The titled hydrochloride was isolated as a white solid.

HRMS (FAB) calculated for M+H⁺: 524.1847. Found 524.1833. Analysis calculated for $C_{30}H_{26}ClN_5O_2 \cdot 1.90HCl$: C, 60.73; H, 4.74; N, 11.80; Found: C, 60.75; H, 4.62; N, 11.10.

Example 81

Preparation of 15-(3-Chlorophenyl)-19,20-dihydro-3-methyl-19-oxo-5H,17H-18,21-ethano-6,10:12,16-dimetheno-22H-imidazo[3,4-h][1,8,11,14] oxatriazacycloeicosine-9-carbonitrile (73), Hydrochloride

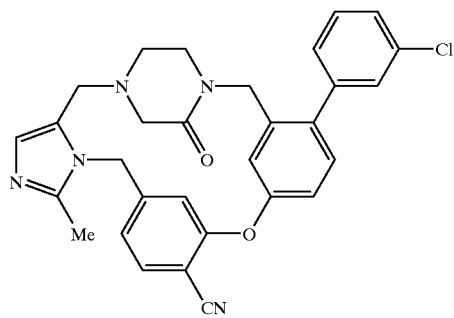

The titled product was prepared from the Example 34 aryl iodide (65.7 mg, 0.133 mmol) using the procedure described for the preparation of Example 76, except that 3-chlorophenylboronic acid was used instead of phenylboronic acid. The titled hydrochloride was isolated as a white solid.

HRMS (FAB) calculated for M+H⁺: 524.1847. Found 524.1845. Analysis calculated for $C_{30}H_{26}ClN_5O_2 \cdot 1.90HCl \cdot 2.00CH_3OH$: C, 58.46; H, 5.50; N, 10.65; Found: C, 58.49; H, 5.18; N, 8.70.

Example 82

Preparation of 15-(4-Chlorophenyl)-19,20-dihydro-3-methyl-19-oxo-5H,17H-18,21-ethano-6,10:12,16-dimetheno-22H-imidazo[3,4-h][1,8,11,14] oxatriazacycloeicosine-9-carbonitrile (74), Dihydrochloride

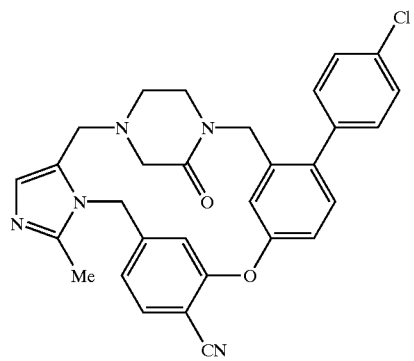

The titled product was prepared from the Example 34 aryl iodide (70.4 mg, 0.143 mmol) using the procedure described for the preparation of Example 76, except that 4-chlorophenylboronic acid was used instead of phenylboronic acid. The titled dihydrochloride was isolated as a white solid.

HRMS (FAB) calculated for M+H⁺: 524.1847. Found 524.1860. Analysis calculated for $C_{30}H_{26}ClN_5O_2 \cdot 1.90HCl \cdot 2.10H_2O$: C, 56.43; H, 5.10; N, 10.97; Found: C, 56.43; H, 5.11; N, 9.00.

Example 83

Preparation of 15-(2,4-Dichlorophenyl)-19,20-dihydro-3-methyl-19-oxo-5H,17H-18,21-ethano-6,10:12,16-dimetheno-22H-imidazo[3,4-h][1,8,11,14] oxatriazacycloeicosine-9-carbonitrile (75), Dihydrochloride

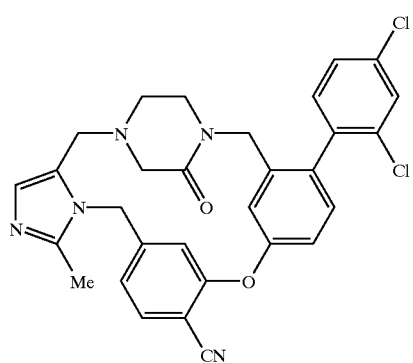

The titled product was prepared from the Example 34 aryl iodide (73 mg, 0.135 mmol) using the procedure described for the preparation of Example 76, except that 2,4-dichlorophenylboronic acid was used instead of phenylboronic acid. The titled dihydrochloride was isolated as a white solid.

HRMS (ES) calculated for M+H⁺: 558.1458. Found 558.1456. Analysis calculated for $C_{30}H_{25}Cl_2N_5O_2 \cdot 2.00HCl \cdot 1.55H_2O \cdot 0.60PPh_3$: C, 60.00; H, 4.83; N, 8.58; Found: C, 60.01; H, 4.98; N, 8.70.

Example 84

Preparation of 15-(3,5-Dichlorophenyl)-19,20-dihydro-3-methyl-19-oxo-5H,17H-18,21-ethano-6,10:12,16-dimetheno-22H-imidazo[3,4-h][1,8,11,14] oxatriazacycloeicosine-9-carbonitrile (76), Dihydrochloride

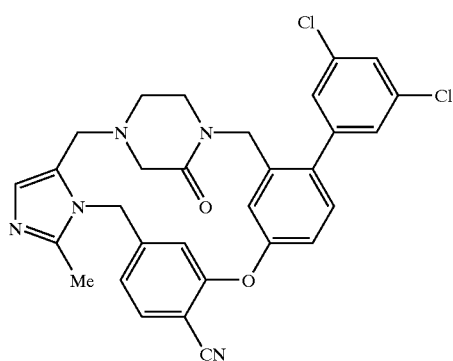

The titled product was prepared from the Example 34 aryl iodide (64.5 mg, 0.120 mmol) using the procedure described for the preparation of Example 76, except that 3,5- dichlorophenylboronic acid was used instead of phenylboronic acid. The titled dihydrochloride was 10 isolated as a white solid.

HRMS (ES) calculated for M+H$^+$: 558.1458. Found 558.1448.

Example 85

Preparation of 19,20-Dihydro-3-methyl-19-oxo-15-(3-thienyl)-5H,17H-18,21-ethano-6,10:12,16-dimetheno-22H-imidazo[3,4-h][1,8,11,14]oxatriazacycloeicosine-9-carbonitrile (77), Hydrochloride

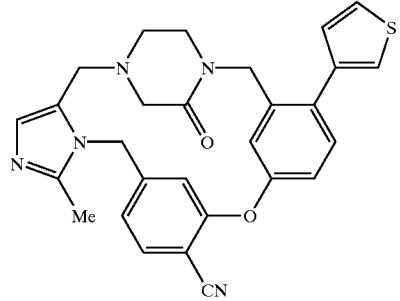

77

The titled product was prepared from the Example 34 aryl iodide (56.9 mg, 0.105 mmol) using the procedure described for the preparation of Example 76, except that 3-thiopheneboronic acid was used instead of phenylboronic acid. The titled hydrochloride was isolated as a white solid.

HRMS (ES) calculated for M+H$^+$: 496.1802. Found 496.1811. Analysis calculated for $C_{28}H_{25}N_5O_2S \cdot 1.40HCl \cdot 2.25CH_3OH$; C, 58.72; H, 5.77; N, 11.32; Found: C, 58.70; H, 5.76; N, 10.57.

Example 86

Preparation of 15-(Benzo[b]furan-2-yl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (78), Dihydrochloride

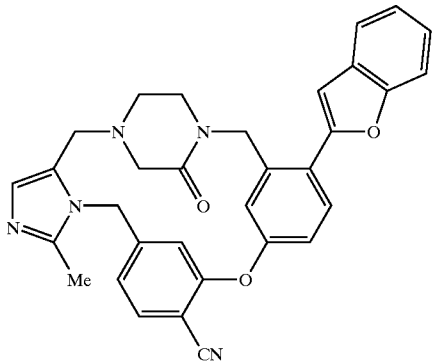

78

The titled product was prepared from the Example 34 aryl iodide (48.2 mg, 0.089 mmol) using the procedure described for the preparation of Example 76, except that benzo[b]furan-2-boronic acid was used instead of phenylboronic acid. The titled dihydrochloride was isolated as a white solid.

HRMS (FAB) calculated for M+H$^+$: 530.2192. Found 530.2167.

Example 87

Preparation of 19,20-Dihydro-15-[(methanesulfonyl)oxy]-19-oxo-5H,17H-18,21-ethano-6,10:12,16-dimetheno-22H-imidazo[3,4-h][1,8,11,14]oxatriazacycloeicosine-9-carbonitrile (79), Dihydrochloride

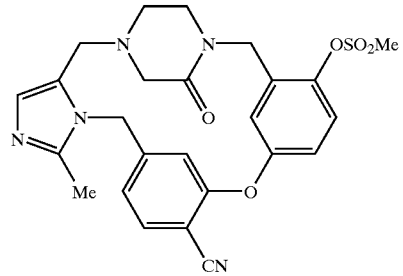

79

Step A: Preparation of 2.5-di-[(Methanesulfonyl)oxy]benzaldehyde

To a solution of 2,5-dihydroxybenzaldehyde (8.22 g, 59.5 mmol) in 100 mL of dichloromethane at 0° C. was added triethylamine (24.8 mL, 178 mmol), followed by dropwise addition of methanesulfonyl chloride (10.1 mL, 130 mmol). After 30 minutes, the solution was concentrated in vacuo, then partitioned between EtOAc and saturated NaHCO$_3$ solution. The organic layer was washed with water and brine, dried (Na$_2$SO$_4$), filtered, and concentrated in vacuo. The product was isolated as a brown oil which was used without further purification.

Step B: Preparation of 1,4-di-[(Methanesulfonyl)oxy]-2-(hydroxymethyl)benzene

To a solution of the product from Step A (17.13 g, 58.2 mmol) in 150 mL of 2:1 THF/ethanol at 0° C. was added sodium borohydride (2.27 g, 60.0 mmol). After 30 minutes, the reaction was carefully quenched by the addition oc saturated NH$_4$Cl solution, then partitioned between EtOAc and saturated NaHCO$_3$ solution. The organic layer was washed with water and brine, dried (Na$_2$SO$_4$), filtered, and concentrated in vacuo. The product was isolated as a yellow oil which was used without further purification.

Step C: Preparation of 1,4-di-[(Methanesulfonyl)oxy]-2-[((methanesulfonyl)oxy)methyl]benzene To a solution of the product from Step B (13.6 g, 45.9 mmol) in 100 mL of dichloromethane at 0° C. was added triethylamine (12.8 mL, 92.1 mmol), followed by dropwise addition of methanesulfonyl chloride (4.30 mL, 55.6 mmol). After 20 minutes, the solution was concentrated in vacuo, then partitioned between EtOAc and saturated NaHCO$_3$ solution. The organic layer was washed with water and brine, dried (Na$_2$SO$_4$), filtered, and concentrated in vacuo. The product was isolated as a brown solid which was used without further purification.

Step D: Preparation of 1-[2,5-di-((Methanesulfonyl)oxy)benzyl]-4-tert-butoxycarbonyl-2-piperazinone The titled compound was prepared from the product of Step C (13.3 g, 35.5 mmol) and the product from Example 32 Step C, using the procedure described in Step D of Example 32. After purification by silica gel chromatography (5% MeOH/CH$_2$Cl$_2$) the product was isolated as an impure mixture.

Step E: Preparation of 1-[2,5-di-((Methanesulfonyl)oxy)benzyl]-2-piperazinone Hydrochloride The titled compound was prepared from the product of Step D (6.07 g) using the procedure described in Step E of Example 32. The product was isolated as an impure mixture.

Step F: Preparation of 4-[1-(4-Cyano-3-fluorobenzyl)-5-imidazolylmethyl]-1-[2,5-di-((methanesulfonyl)oxy)benzyl]-2-piperazinone The titled compound was prepared from the product of Step E (100 mg, 0.241 mmol) and the product aldehyde from Step A of Example 10, using the procedure described in Step F of Example 32. After purification by silica gel chromatography (5% MeOH/CH$_2$Cl$_2$), the product was isolated as a solid.

Step G: Preparation of Compound 79 Dihydrochloride

The titled compound was prepared from the product of Step F (27 mg, 0.045 mmol) using the procedure described in Step G of Example 32. The product was taken up in CH$_2$Cl$_2$ and treated with excess 1 M HCl/ether solution, and concentrated in vacuo to provide the titled product dihydrochloride as a white powder.

HRMS (ES) calculated for M+H$^+$: 508.1649. Found 508.1641.

Example 88

Preparation of 15-Benzyloxy-19,20-dihydro-19-oxo-5H,17H-18,21-ethano-6,10:12,16-dimetheno-22H-imidazo[3,4-h][1,8,11,14]oxatriazacycloeicosine-9-carbonitrile (80), Dihydrochloride

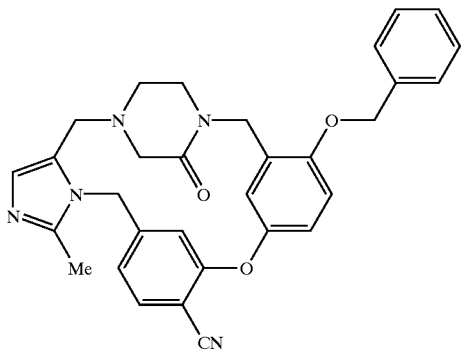

80

Step A: Preparation of 2-Benzyloxy-5-hydroxybenzaldehyde

To a solution of 2,5-dihydroxybenzaldehyde (10.41 g, 75.4 mmol) in 100 mL of DMF was added lithium carbonate (16.71 g, 226 mmol), followed by benzyl bromide (13.5 mL, 113 mmol). The solution was warmed to 60° C. and stirred for 30 hours. The reaction was poured into EtOAc and washed with water, saturated NaHCO$_3$ solution and brine, dried (Na$_2$SO$_4$), filtered, and concentrated in vacuo. The product was isolated as a brown oil which was used without further purification.

Step B: Preparation of 2-Benzyloxy-5-[(2-propenyl)oxy]benzaldehyde

To a solution of the product from Step A (75.4 mmol) in 100 mL of DMF was added potassium carbonate (20.8 g, 150.7 mmol), followed by allyl bromide (11.7 mL, 135 mmol). The reaction was warmed to 60° C. and stirred for one hour. The solution was poured into EtOAc and washed with water, saturated NaHCO$_3$ solution and brine, dried (Na$_2$SO$_4$), filtered, and concentrated in vacuo. The resulting product was purified by silica gel chromatography (20–30% EtOAc/hexane) to provide the titled product, along with unreacted starting material (4.39 g, 26%).

Step C: Preparation of 1-Benzyloxy-2-(hydroxymethyl)-5-[(2-propenyl)oxy]benzene

To a solution of the product from Step B (784 mg, 2.87 mmol) in 5 mL of ethanol at 0° C. was added sodium borohydride (114 mg, 3.01 mmol). After one hour, the reaction was partitioned between EtOAc and saturated NaHCO$_3$ solution. The organic layer was washed with water and brine, dried (Na$_2$SO$_4$), filtered, and concentrated in vacuo. The product was isolated as a yellow oil which was used without further purification.

Step D: Preparation of 1-Benzyloxy-2-[((methanesulfonyl)oxy)-methyl]-5-[(2-propenyl)oxy]benzene The titled compound was prepared from the product of Step C (725 mg, 2.68 mmol) using the procedure described in Step C of Example 87, except that methanesulfonic anhydride was used instead of methanesulfonyl chloride. The product was isolated as an orange oil.

Step E: Preparation of 1-[2-Benzyloxy-5-((2-propenyl)oxy)benzyl]-4-tert-butoxycarbonyl-2-piperazinone The titled compound was prepared from the product of Step D (700 mg, 2.01 mmol) and the product from Example 32 Step C, using the procedure described in Step D of Example 32. After purification by silica gel chromatography (25–50% EtOAc/hexane) the product was isolated as a yellow oil.

Step F: Preparation of 1-[2-Benzyloxy-5-((2-propenyl)oxy)benzyl]-2-piperazinone Hydrochloride The titled compound was prepared from the product of Step E (780 mg, 1.72 mmol) using the procedure described in Step E of Example 32. The product was isolated as a yellow solid.

Step G: Preparation of 4-[1-(4-Cyano-3-fluorobenzyl)-5-imidazolylmethyl]-1-[2-benzyloxy-5-((2-propenyl)oxy)benzyl]-2-piperazinone The titled compound was prepared from the product of Step F (633 mg, 1.63 mmol) and the product aldehyde from Step A of Example 10, using the procedure described in Step F of Example 32. The product was isolated as a yellow solid.

Step H: Preparation of 4-[1-(4-Cyano-3-fluorobenzyl)-5-imidazolylmethyl]-1-[2-hydroxy-5-((2-propenyl)oxy)benzyl]-2-piperazinone To a solution of the product of Step G (800 mg, 1.38 mmol) in 20 mL of THF at room temperature was added Pd(PPh$_3$)$_4$ (203 mg, 0.176 mmol), followed by sodium borohydride (86.2 mg, 2.28 mmol). The reaction was stirred for several hours, then poured into EtOAc and washed with water, saturated NaHCO$_3$ solution and brine, dried (Na$_2$SO$_4$), filtered, and concentrated in vacuo. The crude product was taken up in methanol, filtered, and the solids were dried in vacuo to afford the titled product as an off-white solid.

Step I: Preparation of Compound 80 Dihydrochloride

The titled compound was prepared from the product of Step H (184 mg, 0.266 mmol) using the procedure described in Step G of Example 32 to give 182 mg of crude product. A portion of this was taken up in CH$_2$Cl$_2$ and treated with excess 1 M HCl/ether solution, and concentrated in vacuo to provide the titled product dihydrochloride as a white powder.

HRMS (ES) calculated for M+H$^+$: 520.2343. Found 520.2367. Analysis calculated for C$_{31}$H$_{29}$N$_5$O$_3$.2.00HCl.0.45 H$_2$O: C, 61.99; H, 5.35; N, 11.66; Found: C, 62.01; H, 5.39; N, 10.98.

Example 89

Preparation of 19,20-Dihydro-15-hydroxy-19-oxo-5H,17H-18,21-ethano-6,10:12,16-dimetheno-22H-imidazo[3,4-h][1,8,11,14]oxatriazacycloeicosine-9-carbonitrile (81)

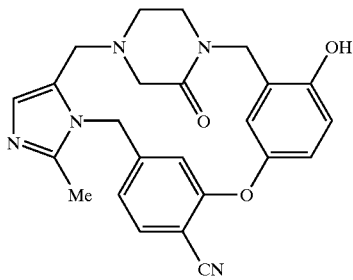

81

To a solution of the Example 88 benzyl ether (147 mg, 0.283 mmol) in 5 mL of ethanol was added 10% palladium on carbon (114 mg). The solution was stirred at room temperature under an atmosphere of hydrogen for 30 hours, then purged with argon. The mixture was filtered through celite, the filter pad was washed with methanol, then with acetone/$CH_2Cl_2$, and the filtrate was concentrated in vacuo to produce the crude material as a white powder.

ES mass spectrum m/e 430.3 (M+1).

Example 90

Preparation of 15-[(Cyclohexylmethyl)oxy]-19,20-dihydro-19-oxo-5H,17H-18,21-ethano-6,10:12,16-dimetheno-22H-imidazo[3,4-h][1,8,11,14]oxatriazacycloeicosine-9-carbonitrile (82), Dihydrochloride

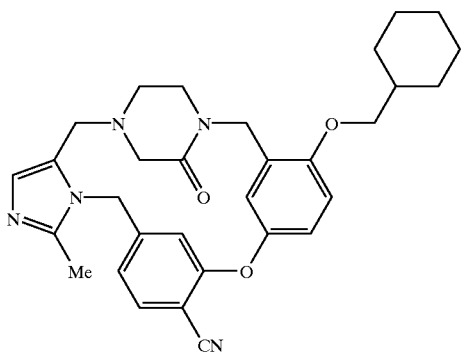

82

To a solution of the Example 89 phenol (375 mg, 0.873 mmol) in 2 mL of DMSO was added cesium carbonate (977 mg, 3.0 mmol) and bromomethylcyclohexane (0.122 mL, 0.874 mmol). The reaction was stirred at room temperature overnight, then poured into EtOAc and washed with water, saturated $NaHCO_3$ solution and brine, dried ($Na_2SO_4$), filtered, and concentrated in vacuo. After purification by silica gel chromatography (5% MeOH/$CH_2Cl_2$), the product was taken up in $CH_2Cl_2$ and treated with excess 1 M HCl/ether solution, and concentrated in vacuo to provide the titled product dihydrochloride as a white powder.

HRMS (ES) calculated for M+H$^+$: 526.2812. Found 526.2835. Analysis calculated for $C_{31}H_{35}N_5O_3 \cdot 2.25HCl \cdot 0.90H_2O$: C, 59.67; H, 6.31; N, 11.23; Found: C, 59.72; H, 6.32; N, 10.27.

Example 91

Preparation of 19,20-Dihydro-19-oxo-15-[(4,4,4-trifluoro-1-butyl)oxy]-5H,17H-18,21-ethano-6,10:12,16-dimetheno-22H-imidazo[3,4-h][1,8,11,14]oxatriazacycloeicosine-9-carbonitrile (83), Dihydrochloride

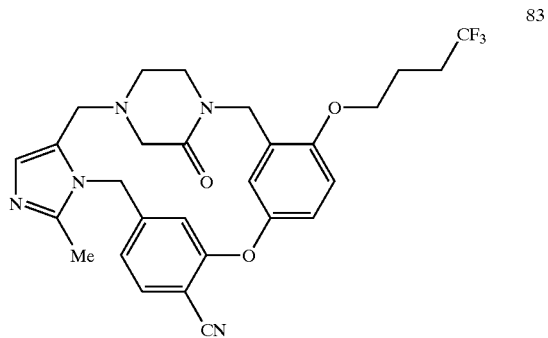

83

The titled product was prepared from the Example 89 phenol (88.9 mg, 0.207 mmol) using the procedure described for the preparation of Example 90, except that 1-iodo-4,4,4-trifluorobutane was used instead of bromomethylcyclohexane. The titled dihydrochloride was isolated as a white solid.

HRMS (ES) calculated for M+H$^+$: 540.2222. Found 540.2221. Analysis calculated for $C_{28}H_{28}N_5O_3F_3 \cdot 2.00HCl \cdot 1.15H_2O$: C, 53.11; H, 5.14; N, 11.06; Found: C, 53.46; H, 5.41; N, 10.67.

Example 92

Preparation of 19,20-Dihydro-19-oxo-15-phenoxy-5H,17H-18,21-ethano-6,10:12,16-dimetheno-22H-imidazo[3,4-h][1,8,11,14]oxatriazacycloeicosine-9-carbonitrile (84), Dihydrochloride

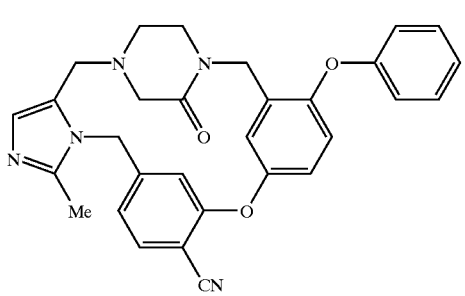

84

To a solution of the Example 89 phenol (24.5 mg, 0.057 mmol) in 0.80 mL of dichloromethane was added powdered 4 Å molecular sieves (78 mg), triethylamine (0.040 mL, 0.28 mmol), phenylboronic acid (11 mg, 0.090 mmol), and Cu(OAc)$_2$ (16.9 mg, 0.093 mmol). The reaction was stirred at room temperature overnight, then poured into EtOAc and washed with water, saturated NaHCO₃ solution and brine, dried (Na₂SO₄), filtered, and concentrated in vacuo. After purification by silica gel chromatography (1–5% MeOH/CH₂Cl₂), the product was taken up in CH₂Cl₂ and treated with excess 1 M HCl/ether solution, and concentrated in vacuo to provide the titled product dihydrochloride as a white powder.

ES mass spectrum m/e 506.3 (M+1). Analysis calculated for $C_{31}H_{29}N_5O_3 \cdot 2.00HCl \cdot 0.45H_2O$: C, 61.99; H, 5.35; N, 11.66; Found: C, 62.01; H, 5.39; N, 10.98.

Example 93

Preparation of 19,20-Dihydro-14-[(methanesulfonyl)oxy]-19-oxo-5H,17H-18,21-ethano-6,10:12,16-dimetheno-22H-imidazo[3,4-h][1,8,11,14]oxatriazacycloeicosine-9-carbonitrile (85), Dihydrochloride

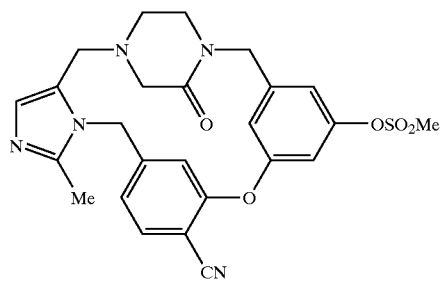

85

Step A: Preparation of 1,3-di-[(Methanesulfonyl)oxy]-5-[((methanesulfonyl)oxy)methyl]benzene To a solution of 3,5-dihydroxybenzyl alcohol (5.23 g, 37.3 mmol) in 80 mL of dichloromethane at 0° C. was added triethylamine (26.0 mL, 187 mmol), followed by methanesulfonic anhydride (26.02 g, 149 mmol). After 3.5 hours, the solution was concentrated in vacuo, then partitioned between EtOAc and saturated NaHCO₃ solution. The organic layer was washed with water and brine, dried (Na₂SO₄), filtered, and concentrated in vacuo. The product was used without further purification.

Step B: Preparation of 1-[3,5-di-((Methanesulfonyl)oxy)benzyl]-4-tert-butoxycarbonyl-2-piperazinone The titled compound was prepared from a portion of the product of Step C (1.37 g, 4.92 mmol) and the product from Example 32 Step C, using the procedure described in Step D of Example 32. Purification by silica gel chromatography (40–60% EtOAc/hexane) gave a mixture of the desired product and the corresponding des-methanesulfonyl adduct. This was taken up in in 10 mL of dichloromethane and cooled to 0° C. Triethylamine was added (0.37 mL), followed by methanesulfonyl chloride (0.154 mL). After one hour, the solution was partitioned between EtOAc and saturated NaHCO₃ solution. The organic layer was washed with water and brine, dried (Na₂SO₄), filtered, and concentrated in vacuo to provide the titled product.

Step C: Preparation of 1-[3,5-di-((Methanesulfonyl)oxy)benzyl]-2-piperazinone Hydrochloride The titled compound was prepared from the product of Step B (453 mg, 0.947 mmol) using the procedure described in Step E of Example 32. The product was isolated as a yellow solid.

Step D: Preparation of 4-[1-(4-Cyano-3-fluorobenzyl)-5-imidazolylmethyl]-1-[3,5-di-((methanesulfonyl)oxy)benzyl]-2-piperazinone The titled compound was prepared from the product of Step C (0.947 mmol) and the product aldehyde from Step A of Example 10, using the procedure described in Step F of Example 32. After purification by silica gel chromatography (5% MeOH/CH₂Cl₂), the product was isolated as a white solid.

Step E: Preparation of Compound 85 Dihydrochloride

The titled compound was prepared from the product of Step D (50.4 mg, 0.083 mmol) using the procedure described in Step G of Example 32. After reversed phase HPLC purification, the product was taken up in CH₂Cl₂ and treated with excess 1 M HCl/ether solution, and concentrated in vacuo to provide the titled product dihydrochloride as a white powder.

HRMS (ES) calculated for M+H⁺: 508.1649. Found 508.1664.

Example 94

Preparation of 14-[(Cyclohexylmethyl)oxy]-19,20-dihydro-19-oxo-5H,17H-18,21-ethano-6,10:12,16-dimetheno-22H-imidazo[3,4-h][1,8,11,14]oxatriazacycloeicosine-9-carbonitrile (86), Dihydrochloride

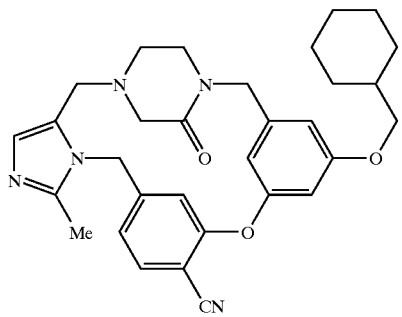

86

To a solution of the bis-mesylate from Step D of Example 93 (43.2 mg, 0.0713 mmol) in 2 mL of DMSO was added cesium carbonate (154 mg, 0.472 mmol), and the reaction was stirred at 80° C. overnight, then cooled to room temperature. Bromomethylcyclohexane (0.011 mL, 0.078 mmol) was added, and the reaction was stirred at room temperature. After 24 hours, an additional portion of bromomethylcyclohexane (0.0025 mL, 0.018 mmol) was added, and the reaction was stirred for another 24 hours. The solution was poured into EtOAc and washed with water, saturated NaHCO₃ solution and brine, dried (Na₂SO₄), filtered, and concentrated in vacuo. After purification by silica gel chromatography (5% MeOH/CH₂Cl₂), the product was taken up in CH₂Cl₂ and treated with excess 1 M HCl/ether solution, and concentrated in vacuo to provide the titled product dihydrochloride as a white powder.

HRMS (ES) calculated for M+H⁺: 526.2812. Found 526.2820. Analysis calculated for $C_{31}H_{35}N_5O_3 \cdot 2.30HCl \cdot 1.40H_2O$: C, 58.66; H, 6.37; N, 11.03; Found: C, 58.63; H, 6.37; N, 9.34.

Example 95

Preparation of 14-[(Cyclopropylmethyl)oxy]-19,20-dihydro-19-oxo-5H,17H-18,21-ethano-6,10:12,16-dimetheno-22H-imidazo[3,4-h][1,8,11,14]oxatriazacycloeicosine-9-carbonitrile (87), Dihydrochloride

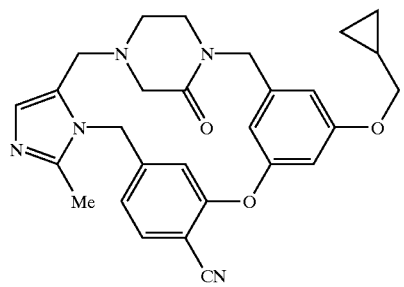

The titled product was prepared from the bis-mesylate from Step D of Example 93 (71.1 mg, 0.117 mmol) using the procedure described for the preparation of Example 94, except that bromomethylcyclopropane was used instead of bromomethylcyclohexane. After purification by silica gel chromatography (1–5% MeOH/CH$_2$Cl$_2$), the product was taken up in CH$_2$Cl$_2$ and treated with excess 1 M HCl/ether solution, and concentrated in vacuo to provide the titled product dihydrochloride as a white powder.

HRMS (ES) calculated for M+H$^+$: 484.2343. Found 484.2350. Analysis calculated for C$_{28}$H$_{29}$N$_5$O$_3$.2.20 HCl.1.00H$_2$O: C, 57.80; H, 5.75; N, 12.04; Found: C, 57.80; H, 5.74; N, 10.44.

Example 96

Preparation of 19,20-Dihydro-19-oxo-14-[(trifluoromethanesulfonyl)oxy]-5H,17H-18,21-ethano-6,10:12,16-dimetheno-22H-imidazo[3,4-h][1,8,11,14]oxatriazacycloeicosine-9-carbonitrile (88)

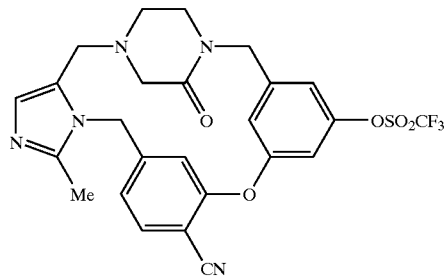

The titled product was prepared from the bis-mesylate from Step D of Example 93 (107.6 mg, 0.178 mmol) using the procedure described for the preparation of Example 94, except that N-phenyltriflimide was used instead of bromomethylcyclohexane. After purification by silica gel chromatography (5% MeOH/CH$_2$Cl$_2$), the product was isolated as a white solid.

ES mass spectrum m/e 562.3 (M+1).

Example 97

Preparation of 14-(3-Cyclopropylethynyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (89), Dihydrochloride

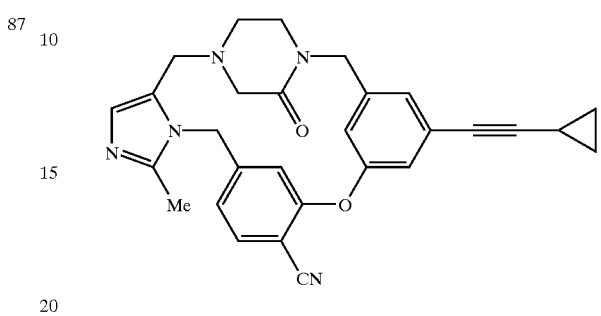

The titled product was prepared from the aryl triflate of Example 96 (57 mg, 0.078 mmol) and the stannane described in Step A of Example 40, using the procedure described in Step B of Example 38. The resulting product was purified by preparative reversed-phase HPLC to give 6.9 mg (18%) as a white solid. This was taken up in CH$_2$Cl$_2$ and treated with excess 1 M HCl/ether solution, and concentrated in vacuo to provide the titled product hydrochloride as a white solid.

HRMS (ES) calculated for M+H$^+$: 478.2237. Found 478.2252.

Example 98

Preparation of 19-oxo-19,20,22,23-tetrahydro-5H-18,21-ethano-12,14-etheno-6,10-metheno-benzo[d]imidazo[4,3-l][1,6,9,13]oxatriazacyclononadecine-9-carbonitrile (90), Dihydrochloride

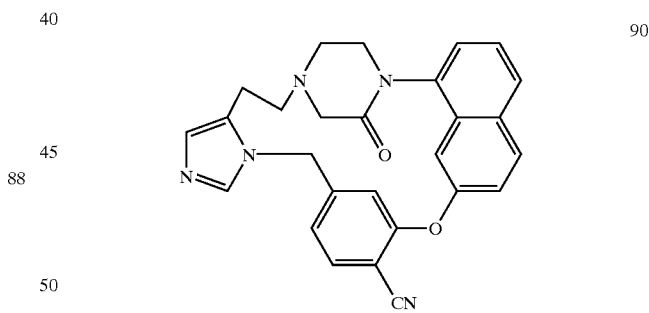

Step A: Preparation of 1-(Triphenylmethyl)-4-[2-(trifluoroacetamido)-1-ethyl]imidazole To a solution of histamine dihydrochloride (20 g, 109 mmol) in 300 mL of dichloromethane at 0° C. was added triethylamine (52.8 mL, 380 mmol), followed by trifluoroacetic anhydride (15.4 mL, 109 mmol). After 30 minutes, 700 mL of dimethylformamide was added, followed by an additional portion of triethylamine (18 mL, 129 mmol) and triphenylmethyl chloride (30.3 g, 109 mmol). The reaction was warmed to room tempeature, stirred for 2 hours, then quenched by the addition of 200 mL of water. The white precipitate was filtered, washed with water, and dried in vacuo to provide the titled product.

Step B: Preparation of 1-(Triphenylmethyl)-4-(2-amino-1-ethyl)imidazole

To a solution of the product from Step A (48.8 g, 109 mmol) in 1L of methanol was added 1M sodium hydroxide solution (325 mL, 325 mmol). Over the course of four days, additional methanol (3 L) and sodium hydroxide solution (325 mL, 325 mmol) were added. The solution was concentrated in vacuo, and partitioned between EtOAc and water. The organic layer was washed with brine, dried ($Na_2SO_4$), filtered, and concentrated in vacuo to provide the titled product.

Step C: Preparation of 1-(Chloroacetamido)-7-hydroxynaphthalene

To a solution of 8-amino-2-naphthol (10.0 g, 62.8 mmol) in 240 mL of 1:1EtOAc/saturated $NaHCO_3$ solution was added chloroacetyl chloride dropwise (5.5 mL, 69.1 mmol). After one hour, the solution was filtered, the layers were separated, and the aqueous layer was extracted with EtOAc. The combined organic layers were washed with brine, dried ($Na_2SO_4$), filtered, and concentrated in vacuo to provide the titled product.

Step D: Preparation of 1-(Chloroacetamido)-7-[(methanesulfonyl)oxy]naphthalene

To a solution of the product from Step C (14.0 g, 59.4 mmol) in 180 mL of dimethylformamide at 0° C. was added triethylamine (26.3 mL, 190 mmol), followed by methanesulfonyl chloride (10.5 mL, 137 mmol). The reaction was stirred overnight, allowing it to warm to room temperature. The solution was poured into EtOAc, washed with saturated $NH_4Cl$ solution, saturated aq. $NaHCO_3$ and brine, dried ($Na_2SO_4$), filtered, and concentrated in vacuo. The resulting product was used without further purification.

Step E: Preparation of N-[7-((Methanesulfonyl)oxy)naphthyl]-2-[N'-(2-(1-triphenylmethyl-4-imidazolyl)ethyl)amino]acetamide To a solution of the product from Step B (25.6 g, 72.7 mmol) in 200 mL of acetonitrile was added diisopropylethylamine (50 mL, 303 mmol), followed by the product from Step D (19.0 g, 60.5 mmol). The reaction was stirred at room temperature overnight, then concentrated in vacuo. The resulting material was partitioned between EtOAc and water, washed with brine, dried ($MgSO_4$), filtered, and concentrated in vacuo to provide the titled product.

Step F: Preparation of N-[7-((Methanesulfonyl)oxy)naphthyl]-2-[N'-(2-hydroxyethyl)-N'-(2-(1-triphenylmethyl-4-imidazolyl)ethyl)amino]acetamide To a solution of the crude product from Step F (60.5 mmol) in 400 mL of methanol was added glycol aldehyde (8.34 g, 69.7 mmol), and sodium cyanoborohydride (6.0 g, 95.1 mmol). The reaction was stirred at room temperature overnight, then concentrated in vacuo. The resulting material was partitioned between EtOAc and water, washed with brine, dried ($MgSO_4$), filtered, and concentrated in vacuo to provide the titled product.

Step G: Preparation of 1-[7-((Methanesulfonyl)oxy)naphthyl]-4-[2-(1-triphenylmethyl-4-imidazolyl)-ethyl]-2-piperazinone To a solution of the product from Step F (60.5 mmol) in 500 mL of tetrahydrofuran was added tributylphosphine (25 mL, 100 mmol). After cooling to 0° C., di-tert-butylazodicarboxylate (23 g, 100 mmol) was added, and the reaction was allowed to come to room temperature for 2 hours. The solution was concentrated in vacuo, partitioned between EtOAc and water, washed with brine, dried ($MgSO_4$), filtered, and concentrated in vacuo to provide the titled product (45.0 g). The crude product was purified by silica gel chromatography (5% $MeOH/CHCl_3$) to provide the pure titled product along with impure fractions.

Step H: Preparation of 4-Bromo-3-fluorobenzoic Acid

To a solution of 4-bromo-3-fluorotoluene (25.0 g, 132 mmol) in 230 mL of 1:1pyridine/water in a 3-necked flask equipped with a mechanical stirrer was added potassium permanganate (46 g, 289 mmol), and the reaction was heated to 70° C. After 1.5 hours. another portion of potassium permanganate (46 g, 289 mmol) was added. After 1.5 hours at 80° C. another portion of potassium permanganate (10 g, 62 mmol) was added. After several hours, the reaction was cooled to room temperature, filtered, and the precipitate was washed with water and ethanol. The filtrate was concentrated in vacuo, taken up in 3N sodium hydroxide solution, acidified with concentrated HCl solution, and filtered. The precipitate was washed with water and dried in vacuo to provide the titled product as a white solid.

Step I: Preparation of 4-Bromo-3-fluorobenzyl Alcohol

To a solution of the product from Step H (14.69 g, 67.0 mmol) in 40 mL of tetrahydrofuran at 0° C. was added borane in THF (141 mL, 141 mmol, 1M) dropwise, keeping the reaction temperature below 5° C. The solution was allowed to warm to room temperature, then stirred for one hour. The reaction was cautiously quenched at 0° C. with 50 mL of water, concentrated in vacuo, and partitioned between EtOAc and water. The aqueous layer was extracted twice with EtOAc, and the combined organic layers were washed with brine, dried ($Na_2SO_4$), filtered, and concentrated in vacuo to provide the titled product.

Step J: Preparation of 4-Cyano-3-fluorobenzyl Alcohol

To a degassed solution of the product from Step I (11.4 g, 55.6 mmol) in 100 mL of DMF was added $Zn(CN)_2$ (3.92 g, 33.4 mmol) and $Pd(PPh_3)_4$ (5.1 g, 4.45 mmol). The reaction was stirred at 90° C. overnight, cooled to room temperature, and concentrated in vacuo. Purification of this material by silica gel chromatography (50% EtOAc/hexane) provided the titled product as a light yellow solid.

Step K: Preparation of 1-[7-((Methanesulfonyl)oxy)naphthyl]-4-[2-(1-(4-cyano-3-fluorobenzyl)-5-imidazolyl)-ethyl]-2-piperazinone To a solution of the product from Step J (15 mg, 0.75 mmol) in 3 mL of dichloromethane at −78° C. was diisopropylethylamine (0.40 mL, 2.28 mmol), followed by triflic anhydride (0.128 mL, 0.76 mmol). After 20 minutes, a solution of the product from Step G (500 mg, 0.762 mmol) in 2 mL of dichloromethane was added, and the reaction was stirred at −78° C. for 30 minutes, and at room temperature for 1.5 hours. After concentrating the reaction in vacuo, 5 mL of methanol was added and the solution was heated at reflux for 30 minutes. The solution was concentrated in vacuo, acidified with 5% HCl solution, triturated with hexane, and partitioned between EtOAc and 20% NaOH solution. The organic layer was washed with brine, dried ($MgSO_4$), filtered, and concentrated in vacuo to provide the titled product.

Step L: Preparation of Compound 90 Dihydrochloride

The titled compound was prepared from the product of Step K (0.75 mmol) using the procedure described in Step G of Example 32. After purification by silica gel chromatography (8–10% $MeOH/CHCl_3$), the product was taken up in $CH_2Cl_2$ and treated with excess 1 M HCl/ether solution, and concentrated in vacuo to provide the titled product dihydrochloride as a white powder.

FAB mass spectrum m/e 450.2 (M+1). Analysis calculated for $C_{27}H_{23}N_5O_2 \cdot 2.00HCl \cdot 2.35H_2O$: C, 57.42; H, 5.30; N, 12.40; Found: C, 57.40; H, 5.33; N, 12.04.

Example 99

Preparation of 9-Bromo-19,20,22,23-tetrahydro-5H-18,21-ethano-12,14-etheno-6,10-metheno-benzo[d]imidazo[4,3-l][1,6,9,13]oxatriazacyclononadecine-19-one (91), Dihydrochloride

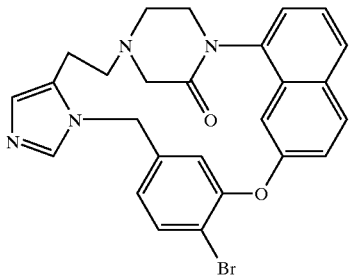

Step A: Preparation of 1-[7-((Methanesulfonyl)oxy)naphthyl]-4-[2-(1-(4-bromo-3-fluorobenzyl)-5-imidazolyl)-ethyl]-2-piperazinone The titled compound was prepared from the product of Step I of Example 98 (1.56 g, 7.61 mmol) and the product of Step G of Example 98 using the procedure described in Step K of Example 98. The crude product was used without further purification.

Step B: Preparation of Compound 91 Dihydrochloride

The titled compound was prepared from the product of Step A (200 mg, 0.33 mmol) using the procedure described in Step G of Example 32, except that the reaction was heated at 120° C. for six hours. After purification by silica gel chromatography (10% MeOH/CHCl$_3$), the product (30 mg, 18%) was taken up in CH$_2$Cl$_2$ and treated with excess 1 M HCl/ether solution, and concentrated in vacuo to provide the titled product dihydrochloride as a white powder.

ES mass spectrum m/e 503.11 (M+1). Analysis calculated for $C_{26}H_{23}BrN_4O_2 \cdot 2.30HCl \cdot 2.30H_2O$: C, 49.67; H, 4.79; N, 8.91; Found: C, 49.82; H, 4.80; N, 8.52.

Example 100

Preparation of 19,20,22,23-Tetrahydro-9-[4-(trifluoromethyl)phenyl]-5H-18,21-ethano-12,14-etheno-6,10-metheno-benzo[d]imidazo[4,3-l][1,6,9,13]oxatriazacyclononadecine-19-one (92), Dihydrochloride

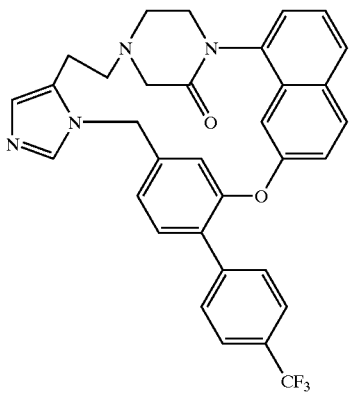

The titled product was prepared from the Example 99 aryl bromide (500 mg, 0.994 mmol) using the procedure described for the preparation of Example 76, except that 4-(trifluoromethyl)phenylboronic acid was used instead of phenylboronic acid. After purification by preparative reversed phase HPLC, the product was taken up in CH$_2$Cl$_2$ and treated with excess 1 M HCl/ether solution, and concentrated in vacuo to provide the titled product dihydrochloride as a white powder.

FAB mass spectrum m/e 569 (M+1). Analysis calculated for $C_{31}H_{29}N_5O_3 \cdot 2.10HCl \cdot 2.00H_2O$: C, 58.18; H, 4.90; N, 8.23; Found: C, 58.42; H, 4.90; N, 7.83.

Example 101

Preparation of 8-Chloro-19-oxo-19,20,22,23-tetrahydro-5H-18,21-ethano-12,14-etheno-6,10-metheno-benzo[d]imidazo[4,3-l][1,6,9,13]oxatriazacyclononadecine-9-carbonitrile (93), Dihydrochloride

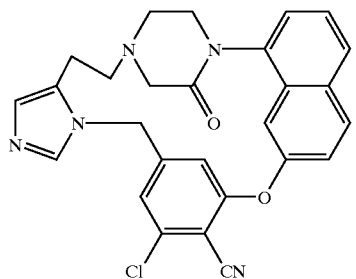

Step A: Preparation of 8-Amino-2-[(tert-butyldiphenylsilyl)oxy]-naphthalene

To a solution of 8-amino-2-naphthol (5.0 g, 31.4 mmol) in 200 mL of dimethylformamide was added imidazole (2.4 g, 34 mmol) and tert-butyldiphenylsilyl chloride (8.6 mL, 33 mmol). After 48 hours, water was added and the reaction was stirred overnight. The solution was partitioned between EtOAc and water, washed with brine, dried (MgSO$_4$), filtered, and concentrated in vacuo to provide the titled product (45.0 g). The crude product was purified by silica gel chromatography (10% EtOAc/hexane) to provide the pure titled product.

Step B: Preparation of 1-(Chloroacetamido)-7-[(tert-butyldiphenylsilyl)oxy]-naphthalene The titled compound was prepared from the product of Step A (6.5 g, 15.8 mmol) using the procedure described in Step C of Example 98. The product was used without further purification.

Step C: Preparation of 1-[7-((tert-Butyldiphenylsilyl)oxy)naphthyl]-4-[2-(1-triphenylmethyl-4-imidazolyl)-ethyl]-2-piperazinone The titled compound was prepared from the product of Step B and the product of Example 98 Step B using the procedures described in Step s E, F, and G of Example 98.

Step D: Preparation of 1-[7-((tert-Butyldiphenylsilyl)oxy)naphthyl]-4-[2-(1-(4-cyano-3,5-dichlorobenzyl)-5-imidazolyl)-ethyl]-2-piperazinone A solution of the product from Step C (500 mg, 0.613 mmol) and the product form Step C of Example 25 (163 mg, 0.613 mmol) in 5 mL of acetonitrile was stirred at room temperature for three days. The reaction was concentrated in vacuo, taken up in 5 mL of methanol, and heated at reflux for one hour. After concentration in vacuo, the crude product was purified by silica gel chromatography (1% NH$_4$OH/10% MeOH/CHCl$_3$) to provide the pure titled product.

Step E: Preparation of Compound 93 Dihydrochloride

165

A solution of the product from Step D (160 mg, 0.211 mmol) in 4 mL of propionitrile was added via syringe pump at a flow rate of 0.03 mL/minute to an 80° C. solution of 40 wt % potassium fluoride on alumina (280 mg) and 18-crown-6 (160 mg, 0.606 mmol) in 46 mL of propionitrile. After several hours, the reaction was cooled to room temperature, concentrated in vacuo, and taken up in EtOAc. The solution was washed with water and brine, dried ($Na_2SO_4$), filtered, and concentrated in vacuo. The resulting product was purified by preparative reversed phase HPLC, taken up in $CH_2Cl_2$ and treated with excess 1 M HCl/ether solution, and concentrated in vacuo to provide the titled product dihydrochloride as a white powder.

HRMS (ES) calculated for M+H$^+$: 484.1535. Found 484.1527. Analysis calculated for $C_{27}H_{22}ClN_5O_2 \cdot 2.00HCl \cdot 0.80H_2O$: C, 56.76; H, 4.52; N, 12.26; Found: C, 56.80; H, 4.97; N, 11.51.

Example 102

Preparation of 3-Methyl-19-oxo-19,20,22,23-tetrahydro-5H-18,21-ethano-12,14-etheno-6,10-metheno-benzo[d]imidazo[4,3-l][1,6,9,13]oxatriaza-cyclononadecine-9-carbonitrile (94), Dihydrochloride

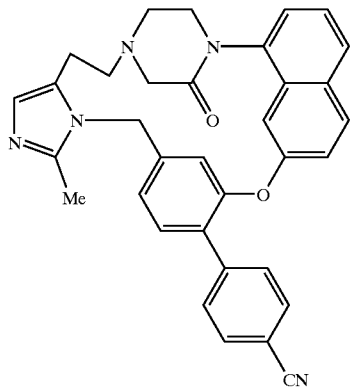

94

The titled compound was prepared using the same procedures described in Example 98, except that 4-(2-aminoethyl)-2-methylimidazole dihydrochloride was used instead of histamine dihydrochloride in Step A. After purification by silica gel chromatography (12% MeOH/CHCl$_3$), the product was taken up in $CH_2Cl_2$ and treated with excess 1 M HCl/ether solution, and concentrated in vacuo to provide the titled product dihydrochloride as a white powder.

FAB mass spectrum m/e 464.21 (M+1). Analysis calculated for $C_{28}H_{25}N_5O_2 \cdot 2.45HCl \cdot 2.15H_2O$: C, 56.84; H, 5.41; N, 11.84; Found: C, 56.99; H, 5.42; N, 11.45.

166

Example 103

Preparation of 18-oxo-18,19,20,21,22,23-Hexaahydro-5H-19,22-ethano-12,14-etheno-6,10-metheno-benzo[d]imidazo[4,3-l][1,7,10,13] oxatriazacyclononadecine-9-carbonitrile (95), Dihydrochloride

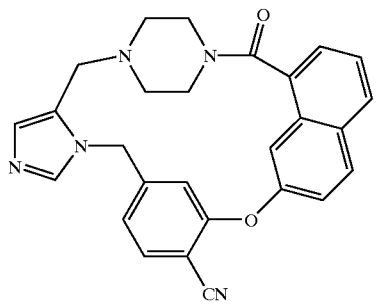

95

Step A: 8-Iodo-2-naphthol

8-Amino-2-naphthol (5.0 g, 31.4 mmol) was dissolved in THF (25 mL) and 3 N aqueous HCl (50 mL) was added. The mixture was cooled to 0° C. then a solution of NaNO$_2$ (2.38 g, 34.5 mmol) in H$_2$O (10 mL) was added. The resulting mixture was stirred at 0° C. for 40 min, then a solution of KI (20.9 g, 126 mmol) in H$_2$O (15 mL) was added, and stirring was continued for 30 min. The reaction mixture was extracted with EtOAc (2×200 mL). The combined organic extracts were washed with water (100 mL), then brine (100 mL), then dried over Na$_2$SO$_4$, filtered, and concentrated in vacuo. The residue was purified by flash column chromatography on silica, eluting with hexane—10% EtOAc to yield the desired product.

Step B: 2-Benzyloxy-8-iodonaphthalene

To a solution of the product from Step A (1.18 g, 4.37 mmol) in 20 mL of DMF was added cesium carbonate (2.48 g, 8.74 mmol) and benzyl bromide (0.52 mL, 4.37 mmol). After stirring overnight at room temperature, the reaction was poured into EtOAc and water, washed with 5% NaOH solution, water, 10% NaHSO$_3$ solution and brine, dried over MgSO$_4$, filtered, and concentrated in vacuo. The residue was purified by flash column chromatography on silica gel (5% EtOAc/hexane) to yield the desired product as a pink solid.

Step C: 7-Benzyloxy-1-naphthoic Acid

To a solution of the product from Step B (1.29 g, 3.58 mmol) in 20 mL of dry THF at −78° C. was added tert-butyllithium in pentane (4.2 mL, 7.16 mmol, 1.7 M). After stirring for 5 minutes at −78° C., carbon dioxide gas was bubbled through the solution for 5 minutes, and the reaction was allowed to warm to room temperature over one hour. After an additional 2 hours, the solution was concentrated in vacuo, then taken up in EtOAc and water. After acidifying to pH~1, the aqueous layer was extracted with EtOAc, and the combined organic layers were washed with brine, dried over MgSO$_4$, filtered, and concentrated in vacuo. The product was isolated as a yellow solid.

Step D: Preparation of 1-tert-Butyloxycarbonyl-4-(7-benzyloxy-1-naphthoyl)-piperazine To the product from Step C (3.58 mmol), N-tert-butoxycarbonylpiperazine (733 mg, 3.93 mmol), EDC hydrochloride (750 mg, 3.93 mmol), HOBT (483 mg, 3.58 mmol), and triethylamine (0.498 mL, 3.58 mmol) were stirred in dry DMF (15 mL) at room temperature for two days. After concentration in vacuo, the residue was partitioned between EtOAc and 50% NaHCO$_3$ solution, washed with water and brine, dried over MgSO₄, filtered, and concentrated in vacuo. The residue was purified by flash column chromatography on silica gel (30% EtOAc/hexane) to yield the desired product as a white foam.

Step E: Preparation of 1-tert-Butyloxycarbonyl-4-(7-hydroxy-1-naphthoyl)-piperazine To the product from Step D (1.10 g, 2.46 mmol) in 20 mL of methanol was added 20% palladium hydroxide on carbon (940 mg). The solution was stirred at room temperature under an atmosphere of hydrogen for 1.5 hours, then purged with argon. The mixture was filtered through celite, the filter pad was washed with methanol, and the filtrate was concentrated in vacuo to produce the crude material as a white solid.

Step F: Preparation of 1-tert-Butyloxycarbonyl-4-[7-(methanesulfonyl)oxy-1-naphthoyl]-piperazine To a solution of the product from Step E (426 mg, 1.19 mmol) in 5 mL of DMF at 0° C. was added triethylamine (0.532 mL, 3.82 mmol), followed by methanesulfonyl chloride (0.212 mL, 2.73 mmol). The reaction was stirred at room temperature overnight, then partitioned between EtOAc and 50% NaHCO₃ solution. The organic layer was washed with water and brine, dried (MgSO₄), filtered, and concentrated in vacuo. The product was isolated as a yellow gum which was used without further purification.

Step G: Preparation of 1-[7-(Methanesulfonyl)oxy-1-naphthoyl]-piperazine Trifluoroacetate To a solution of the product from Step F (560 mg, 1.20 mmol) in dichloromethane (40 mL) at 0° C. was added trifluoroacetic acid (10 mL). The solution was stirred for 2 hours and then concentrated in vacuo to yield the titled compound.

Step H: Preparation of 4-[1-(4-Cyano-3-fluorobenzyl)-5-imidazolylmethyl]-1-[(3-(methanesulfonyloxy)phenyl)-acetyl]piperazine To a solution of the product from Step G (348 mg, 1.04 mmol) and the aldehyde from Example 1Step G (445 mg, 1.50 mmol) in 8 mL of 1,2-dichloroethane was added 4A powdered molecular sieves (200 mg), followed by sodium triacetoxyborohydride (440 mg, 2.08 mmol). The reaction was stirred overnight, and a second portion of sodium triacetoxyborohydride (105 mg, 0.502 mmol) was added. After 4 days the reaction was poured into EtOAc, washed with sat. aq. NaHCO₃ and brine, dried (Na₂SO₄), filtered, and concentrated in vacuo. The crude product was purified by silica gel chromatography (1% NH₄OH/4% MeOH/CHCl₃) to provide the pure titled product.

Step I: Preparation of Compound 95 Dihydrochloride

The titled compound was prepared from the product of Step H (50 mg, 0.091 mmol) using the procedure described in Step E of Example 27, except that the syringe pump addition was done over a one hour interval. The crude product was purified on a C₁₈ preparative HPLC column and purified with a mixed gradient of 5%–95% acetonitrile/0.1% TFA; 95%–5%/0.1% aqueous TFA over 15 min. The titled compound was isolated after conversion to the dihydrochloride salt.

FAB mass spectrum m/e 450.2 (M+1). Analysis calculated for $C_{27}H_{23}N_5O_2 \cdot 2.00HCl \cdot 0.30H_2O$: C, 61.43; H, 4.89; N, 13.27; Found: C, 61.49; H, 4.96; N, 12.37.

Example 104

Preparation of 18-oxo-18,19,20,21,22,23-Hexaahydro-5H-19,22-ethano-12,14-etheno-6,10-metheno-24H-benzo[d]imidazo[4,3-m][1,7,10,14] oxatriazacycloeicosine-9-carbonitrile (96), Trihydrochloride

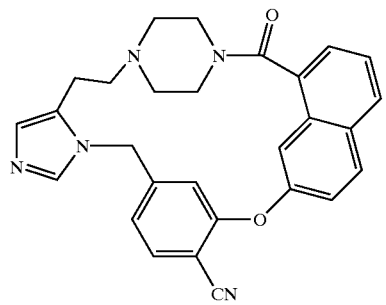

96

Step A: Preparation of 1-[2-(1-Triphenymethyl-4-imidazolyl)ethyl]-piperazine

A solution of 4-(2-chloroethyl)-1-(triphenylmethyl) imidazole (5.89 g, 15.8 mmol) and piperazine (27.2 g, 316 mmol) in ethanol (80 mL) were heated to reflux for 2 hours. The solvent was removed in vacuo and the residue partitioned between methylene chloride and saturated sodium bicarbonate. The organic layer was separated, washed with brine, dried (Na₂SO₄), filtered, and concentrated in vacuo to provide the titled product as a yellow oil which was sufficiently pure for use in the next step.

Step B: Preparation of 1-tert-Butoxycarbonyl-4-[2-(1-triphenymethyl-4-imidazolyl)ethyl]piperazine To a solution of the product from Step A (6.67 g, 15.8 mmol) and diisopropylethylamine (4.12 mL, 23.7 mmol) in methylene chloride (50 mL) was added di-tert-butyl dicarbonate (3.44 g, 15.8 mmol) in one portion. The reaction mixture was stirred overnight, then poured onto saturated sodium bicarbonate. The organic layer was separated, washed with brine, dried (Na₂SO₄), filtered, and concentrated in vacuo to provide the titled product as a yellow gum which was sufficiently pure for use in the next step.

Step C: Preparation of 1-tert-Butoxycarbonyl-4-[2-(1-(4-cyano-3-fluorobenzyl)-5-imidazolyl)ethyl]piperazine Trifluoromethanesulfonic anhydride (2.73 mL, 16.3 mmol) was added to a solution of the product from Step B (8.25 g, 15.8 mmol), the product of Step J of Example 98 (2.39 g, 15.8 mmol), and diisopropylethylamine (3.02 mL, 17.4 mmol) in methylene chloride (30 mL) at −78° C. The solution was slowly warmed to room temperature overnight and then concentrated in vacuo. The residue was dissolved in methanol (50 mL) and heated to reflux for 2 hours and then reconcentrated in vacuo. The residue was partitioned between saturated sodium bicarbonate and methylene chloride. The organic layer was separated, dried (Na₂SO₄), filtered, and concentrated in vacuo. The crude product was chromatographed on silica gel with 5–20% methanol in methylene chloride from which the title compound was isolated as a white solid.

Step D: Preparation of 1-[2-(1-(4-Cyano-3-fluorobenzyl)-5-imidazolyl)ethyl]piperazine, Trihydrochloride A solution of the product from Step C (6.53 g, 15.8 mmol) in ethyl acetate (20 mL) was saturated with HCl gas. The solution was stirred for 1.5 hours and then concentrated in vacuo to yield the titled compound as a white solid.

Step E: 7-(Triisopropylsilyloxy)-1-iodonaphthalene

To a solution of 8-iodo-2-naphthol, as described in Step A of Example 103 (2.75 g, 10.2 mmol) in dry DMF (25 mL), under argon, were added imidazole (1.39 g, 20.4 mmol) and triisopropylsilyl chloride (2.55 g, 13.2 mmol). The resulting mixture was stirred at ambient temperature for 4 hrs, then quenched with 10% aqueous citric acid (100 mL) and extracted with EtOAc (2×100 mL). The combined organic extracts were washed with water (50 mL), then brine (50 mL), then dried over $Na_2SO_4$, filtered, and concentrated in vacuo. The residue was purified by flash column chromatography on silica, eluting with $CH_2Cl_2$—50% hexane to yield the desired product as a white solid.

Step F: 7-(Triisopropylsilyloxy)-1-naphthoic Acid

To a solution of 7-(triisopropylsilyloxy)-1-iodonaphthalene, as described in Step E, (3.95 g, 9.26 mmol) in dry THF (60 mL) at −78° C., under argon, was added tert-butyllithium (10.9 mL of a 1.7 M solution in pentane, 18.53 mmol), dropwise. The resulting mixture was stirred at −78° C. for 1 hr, then an excess of $CO_2$ (g) was bubbled in over 5 min. The mixture was allowed to warm to ambient temperature and stirred for 18 hrs. The reaction mixture was poured into $H_2O$ (100 mL) and EtOAc (200 mL). The aqueous layer was adjusted to pH=2–3 by addition of 1.0 N aqueous HCl, and the EtOAc layer was extracted, then dried over $Na_2SO_4$, filtered, and concentrated in vacuo to provide the titled compound, which was of sufficient purity to use in the next step.

Step G: Preparation of 4-[2-(1-(4-Cyano-3-fluorobenzyl)-5-imidazolyl)ethyl]-1-(7-triisopropylsilyloxy-1-naphthoyl)-piperazine The product from Step D (66.1 mg, 0.156 mmol), 7-triisopropylsilyloxy-1-naphthoic acid from Step F (53.8 mg, 0.156 mmol), EDC hydrochloride (33.0 mg, 0.172 mmol), HOBT (23.2 mg, 0.172 mmol), and N,N-diisopropylethylamine (0.136 mL, 0.781 mmol) were stirred in dry, degassed DMF (0.5 mL) at 20° C. overnight. The reaction was stirred overnight and then injected onto a $C_{18}$ preparative HPLC column and purified with a mixed gradient of 5%–95% acetonitrile/0.1% TFA; 95%–5%/0.1% aqueous TFA over 15 min. The title compound was isolated after conversion to the free base.

Step H: Preparation of Compound 96 Trihydrochloride

A solution of the product from Step G, potassium fluoride (40 wt % on alumina, 20.0 mg), and 18-crown-6 (5.0 mg) in acetonitrile (1 mL) was heated to 65° C. for 48 hrs. The reaction mixture was poured onto saturated sodium bicarbonate and extracted with methylene chloride (3×10 mL). The combined organic layers were dried ($Na_2SO_4$), filtered, and concentrated in vacuo. The crude product was purified on a $C_{18}$ preparative HPLC column and purified with a mixed gradient of 5%–95% acetonitrile/0.1% TFA; 95%–5%/0.1% aqueous TFA over 15 min. The title compound was isolated after conversion to the trihydrochloride salt.

ES mass spectrum m/e 464 (M+1). Analysis calculated for $C_{28}H_{25}N_5O_2 \cdot 3.90HCl \cdot 0.80EtOAc$: C, 55.41; H, 5.26; N, 10.36; Found: C, 55.36; H, 5.23; N, 10.34.

Example 105

Preparation of 15-Bromo-18-oxo-18,19,20,21,22,23-hexaahydro-5H-19,22-ethano-12,14-etheno-6,10-metheno-24H-benzo[d]imidazo[4,3-m][1,7,10,14] oxatriazacycloeicosine-9-carbonitrile (97), Trihydrochloride

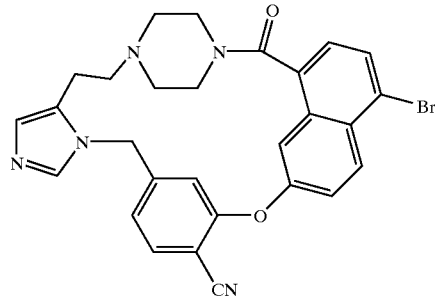

97

Step A: 8-(tert-Butoxycarbonylamino)-2-naphthol

A mixture of 8-amino-2-naphthol (50.6 g, 0.318 mol) and di-tert-butyl dicarbonate (72.8 g, 0.334 mol) in $CH_2Cl_2$ (1.4 L) and THF (1 L) was heated to reflux for 36 hrs. The mixture was allowed to cool to ambient temperature, then filtered and concentrated in vacuo. The residue was purified by flash column chromatography on silica, eluting with a gradient of $CH_2Cl_2$—0 to 10% ethyl acetate to yield the desired product as a light brown solid.

Step B: 1-(tert-Butoxycarbonylamino)-7-[(methanesulfonyl)oxy]-naphthalene

A mixture of the product from Step A (4.05 g, 15.6 mmol) and triethylamine (3.30 mL, 23.7 mmol) was stirred in dry $CH_2Cl_2$ (150 mL), under argon, at 0° C. and methanesulfonic anhydride (2.99 g, 17.2 mmol) was added in one portion. The resulting mixture was stirred at 0° C. for 20 min, then poured into saturated aqueous $NaHCO_3$ (100 mL) and the $CH_2Cl_2$ layer was extracted. The aqueous layer was extracted further with $CH_2Cl_2$ (100 mL). The combined organic extracts were dried over $Na_2SO_4$, filtered, and concentrated in vacuo to provide the titled compound as a pale solid.

Step C: 4-Bromo-1-(tert-butoxycarbonylamino)-7-[(methanesulfonyl)oxy]naphthalene To a stirred solution of the product from Step B, (2.05 g, 6.08 mmol) in acetic acid (50 mL) was added N-bromosuccinimide (1.14 g, 6.38 mmol) in one portion. The reaction mixture was stirred at ambient temperature for 2 hrs, then $H_2O$ (100 mL) and $CH_2Cl_2$ (100 mL) were added and the resulting mixture was cooled to 0° C. The aqueous layer was adjusted to pH of about 7 by addition of 10 N aqueous NaOH and the organic layer was extracted. The aqueous phase was extracted with a further portion of $CH_2Cl_2$ (100 mL), and the combined organic extracts were dried over $Na_2SO_4$, filtered, and concentrated in vacuo. The residue was triturated with 1:1 hexane-EtOAc to provide the titled product as a grey solid.

Step D: 1-Amino-4-bromo-7-[(methanesulfonyl)oxy]-naphthalene Hydrochloride

A solution of the product from Step C (4.60 g, 11.0 mmol) in ethyl acetate (200 mL) was saturated with HCl gas. The solution was stirred for 30 hours and then concentrated in vacuo to yield the titled compound as a brown solid.

Step E: 5-Bromo-8-iodo-2-[(methanesulfonyl)oxy]-naphthalene

To a solution of the product from Step D (1.50 g, 4.25 mmol) in 16 mL of 1:1THF/3M HCl solution at 0° C. was added NaNO₂ as a 40 wt % solution in water (0.626 mL, 4.68 mmol). After 15 minutes, a solution of potassium iodide (2.12 g, 12.76 mmol) in 5 mL of water was added, and the solution was stirred for 3 hours. The reaction was poured into dichloromethane and water, the aqueous layer was extracted with dichloromethane, and the combined organic extracts were dried over Na₂SO₄, filtered, and concentrated in vacuo. The residue was purified by flash column chromatography on silica gel (20–30% EtOAc/hexane) to yield the desired product as a white solid.

Step F: Methyl 4-Bromo-7-[(methanesulfonyl)oxy] naphthoate

To a solution of the the product from Step E (954 mg, 2.23 mmol) in 7 mL of methanol and 7 mL of DMSO was added triethylamine (1.56 mL, 11.2 mmol), Pd(OAc)₂ (25.1 mg, 0.11 mmol), and 1,3-bis-(diphenylphosphine)propane (46 mg, 0.11 mmol). The reaction was heated at 50° C. under an atmosphere of carbon monoxide for 3 hours, and cooled to room temperature. The solution was poured into water and extracted with 3× dichloromethane. The combined organic extracts were dried over Na₂SO₄, filtered, and concentrated in vacuo to give the product which was used without further purification.

Step G: 4-Bromo-7-hydroxynaphthoic Acid

To a solution of the the product from Step F (802 mg, 2.23 mmol) in 50 mL of THF was added 10 mL of 2N NaOH solution, and the reaction was heated at reflux overnight. The solution was acidified with 1N HCl and extracted with 3× EtOAc. The combined organic extracts were dried over Na₂SO₄, filtered, and concentrated in vacuo to give a solid, which was triturated with dichloromethane to give the titled product.

Step H: Preparation of 4-[2-(1-(4-Cyano-3-fluorobenzyl)-5-imidazolyl)ethyl]-1-(4-bromo-7-hydroxy-1-naphthoyl)-piperazine The titled compound was prepared from the product of Step G (220 mg, 0.823 mmol) and the product of Step D of Example 104 (348 mg, 0.823 mmol) using the procedure described in Step G of Example 104. The crude product was purified on a C₁₈ preparative HPLC column to give the titled product after conversion to the free base.

Step I: Preparation of Compound 97 Trihydrochloride

The titled compound was prepared from the product of Step H (36.1 mg, 0.064 mmol) using the procedure described in Step H of Example 104. The crude product was purified on a C₁₈ preparative HPLC column and purified with a mixed gradient of 5%–95% acetonitrile/0.1% TFA; 95%–5%/0.1% aqueous TFA over 15 min. The titled compound was isolated after conversion to the trihydrochloride salt.

ES mass spectrum m/e 542.2 (M+1). Analysis calculated for $C_{28}H_{24}BrN_5O_2 \cdot 3.15HCl \cdot 0.35Et_2O$: C, 51.68; H, 4.52; N, 10.25; Found: C, 51.69; H, 4.89; N, 10.26.

Example 106

Preparation of 5,6,20,21,22,23,24,25-Octahydro-21-oxo-7H-20,23-ethano-14,16-etheno-8,12-metheno-benzo[d]imidazo[4,3-l][1,6,9,13]oxatriaza-cycloheneicosine-11-carbonitrile (98), Dihydrochloride

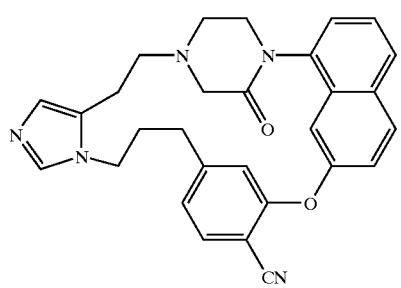

98

Step A Preparation of 4-Cyano-3-fluorobenzaldehyde

To a solution of the alcohol from Step J of Example 98 (1.00 g, 6.62 mmol) in 15 mL of DMSO was added triethylamine (3.68 mL, 26.4 mmol), then SO₃-pyridine complex (2.64 g, 16.5 mmol). After 30 minutes, the reaction was poured into EtOAc, washed with water and brine, dried (Na₂SO₄), filtered, and concentrated in vacuo to provide the aldehyde which was sufficiently pure for use in the next step without further purification.

Step B: Preparation of trans-Ethyl 3-(4-Cyano-3-fluorophenyl)-2-propenoate

A solution of the product from Step A (970 mg, 6.5 mmol) and (carbethoxymethylene)triphenylphosphorane (2.3 g, 6.5 mmol) was heated at reflux in 50 mL of toluene overnight. The reaction was concentrated in vacuo, triturated with ether, and filtered. The filtrate was concentrated in vacuo, and purified by flash column chromatography on silica gel (15% EtOAc/hexane) to yield the desired product as a white solid.

Step C: Preparation of Ethyl 3-(4-Cyano-3-fluorophenyl) propanoate

To a solution of the product from Step B (1.3 g, 5.9 mmol) in 30 mL of methanol was added 10% palladium on carbon (130 mg). The solution was stirred at room temperature under an atmosphere of hydrogen for 2 hours, then purged with argon. The mixture was filtered through celite, the filter pad was washed with methanol, and the filtrate was concentrated in vacuo. The crude product was purified on a C₁₈ preparative HPLC column to give the titled product after conversion to the free base.

ES mass spectrum m/e 221.1 (M+1).

Step D: Preparation of 2-Fluoro-4-(3-hydroxy-1-propyl) benzonitrile

To a solution of the product from Step C (140 mg, 0.71 mmol) in 3.5 mL of ethanol at 0° C. was added sodium borohydride (84 mg, 2.1 mmol). After 45 minutes, another portion of sodium borohydride was added, and the mixture was stirred overnight. The reaction was quenched with saturated NH₄Cl solution, concentrated in vacuo, and partitioned between EtOAc and saturated NaHCO₃ solution. The organic layer was washed with brine, dried (Na₂SO₄), filtered, and concentrated in vacuo to provide the alcohol which was sufficiently pure for use in the next step without further purification.

Step E: Preparation of 1-[7-((tert-Butyldiphenylsilyl)oxy) naphthyl]-4-[2-(1-(3-(4-cyano-3-fluorophenyl)-1-propyl)-5-imidazolyl-ethyl]-2-piperazinone The titled compound was prepared from the product of Step D (80 mg, 0.45 mmol) and the product of Step C of Example 101 (364 mg, 0.447 mmol) using the procedure described in Step K of Example 98. The crude product was purified on a $C_{18}$ preparative HPLC column to give the titled product after conversion to the free base.

Step F: Preparation of Compound 98 Dihydrochloride

The titled compound was prepared from the product of Step E (50 mg, 0.070 mmol) using the procedure described in Step E of Example 101. The crude product was purified on a $C_{18}$ preparative HPLC column and purified with a mixed gradient of 5%–95% acetonitrile/0.1% TFA; 95%–5%/0.1% aqueous TFA over 15 min. The titled compound was isolated after conversion to the dihydrochloride salt.

ES mass spectrum m/e 478.3 (M+1). Analysis calculated for $C_{29}H_{27}N_5O_2 \cdot 2.00HCl \cdot 1.90H_2O$: C, 59.57; H, 5.65; N, 11.98; Found: C, 59.56; H, 6.09; N, 10.35.

Example 107

Preparation of 15-Chloro-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (99), Dihydrochloride

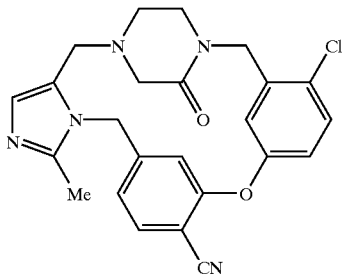

99

The titled compound was prepared from 4-chloro-3-methylphenol using the procedures described in Step s A through G of Example 32, except that in Step F the aldehyde was substituted with the product aldehyde from Step A of Example 10. The resulting product was isolated as a white solid. This was taken up in $CH_2Cl_2$ and treated with excess 1 M HCl/ether solution, and concentrated in vacuo to provide the titled product hydrochloride as a white powder.

HRMS (ES) calculated for M+H$^+$: 448.1535. Found 448.1514.

Example 108

In Vitro Inhibition of ras Farnesyl Transferase

Transferase Assays. Isoprenyl-protein transferase activity assays are carried out at 30° C. unless noted otherwise. A typical reaction contains (in a final volume of 50 µL): [$^3$H]farnesyl diphosphate, Ras protein, 50 mM HEPES, pH 7.5, 5 mM $MgCl_2$, 5 mM dithiothreitol, 10 µM $ZnCl_2$, 0.1% polyethyleneglycol (PEG) (15,000–20,000 mw) and isoprenyl-protein transferase. The FPTase employed in the assay is prepared by recombinant expression as described in Omer, C. A., Kral, A. M., Diehl, R. E., Prendergast, G. C., Powers, S., Allen, C. M., Gibbs, J. B. and Kohl, N. E. (1993) Biochemistry 32:5167–5176. After thermally pre-equilibrating the assay mixture in the absence of enzyme, reactions are initiated by the addition of isoprenyl-protein transferase and stopped at timed intervals (typically 15 min) by the addition of 1 M HCl in ethanol (1 mL). The quenched reactions are allowed to stand for 15 m (to complete the precipitation process). After adding 2 mL of 100% ethanol, the reactions are vacuum-filtered through Whatman GF/C filters. Filters are washed four times with 2 mL aliquots of 100% ethanol, mixed with scintillation fluid (10 mL) and then counted in a Beckman LS3801scintillation counter.

For inhibition studies, assays are run as described above, except inhibitors are prepared as concentrated solutions in 100% dimethyl sulfoxide and then diluted 20-fold into the enzyme assay mixture. Substrate concentrations for inhibitor $IC_{50}$ determinations are as follows: FTase, 650 nM Ras-CVLS (SEQ.ID.NO.: 2), 100 nM farnesyl diphosphate.

The compounds of the instant invention are tested for inhibitory activity against human FPTase by the assay described above.

The compounds of the instant invention described in the above Examples 1–105 were tested for inhibitory activity against human FPTase by the assay described above and were found to have an $IC_{50}$ of ≦5 µM.

Example 109

Modified in Vitro GGTase Inhibition Assay

The modified geranylgeranyl-protein transferase inhibition assay is carried out at room temperature. A typical reaction contains (in a final volume of 50 µL): [$^3$H] geranylgeranyl diphosphate, biotinylated Ras peptide, 50 mM HEPES, pH 7.5, a modulating anion (for example 10 mM glycerophosphate or 5 mM ATP), 5 mM $MgCl_2$, 10 µM $ZnCl_2$, 0.1% PEG (15,000–20,000 mw), 2 mM dithiothreitol, and geranylgeranyl-protein transferase type I(GGTase). The GGTase-type I enzyme employed in the assay is prepared as described in U.S. Pat. No. 5,470,832, incorporated by reference. The Ras peptide is derived from the K4B-Ras protein and has the following sequence: biotinyl-GKKKKKKSKTKCVIM (single amino acid code) (SEQ.ID.NO.: 3). Reactions are initiated by the addition of GGTase and stopped at timed intervals (typically 15 min) by the addition of 200 µL of a 3 mg/mL suspension of streptavidin SPA beads (Scintillation Proximity Assay beads, Amersham) in 0.2 M sodium phosphate, pH 4, containing 50 mM EDTA, and 0.5% BSA. The quenched reactions are allowed to stand for 2 hours before analysis on a Packard TopCount scintillation counter.

For inhibition studies, assays are run as described above, except inhibitors are prepared as concentrated solutions in 100% dimethyl sulfoxide and then diluted 25-fold into the enzyme assay mixture. $IC_{50}$ values are determined with Ras peptide near $K_M$ concentrations. Enzyme and substrate concentrations for inhibitor $IC_{50}$ determinations are as follows: 75 pM GGTase-I, 1.6 µM Ras peptide, 100 nM geranylgeranyl diphosphate.

The compounds of the instant invention, including those compounds described in the above Examples 1–107, are tested for inhibitory activity against human GGTase-type I by the assay described above.

Example 110

Cell-based in Vitro ras Farnesylation Assay

The cell line used in this assay is a v-ras line derived from either Rat1 or $NIH_3T3$ cells, which expressed viral Ha-ras p21. The assay is performed essentially as described in DeClue, J. E. et al., Cancer Research 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labeled in 3 ml methionine-free DMEM supplemented with 10% regular DMEM, 2% fetal bovine serum and 400 μCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., *J. Virol.* 43:294–304, (1982)). Following a 2 hour antibody incubation at 4° C., 200 μl of a 25% suspension of protein A-Sepharose coated with rabbit anti rat IgG is added for 45 min. The immuno-precipitates are washed four times with IP buffer (20 nM HEPES, pH 7.5/1 mM EDTA/1% Triton X-100.0.5% deoxycholate/0.1%/SDS/0.1M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 111

Cell-based in Vitro Growth Inhibition Assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10$^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

Example 112

Construction of SEAP Reporter Plasmid pDSE100

The SEAP reporter plasmid, pDSE100 was constructed by ligating a restriction fragment containing the SEAP coding sequence into the plasmid pCMV-RE-AKI. The SEAP gene is derived from the plasmid pSEAP2-Basic (Clontech, Palo Alto, Calif.). The plasmid pCMV-RE-AKI was constructed by Deborah Jones (Merck) and contains 5 sequential copies of the 'dyad symmetry response element' cloned upstream of a 'C.AT-TATA' sequence derived from the cytomegalovirus immediate early promoter. The plasmid also contains a bovine growth hormone poly-A sequence.

The plasmid, pDSE100 was constructed as follows. A restriction fragment encoding the SEAP coding sequence was cut out of the plasmid pSEAP2-Basic using the restriction enzymes EcoR1 and HpaI. The ends of the linear DNA fragments were filled in with the Klenow fragment of *E. coli* DNA Polymerase I. The 'blunt ended' DNA containing the SEAP gene was isolated by electrophoresing the digest in an agarose gel and cutting out the 1694 base pair fragment. The vector plasmid pCMV-RE-AKI was linearized with the restriction enzyme Bgl-II and the ends filled in with Klenow DNA Polymerase I. The SEAP DNA fragment was blunt end ligated into the pCMV-RE-AKI vector and the ligation products were transformed into DH5-alpha *E. coli* cells (Gibco-BRL). Transformants were screened for the proper insert and then mapped for restriction fragment orientation. Properly oriented recombinant constructs were sequenced across the cloning junctions to verify the correct sequence. The resulting plasmid contains the SEAP coding sequence downstream of the DSE and CAT-TATA promoter elements and upstream of the BGH poly-A sequence.

Alternative Construction of SEAP Reporter Plasmid. pDSE101

The SEAP repotrer plasmid, pDSE101 is also constructed by ligating a restriction fragment containing the SEAP coding sequence into the plasmid pCMV-RE-AKI. The SEAP gene is derived from plasmid pGEM7zf(-)/SEAP.

The plasmid pDSE101 was constructed as follows: A restriction fragment containing part of the SEAP gene coding sequence was cut out of the plasmid pGEM7zf(-)/SEAP using the restriction enzymes Apa I and KpnI. The ends of the linear DNA fragments were chewed back with the Klenow fragment of *E. coli* DNA Polymerase I. The "blunt ended" DNA containing the truncated SEAP gene was isolated by electrophoresing the digest in an agarose gel and cutting out the 1910 base pair fragment. This 1910 base pair fragment was ligated into the plasmid pCMV-RE-AKI which had been cut with Bgl-II and filled in with *E. coli* Klenow fragment DNA polymerase. Recombinant plasmids were screened for insert orientation and sequenced through the ligated junctions. The plasmid pCMV-RE-AKI is derived from plasmid pCMVIE-AKI-DHFR (Whang, Y., Silberklang, M., Morgan, A., Munshi, S., Lenny, A. B., Ellis, R. W., and Kieff, E. (1987) J. Virol., 61, 1796–1807) by removing an EcoRI fragment containing the DHFR and Neomycin markers. Five copies of the fos promoter serum response element were inserted as described previously (Jones, R. E., Defeo-Jones, D., McAvoy, E. M., Vuocolo, G. A., Wegrzyn, R. J., Haskell, K. M. and Oliff, A. (1991) Oncogene, 6, 745–751) to create plasmid pCMV-RE-AKI.

The plasmid pGEM7zf(-)/SEAP was constructed as follows. The SEAP gene was PCRed, in two segments from a human placenta cDNA library (Clontech) using the following oligos.

Sense strand N-terminal SEAP: 5'
  GAGAGGGAATTCGGGCCCTTCCTGCAT GCTGCT-GCTGCTGCTGCTGCTGGGC 3' (SEQ.ID.NO.:4)
Antisense strand N-terminal SEAP: 5'
  GAGAGAGCTCGAGGTTAACCCGGGT GCGCG-GCGTCGGTGGT 3' (SEQ.ID.NO.:5)
Sense strand C-terminal SEAP: 5'
  GAGAGAGTCTAGAGTTAACCCGTGGTCC CCGCGTTGCTTCCT 3' (SEQ.ID.NO.:6)
Antisense strand C-terminal SEAP: 5'
  GAAGAGGAAGCTTGGTACCGCCACTG GGCTG-TAGGTGGTGGCT 3' (SEQ.ID.NO.:7)

The N-terminal oligos (SEQ.ID.NO.: 4 and SEQ.ID.NO.: 5) were used to generate a 1560 bp N-terminal PCR product that contained EcoRI and HpaI restriction sites at the ends.

The Antisense N-terminal oligo (SEQ.ID.NO.: 5) introduces an internal translation STOP codon within the SEAP gene along with the HpaI site. The C-terminal oligos (SEQ.ID.NO.: 6 and SEQ.ID.NO.: 7) were used to amplify a 412 bp C-terminal PCR product containing HpaI and HindIII restriction sites. The sense strand C-terminal oligo (SEQ.ID.NO.: 6) introduces the internal STOP codon as well as the HpaI site. Next, the N-terminal amplicon was digested with EcoRI and HpaI while the C-terminal amplicon was digested with HpaI and HindIII. The two fragments comprising each end of the SEAP gene were isolated by electro-phoresing the digest in an agarose gel and isolating the 1560 and 412 base pair fragments. These two fragments were then co-ligated into the vector pGEM7zf(−) (Promega) which had been restriction digested with EcoRI and HindIII and isolated on an agarose gel. The resulting clone, pGEM7zf(−)/SEAP contains the coding sequence for the SEAP gene from amino acids.

Construction of a Constitutively Expressing SEAP Plasmid pCMV-SEAP-A

An expression plasmid constitutively expressing the SEAP protein was created by placing the sequence encoding a truncated SEAP gene downstream of the cytomegalovirus (CMV) IE-1 promoter. The expression plasmid also includes the CMV intron A region 5' to the SEAP gene as well as the 3' untranslated region of the bovine growth hormone gene 3' to the SEAP gene.

The plasmid pCMVIE-AKI-DHFR (Whang, Y., Silberklang, M., Morgan, A., Munshi, S., Lenny, A. B., Ellis, R. W., and Kieff, E. (1987) J. Virol., 61:1796–1807) containing the CMV immediate early promoter was cut with EcoRi generating two fragments. The vector fragment was isolated by agarose electrophoresis and religated. The resulting plasmid is named pCMV-AKI. Next, the cytomegalovirus intron A nucleotide sequence was inserted downstream of the CMV IE1 promter in pCMV-AKI. The intron A sequence was isolated from a genomic clone bank and subcloned into pBR322 to generate plasmid p16T-286. The intron A sequence was mutated at nucleotide 1856 (nucleotide numbering as in Chapman, B. S., Thayer, R. M., Vincent, K. A. and Haigwood, N. L., Nuc. Acids Res. 19, 3979–3986) to remove a SacI restriction site using site directed mutagenesis. The mutated intron A sequence was PCRed from the plasmid p16T-287 using the following oligos.

Sense strand: 5' GGCAGAGCTCGTTTAGTGAACCGT-CAG 3' (SEQ.ID.NO.: 8)

Antisense strand: 5' GAGAGATCTCAAGGACGGT-GACTGCAG 3' (SEQ.ID.NO.: 9)

These two oligos generate a 991 base pair fragment with a SacI site incorporated by the sense oligo and a Bgl-II fragment incorporated by the antisense oligo. The PCR fragment is trimmed with SacI and Bgl-II and isolated on an agarose gel. The vector pCMV-AKI is cut with SacI and Bgl-II and the larger vector fragment isolated by agarose gel electrophoresis. The two gel isolated fragments are ligated at their respective SacI and Bgl-II sites to create plasmid pCMV-AKI-InA.

The DNA sequence encoding the truncated SEAP gene is inserted into the pCMV-AKI-InA plasmid at the Bgl-II site of the vector. The SEAP gene is cut out of plasmid pGEM7zf (−)/SEAP (described above) using EcoRI and HindIII. The fragment is filled in with Klenow DNA polymerase and the 1970 base pair fragment isolated from the vector fragment by agarose gel electrophoresis. The pCMV-AKI-InA vector is prepared by digesting with Bgl-II and filling in the ends with Klenow DNA polymerase. The final construct is generated by blunt end ligating the SEAP fragment into the pCMV-AKI-InA vector. Transformants were screened for the proper insert and then mapped for restriction fragment orientation. Properly oriented recombinant constructs were sequenced across the cloning junctions to verify the correct sequence. The resulting plasmid, named pCMV-SEAP-A (deposited in the ATCC under Budapest Treaty on Aug. 27, 1998, and designated ATCC), contains a modified SEAP sequence downstream of the cytomegalovirus immediately early promoter IE-1 and intron A sequence and upstream of the bovine growth hormone poly-A sequence. The plasmid expresses SEAP in a constitutive manner when transfected into mammalian cells.

Alternative Construction of a Constitutively Expressing SEAP Plasmid pCMV-SEAP-B An expression plasmid constitutively expressing the SEAP protein can be created by placing the sequence encoding a truncated SEAP gene downstream of the cytomegalovirus (CMV) IE-1 promoter and upstream of the 3' unstranslated region of the bovine growth hormone gene.

The plasmid pCMVIE-AKI-DHFR (Whang, Y., Silberklang, M., Morgan, A., Munshi, S., Lenny, A. B., Ellis, R. W., and Kieff, E. (1987) J. Virol., 61:1796–1807) containing the CMV immediate early promoter and bovine growth hormone poly-A sequence can be cut with EcoRI generating two fragments. The vector fragment can be isolated by agarose electrophoresis and religated. The resulting plasmid is named pCMV-AKI. The DNA sequence encoding the truncated SEAP gene can be inserted into the pCMV-AKI plasmid at a unique Bgl-II in the vector. The SEAP gene is cut out of plasmid pGEMzf(−)/SEAP (described above) using EcoRI and HindIII. The fragments are filled in with Klenow DNA polymerase and the 1970 base pair fragment is isolated from the vector fragment by agarose gel electrophoresis. The pCMV-AKI vector is prepared by digesting with Bgl-II and filling in the ends with Klenow DNA polymerase. The final construct is generated by blunt end ligating the SEAP fragment into the vector and transforming the ligation reaction into E. coli DH5µ cells. Transformants can then be screened for the proper insert and mapped for restriction fragment orientation. Properly oriented recombinant constructs would be sequenced across the cloning junctions to verify the correct sequence. The resulting plasmid, named pCMV-SEAP-B contains a modified SEAP sequence downstream of the cytomegalovirus immediate early promoter, IE1, and upstream of a bovine growth hormone poly-A sequence. The plasmid would express SEAP in a constitutive nammer when transfected into mammalian cells.

Cloning of a Myristylated Viral-H-ras Expression Plasmid pSMS600

A DNA fragment containing viral-H-ras can be PCRed from plasmid "HB-11 (deposited in the ATCC under Budapest Treaty on Aug. 27, 1997, and designated ATCC 209,218) using the following oligos.

Sense Strand:
5 ' TCTCCTCGAGGCCACCATGGGGAGTAG-CAAGAGCAAGCCTAA GGACCCCAGC-CAGCGCCGGATGACAGAATACAAGCT-TGTGGTG G 3'. (SEQ.ID.NO.: 10)

Antisense:
5° CACATCTAGATCAGGACAGCACAGACT-TGCAGC 3'. (SEQ.ID.NO.: 11)

A sequence encoding the first 15 aminoacids of the v-src gene, containing a myristylation site, is incorporated into the sense strand oligo. The sense strand oligo also optimizes the 'Kozak' translation initiation sequence immediately 5' to the ATG start site. To prevent prenylation at the viral-ras C-terminus, cysteine 186 would be mutated to a serine by substituting a G residue for a C residue in the C-terminal antisense oligo. The PCR primer oligos introduce an XhoI site at the 5' end and a XbaI site at the 3' end. The XhoI-XbaI fragment can be ligated into the mammalian expression plasmid pCI (Promega) cut with XhoI and XbaI. This results in a plasmid, pSMS600, in which the recombinant myr-viral-H-ras gene is constitutively transcribed from the CMV promoter of the pCI vector.

Cloning of a Viral-H-ras-CVLL Expression Plasmid pSMS601

A viral-H-ras clone with a C-terminal sequence encoding the amino acids CVLL can be cloned from the plasmid "HB-11" by PCR using the following oligos.
Sense Strand:
5' TCTCCTCGAGGCCACCATGACAGAATACA AGCTTGTGGTGG-3' (SEQ.ID.NO.: 12)
Antisense Strand:
5' CACTCTAGACTGGTGTCAGAGCAGCACACACT TGCAGC-3' (SEQ.ID.NO.: 13)

The sense strand oligo optimizes the 'Kozak' sequence and adds an XhoI site. The antisense strand mutates serine 189 to leucine and adds an XbaI site. The PCR fragment can be trimmed with XhoI and XbaI and ligated into the XhoI-XbaI cut vector pCI (Promega). This results in a plasmid, pSMS601, in which the mutated viral-H-ras-CVLL gene is constitutively transcribed from the CMV promoter of the pCI vector.

Cloning of Cellular-H-ras-Leu61 Expression Plasmid pSMS620

The human cellular-H-ras gene can be PCRed from a human cerebral cortex cDNA library (Clontech) using the following oligonucleotide primers.
Sense Strand:
5'-GAGAGAATTCGCCACCATGACGGAATATAA GCTGGTGG-3' (SEQ.ID.NO.: 14)
Antisense Strand:
5'-GAGAGTCGACGCGTCAGGAGAGCACACAC TTGC-3' (SEQ.ID.NO.: 15)

The primers will amplify a c-H-Ras encoding DNA fragment with the primers contributing an optimized 'Kozak' translation start sequence, an EcoRI site at the N-terminus and a Sal I site at the C-terminal end. After trimming the ends of the PCR product with EcoRI and Sal I, the c-H-ras fragment can be ligated ligated into an EcoRI-Sal I cut mutagenesis vector pAlter-1 (Promega). Mutation of glutamine-61 to a leucine can be accomplished using the manufacturer's protocols and the following oligo-nucleotide:
5'-CCGCCGGCCTGGAGGAGTACAG-3' (SEQ.ID.NO.: 16)

After selection and sequencing for the correct nucleotide substitution, the mutated c-H-ras-Leu61 can be excised from the pAlter-1 vector, using EcoRi and Sal I, and be directly ligated into the vector pCI (Promega) which has been digested with EcoRI and Sal I. The new recombinant plasmid, pSMS620, will constitutively transcribe c-H-ras-Leu61 from the CMV promoter of the pCI vector.

Cloning of a c-N-ras-Val-12 Expression Plasmid pSMS630

The human c-N-ras gene can be PCRed from a human cerebral cortex cDNA library (Clontech) using the following oligonucleotide primers.

Sense Strand:
5'-GAGAGAATTCGCCACCATGACTGAGTACA AACTGGTGG-3' (SEQ.ID.NO.: 17)
Antisense Strand:
5'-GAGAGTCGACTTGTTACATCACCACACATGGC-3' (SEQ.ID.NO.: 18)

The primers will amplify a c-N-Ras encoding DNA fragment with the primers contributing an optimized 'Kozak' translation start sequence, an EcoRI site at the N-terminus and a Sal I site at the C-terminal end. After trimming the ends of the PCR product with EcoRI and Sal I, the c-N-ras fragment can be ligated into an EcoRI-Sal I cut mutagenesis vector pAlter-1 (Promega). Mutation of glycine-12 to a valine can be accomplished using the manufacturer's protocols and the following oligonucleotide:
5'-GTTGGAGCAGTTGGTGTTGGG-3' (SEQ.ID.NO.: 19)

After selection and sequencing for the correct nucleotide substitution, the mutated c-N-ras-Val-12 can be excised from the pAlter-1 vector, using EcoRI and Sal I, and be directly ligated into the vector pCI (Promega) which has been digested with EcoRI and Sal I. The new recombinant plasmid, pSMS630, will constitutively transcribe c-N-ras-Val-12 from the CMV promoter of the pCI vector.

Cloning of a c-K4B-ras-Val-12 Expression Plasmid pSMS640

The human c-K4B-ras gene can be PCRed from a human cerebral cortex cDNA library (Clontech) using the following oligo-nucleotide primers.

Sense Strand:
5'-GAGAGGTACCGCCACCATGACTGAATATA AACTTGTGG-3' (SEQ.ID.NO.: 20)
Antisense Strand:
5'-CTCTGTCGACGTATTTACATAATTACACAC TTGTC-3' (SEQ.ID.NO.: 21)

The primers will amplify a c-K4B-Ras encoding DNA fragment with the primers contributing an optimized 'Kozak' translation start sequence, a KpnI site at the N-terminus and a Sal I site at the C-terminal end. After trimming the ends of the PCR product with Kpn I and Sal I, the c-K4B-ras fragment can be ligated into a KpnI-Sal I cut mutagenesis vector pAlter-1 (Promega). Mutation of cysteine-12 to a valine can be accomplished using the manufacturer's protocols and the following oligonucleotide:
5'-GTAGTTGGAGCTGTTGGCGTAGGC-3' (SEQ.ID.NO.: 22)

After selection and sequencing for the correct nucleotide substitution, the mutated c-K4B-ras-Val-12 can be excised from the pAlter-1 vector, using KpnI and Sal I, and be directly ligated into the vector pCI (Promega) which has been digested with KpnI and Sal I. The new recombinant plasmid will constitutively transcribe c-K4B-ras-Val-12 from the CMV promoter of the pCI vector.

Cloning of c-K-ras4A-Val-12 Expression Plasmid pSMS650

The human c-K4A-ras gene can be PCRed from a human cerebral cortex cDNA library (Clontech) using the following oligo-nucleotide primers.

Sense Strand:
5'-GAGAGGTACCGCCACCATGACTGAATA
TAAACTTGTGG-3' (SEQ.ID.NO.: 23)
Antisense Strand:
5'-CTCTGTCGACAGATTACATTATAATGCAT
TTTTAATTTTCACA C-3' (SEQ.ID.NO.: 24)

The primers will amplify a c-K4A-Ras encoding DNA fragment with the primers contributing an optimized 'Kozak' translation start sequence, a KpnI site at the N-terminus and a Sal I stite at the C-terminal end. After trimming the ends of the PCR product with Kpn I and Sal I, the c-K-ras4A fragment can be ligated into a KpnI-Sal I cut mutagenesis vector pAlter-1 (Promega). Mutation of cysteine-12 to a valine can be accomplished using the manufacturer's protocols and the following oligonucleotide:

5'-GTAGTTGGAGCTGTTGGCGTAGGC-3' (SEQ.ID. NO.: 25)

After selection and sequencing for the correct nucleotide substitution, the mutated c-K4A-ras-Val-12 can be excised from the pAlter-1 vector, using KpnI and Sal I, and be directly ligated into the vector pCI (Promega) which has been digested with KpnI and Sal I. The new recombinant plasmid, pSMS650, will constitutively transcribe c-K4A-ras-Val-12 from the CMV promoter of the pCI vector.

SEAP Assay

Human C33A cells (human epitheial carcenoma—ATTC collection) are seeded in 10 cm tissue culture plates in DMEM+10% fetal calf serum+1×Pen/Strep+1×glutamine+ 1×NEAA. Cells are grown at 37° C. in a 5% $CO_2$ atmosphere until they reach 50–80% of confluency.

The transient transfection is performed by the $CaPO_4$ method (Sambrook et al., 1989). Thus, expression plasmids for H-ras, N-ras, K-ras, Myr-ras or H-ras-CVLL are co-precipitated with the DSE-SEAP reporter construct. (A ras expression plasmid is not included when the cell is transfected with the pCMV-SEAP plasmid.) For 10 cm plates 600 μl of $CaCl_2$-DNA solution is added dropwise while vortexing to 600 μl of 2×HBS buffer to give 1.2 ml of precipitate solution (see recipes below). This is allowed to sit at room temperature for 20 to 30 minutes. While the precipitate is forming, the media on the C33A cells is replaced with DMEM (minus phenol red; Gibco cat. No. 31053-028)+0.5% charcoal stripped calf serum+1×(Pen/ Strep, Glutamine and nonessential aminoacids). The $CaPO_4$-DNA precipitate is added dropwise to the cells and the plate rocked gently to distribute. DNA uptake is allowed to proceed for 5–6 hrs at 37° C. under a 5% $CO_2$ atmosphere.

Following the DNA incubation period, the cells are washed with PBS and trypsinized with 1 ml of 0.05% trypsin. The 1 ml of trypsinized cells is diluted into 10 ml of phenol red free DMEM+0.2% charcoal stripped calf serum+ 1× (Pen/Strep, Glutamine and NEAA). Transfected cells are plated in a 96 well microtiter plate (100 μl/well) to which drug, diluted in media, has already been added in a volume of 100 μl. The final volume per well is 200 μl with each drug concentration repeated in triplicate over a range of half-log steps.

Incubation of cells and drugs is for 36 hrs at 370 under $CO_2$. At the end of the incubation period, cells are examined micro-scopically for evidence of cell distress. Next, 100 μl of media containing the secreted alkaline phosphatase is removed from each well and transferred to a microtube array for heat treatment at 65° C. for 1 hr to inactivate endogenous alkaline phosphatases (but not the heat stable secreted phosphatase).

The heat treated media is assayed for alkaline phosphatase by a luminescence assay using the luminescence reagent CSPD® Tropix, Bedford, Mass.). A volume of 50 μl media is combined with 200 μl of CSPD cocktail and incubated for 60 minutes at room temperature. Luminesence is monitored using an ML2200 microplate luminometer (Dynatech). Luminescence reflects the level of activation of the fos reporter construct stimulated by the transiently expressed protein.

$DNA-CaPO_4$ Precipitate for 10 cm. Plate of Cells

| | |
|---|---|
| Ras expression plasmid (1 μg/μl) | 10 μl |
| DSE-SEAP Plasmid (1 μg/μl) | 2 μl |
| Sheared Calf Thymus DNA (1 μg/μl) | 8 μl |
| 2M $CaCl_2$ | 74 μl |
| $dH_2O$ | 506 μl |

2×HBS Buffer 280 mM NaCl
10 mM KCl
1.5 mM $Na_2HPO_4$ $2H_2O$
12 mM dextrose
50 mM HEPES
Final pH=7.05

Luminesence Buffer (26 ml)

| | |
|---|---|
| Assay Buffer | 20 ml |
| Emerald Reagent ™ (Tropix) | 2.5 ml |
| 100 mM homoarginine | 2.5 ml |
| CSPD Reagent ® (Tropix) | 1.0 ml |

Assay Buffer

Add 0.05M $Na_2CO_3$ to 0.05M $NaHCO_3$ to obtain pH 9.5. Make 1 mM in $MgCl_2$

Example 113

The processing assays employed are modifications of that described by DeClue et al [Cancer Research 51, 712–717, 1991].

K4B-Ras Processing Inhibition Assay

PSN-1 (human pancreatic carcinoma) or viral-K4-B-ras-transformed Rat1 cells are used for analysis of protein processing. Subconfluent cells in 100 mm dishes are fed with 3.5 ml of media (methionine-free RPMI supplemented with 2% fetal bovine serum or cysteine-free/methionine-free DMEM supplemented with 0.035 ml of 200 mM glutamine (Gibco), 2% fetal bovine serum, respectively) containing the desired concentration of test compound, lovastatin or solvent alone. Cells treated with lovastatin (5–10 μM), a compound that blocks Ras processing in cells by inhibiting a rate-limiting step in the isoprenoid biosynthetic pathway, serve as a positive control. Test compounds are prepared as 1000× concentrated solutions in DMSO to yield a final solvent concentration of 0.1%. Following incubation at 37° C. for two hours 204 μCi/ml [$^{35}$S]Pro-Mix (Amersham, cell labeling grade) is added.

After introducing the label amino acid mixture, the cells are incubated at 37° C. for an additional period of time (typically 6 to 24 hours). The media is then removed and the cells are washed once with cold PBS. The cells are scraped into 1 ml of cold PBS, collected by centrifugation (10,000×g for 10 sec at room temperature), and lysed by vortexing in 1 ml of lysis buffer (1% Nonidet P-40, 20 mM HEPES, pH 7.5, 150 mM NaCl, 1 mM EDTA, 0.5% deoxycholate, 0.1% SDS, 1 mM DTT, 10 µg/ml AEBSF, 10 µg/ml aprotinin, 2 µg/ml leupeptin and 2 µg/ml antipain). The lysate is then centrifuged at 15,000×g for 10 min at 4° C. and the supernatant saved.

For immunoprecipitation of Ki4B-Ras, samples of lysate supernatant containing equal amounts of protein are utilized. Protein concentration is determined by the bradford method utilizing bovine serum albumin as a standard. The appropriate volume of lysate is brought to 1 ml with lysis buffer lacking DTT and 8 µg of the pan Ras monoclonal antibody, Y13-259, added. The protein/antibody mixture is incubated on ice at 4° C. for 24 hours. The immune complex is collected on pansorbin (Calbiochem) coated with rabbit antiserum to rat IgG (Cappel) by tumbling at 4° C. for 45 minutes. The pellet is washed 3 times with 1 ml of lysis buffer lacking DTT and protease inhibitors and resuspended in 100 µl elution buffer (10 mM Tris pH 7.4, 1% SDS). The Ras is eluted from the beads by heating at 95° C. for 5 minutes, after which the beads are pelleted by brief centrifugation (15,000×g for 30 sec. at room temperature).

The supernatant is added to 1 ml of Dilution Buffer 0.1% Triton X-100, 5 mM EDTA, 50 mM NaCl, 10 mM Tris pH 7.4) with 2 µg Kirsten-ras specific monoclonal antibody, c-K-ras Ab-1 (Calbiochem). The second protein/antibody mixture is incubated on ice at 4° C. for 1–2 hours. The immune complex is collected on pansorbin (Calbiochem) coated with rabbit antiserum to rat IgG (Cappel) by tumbling at 4° C. for 45 minutes. The pellet is washed 3 times with 1 ml of lysis buffer lacking DTT and protease inhibitors and resuspended in Laemmli sample buffer. The Ras is eluted from the beads by heating at 95° C. for 5 minutes, after which the beads are pelleted by brief centrifugation. The supernatant is subjected to SDS-PAGE on a 12% acrylamide gel (bis-acrylamide:acrylamide, 1:100), and the Ras visualized by fluorography.

hDJ Processing Inhibition Assay

PSN-1 cells are seeded in 24-well assay plates. For each compound to be tested, the cells are treated with a minimum of seven concentrations in half-log steps. The final solvent (DMSO) concentration is 0.1%. A vehicle-only control is included on each assay plate. The cells are treated for 24 hours at 37° C./5% $CO_2$.

The growth media is then aspirated and the samples are washed with PBS. The cells are lysed with SDS-PAGE sample buffer containing 5% 2-mercaptoethanol and heated to 95° C. for 5 minutes. After cooling on ice for 10 minutes, a mixture of nucleases is added to reduce viscosity of the samples.

The plates are incubated on ice for another 10 minutes. The samples are loaded onto pre-cast 8% acrylamide gels and electrophoresed at 15 mA/gel for 3–4 hours. The samples are then transferred from the gels to PVDF membranes by Western blotting.

The membranes are blocked for at least 1 hour in buffer containing 2% nonfat dry milk. The membranes are then treated with a monoclonal antibody to hDJ-2 (Neomarkers Cat. #MS-225), washed, and treated with an alkaline phosphatase-conjugated secondary antibody. The membranes are then treated with a fluorescent detection reagent and scanned on a phosphorimager.

For each sample, the percent of total signal corresponding to the unprenylated species of hDJ (the slower-migrating species) is calculated by densitometry. Dose-response curves and $EC_{50}$ values are generated using 4-parameter curve fits in SigmaPlot software.

Example 114

Rap1 Processing Inhibition Assay

Protocol A:

Cells are labeled, incubated and lysed as described in Example 113.

For immunoprecipitation of Rap1, samples of lysate supernatant containing equal amounts of protein are utilized. Protein concentration is determined by the bradford method utilizing bovine serum albumin as a standard. The appropriate volume of lysate is brought to 1 ml with lysis buffer lacking DTT and 2 µg of the Rap1 antibody, Rap1/Krev1 (121) (Santa Cruz Biotech), is added. The protein/antibody mixture is incubated on ice at 4° C. for 1 hour. The immune complex is collected on pansorbin (Calbiochem) by tumbling at 4° C. for 45 minutes. The pellet is washed 3 times with 1 ml of lysis buffer lacking DTT and protease inhibitors and resuspended in 100 µl elution buffer (10 mM Tris pH 7.4, 1% SDS). The Rap1 is eluted from the beads by heating at 95° C. for 5 minutes, after which the beads are pelleted by brief centrifugation (15,000×g for 30 sec. at room temperature).

The supernatant is added to 1 ml of Dilution Buffer (0.1% Triton X-100, 5 mM EDTA, 50 mM NaCl, 10 mM Tris pH 7.4) with 2 µg Rap1 antibody, Rap1/Krev1 (121) (Santa Cruz Biotech). The second protein/antibody mixture is incubated on ice at 4° C. for 1–2 hours. The immune complex is collected on pansorbin (Calbiochem) by tumbling at 4° C. for 45 minutes. The pellet is washed 3 times with 1 ml of lysis buffer lacking DTT and protease inhibitors and resuspended in Laemmli sample buffer. The Rap1 is eluted from the beads by heating at 95° C. for 5 minutes, after which the beads are pelleted by brief centrifugation. The supernatant is subjected to SDS-PAGE on a 12% acrylamide gel (bis-acrylamide:acrylamide, 1:100), and the Rap1 visualized by fluorography.

Protocol B:

PSN-1 cells are passaged every 3–4 days in 10 cm plates, splitting near-confluent plates 1:20 and 1:40. The day before the assay is set up, 5×10⁶ cells are plated on 15 cm plates to ensure the same stage of confluency in each assay. The media for these cells is RPM1 1640 (Gibco), with 15% fetal bovine serum and 1×Pen/Strep antibiotic mix.

The day of the assay, cells are collected from the 15 cm plates by trypsinization and diluted to 400,000 cells/ml in media. 0.5 ml of these diluted cells are added to each well of 24-well plates, for a final cell number of 200,000 per well. The cells are then grown at 37° C. overnight.

The compounds to be assayed are diluted in DMSO in ½-log dilutions. The range of final concentrations to be assayed is generally 0.1–100 µM. Four concentrations per compound is typical. The compounds are diluted so that each concentration is 1000× of the final concentration (i.e., for a 10 µM data point, a 10 mM stock of the compound is needed).

2 µL of each 1000× compound stock is diluted into 1 ml media to produce a 2× stock of compound. A vehicle control solution (2 µL DMSO to 1 ml media), is utilized. 0.5 ml of the 2× stocks of compound are added to the cells.

After 24 hours, the media is aspirated from the assay plates. Each well is rinsed with 1 ml PBS, and the PBS is aspirated. 180 μL SDS-PAGE sample buffer (Novex) containing 5% 2-mercaptoethanol is added to each well. The plates are heated to 100° C. for 5 minutes using a heat block containing an adapter for assay plates. The plates are placed on ice. After 10 minutes, 20 μL of an RNAse/DNase mix is added per well. This mix is 1 mg/ml DNaseI (Worthington Enzymes), 0.25 mg/ml Rnase A (Worthington Enzymes), 0.5M Tris-HCl pH8.0 and 50 mM $MgCl_2$. The plate is left on ice for 10 minutes. Samples are then either loaded on the gel, or stored at −70° C. until use.

Each assay plate (usually 3 compounds, each in 4-point titrations, plus controls) requires one 15-well 14% Novex gel. 25 μl of each sample is loaded onto the gel. The gel is run at 15 mA for about 3.5 hours. It is important to run the gel far enough so that there will be adequate separation between 21 kd (Rap1) and 29 kd (Rab6).

The gels are then transferred to Novex pre-cut PVDF membranes for 1.5 hours at 30V (constant voltage). Immediately after transferring, the membranes are blocked overnight in 20 ml Western blocking buffer (2% nonfat dry milk in Western wash buffer (PBS+0.1% Tween-20). If blocked over the weekend, 0.02% sodium azide is added. The membranes are blocked at 4° C. with slow rocking.

The blocking solution is discarded and 20 ml fresh blocking solution containing the anti Rap1a antibody (Santa Cruz Biochemical SC1482) at 1:1000 (diluted in Western blocking buffer) and the anti Rab6 antibody (Santa Cruz Biochemical SC310) at 1:5000 (diluted in Western blocking buffer) are added. The membranes are incubated at room temperature for 1 hour with mild rocking. The blocking solution is then discarded and the membrane is washed 3 times with Western wash buffer for 15 minutes per wash. 20 ml blocking solution containing 1:1000 (diluted in Western blocking buffer) each of two alkaline phosphatase conjugated antibodies (Alkaline phosphatase conjugated Anti-goat IgG and Alkaline phosphatase conjugated anti-rabbit IgG [Santa Cruz Biochemical]) is then added. The membrane is incubated for one hour and washed 3× as above.

About 2 ml per gel of the Amersham ECF detection reagent is placed on an overhead transparency (ECF) and the PVDF membranes are placed face-down onto the detection reagent. This is incubated for one minute, then the membrane is placed onto a fresh transparency sheet.

The developed transparency sheet is scanned on a phosphorimager and the Rap1a Minimum Inhibitory Concentration is determined from the lowest concentration of compound that produces a detectable Rap1a Western signal. The Rap1a antibody used recognizes only unprenylated/unprocessed Rap1a, so that the precence of a detectable Rap1a Western signal is indicative of inhibition of Rap1a prenylation.

Protocol C:

This protocol allows the determination of an $EC_{50}$ for inhibition of processing of Rap1a. The assay is run as described in Protocol B with the following modifications. 20 μl of sample is run on pre-cast 10–20% gradient acrylamide mini gels (Novex Inc.) at 15 mA/gel for 2.5–3 hours. Prenylated and unprenylated forms of Rap1a are detected by blotting with a polyclonal antibody (Rap1/Krev-1 Ab#121; Santa Cruz Research Products #sc-65), followed by an alkaline phosphatase-conjugated anti-rabbit IgG antibody. The percentage of unprenylated Rap1a relative to the total amount of Rap1a is determined by peak integration using Imagequant® software (Molecular Dynamics). Unprenylated Rap1a is distinguished from prenylated protein by virtue of the greater apparent molecular weight of the prenylated protein. Dose-response curves and $EC_{50}$ values are generated using 4-parameter curve fits in SigmaPlot software.

Example 115

In Vivo Tumor Growth Inhibition Assay (Nude Mouse)

In vivo efficacy as an inhibitor of the growth of cancer cells may be confirmed by several protocols well known in the art. Examples of such in vivo efficacy studies are described by N. E. Kohl et al. (Nature Medicine, 1:792–797 (1995)) and N. E. Kohl et al. (Proc. Nat. Acad. Sci. U.S.A., 91:9141–9145 (1994)).

Rodent fibroblasts transformed with oncogenically mutated human Ha-ras or Ki-ras ($10^6$ cells/animal in 1 ml of DMEM salts) are injected subcutaneously into the left flank of 8–12 week old female nude mice (Harlan) on day 0. The mice in each oncogene group are randomly assigned to a vehicle, compound or combination treatment group. Animals are dosed subcutaneously starting on day 1 and daily for the duration of the experiment. Alternatively, the farnesyl-protein transferase inhibitor may be administered by a continuous infusion pump. Compound, compound combination or vehicle is delivered in a total volume of 0.1 ml. Tumors are excised and weighed when all of the vehicle-treated animals exhibited lesions of 0.5–1.0 cm in diameter, typically 11–15 days after the cells were injected. The average weight of the tumors in each treatment group for each cell line is calculated.

What is claimed is:
1. A compound of the formula A:

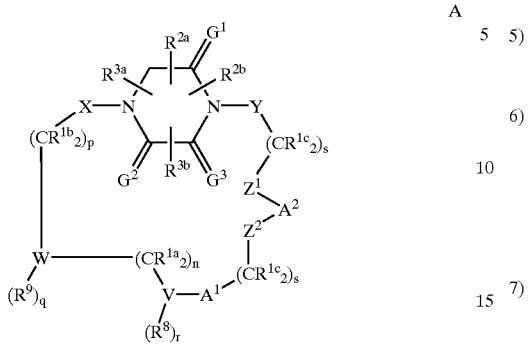

wherein:

$R^{1a}$, $R^{1b}$, $R^{1c}$ and $R^{1d}$ are independently selected from:
  a) hydrogen,
  b) aryl, heterocycle, cycloalkyl, alkenyl, alkynyl, $R^{10}O$—, $R^{11}S(O)_m$—, $R^{10}C(O)NR^{10}$—, $(R^{10})_2N$—C(O)—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—,
  c) unsubstituted or substituted $C_1$–$C_6$ alkyl wherein the substitutent on the substituted $C_1$–$C_6$ alkyl is selected from unsubstituted or substituted aryl, heterocyclic, cycloalkyl, alkenyl, alkynyl, $R^{10}O$—, $R^{11}S(O)_m$—, $R^{10}C(O)NR^{10}$—, $(R^{10})_2N$—C(O)—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—; or two $R^{1a}$s, two $R^{1b}$s, two $R^{1c}$s or two $R^{1d}$s, on the same carbon atom may be combined to form —$(CH_2)_t$—;

$R^{2a}$, $R^{2b}$, $R^{3a}$ and $R^{3b}$ are independently selected from H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

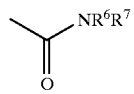

or

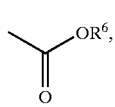

wherein the substituted group is substituted with one or more of:
1) aryl or heterocycle, unsubstituted or substituted with:
  a) $C_{1-4}$ alkyl,
  b) $(CH_2)_pOR^6$,
  c) $(CH_2)_pNR^6R^7$,
  d) halogen,
  e) CN, 2) $C_{3-6}$ cycloalkyl,
3) $OR^6$,
4) $SR^4$, $S(O)R^4$, $SO_2R^4$, 5) 

6) 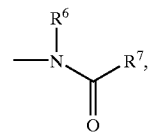

7) 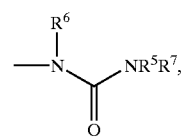

8) 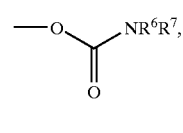

9) 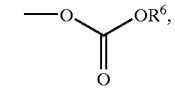

10) 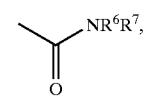

11) 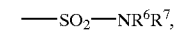

12) 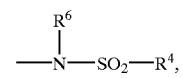

13) 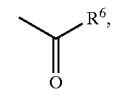

14) 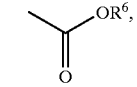

15) $N_3$, or

16) F; or $R^{2a}$ and $R^{3a}$ are attached to the same C atom and are combined to form —$(CH_2)_u$— wherein one of the carbon atoms is optionally replaced by a moiety selected from O, $S(O)_m$, —NC(O)—, and —$N(COR^{10})$—; and $R^{2a}$ and $R^{3a}$ are optionally attached to the same carbon atom;

$R^4$ is selected from $C_{1-4}$ alkyl, $C_{3-6}$ cycloalkyl, heterocycle, aryl, unsubstituted or substituted with:

a) $C_{1-4}$alkoxy,
b) aryl or heterocycle,
c) halogen,
d) HO,
e)

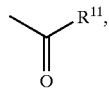

f) —$SO_2R^{11}$,
g) $N(R^{10})_2$, or
h) $C_{1-4}$ perfluoroalkyl;

$R^5$, $R^6$ and $R^7$ are independently selected from:
1) hydrogen,
2) $R^{10}C(O)$—, or $R^{10}OC(O)$—, and
3) $C_1$–$C_6$ alkyl, $C_2$–$C_6$ alkenyl, $C_2$–$C_6$ alkynyl, $C_{3-6}$ cycloalkyl, heterocycle, aryl, aroyl, heteroaroyl, arylsulfonyl, heteroarylsulfonyl, $C_6$–$C_{10}$ multicyclic alkyl ring, unsubstituted or substituted with one or more substituents selected from:
   a) $R^{10}O$—,
   b) aryl or heterocycle,
   c) halogen,
   d) $R^{10}C(O)NR^{10}$—,
   e)

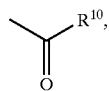

f) —$SO_2R^{11}$,
g) $N(R^{10})_2$,
h) $C_{3-6}$ cycloalkyl,
i) $C_6$–$C_{10}$ multicyclic alkyl ring,
j) $C_1$–$C_6$ perfluoroalkyl,
k) $(R^{10})_2N$—$C(NR^{10})$—,
l) $R^{10}OC(O)$—,
m) $R^{11}OC(O)NR^{10}$—,
n) CN, and
o) $NO_2$; or $R^6$ and $R^7$ may be joined in a ring; and independently, $R^5$ and $R^7$ may be joined in a ring;

$R^8$ is independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $R^{10}OC(O)$—, $N_3$, —$N(R^{10})_2$, or $R^{11}OC(O)NR^{10}$—, and
c) $C_1$–$C_6$ alkyl unsubstituted or substituted by unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NH$—, $(R^{10})_2NC(O)$—, $R^{10}{}_2N$—$C(NR^{10})$—, CN, $R^{10}C(O)$—, $R^{10}OC(O)$—, $N_3$, —$N(R^{10})_2$, or $R^{10}OC(O)NH$—;

$R^9$ is selected from:
a) hydrogen,
b) $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $R^{10}OC(O)$—, $N_3$, —$N(R^{10})_2$, or $R^{11}OC(O)NR^{10}$—, and c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $R^{10}OC(O)$—, $N_3$, —$N(R^{10})_2$, or $R^{11}OC(O)NR^{10}$—;

$R^{10}$ is independently selected from hydrogen, $C_1$–$C_6$ alkyl, benzyl, unsubstituted or substituted aryl and unsubstituted or substituted heterocycle;

$R^{11}$ is independently selected from $C_1$–$C_6$ alkyl unsubstituted or substituted aryl and unsubstituted or substituted heterocycle;

$R^{12}$ is independently selected from hydrogen, $C_1$–$C_6$ alkyl, $C_1$–$C_3$ perfluoroalkyl, unsubstituted or substituted benzyl, unsubstituted or substituted aryl, unsubstituted or substituted heterocycle, and $C_1$–$C_6$ alkyl substituted with unsubstituted or substituted aryl or unsubstituted or substituted heterocycle;

$A^1$ is O;

$A^2$ is a bond;

$G^1$, $G^2$ and $G^3$ are independently selected from $H_2$ and O;

W is imidazolyl;

V is aryl;

X and Y are independently selected from a bond and —C(=O)—;

$Z^1$ is selected from unsubstituted or substituted aryl, wherein the substituted aryl is substituted with one or more of:
1) $C_{1-8}$ alkyl, $C_{2-8}$ alkenyl or $C_{2-8}$ alkynyl, unsubstituted or substituted with:
   a) $C_{1-4}$alkoxy,
   b) $NR^6R^7$,
   c) $C_{3-6}$ cycloalkyl,
   d) aryl or heterocycle,
   e) HO,
   f) —$S(O)_mR^4$,
   g) —$C(O)NR^6R^7$,
   h) —$Si(C_{1-4}$ alkyl$)_3$, or
   i) $C_{1-4}$ perfluoroalkyl;
2) substituted or unsubstituted aryl or substituted or unsubstituted heterocycle,
3) halogen,
4) $OR^6$,
5) $NR^6R^7$,
6) CN,
7) $NO_2$,
8) $CF_3$;
9) —$S(O)_mR^4$,
10) —$OS(O)_2R^4$,
11) —$C(O)NR^6R^7$,
12) —$C(O)OR^6$, or
13) $C_3$–$C_6$ cycloalkyl;

$Z^2$ is a bond;

m is 0, 1 or 2;

n is 0, 1, 2, 3 or 4;

p is 0, 1, 2, 3 or 4;

q is 1 or 2;

r is 0 to 5;

s is independently 0, 1, 2 or 3;

t is 2 to 6; and u is 4 or 5;

or a pharmaceutically acceptable salt or stereoisomer thereof.

2. The compound according to claim 1 of the formula A:

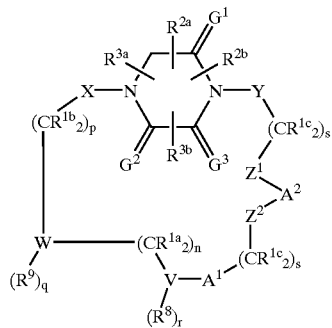

wherein:

$R^{1a}$, $R^{1b}$, $R^{1c}$ and $R^{1d}$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—,
c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

$R^{2a}$, $R^{2b}$, $R^{3a}$ and $R^{3b}$ are independently selected from H; unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

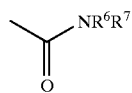

or

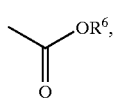

wherein the substituted group is substituted with one or more of:
1) aryl or heterocycle, unsubstituted or substituted with:
   a) $C_{1-4}$ alkyl,
   b) $(CH_2)_pOR^6$,
   c) $(CH_2)_pNR^6R^7$,
   d) halogen,
   e) CN,
2) $C_{3-6}$ cycloalkyl,
3) $OR^6$,
4) $SR^4$, $S(O)R^4$, $SO_2R^4$,

5) —$NR^6R^7$,

6)

$$\ce{-N(R^6)-C(=O)-R^7}$$

7)

$$\ce{-N(R^6)-C(=O)-NR^5R^7}$$

8)

$$\ce{-O-C(=O)-NR^6R^7}$$

9)

$$\ce{-O-C(=O)-OR^6}$$

10)

$$\ce{-C(=O)-NR^6R^7}$$

11) —$SO_2$—$NR^6R^7$,

12)

$$\ce{-N(R^6)-SO_2-R^4}$$

13)

$$\ce{-C(=O)-R^6}$$

14)

$$\ce{-C(=O)-OR^6}$$

15) $N_3$, or

16) F; or $R^2$ and $R^3$ are attached to the same C atom and are combined to form —$(CH_2)_u$— wherein one of the carbon atoms is optionally replaced by a moiety selected from O, $S(O)_m$, —NC(O)—, and —$N(COR^{10})$—,
and $R^2$ and $R^3$ are optionally attached to the same carbon atom;

$R^4$ is selected from $C_{1-4}$ alkyl, $C_{3-6}$ cycloalkyl, heterocycle, aryl, unsubstituted or substituted with:
   a) $C_{1-4}$ alkoxy,
   b) aryl or heterocycle, c) halogen,
d) HO,
e)

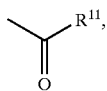

f) —SO$_2$R$^{11}$, or
g) N(R$^{10}$)$_2$;

R$^5$, R$^6$ and R$^7$ are independently selected from H; C$_{1-4}$ alkyl, C$_{3-6}$ cycloalkyl, heterocycle, aryl, aroyl, heteroaroyl; arylsulfonyl, heteroarylsulfonyl, unsubstituted or substituted with:
a) C$_{1-4}$ alkoxy,
b) aryl or heterocycle,
c) halogen,
d) HO,
e)

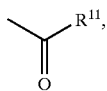

f) —SO$_2$R$^1$, or
g) N(R$^{10}$)$_2$; or

R$^6$ and R$^7$ may be joined in a ring; and independently, R$^5$ and R$^7$ may be joined in a ring;

R$^8$ is independently selected from:
a) hydrogen,
b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, R$^{10}$OC(O)—, N$_3$, —N(R$^{10}$)$_2$, or R$^{11}$OC(O)NR$^{10}$—, and
c) C$_1$–C$_6$ alkyl unsubstituted or substituted by unsubstituted or substituted aryl, unsubstituted or substituted heterocycle, C$_3$–C$_{10}$ cycloalkyl, C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NH—, (R$^{10}$)$_2$NC(O)—, R$^{10}$$_2$N—C(NR$^{10}$)—, CN, R$^{10}$C(O)—, R$^{10}$OC(O)—, N$_3$, —N(R$^{10}$)$_2$, or R$^{10}$OC(O)NH—;

R$^9$ is selected from:
a) hydrogen,
b) C$_2$–C$_6$ alkenyl, C$_2$–C$_6$ alkynyl, perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, R$^{10}$C(O)—, N$_3$, —N(R$^{10}$)$_2$, or R$^{11}$OC(O)NR$^{10}$—, and
c) C$_1$–C$_6$ alkyl unsubstituted or substituted by perfluoroalkyl, F, Cl, Br, R$^{10}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, R$^{10}$C(O)—, N$_3$, —N(R$^{10}$)$_2$, or R$^{11}$OC(O)NR$^{10}$—;

R$^{10}$ is independently selected from hydrogen, C$_1$–C$_6$ alkyl, benzyl, unsubstituted or substituted aryl and unsubstituted or substituted heterocycle;

R$^{11}$ is independently selected from C$_1$–C$_6$ alkyl unsubstituted or substituted aryl and unsubstituted or substituted heterocycle;

A$^1$ is O;
A$^2$ is a bond;

G$^1$, G$^2$ and G$^3$ are independently selected from H$_2$ and O;
W is imidazolyl;
V is phenyl;
X and Y are independently selected from a bond and —C(=O)—;
Z$^1$ is selected from unsubstituted or substituted phenyl and unsubstituted or substituted naphthyl, wherein the substituted phenyl or substituted naphthyl is substituted with one or more of:
1) C$_{1-4}$ alkyl, unsubstituted or substituted with:
   a) C$_{1-4}$ alkoxy,
   b) NR$^6$R$^7$,
   c) C$_{3-6}$ cycloalkyl,
   d) aryl or heterocycle,
   e) HO,
   f) —S(O)$_m$R$^4$, or
   g) —C(O)NR$^6$R$^7$,
2) aryl or heterocycle,
3) halogen,
4) OR$^6$,
5) NR$^6$R$^7$,
6) CN,
7) NO$_2$,
8) CF$_3$,
9) —S(O)$_m$R$^4$,
10) —C(O)NR$^6$R$^7$, or
11) C$_3$–C$_6$ cycloalkyl;

Z$^2$ is a bond;
m is 0, 1 or 2;
n is 0, 1, 2, 3 or 4;
p is 0, 1, 2, 3 or 4;
q is 1 or 2;
r is 0 to 5;
s is independently 0, 1, 2 or 3; and
u is 4 or 5;
or a pharmaceutically acceptable salt or stereoisomer thereof.

3. The compound according to claim 1 of the formula B:

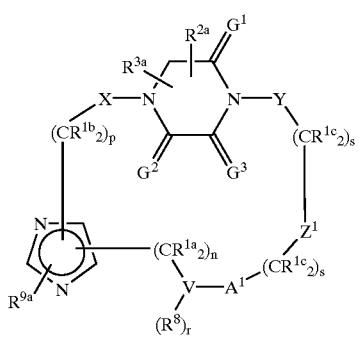

wherein:
R$^{1a}$, R$^{1b}$ and R$^{1c}$ is independently selected from:
a) hydrogen,
b) aryl, heterocycle, cycloalkyl, R$^{10}$O—, —N(R$^{10}$)$_2$ or C$_2$–C$_6$ alkenyl, and
c) C$_1$–C$_6$ alkyl unsubstituted or substituted by aryl, heterocycle, cycloalkyl, alkenyl, R$^{10}$O—, or —N(R$^{10}$)$_2$;
or two R$^{1b}$s, two R$^{1c}$s or two R$^{1d}$s, on the same carbon atom may be combined to form —(CH$_2$)$_t$—;

R$^{3a}$ is selected from H and CH$_3$;

$R^{2a}$ is selected from H;

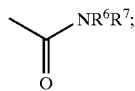

and $C_{1-5}$ alkyl, unbranched or branched, unsubstituted or substituted with one or more of:
1) aryl,
2) heterocycle,
3) $OR^6$,
4) $SR^4$, $SO_2R^4$, or

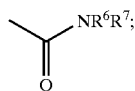

and any two of $R^{2a}$ and $R^{3a}$ are optionally attached to the same carbon atom;

$R^4$ is selected from $C_{1-4}$ alkyl and $C_{3-6}$ cycloalkyl, unsubstituted or substituted with:
a) $C_{1-4}$ alkoxy,
b) halogen, or
c) aryl or heterocycle;

$R^6$ and $R^7$ are independently selected from H; $C_{1-6}$ alkyl, $C_{3-6}$ cycloalkyl, $C_6$–$C_{10}$ multicyclic alkyl ring, heterocycle, aryl, aroyl, heteroaroyl, arylsulfonyl, heteroarylsulfonyl, unsubstituted or substituted with one or two:
a) $C_{1-4}$ alkoxy,
b) aryl or heterocycle,
c) halogen,
d) HO,
e)

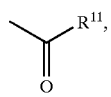

f) $-SO_2R^{11}$,
g) $N(R^{10})_2$,
h) $C_{3-6}$ cycloalkyl,
i) $C_6$–$C_{10}$ multicyclic alkyl ring; or $R^8$ is independently selected from:
a) hydrogen,
b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{12}O-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and
c) $C_1$–$C_6$ alkyl substituted by: unsubstituted or substituted aryl, $C_1$–$C_6$ perfluoroalkyl, $R^{10}O-$, $R^{10}C(O)NR^{10}-$, $(R^{10})_2N-C(NR^{10})$, $R^{10}C(O)-$, $N(R^{10})_2$, or $R^{11}OC(O)NR^{10}-$;

$R^{9a}$ is hydrogen or methyl;

$R^{10}$ is independently selected from hydrogen, $C_1$–$C_6$ alkyl, benzyl and unsubstituted or substituted aryl;

$R^{11}$ is independently selected from $C_1$–$C_6$ alkyl and unsubstituted or substituted aryl;

$R^{12}$ is independently selected from hydrogen, $C_1$–$C_6$ alkyl, unsubstituted or substituted benzyl, unsubstituted or substituted aryl, unsubstituted or substituted heterocycle, and $C_1$–$C_6$ alkyl substituted with unsubstituted or substituted aryl or unsubstituted or substituted heterocycle;

$A^1$ is O;

$G^1$, $G^2$ and $G^3$ are independently selected from $H_2$ and O;

V is phenyl;

X is a bond or $-C(=O)-$;

Y is a bond or $-C(=O)-$;

$Z^1$ is selected from unsubstituted or substituted phenyl and unsubstituted or substituted naphthyl, wherein the substituted phenyl or substituted naphthyl is substituted with one or more of:
1) $C_{1-8}$ alkyl, $C_{2-8}$ alkenyl or $C_{2-8}$ alkynyl, unsubstituted or substituted with:
 a) $C_{1-4}$ alkoxy,
 b) $NR^6R^7$,
 c) $C_{3-6}$ cycloalkyl,
 d) aryl or heterocycle,
 e) HO,
 f) $-S(O)_mR^4$,
 g) $-C(O)NR^6R^7$,
 h) $-Si(C_{1-4}$ alkyl$)_3$, or
 i) $C_{1-4}$ perfluoroalkyl;
2) substituted or unsubstituted aryl or substituted or unsubstituted heterocycle,
3) halogen,
4) $OR^6$,
5) $NR^6R^7$,
6) CN,
7) $NO_2$,
8) $CF_3$,
9) $-S(O)_mR^4$,
10) $-OS(O)_2R^4$,
11) $-C(O)NR^6R^7$,
12) $-C(O)OR^6$, or
13) $C_3$–$C_6$ cycloalkyl;

m is 0, 1 or 2;
n is 0, 1, 2, 3 or 4;
p is 0, 1, 2, 3 or 4;
r is 0 to 5; and
s is independently 0, 1, 2 or 3;
or a pharmaceutically acceptable salt or stereoisomer thereof.

4. The compound according to claim 3 of the formula C-1:

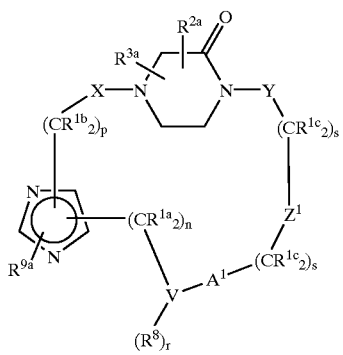

C-1 wherein:
$R^{1a}$, $R^{1b}$ and $R^{1c}$ is independently selected from:
a) hydrogen,
b) aryl, heterocycle, cycloalkyl, $R^{10}O-$, $-N(R^{10})_2$ or $C_2$–$C_6$ alkenyl, and
c) $C_1$–$C_6$ alkyl unsubstituted or substituted by aryl, heterocycle, cycloalkyl, alkenyl, $R^{10}O-$, or $-N(R^{10})_2$;

$R^{3a}$ is selected from H and $CH_3$;
$R^{2a}$ is selected from H;

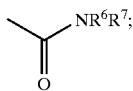

and $C_{1-5}$ alkyl, unbranched or branched, unsubstituted or substituted with one or more of:
1) aryl,
2) heterocycle,
3) $OR^6$,
4) $SR^4$, $SO_2R^4$, or

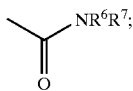

and any two of $R^{2a}$ and $R^{3a}$ are optionally attached to the same carbon atom, $R^4$ is selected from $C_{1-4}$ alkyl and $C_{3-6}$ cycloalkyl, unsubstituted or substituted with:
a) $C_{1-4}$ alkoxy,
b) halogen, or
c) aryl or heterocycle;

$R^6$ and $R^7$ are independently selected from H; $C_{1-6}$ alkyl, $C_{3-6}$ cycloalkyl, $C_6$–$C_{10}$ multicyclic alkyl ring, heterocycle, aryl, aroyl, heteroaroyl, arylsulfonyl, heteroarylsulfonyl, unsubstituted or substituted with one or two:
a) $C_{1-4}$ alkoxy,
b) aryl or heterocycle,
c) halogen,
d) HO,
e)

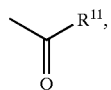

f) $-SO_2R^{11}$,
g) $N(R^{10})_2$,
h) $C_{3-6}$ cycloalkyl,
i) $C_6$–$C_{10}$ multicyclic alkyl ring; or $R^8$ is independently selected from:
a) hydrogen,
b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{12}O-$, $R^{10}C(O)NR^{10}-$, CN, $NO_2$, $(R^{10})_2N-C(NR^{10})-$, $R^{10}C(O)-$, $-N(R^{10})_2$, or $R^{11}OC(O)NR^{10}-$, and
c) $C_1$–$C_6$ alkyl substituted by unsubstituted or substituted aryl, $C_1$–$C_6$ perfluoroalkyl, $R^{10}O-$, $R^{10}C(O)NR^{10}-$, $(R^{10})_2N-C(NR^{10})-$, $R^{10}C(O)-$, $-N(R^{10})_2$, or $R^{11}OC(O)NR^{10}-$;

$R^{9a}$ is hydrogen or methyl;
$R^{10}$ is independently selected from hydrogen, $C_1$–$C_6$ alkyl, benzyl and unsubstituted or substituted aryl;
$R^{11}$ is independently selected from $C_1$–$C_6$ alkyl and unsubstituted or substituted aryl;
$R^{12}$ is independently selected from hydrogen, $C_1$–$C_6$ alkyl, unsubstituted or substituted benzyl, unsubstituted or substituted aryl, unsubstituted or substituted heterocycle, and $C_1$–$C_6$ alkyl substituted with unsubstituted or substituted aryl or unsubstituted or substituted heterocycle;

$A^1$ is O;
V is phenyl;
X is a bond or $-C(=O)-$;
Y is a bond or $-C(=O)-$;
$Z^1$ is selected from unsubstituted or substituted phenyl and unsubstituted or substituted naphthyl, wherein the substituted phenyl or substituted naphthyl is substituted with one or more of:
1) $C_{1-8}$ alkyl, $C_{2-8}$ alkenyl or $C_{2-8}$ alkynyl, unsubstituted or substituted with:
 a) $C_{1-4}$ alkoxy,
 b) $NR^6R^7$,
 c) $C_{3-6}$ cycloalkyl,
 d) aryl or heterocycle,
 e) HO,
 f) $-S(O)_mR^4$,
 g) $-C(O)NR^6R^7$,
 h) $-Si(C_{1-4} alkyl)_3$, or
 i) $C_{1-4}$ perfluoroalkyl;
2) substituted or unsubstituted aryl or substituted or unsubstituted heterocycle,
3) halogen,
4) $OR^6$,
5) $NR^6R^7$,
6) CN,
7) $NO_2$,
8) $CF_3$,
9) $-S(O)_mR^4$,
10) $-OS(O)_2R^4$,
11) $-C(O)NR^6R^7$,
12) $-C(O)OR^6$, or
13) $C_3$–$C_6$ cycloalkyl;

m is 0, 1 or 2;
n is 0, 1, 2, 3 or 4;
p is 0, 1, 2, 3 or 4;
r is 0 to 5; and
s is independently 0, 1, 2 or 3;
or a pharmaceutically acceptable salt or stereoisomer thereof.

5. The compound according to claim 4 of the formula D:

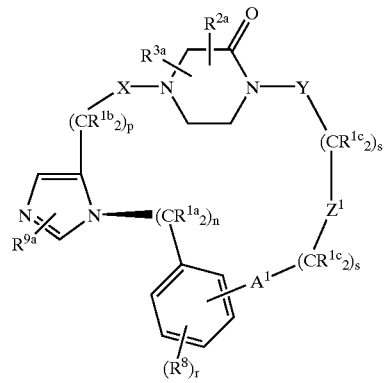

wherein:
$R^{1a}$, $R^{1b}$ and $R^{1c}$ is independently selected from:
a) hydrogen,
b) aryl, heterocycle, cycloalkyl, $R^{10}O-$, $-N(R^{10})_2$ or $C_2$–$C_6$ alkenyl, and c) $C_1$–$C_6$ alkyl unsubstituted or substituted by aryl, heterocycle, cycloalkyl, alkenyl, $R^{10}O$—, or —$N(R^{10})_2$;

$R^{3a}$ is selected from H and $CH_3$;

$R^{2a}$ is selected from H;

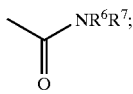

and $C_{1-5}$ alkyl, unbranched or branched, unsubstituted or substituted with one or more of:
1) aryl,
2) heterocycle,
3) $OR^6$,
4) $SR^4$, $SO_2R^4$, or
5)

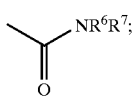

and any two of $R^2$ and $R^3$ are optionally attached to the same carbon atom;

$R^4$ is selected from $C_{1-4}$ alkyl and $C_{3-6}$ cycloalkyl, unsubstituted or substituted with:
a) $C_{1-4}$ alkoxy,
b) halogen, or
c) aryl or heterocycle;

$R^6$ and $R^7$ are independently selected from H; $C_{1-6}$ alkyl, $C_{3-6}$ cycloalkyl, $C_6$–$C_{10}$ multicyclic alkyl ring, heterocycle, aryl, aroyl, arylsulfonyl, unsubstituted or substituted with one or two:
a) $C_{1-4}$ alkoxy,
b) aryl or
c) halogen,
d) HO,
e)

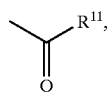

f) —$SO_2R^{11}$,
g) $N(R^{10})_2$,
h) $C_{3-6}$ cycloalkyl,
i) $C_6$–$C_{10}$ multicyclic alkyl ring; or $R^8$ is independently selected from:
a) hydrogen,
b) unsubstituted or substituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^{12}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by unsubstituted or substituted aryl, $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

$R^{9a}$ is hydrogen or methyl;

$R^{10}$ is independently selected from hydrogen, $C_1$–$C_6$ alkyl, benzyl and unsubstituted or substituted aryl;

$R^{11}$ is independently selected from $C_1$–$C_6$ alkyl and unsubstituted or substituted aryl;

$R^{12}$ is independently selected from hydrogen, $C_1$–$C_6$ alkyl, unsubstituted or substituted benzyl, unsubstituted or substituted aryl, unsubstituted or substituted heterocycle, and $C_1$–$C_6$ alkyl substituted with unsubstituted or substituted aryl or unsubstituted or substituted heterocycle;

$A^1$ is O;

X is a bond;

Y is a bond;

$Z^1$ is selected from unsubstituted or substituted phenyl and unsubstituted or substituted naphthyl, wherein the substituted phenyl or substituted naphthyl is substituted with one or more of:
1) $C_{1-8}$ alkyl, $C_{2-8}$ alkenyl or $C_{2-8}$ alkynyl, unsubstituted or substituted with:
   a) $C_{1-4}$ alkoxy,
   b) $NR^6R^7$,
   c) $C_{3-6}$ cycloalkyl,
   d) aryl or heterocycle,
   e) HO,
   f) —$S(O)_mR^4$,
   g) —$C(O)NR^6R^7$,
   h) —$Si(C_{1-4}\ alkyl)_3$, or
   i) $C_{1-4}$ perfluoroalkyl;
2) substituted or unsubstituted aryl or substituted or unsubstituted heterocycle,
3) halogen,
4) $OR^6$,
5) $NR^6R^7$,
6) CN,
7) $NO_2$,
8) $CF_3$,
9) —$S(O)_mR^4$,
10) —$OS(O)_2R^4$,
11) —$C(O)NR^6R^7$,
12) —$C(O)OR^6$, or
13) $C_3$–$C_6$ cycloalkyl;

m is 0, 1 or 2;

n is 0, 1, 2, 3 or 4;

p is 0, 1, 2, 3 or 4;

r is 0 to 5; and s is independently 0, 1, 2 or 3;

or a pharmaceutically acceptable salt or stereoisomer thereof.

6. The compound according to claim 4 of the formula E:

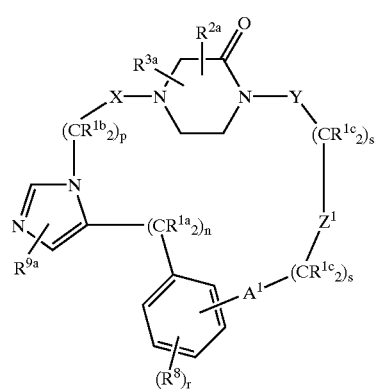

E wherein:
R$^{1a}$, R$^{1b}$ and R$^{1c}$ is independently selected from:
a) hydrogen,
b) aryl, heterocycle, cycloalkyl, R$^{10}$O—, —N(R$^{10}$)$_2$ or C$_2$–C$_6$ alkenyl, and
c) C$_1$–C$_6$ alkyl unsubstituted or substituted by aryl, heterocycle, cycloalkyl, alkenyl, R$^{10}$O—, or —N(R$^{10}$)$_2$;

R$^{3a}$ is selected from H and CH$_3$;
R$^{2a}$ is selected from H;

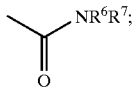

and C$_{1-5}$ alkyl, unbranched or branched, unsubstituted or substituted with one or more of:
1) aryl,
2) heterocycle,
3) OR$^6$,
4) SR$^4$, SO$_2$R$^4$, or
5)

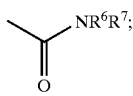

and any two of R$^{2a}$ and R$^{3a}$ are optionally attached to the same carbon atom;
R$^4$ is selected from C$_{1-4}$ alkyl and C$_{3-6}$ cycloalkyl, unsubstituted or substituted with:
a) C$_{1-4}$ alkoxy,
b) halogen, or
c) aryl or heterocycle;
R$^6$ and R$^7$ are independently selected from H; C$_{1-6}$ alkyl, C$_{3-6}$ cycloalkyl, C$_6$–C$_{10}$ multicyclic alkyl ring, aryl, aroyl, arylsulfonyl, unsubstituted or substituted with one or two:
a) C$_{1-4}$ alkoxy,
b) aryl,
c) halogen,
d) HO,
e)

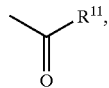

f) —SO$_2$R$^{11}$,
g) N(R$^{10}$)$_2$,
h) C$_{3-6}$ cycloalkyl,
i) C$_6$–C$_{10}$ multicyclic alkyl ring; or
R$^8$ is independently selected from:
a) hydrogen,
b) unsubstituted or substituted aryl, C$_1$–C$_6$ alkyl, C$_2$–C$_6$ alkenyl, C$_2$–C$_6$ alkynyl, C$_1$–C$_6$ perfluoroalkyl, F, Cl, R$^{12}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
c) C$_1$–C$_6$ alkyl substituted by unsubstituted or substituted aryl, C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

R$^{9a}$ is hydrogen or methyl;
R$^{10}$ is independently selected from hydrogen, C$_1$–C$_6$ alkyl, benzyl and unsubstituted or substituted aryl;
R$^{11}$ is independently selected from C$_1$–C$_6$ alkyl and unsubstituted or substituted aryl;
A$^1$ is O;
X is a bond;
Y is a bond;
Z$^1$ is selected from unsubstituted or substituted phenyl and unsubstituted or substituted naphthyl, wherein the substituted phenyl or substituted naphthyl is substituted with one or more of:
1) C$_{1-8}$ alkyl, C$_{2-8}$ alkenyl or C$_{2-8}$ alkynyl, unsubstituted or substituted with:
a) C$_{1-4}$ alkoxy,
b) NR$^6$R$^7$,
c) C$_{3-6}$ cycloalkyl,
d) aryl or heterocycle,
e) HO,
f) —S(O)$_m$R$^4$,
g) —C(O)NR$^6$R$^7$,
h) —Si(C$_{1-4}$ alkyl)$_3$, or
i) C$_{1-4}$ perfluoroalkyl;
2) substituted or unsubstituted aryl or substituted or unsubstituted heterocycle,
3) halogen,
4) OR$^6$,
5) NR$^6$R$^7$,
6) CN,
7) NO$_2$,
8) CF$_3$,
9) —S(O)$_m$R$^4$,
10) —OS(O)$_2$R$^4$,
11) —C(O)NR$^6$R$^7$,
12) —C(O)OR$^6$, or
13) C$_3$–C$_6$ cycloalkyl;
m is 0, 1 or 2;
n is 0, 1, 2, 3 or 4;
p is 0, 1, 2, 3 or 4;
r is 0 to 5; and
s is independently 0, 1, 2 or 3;
or a pharmaceutically acceptable salt or stereoisomer thereof.

7. A compound which is selected from:
19,20-Dihydro-19-oxo-5H,17H-18,21-ethano-6,10:12,16-dimetheno-22H-imidazo[3,4-h][1,8,11,14]oxatriazacycloeicosine-9-carbonitrile (1), (±)-19,20-Dihydro-19-oxo-5H-18,21-ethano-12,14-etheno-6,10-metheno-22H-benzo[d]imidazo[4,3-k][1,6,9,12]oxatriaza-cyclooctadecine-9-carbonitrile (6), (+)-19,20-Dihydro-19-oxo-5H-18,21-ethano-12,14-etheno-6,10-metheno-22H-benzo[d]imidazo[4,3-k][1,6,9,12]oxatriazacyclooctadecine-9-carbonitrile ((+)-6), (−)-19,20-Dihydro-19-oxo-5H-18,21-ethano-12,14-etheno-6,10-metheno-22H-benzo[d]imidazo[4,3-k][1,6,9,12]oxatriazacyclooctadecine-9-carbonitrile ((−)-6), 19,20-dihydro-5H,17H-18,21-Ethano-6,10:12,16-dimetheno-22H-imidazo[3,4-h][1,8,11,14]oxatriazacycloeicosin-20-one (7), (±)-19,20-Dihydro-3-methyl-19-oxo-5H-18,21-ethano-12,14-etheno-6,10-metheno-22H-benzo[d]imidazo[4,3-k][1,6,9,12]oxatriazacyclooctadecine-9-carbonitrile (8), (+)-19,20-Dihydro-3-methyl-19-oxo-5H-18,21-ethano-12,14-etheno-6,10-metheno-22H-benzo[d]imidazo[4,3-k][1,6,9,12]oxatriaza-cyclooctadecine-9-carbonitrile ((+)-8), (−)-19,20-Dihydro-3-methyl-19-oxo-5H-18,21-ethano-12,14-etheno-6,10-metheno-22H-benzo[d]imidazo[4,3-k][1,6,9,12]oxatriaza-cyclooctadecine-9-carbonitrile ((−)-8), (+)-19,20-Dihydro-19,22-dioxo-5H-18,21-ethano-12,14-etheno-6,10-metheno-22H-benzo[d]imidazo[4,3-k][1,6,9,12]oxatriazacyclooctadecine-9-carbonitrile (10), (+)-19,20-Dihydro-19,22-dioxo-5H-18,21-ethano-12,14-etheno-6,10-metheno-22H-benzo[d]imidazo[4,3-k][1,6,9,12]oxatriazacyclooctadecine-9-carbonitrile ((+)-10), (−)-19,20-Dihydro-19,22-dioxo-5H-18,21-ethano-12,14-etheno-6,10-metheno-22H-benzo[d]imidazo[4,3-k][1,6,9,12]oxatriazacyclooctadecine-9-carbonitrite ((−)-10), (+)-1-Bromo-19,20-dihydro-19-oxo-5H-18,21-ethano-12,14-etheno-6,10-metheno-22H-benzo[d]imidazo[4,3-k][1,6,9,12]oxatriazacyclooctadecine-9-carbonitrile (11), (+)-1-Bromo-19,20-dihydro-3-methyl-19-oxo-5H-18,21-ethano-12,14-etheno-6,10-metheno-22H-benzo[d]imidazo[4,3-k][1,6,9,12]oxatriaza-cyclooctadecine-9-carbonitrile (12), (−)-1-Bromo-19,20-dihydro-3-methyl-19-oxo-5[-18,21-ethano-12,14-etheno-6,10-metheno-22H-benzo[d]imidazo[4,3-k][1,6,9,12]oxatriazacyclo-octadecine-9-carbonitrile (12), 19,20-Dihydro-5H-18,21-ethano-12,14-etheno-6,10-metheno-22H-benzo[d]imidazo[4,3-k][1,6,9,12]oxatriaza-cyclooctadecine-9-carbonitrile (13)

(±)(5RS)-19,20-Dihydro-5-methyl-19-oxo-5H-18,21-ethano-12,14-etheno-6,10-metheno-22H-benzo[d]imidazo[4,3-k][1,6,9,12]oxatriaza-cyclooctadecine-9-carbonitrile (14), (5R,R)-19,20-Dihydro-5S-methyl-19-oxo-5H-18,21-ethano-12,14-etheno-6,10-metheno-22H-benzo[d]imidazo[4,3-k][1,6,9,12]oxatriaza-cyclooctadecine-9-carbonitrile, (5S,S)-19,20-Dihydro-5S-methyl-19-oxo-5H-18,21-ethano-12,14-etheno-6,10-metheno-22H-benzo[d]imidazo[4,3-k][1,6,9,12]oxatriaza-cyclooctadecine-9-carbonitrile, (5R,S)-19,20-Dihydro-5R-methyl-19-oxo-5H-18,21-ethano-12,14-etheno-6,10-metheno-22H-benzo[d]imidazo[4,3-k][1,6,9,12]oxatriaza-cyclooctadecine-9-carbonitrile, (5S,R)-19,20-Dihydro-5-methyl-19-oxo-5H-18,21-ethano-12,14-etheno-6,10-metheno-22H-benzo[d]imidazo[4,3-k][1,6,9,12]oxatriaza-cyclooctadecine-9-carbonitrile, (+)-18,19-Dihydro-18-oxo-5H-6,9:11,13-dietheno-17,20-ethano-9H,21H-benzo[d]imidazo[4,3-k][1,6,9,12]oxatriaza-cyclooctadecine-8-carbonitrile (16), (R,R)-18,19-Dihydro-18-oxo-5H-6,9:11,13-dietheno-17,20-ethano-9H,21H-benzo[d]imidazo[4,3-k][1,6,9,12]oxatriaza-cycloheptadecine-8-carbonitrile, (R,S)-18,19-Dihydro-18-oxo-5H-6,9:11,13-dietheno-17,20-ethano-9H,21H-benzo[d]imidazo[4,3-k][1,6,9,12]oxatriaza-cycloheptadecine-8-carbonitrile, (S,R)-18,19-Dihydro-18-oxo-5H-6,9:11,13-dietheno-17,20-ethano-9H,21H-benzo[d]imidazo[4,3-k][1,6,9,12]oxatriaza-cycloheptadecine-8-carbonitrile, (S,S)-18,19-Dihydro-18-oxo-5H-6,9:11,13-dietheno-17,20-ethano-9H,21H-benzo[d]imidazo[4,3-k][1,6,9,12]oxatriaza-cycloheptadecine-8-carbonitrile, 8-Chloro-19,20-dihydro-19-oxo-5H-18,21-ethano-12,14-etheno-6,10-metheno-22H-benzo[d]imidazo[4,3-k][1,6,9,12]oxatriaza-cyclooctadecine-9-carbonitrile (19), 19,20-Dihydro-19-oxo-8-phenoxy-5H-18,21-ethano-12,14-etheno-6,10-metheno-22H-benzo[d]imidazo[4,3-k][1,6,9,12]oxatriaza-cyclooctadecine-9-carbonitrile (20), 18-Oxo-17,18,20,21-tetrahydro-5H-19,22-ethano-6,10:12,16-dimetheno-23H-imidazo[3,4-h][1,8,11,14]oxatriazacycloheneicosine-9-carbonitrile (21), Spiro[cyclohexane-1',17–18-oxo-17,18,20,21-tetrahydro-5H-19,22-ethano-6,10:12,16-dimetheno-23H-imidazo[3,4-h][1,8,11,14]oxatriazacycloheneicosine-9-carbonitrile] (22), (+)-19,20-Dihydro-19-oxo-17-propyl-5H,17H-18,21-ethano-6,10:12,16-dimetheno-22H-imidazo[3,4-h][1,8,11,14]oxatriaza-cycloeicosine-9-carbonitrile (23), (+)-19,20-Dihydro-19-oxo-17-propyl-5H,17H-18,21-ethano-6,10:12,16-dimetheno-22H-imidazo[3,4-h][1,8,11,14]oxatriaza-cycloeicosine-9-carbonitrile ((+)-23), (−)-19,20-Dihydro-19-oxo-17-propyl-5H,17H-18,21-ethano-6,10:12,16-dimetheno-22H-imidazo(3,4-h][1,8,11,14]oxatriaza-cycloeicosine-9-carbonitrile ((−)-23), 15-Bromo-19,20-dihydro-19-oxo-5H,17H-18,21-ethano-6,10:12,16-dimetheno-22H-imidazo(3,4-h][1,8,11,14]oxatriaza-cycloeicosine-9-carbonitrile (24), 15-Bromo-19,20-dihydro-3-methyl-19-oxo-5H,17H-18,21-ethano-6,10:12,16-dimetheno-22H-imidazo[3,4-h][1,8,11,14]oxatriaza-cycloeicosine-9-carbonitrile (25), 19,20-Dihydro-15-iodo-3-methyl-19-oxo-5H,17H-18,21-ethano-6,10:12,16-dimetheno-22H-imidazo[3,4-h][1,8,11,14]oxatriaza-cycloeicosine-9-carbonitrile (26), 19,20-Dihydro-3-methyl-19-oxo-5H,17H-18,21-ethano-12,16-imino-6,10-metheno-22H-imidazo[3,4-h][1,8,11,14]oxatriaza-cycloeicosine-9-carbonitrile (27), 15-Bromo-19,20-dihydro-3-methyl-19-oxo-5H,17H-18,21-ethano-12,16-imino-6,10-metheno-22H-imidazo[3,4-h][1,8,11,14]oxatriaza-cycloeicosine-9-carbonitrile (28), 15-Bromo-19,20-dihydro-3-methyl-17-oxo-5H,17H-18,21-ethano-6,10:12,16-dimetheno-22H-imidazo[3,4-h][1,8,11,14]oxatriaza-cycloeicosine-9-carbonitrile (29), 15-[(2-Cyclobutyl)ethynyl]-19,20-dihydro-3-methyl-17-oxo-5H,17H-18,21-ethano-6,10:12,16-dimetheno-22H-imidazo[3,4-h][1,8,11,14]oxatriazacycloeicosine-9-carbonitrile (30), 15-[(2-Cyclobutyl)ethyl]-19,20-dihydro-3-methyl-17-oxo-5H,17H-18,21-ethano-6,10:12,16-dimetheno-22H-imidazo[3,4-h][1,8,11,14]oxatriazacycloeicosine-9-carbonitrile (31), 15-[(2-Cyclopropyl)ethyl]-19,20-dihydro-3-methyl-17-oxo-5H,17H-18,21-ethano-6,10:12,16-dimetheno-22H-imidazo[3,4-h][1,8,11,14]oxatriazacycloeicosine-9-carbonitrile (32), 19,20-Dihydro-15-(3,3-dimethyl-1-butynyl)-19-oxo-5H,17H-18,21-ethano-6,10:12,16-dimetheno-22H-imidazo[3,4-h] (1,8,11,14)oxatriazacycloeicosine-9-carbonitrile (33), 19,20-Dihydro-I9-oxo-15-(2-phenylethynyl)-5H,17H-18,21-ethano-6,10:12,16-dimetheno-22H-imidazo[3,4-h][1,8,11,14]oxatriazacycloeicosine-9-carbonitrile (34), 15-(Cyclohexylethynyl)-19,20-dihydro-19-oxo-5H,17H-18,21-ethano-6,10:12,16-dimetheno-22H-imidazo[3,4-h][1,8,11,14]oxatriaza-cycloeicosine-9-carbonitrile (35), 19,20-Dihydro-19-oxo-15-[2-(trimethylsilyl)ethynyl]-5H,17H-18,21-ethano-6,10:12,16-dimetheno-22H-imidazo[3,4-h][1,8,11,14]oxatriazacycloeicosine-9-carbonitrile (36), 19,20-Dihydro-15-(ethynyl)-19-oxo-5H,17H-18,21-ethano-6,10:12,16-dimetheno-22H-imidazo[3,4-h][1,8,11,14]oxatriazacycloeicosine-9-carbonitrile (37), 19,20-Dihydro-3-methyl-19-oxo-5H,17H-18,21-ethano-6,10:12,16-dimetheno-22H-imidazo[3,4-h][1,8,11,14]oxatriaza-cycloeicosine-9-carbonitrile (38), 15-(Cyclohexylethynyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (39), 19,20-Dihydro-3-methyl-15-(1-octynyl)-19-oxo-5H,17H-18,21-ethano-6,10:12,16-dimetheno-22H-imidazo[3,4-h][1,8,11,14]oxatriaza-cycloeicosine-9-carbonitrile (40), 15-(3-Cyclohexyl-1-propynyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (41), 15-(3-Cyclobutylethynyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (42), 15-(3-Cyclopropylethynyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (43), 19,20-Dihydro-3-methyl-19-oxo-15-(5,5,5-trifluoro-1-pentynyl)-5H,17H-18,21-ethano-6,10:12,16-dimetheno-22H-imidazo[3,4-h][1,8,11,14]oxatriazacycloeicosine-9-carbonitrile (44), 19,20-Dihydro-3-methyl-19-oxo-15-(5,5,5-trifluoro-1-pentynyl)-5H,17H-18,21-ethano-12,16-imino-6,10-metheno-22H-imidazo[3,4-h][1,8,11,14]oxatriazacycloeicosine-9-carbonitrile (45), 19,20-Dihydro-19-oxo-15-(2-propenyl)-5H,17H-18,21-ethano-6,10:12,16-dimetheno-22H-imidazo[3,4-h][1,8,11,14]oxatriaza-cycloeicosine-9-carbonitrile (46), 19,20-Dihydro-3-methyl-19-oxo-15-(2-propenyl)-5H,17H-18,21-ethano-6,10:12,16-dimetheno-22H-imidazo[3,4-h][1,8,11,14]oxatriazacycloeicosine-9-carbonitrile (47), 15-(Cyclopropyl)methyl-19,20-dihydro-19-oxo-5H,17H-18,21-ethano-6,10:12,16-dimetheno-22H-imidazo[3,4-h][1,8,11,14]oxatriazacycloeicosine-9-carbonitrile (48), 19,20-Dihydro-15-methyl-19-oxo-5H,17H-18,21-ethano-6,10:12,16-dimetheno-22H-imidazo[3,4-h][1,8,11,14]oxatriaza-cycloeicosine-9-carbonitrile (49), 19,20-Dihydro-3-methyl-19-oxo-15-pentyl-5H,17H-18,21-ethano-12,16-imino-6,10-metheno-22H-imidazo[3,4-h][1,8,11,14]oxatriazacycloeicosine-9-carbonitrile (50), 19,20-Dihydro-15-(3,3-dimethyl-1-butyl)-19-oxo-5H,17!]-18,21-ethano-6,10:12,16-dimetheno-22H-imidazo[3,4-h][1,8,11,14]oxatriazacycloeicosine-9-carbonitrile (51), 15-(2-Cyclohexyl-1-ethyl)-19,20-dihydro-19-oxo-5H,17H-18,21-ethano-6,10:12,16-dimetheno-22H-imidazo[3,4-h][1,8,11,14]oxatriazacycloeicosine-9-carbonitrile (52), 19,20-Dihydro-15-ethyl-19-oxo-5H,17H-18,21-ethano-6,10:12,16-dimetheno-22H-imidazo[3,4-h][1,8,11,14]oxatriazacycloeicosine-9-carbonitrile (53), 19,20-Dihydro-19-oxo-15-propyl-5H,17H-18,21-ethano-6,10:12,16-dimetheno-22H-imidazo[3,4-h][1,8,11,14]oxatriazacycloeicosine-9-carbonitrile (54), 19,20-Dihydro-3-methyl-15-octyl-19-oxo-5H,17H-18,21-ethano-6,10:12,16-dimetheno-22H-imidazo[3,4-h][1,8,11,14]oxatriazacycloeicosine-9-carbonitrile (55), 15-(2-Cyclohexyl-1-ethyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (56), cis-15-(2-Cyclopropyl-1-ethenyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (57), 15-(2-Cyclopropyl-1-ethyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (58), 19,20-Dihydro-3-methyl-19-oxo-15-(5,5,5-trifluoropentyl)-5H,17H-18,21-ethano-6,10:12,16-dimetheno-22H-imidazo[3,4-h][1,8,11,14]oxatriazacycloeicosine-9-carbonitrile (59), 19,20-Dihydro-3-methyl-19-oxo-15-(5,5,5-trifluoropentyl)-5H,17H-18,21-ethano-12,16-imino-6,10-metheno-22H-imidazo[3,4-h][1,8,11,14]oxatriazacycloeicosine-9-carbonitrile (60), 9-Cyano-19,20-dihydro-19-oxo-5H,17H-18,21-ethano-6,10:12,16-dimetheno-22H-imidazo[3,4-h][1,8,11,14]oxatriaza-cycloeicosine-15-carboxylic acid methyl ester (61), 9-Cyano-19,20-dihydro-19-oxo-5H,17H-18,21-ethano-6,10:12,16-dimetheno-22H-imidazo[3,4-h][1,8,11,14]oxatriaza-cycloeicosine-15-carboxylate,lithium salt (62)

N-(2-Adamantyl)-9-cyano-19,20-dihydro-19-oxo-5H,17H-18,21-ethano-6,10:12,16-dimetheno-22H-imidazo[3,4-h][1,8,11,14]oxatriazacycloeicosine-15-carboxamide (63), (±)-19,20-Dihydro-15-(2,3-dihydroxy-1-propyl)-19-oxo-5H,17H-18,21-ethano-6,10:12,16-dimetheno-22H-imidazo[3,4-h][1,8,11,14]oxatriazacycloeicosine-9-carbonitrile (64), (+)-19,20-Dihydro-15-(2,3-dihydroxy-1-propyl)-3-methyl-19-oxo-5H,17H-18,21-ethano-6,10:12,16-dimetheno-22H-imidazo[3,4-h][1,8,11,14]oxatriazacycloeicosine-9-carbonitrile (65)

(+)-19,20-Dihydro-15-[(2,2-dimethyl-1,3-dioxolano)-4-methyl]-19-oxo-5H,17H-18,21-ethano-6,10:12,16-dimetheno-22H-imidazo[3,4-h][1,8,11,14]oxatriazacyclocicosine-9-carbonitrile (66)

(+)-19,20-Dihydro-15-[(2,2-dimethyl-1,3-dioxolano)-4-methyl]-3-methyl-19-oxo-5H,17H-18,21-ethano-6,10:12,16-dimetheno-22H-imidazo[3,4-h][1,8,11,14]oxatriazacycloeicosine-9-carbonitrile (67)

19,20-Dihydro-3-methyl-19-oxo-15-phenyl-5H,17H-18,21-ethano-6,10:12,16-dimetheno-22H-imidazo[3,4-h][1,8,11,14]oxatriazacycloeicosine-9-carbonitrile (68), 19,20-Dihydro-15-(2-methoxyphenyl)-3-methyl-19-oxo-5H,17H-18,21-ethano-6,10:12,16-dimetheno-22H-imidazo[3,4-h][1,8,11,14]oxatriazacycloeicosine-9-carbonitrile (69), 19,20-Dihydro-15-(3-methoxyphenyl)-3-methyl-19-oxo-5H,17H-18,21-ethano-6,10:12,16-dimetheno-22H-imidazo[3,4-h][1,8,11,14]oxatriazacycloeicosine-9-carbonitrile (70), 19,20-Dihydro-15-(4-methoxyphenyl)-3-methyl-19-oxo-5H,17H-18,21-ethano-6,10:12,16-dimetheno-22H-imidazo[3,4-h][1,8,11,14]oxatriazacycloeicosine-9-carbonitrile (71), 15-(2-Chlorophenyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (72), 15-(3-Chlorophenyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (73), 15-(4-Chlorophenyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (74), 15-(2,4-Dichlorophenyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (75), 15-(3,5-Dichlorophenyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (76), 19,20-Dihydro-3-methyl-19-oxo-15-(3-thienyl)-5H,17H-18,21-ethano-6,10:12,16-dimetheno-22H-imidazo[3,4-h][1,8,11,14]oxatriazacycloeicosine-9-carbonitrile (77), 15-(Benzo[b]furan-2-yl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (78), 19,20-Dihydro-15-[(methanesulfonyl)oxy]-19-oxo-5H,17H-18,21-ethano-6,10:12,16-dimetheno-22H-imidazo[3,4-h][1,8,11,14]oxatriazacycloeicosine-9-carbonitrile (79), 15-Benzyloxy-19,20-dihydro-19-oxo-5H,17H-18,21-ethano-6,10:12,16-dimetheno-22H-imidazo[3,4-h][1,8,11,14]oxatriazacycloeicosine-9-carbonitrile (80), 19,20-Dihydro-15-hydroxy-19-oxo-5H,17H-18,21-ethano-6,10:12,16-dimetheno-22H-imidazo[3,4-h][1,8,11,14]oxatriaza-cycloeicosine-9-carbonitrile (81)

15-[(Cyclohexylmethyl)oxy]-19,20-dihydro-19-oxo-5H,17H-18,21-ethano-6,10:12,16-dimetheno-22H-imidazo[3,4-h][1,8,11,14]oxatriazacycloeicosine-9-carbonitrile (82), 19,20-Dihydro-19-oxo-15-[(4,4,4-trifluoro-1-butyl)oxy]-5H,17H-18,21-ethano-6,10:12,16-dimetheno-22H-imidazo[3,4-h][1,8,11,14]oxatriazacycloeicosine-9-carbonitrile (83), 19,20-Dihydro-19-oxo-15-phenoxy-5H,17H-18,21-ethano-6,10:12,16-dimetheno-22H-imidazo[3,4-h][1,8,11,14]oxatriaza-cycloeicosine-9-carbonitrile (84), 19,20-Dihydro-14-[(methanesulfonyl)oxy]-19-oxo-5H,17H-18,21-ethano-6,10:12,16-dimetheno-22H-imidazo[3,4-h][1,8,11,14]oxatriazacycloeicosine-9-carbonitrile (85), 14-[(Cyclohexylmethyl)oxy]-19,20-dihydro-19-oxo-5H,17H-18,21-ethano-6,10:12,16-dimetheno-22H-imidazo[3,4-h][1,8,11,14]oxatriazacycloeicosine-9-carbonitrile (86), 14-[(Cyclopropylmethyl)oxy]-19,20-dihydro-19-oxo-5H,17H-18,21-ethano-6,10:12,16-dimetheno-22H-imidazo[3,4-h][1,8,11,14]oxatriazacycloeicosine-9-carbonitrile (87), 19,20-Dihydro-19-oxo-14-[(trifluoromethanesulfonyl)oxy]-5H,17H-18,21-ethano-6,10:12,16-dimetheno-22H-imidazo[3,4-h][1,8,11,14]oxatriazacycloeicosine-9-carbonitrile (88), 14-(3-Cyclopropylethynyl)-19,20-dihydro-3-methyl-19-oxo-5H,17H-18,21-ethano-6,10:12,16-dimetheno-22H-imidazo[3,4-h][1,8,11,14]oxatriazacycloeicosine-9-carbonitrile (89), 19-Oxo-19,20,22,23-tetrahydro-5H-18,21-ethano-12,14-etheno-6,10-metheno-benzo[d]imidazo[4,3l][1,6,9,13]oxatriaza-cyclononadecine-9-carbonitrile (90), 9-Bromo-19,20,22,23-tetrahydro-5H-18,21-ethano-12,14-etheno-6,10-metheno-benzo[d]imidazo[4,3l][1,6,9,13]oxatriaza-cyclononadecine-19-one (91), 19,20,22,23-Tetrahydro-9-[4-(trifluoromethyl)phenyl]-5H-18,21-ethano-12,14-etheno-6,10-metheno-benzo[d]imidazo[4,3-l][1,6,9,13]oxatriazacyclononadecine-19-one (92), 8-Chloro-19-oxo-19,20,22,23-tetrahydro-5H-18,21-ethano-12,14-etheno-6,10-metheno-benzo[d]imidazo[4,3l][1,6,9,13]oxatriaza-cyclononadecine-9-carbonitrile (93), 3-Methyl-19-oxo-19,20,22,23-tetrahydro-5H-18,21-ethano-12,14-etheno-6,10-metheno-benzo[d]imidazo[4,3l][1,6,9,13]oxatriaza-cyclononadecine-9-carbonitrile (94), 18-Oxo-18,19,20,21,22,23-hexaahydro-5H-19,22-ethano-12,14-etheno-6,10-metheno-benzo[d]imidazo[4,3l][1,7,10,13]oxatriaza-cyclononadecine-9-carbonitrile (95), 18-Oxo-18,19,20,21,22,23-hexaahydro-5H-19,22-ethano-12,14-etheno-6,10-metheno-24H-benzo[d]imidazo[4,3-m][1,7,10,14]oxatriazacycloeicosine-9-carbonitrile (96), 15-Bromo-18-oxo-18,19,20,21,22,23-hexaahydro-5H-19,22-ethano-12,14-etheno-6,10-metheno-24H-benzo[d]imidazo[4,3-m][1,7,10,14]oxatriazacycloeicosine-9-carbonitrile (97), 5,6,20,21,22,23,24,25-Octahydro-21-Oxo-7H-20,23-ethano-14,16-etheno-8,12-metheno-benzo[d]imidazo[4,3l][1,6,9,13]oxatriaza-cycloheneicosine-11-carbonitrile (98), 15-Chloro-19,20-dihydro-3-methyl-19-oxo-5H,17H-18,21-ethano-6,10:12,16-dimetheno-22H-imidazo[3,4-h][1,8,11,14]oxatriaza-cycloeicosine-9-carbonitrile (99),

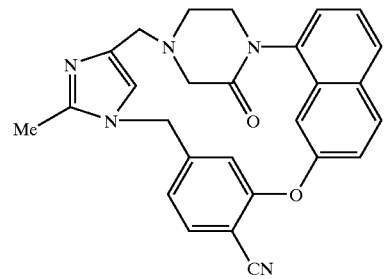

or a pharmaceutically acceptable salt or stereoisomer thereof.

8. The compound according to claim 7 which is:
(+)-19,20-Dihydro-1,9-oxo-5H-18,21-ethano-12,14-etheno-6,10-metheno-22H-benzo[d]imidazo[4,3-k][1,6,9,12]oxatriazacyclooctadecine-9-carbonitrile ((+)-6),

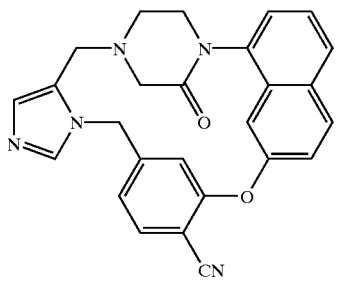

or a pharmaceutically acceptable salt or stereoisomer thereof.

9. The compound according to claim 7 which is:
15-Bromo-19,20-dihydro-3-methyl-19-oxo-5H,17H-18,21-ethano-6,10:12,16-dimetheno-22H-imidazo[3,4-h][1,8,11,14]oxatriaza-cycloeicosine-9-carbonitrile (25)

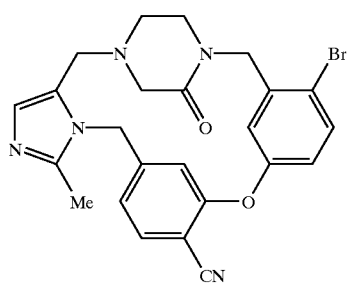

or a pharmaceutically acceptable salt or stereoisomer thereof.

10. The compound according to claim 7 which is:
15-[(2-Cyclobutyl)ethyl]-19,20-dihydro-3-methyl-17-oxo-5H,17H-18,21-ethano-6,10:12,16-dimetheno-22H-imidazo[3,4-h][1,8,11,14]oxatriazacycloeicosine-9-carbonitrile (31),

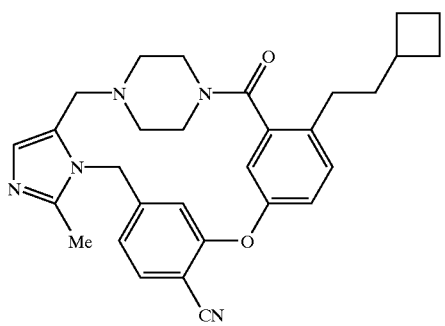

or a pharmaceutically acceptable salt or stereoisomer thereof.

11. The compound according to claim 7 which is:
19,20-Dihydro-3-methyl-19-oxo-15-(5,5,5-trifluoropentyl)-5H,17H-18,21-etheno-6,10:12,16-dimetheno-22H-imidazo[3,4-h][1,8,11,14]oxatriazacycloeicosine-9-carbonitrile (59)

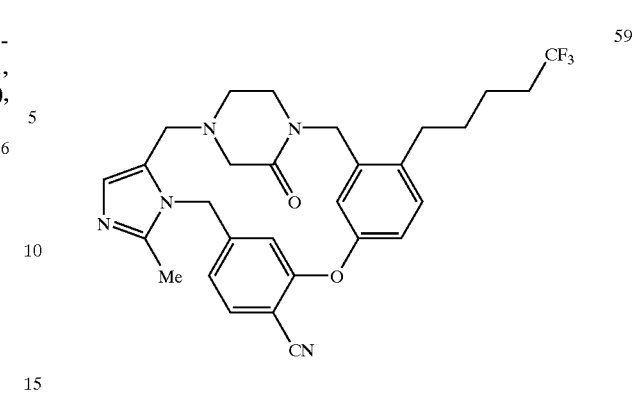

or a pharmaceutically acceptable salt or stereoisomer thereof.

12. The compound according to claim 7 which is:
19-Oxo-19,20,22,23-tetrahydro-5H-18,21-ethano-12,14-etheno-6,10-metheno-benzo[d]imidazo[4,3l][1,6,9,13]oxatriaza-cyclononadecine-9-carbonitrile (90)

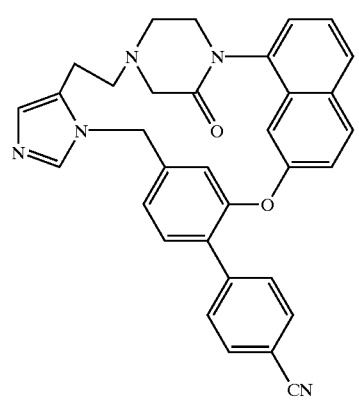

or a pharmaceutically acceptable salt or stereoisomer thereof.

13. The compound according to claim 7 which is:
18-Oxo-18,19,20,21,22,23-hexaahydro-5H-19,22-ethano-12,14-etheno-6,10-metheno-24H-benzo[d]imidazo[4,3-m][1,7,10,14]oxatriazacycloeicosine-9-carbonitrile (96)

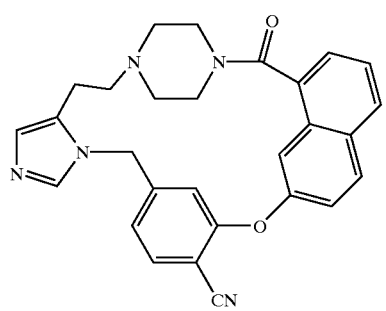

or a pharmaceutically acceptable salt or stereoisomer thereof.

14. A pharmaceutical composition comprising a pharmaceutical carrier, and dispersed therein, a therapeutically effective amount of a compound of claim 1.

15. A pharmaceutical composition comprising a pharmaceutical carrier, and dispersed therein, a therapeutically effective amount of a compound of claim 7.

16. A pharmaceutical composition comprising a pharmaceutical carrier, and dispersed therein, a therapeutically effective amount of a compound of claim 8.

17. A process for making a pharmaceutical composition comprising combining a compound of claim 1 and a pharmaceutically acceptable carrier.

* * * * *